United States Patent
Dasseux et al.

(10) Patent No.: US 10,941,095 B2
(45) Date of Patent: *Mar. 9, 2021

(54) HYDROXYL COMPOUNDS AND COMPOSITIONS FOR CHOLESTEROL MANAGEMENT AND RELATED USES

(71) Applicant: Esperion Therapeutics, Inc., Ann Arbor, MI (US)

(72) Inventors: Jean-Louis H. Dasseux, Toulouse (FR); Carmen D. Oniciu, Toulouse (FR)

(73) Assignee: Esperion Therapeutics, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/142,547

(22) Filed: Sep. 26, 2018

(65) Prior Publication Data

US 2019/0263742 A1  Aug. 29, 2019

Related U.S. Application Data

(60) Continuation of application No. 15/487,623, filed on Apr. 14, 2017, now Pat. No. 10,118,881, which is a continuation of application No. 14/674,028, filed on Mar. 31, 2015, now Pat. No. 9,624,152, which is a continuation of application No. 13/925,818, filed on Jun. 24, 2013, now Pat. No. 9,000,041, which is a continuation of application No. 13/470,825, filed on May 14, 2012, now Pat. No. 8,497,301, which is a
(Continued)

(51) Int. Cl.
*C07C 31/27* (2006.01)
*C07C 61/12* (2006.01)
(Continued)

(52) U.S. Cl.
CPC .......... *C07C 31/27* (2013.01); *A61K 31/191* (2013.01); *A61K 31/194* (2013.01); *A61K 31/20* (2013.01); *A61K 31/23* (2013.01); *C07C 31/20* (2013.01); *C07C 31/22* (2013.01); *C07C 31/24* (2013.01); *C07C 33/26* (2013.01); *C07C 47/19* (2013.01); *C07C 47/34* (2013.01); *C07C 59/01* (2013.01); *C07C 59/105* (2013.01); *C07C 59/11* (2013.01); *C07C 59/245* (2013.01); *C07C 59/285* (2013.01); *C07C 59/29* (2013.01); *C07C 59/46* (2013.01); *C07C 59/48* (2013.01); *C07C 59/54* (2013.01); *C07C 61/12* (2013.01); *C07C 62/02* (2013.01); *C07C 62/06* (2013.01); *C07C 65/17* (2013.01); *C07C 69/003* (2013.01); *C07C 69/017* (2013.01); *C07C 69/675* (2013.01); *C07C 69/757* (2013.01); *C07C 255/00* (2013.01); *C07C 309/08* (2013.01); *C07C 309/24* (2013.01); *C07C 309/25* (2013.01); *C07D 213/80* (2013.01); *C07D 257/04* (2013.01); *C07D 261/08* (2013.01); *C07D 261/12* (2013.01); *C07D 305/12* (2013.01); *C07D 307/33* (2013.01);
(Continued)

(58) Field of Classification Search
CPC ....... C07C 31/27; C07C 59/01; C07C 255/00; C07C 309/24; C07C 309/08; C07C 69/017; C07C 69/003; C07C 69/675; C07C 47/19; C07C 33/26; A61K 31/191; A61K 31/20; A61K 31/23; A61K 31/194; C07D 309/30; C07D 307/33; C07D 305/12; C07D 261/08; C07D 257/04; C07D 495/04; C07F 9/242; C07F 9/2408; C07F 9/12; C07F 9/11
See application file for complete search history.

(56) References Cited

U.S. PATENT DOCUMENTS

3,152,148 A    10/1964  Easterly et al.
3,441,605 A     4/1969  Blake
(Continued)

FOREIGN PATENT DOCUMENTS

EP    0284108 A2    9/1988
EP    1047421 A2   11/2000
(Continued)

OTHER PUBLICATIONS

Ackerly, et al., 1995, "A novel approach to dual-acting thromboxane receptor antagonist/synthase inhibitors based on the link of 1,3-dioxane-thrombaxane receptor antagonists and -thromboxane synthase inhibitors", J. Med. Chem. 38:1608-1628.
(Continued)

*Primary Examiner* — Sudhakar Katakam
(74) *Attorney, Agent, or Firm* — Goodwin Procter LLP

(57) ABSTRACT

The present invention relates to novel hydroxyl compounds, compositions comprising hydroxyl compounds, and methods useful for treating and preventing a variety of diseases and conditions such as, but not limited to aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, obesity, oxysterol elimination in bile, pancreatitis, pancreatitius, Parkinson's disease, a peroxisome proliferator activated receptor-associated disorder, phospholipid elimination in bile, renal disease, septicemia, metabolic syndrome disorders (e.g., Syndrome X), thrombotic disorder. Compounds and methods of the invention can also be used to modulate C reactive protein or enhance bile production in a patient. In certain embodiments, the compounds, compositions, and methods of the invention are useful in combination therapy with other therapeutics, such as hypocholesterolemic and hypoglycemic agents.

24 Claims, No Drawings

Related U.S. Application Data continuation of application No. 12/870,184, filed on Aug. 27, 2010, now abandoned, which is a division of application No. 11/680,105, filed on Feb. 28, 2007, now Pat. No. 7,812,199, which is a division of application No. 10/743,470, filed on Dec. 23, 2003, now Pat. No. 7,335,799.

(60) Provisional application No. 60/441,795, filed on Jan. 23, 2003.

(51) Int. Cl.

| | | |
|---|---|---|
| C07C 47/34 | (2006.01) |
| C07C 309/25 | (2006.01) |
| C07F 9/24 | (2006.01) |
| C07D 261/12 | (2006.01) |
| C07C 59/105 | (2006.01) |
| C07C 33/26 | (2006.01) |
| C07C 47/19 | (2006.01) |
| C07C 69/675 | (2006.01) |
| C07C 69/003 | (2006.01) |
| C07C 69/017 | (2006.01) |
| C07C 309/08 | (2006.01) |
| C07F 9/11 | (2006.01) |
| C07C 309/24 | (2006.01) |
| C07F 9/12 | (2006.01) |
| C07D 495/04 | (2006.01) |
| C07C 255/00 | (2006.01) |
| C07D 257/04 | (2006.01) |
| C07D 261/08 | (2006.01) |
| C07D 305/12 | (2006.01) |
| C07D 307/33 | (2006.01) |
| C07C 59/01 | (2006.01) |
| C07D 309/30 | (2006.01) |
| A61K 31/194 | (2006.01) |
| A61K 31/23 | (2006.01) |
| A61K 31/20 | (2006.01) |
| A61K 31/191 | (2006.01) |
| C07C 31/20 | (2006.01) |
| C07C 31/22 | (2006.01) |
| C07C 31/24 | (2006.01) |
| C07C 59/11 | (2006.01) |
| C07C 59/285 | (2006.01) |
| C07C 59/29 | (2006.01) |
| C07C 59/46 | (2006.01) |
| C07C 59/48 | (2006.01) |
| C07C 59/54 | (2006.01) |
| C07C 62/06 | (2006.01) |
| C07C 65/17 | (2006.01) |
| C07C 69/757 | (2006.01) |
| C07D 213/80 | (2006.01) |
| C07D 309/10 | (2006.01) |
| C07D 309/12 | (2006.01) |
| C07D 405/12 | (2006.01) |
| C07F 9/09 | (2006.01) |
| C07F 9/117 | (2006.01) |
| C07F 9/44 | (2006.01) |
| C07C 59/245 | (2006.01) |
| C07C 62/02 | (2006.01) |

(52) U.S. Cl.
CPC ......... *C07D 309/10* (2013.01); *C07D 309/12* (2013.01); *C07D 309/30* (2013.01); *C07D 405/12* (2013.01); *C07D 495/04* (2013.01); *C07F 9/093* (2013.01); *C07F 9/094* (2013.01); *C07F 9/11* (2013.01); *C07F 9/117* (2013.01); *C07F 9/12* (2013.01); *C07F 9/242* (2013.01); *C07F 9/2408* (2013.01); *C07F 9/2416* (2013.01); *C07F 9/2425* (2013.01); *C07F 9/4423* (2013.01); *C07C 2601/02* (2017.05); *C07C 2601/04* (2017.05); *C07C 2601/08* (2017.05)

(56) References Cited

U.S. PATENT DOCUMENTS

| | | |
|---|---|---|
| 3,773,946 A | 11/1973 | Creger |
| 3,930,024 A | 12/1975 | Creger |
| 4,281,200 A | 7/1981 | Snoble |
| 4,287,200 A | 9/1981 | Kawamatsu et al. |
| 4,584,321 A | 4/1986 | Manghisi et al. |
| 4,613,593 A | 9/1986 | Yamatsu et al. |
| 4,634,119 A | 1/1987 | Pesthy |
| 4,634,719 A | 1/1987 | Takaishi et al. |
| 4,639,344 A | 1/1987 | Ueno et al. |
| 4,689,344 A | 8/1987 | Bar-Tana |
| 4,711,896 A | 12/1987 | Bar-Tana et al. |
| 4,714,762 A | 12/1987 | Hoefle et al. |
| 4,896,344 A | 1/1990 | Grady et al. |
| 5,166,174 A | 11/1992 | Ueno et al. |
| 5,225,439 A | 7/1993 | Ueno et al. |
| 5,284,858 A | 2/1994 | Ueno et al. |
| 5,380,709 A | 1/1995 | Ueno et al. |
| 5,428,062 A | 6/1995 | Ueno et al. |
| 5,502,198 A | 3/1996 | Picard et al. |
| 5,504,073 A | 4/1996 | Homan |
| 5,570,569 A | 11/1996 | Masuda |
| 5,578,639 A | 11/1996 | Homan |
| 5,633,287 A | 5/1997 | Lee et al. |
| 5,648,387 A | 7/1997 | Bisgaier et al. |
| 5,750,569 A | 5/1998 | Bisgaier et al. |
| 5,756,344 A | 5/1998 | Onda et al. |
| 5,756,544 A | 5/1998 | Bisgaier et al. |
| 5,783,600 A | 7/1998 | Bisgaier et al. |
| 5,834,596 A | 11/1998 | Ageland et al. |
| 5,886,034 A | 3/1999 | Ueno et al. |
| 5,968,963 A | 10/1999 | Homan |
| 5,981,595 A | 11/1999 | Picard et al. |
| 6,004,925 A | 12/1999 | Dasseux et al. |
| 6,017,905 A | 1/2000 | Roark et al. |
| 6,037,323 A | 3/2000 | Dasseux et al. |
| 6,093,719 A | 7/2000 | Bocan |
| 6,093,744 A | 7/2000 | Lee et al. |
| 6,124,309 A | 9/2000 | Bocan |
| 6,143,755 A | 11/2000 | Bocan |
| 6,362,236 B1 | 3/2002 | Aviram et al. |
| 6,410,802 B1 | 6/2002 | Dasseux et al. |
| 6,459,003 B1 | 10/2002 | Dasseux et al. |
| 6,506,799 B1 | 1/2003 | Dasseux |
| 6,646,170 B2 | 11/2003 | Dasseux et al. |
| 6,673,780 B2 | 1/2004 | Dasseux et al. |
| 6,699,910 B2 | 3/2004 | Dasseux et al. |
| 6,703,422 B2 | 3/2004 | Dasseux et al. |
| 6,713,507 B2 | 3/2004 | Dasseux et al. |
| 6,790,953 B2 | 9/2004 | Dasseux et al. |
| 6,831,105 B2 | 12/2004 | Dasseux |
| 6,909,014 B2 | 6/2005 | Dasseux et al. |
| 7,119,221 B2 | 10/2006 | Dasseux et al. |
| 7,192,940 B2 | 3/2007 | Dasseux et al. |
| 7,304,093 B2 | 12/2007 | Dasseux et al. |
| 7,335,689 B2 | 2/2008 | Dasseux et al. |
| 7,335,799 B2 | 2/2008 | Dasseux et al. |
| 7,405,226 B2 | 7/2008 | Dasseux et al. |
| 7,576,130 B2 | 8/2009 | Dasseux et al. |
| 7,705,177 B2 | 4/2010 | Oniciu et al. |
| 7,812,199 B2 | 10/2010 | Dasseux et al. |
| 7,838,554 B2 | 11/2010 | Dasseux et al. |
| 8,067,466 B2 | 11/2011 | Dasseux et al. |
| 8,084,498 B2 | 12/2011 | Dasseux et al. |
| 8,153,690 B2 | 4/2012 | Dasseux et al. |
| 8,309,604 B2 | 11/2012 | Dasseux et al. |
| 8,497,301 B2 * | 7/2013 | Dasseux ............ C07C 31/22 514/558 |

(56) References Cited

U.S. PATENT DOCUMENTS

| | | | |
|---|---|---|---|
| 8,623,915 B2 | 1/2014 | Dasseux et al. | |
| 8,642,653 B2 | 2/2014 | Dasseux et al. | |
| 9,000,041 B2* | 4/2015 | Dasseux | A61K 31/194 |
| | | | 514/558 |
| 9,006,290 B2 | 4/2015 | Dasseux et al. | |
| 9,452,964 B2 | 9/2016 | Dasseux et al. | |
| 9,624,152 B2* | 4/2017 | Dasseux | A61K 31/23 |
| 10,047,028 B2 | 8/2018 | Dasseux et al. | |
| 10,118,881 B2* | 11/2018 | Dasseux | A61K 31/191 |
| 2004/0214777 A1 | 10/2004 | McGrath | |
| 2004/0214887 A1 | 10/2004 | Dasseux et al. | |
| 2005/0043278 A1 | 2/2005 | Dasseux et al. | |
| 2005/0119333 A1 | 6/2005 | Dasseux | |
| 2005/0214887 A1 | 9/2005 | Emori et al. | |
| 2007/0155704 A1 | 7/2007 | Dasseux et al. | |
| 2007/0179120 A1 | 8/2007 | Dasseux et al. | |
| 2008/0249166 A1 | 10/2008 | Dasseux et al. | |
| 2009/0024789 A1 | 1/2009 | Rajan et al. | |
| 2009/0247489 A1 | 10/2009 | Dasseux et al. | |
| 2012/0129930 A1 | 5/2012 | Dasseux et al. | |
| 2012/0225908 A1 | 9/2012 | Dasseux et al. | |
| 2015/0344388 A1 | 12/2015 | Dasseux et al. | |
| 2015/0344389 A1 | 12/2015 | Dasseux et al. | |
| 2019/0084908 A1 | 3/2019 | Dasseux et al. | |

FOREIGN PATENT DOCUMENTS

| | | |
|---|---|---|
| FR | 1545224 A | 11/1968 |
| GB | 1196594 A | 7/1970 |
| GB | 1196595 A | 7/1970 |
| GB | 1196596 A | 7/1970 |
| GB | 1196597 A | 7/1970 |
| GB | 1196598 A | 7/1970 |
| WO | WO-9630328 A1 | 10/1996 |
| WO | WO-9830530 A1 | 7/1998 |
| WO | WO-9900116 A2 | 1/1999 |
| WO | WO-9926583 A2 | 6/1999 |
| WO | WO-2004067489 A2 | 8/2004 |

OTHER PUBLICATIONS

Acton, et al., 1996, "Identification of scavenger receptor SR-B1 as high density lipoprotein receptor", Science. 271(5248):518-20.

Ahrens, et al., 1967, "A direct method for preparing pyridoxal and 4-pyridoxic acid (1)", J. Heterocyl. Chem. 4:625-26.

Alexander, K., et al., 1948, "4.4-Dichlorodibutyl ether and its derivatives from tetrahydrofuran", J. Am. Chem. Soc. 70:1839-42.

Badimon, et al., 1992, "Role of High density lipoproteins in the regression of atherosclerosis", Circulation 85 (Suppl);11186-94.

Bailey, et al. "Convenient general method for the preparation of primary alkyllithiums by lithium-iodine exchange," (1990) J. Org. Chem. vol. 55, No. 19, pp. 5404-5406.

Barrans, et al., 1996, "Pre-beta HDL; structure and metabolism", Biochim, Biophys. Acta. 1300(2):73-85.

Becker, et al., 1982, "Intramolecular photoaddition of terminal allenes to conjugated cyclohexenones", J. Org. Chem. 47:3297-3310.

Beilstein Report for Compound Beilstein Registry No. 1741087, based in part on Crisan et al. (1956), Ann. Chim, (Paris), 13(1): 436-459.

Beilstein Report for Compound Beilstein Registry No. 1778991, based in part on Pechmann (1904), Chem. Ber., 37: 3819.

Beilstein Report for Compound Beilstein Registry No. 1784568, based in part on English (1941), J. Am. Chem. Soc., 63 (4): 941-943.

Beilstein Report for Compound Beilstein Registry No. 2961112, based in part on Lardelli et al. (1967), Recl. Trav. Chim., 86: 481-503.

Beilstein Report for Compound Beilstein Registry No. 5836264, based in part on Weber et al. (1992), J. Med. Chem., 35(21): 3755-3773.

Beilstein Report for Compound Beilstein Registry No. 7473723, based in part on Rieke et al. (1996), J. Org. Chem., 61(8): 2726-2730.

Beilstein Report for Compound, Beilstein Registry No. 5815199 based in part on Weber et al. (1992), J. Med. Chem., 35(21): 3755-3773.

Bernady, et al. "Prostaglandins and congeners. 20. Synthesis of prostaglandins via conjugate addition of lithium trans-1-alkenyltrialkylalanate reagents. A novel reagent for conjugate 1,4-additions," J. Org. Chem. (1979) vol. 44, No. 9, pp. 1438-1447.

Bhanot, et al "Synthetic studies on Terpenoids. 5. Syntheses of γ- and δ-Lactones from β-(2,7-Dimethyl-1,2-dihdroxycycloheptyl)propionic Acid," J. Org. Chem. (1977) vol. 42, pp. 1623-1627.

Bicking, et al., "11,12-Secoprostaglandins. 1. Acylhydroxyalkanoic acids and related compounds", J. Med. Chem., 1977, pp. 35-43, vol. 20.

Bisgaier, et al., 1997, "Attenuation of plasma low density lipoprotein cholesterol by select 3-hydroxy-3-methylglutaryl coenzyme A reductase inhibitors in mice of low density lipoprotein receptors", J. Lipid Res. 38 (12):2502-2515.

Bisgaier, et al., 1998, "A novel compound that elevates high density lipoprotein and activates the peroxisome proliferator activated receptor", J. Lipid Res. 39(1):17-30.

Blatt ed., 1943, "Gilbert Sulfonation and Related Reactions" pp. 135-142, 160-165; Org. Synth. Coll. vol. II, Wiley, NY and Org. Synth. Coll. vol. IV, 1963, Wiley NY 529-531.

Blatt, et al., "The reducing action of Grignard reagent and the synthesis of tertiary aliphatic carbinols", J. Org. Chem., 1932, pp. 1495-1499, vol. 54.

Bohme, V. and Lener, W., 1955, Annalen der Chemie, 595;169-178 (English language abstract).

Bongini, et al., 1979 "A simple and practical method for tetrahydropyranylation of alcohols and phenols", Synthesis 618-620.

Brown, et al. "Selective reductions. 26. Lithuim triethylborohydride as an exceptionally powerful and selective reducing agent in organic synthesis. Exploration of the reactions with selected organic compounds containing representative functional groups," J. Org. Chem. (1980) vol. 45, No. 1, pp. 1-12.

Brown, H. C. et al."Hydroboration. 67. Cyclic hydroboration of acyclic alpha,omega-dienes with 9-borabicyclo[3.3.1]nonane/borane-dimethyl sulfide," J. Org. Chem. (1984) vol. 49, No. 6, pp. 1072-1078.

Brown, H. C. et al."Selective reductions. VII. Reaction of lithium trimethoxyaluminohydride with selected organic compounds containing representative functional groups," J. Am. Chem. Soc. (1965) vol. 87, No. 24, pp. 5614-5620.

Bruce, et al., 1998, "Plasma lipid transfer proteins, high-density lipoproteins, and reverse cholesterol transport", Annu Rev Nutr. 1998;18:297-330.

Campagna, et al., 1994, "Cyclic Amidine Analogues of Taurine and Homotaurine; Synthesis and Effects on Rat Skeletal Muscle", Farmaco, Ed. Sci 49:653-658.

Cerny, et al., 1969, "Properties of Sodium Bis-(2-Methoxyethoxy)-Aluminum Hydride", Collect Czech Chem Comm. 34:1025-33.

Chadwick, et al., 1979, "Reaction between N-Alkylpyroles and Alkyllithium Reagents" J. Chem Soc., Perkin Trans. 12845.

Chaikin, et al., 1949, "Lithium Borohydride as a Reducing Agent", J. Am. Chem. Soc. 71:3245-48.

Chen, et al., 1998, "Asymmetric total synthesis of phosphatidylinositol 3-phosphate and 4-phosphate derivatives", J. Org. Chem. 63:6511-22.

Comins, et al., 1981, "A one pot synthesis of unsymmetrical secondary alcohols from two grignard reagents", Tetrahedron Lett. 22:1085-88.

Corbridge, 1985, "Phosphorus: An Outline of its Chemistry, Biochemistry and Technology", Studies in Inorganic Chemistry, 3rd ed, pp. 357-395.

Corey, et al., 1967, "A useful method for the conversion of alcohols into iodides", J. Org. Chem. 32:4160-4161.

(56) References Cited

OTHER PUBLICATIONS

Corey, et al., 1979, "Useful procedures for the oxidation of alcohols involving pyridinum dichromate in aprotic media", Tetrahedron Lett. 5:399-402.
Corothers, 1924, "Platinum oxide as a catalyst in the reduction of organic compounds. V. The preparation of primary alcohols by the catalytic hydrogenation of aldehydes," J. Am. Chem. Soc. 46:1675-83.
Dalton, J.C. et al. (1971) "Type I and Type II Photochemical Reactions of Some Five- and Six-Membered Cycloalkanones," J. Am. Chem. Soc., 93 (26): 7213-21.
Danheiser, et al., 1991, "A Practical and Efficient Method for Synthesis of β-Lactones", J. Org. Chem. 58:1176-65.
Dansky HM, Fisher Ea, 1999, "High-density lipoprotein and plaque regression: the good cholesterol gets even better", Circulation 100(17): 1762-3.
Decossin, et al., 1997, "Subclasses of LpA-I in coronary artery disease: distribution and cholesterol efflux ability", Eur J Clin Invest. 27(4):299-307.
Desarlo, et al., 1971, "Isoxazolin-5-one", J. Chem Soc. 88-89.
Eaton, et al., 1972, "Hydroxypropylation", J. Org. Chem. 37:1947-50.
Ehlinger, et al., 1980, "Silicon in Synthesis. 10. The (trimethylsiyl)allyl Anion: A. beta-Acyl anion equivalent for the conversion of aldehydes and ketones into gamma-lactone", J. Am. Chem. Soc. 102:5004-11.
Eisch, et al. 1978, "Synthesis of lactones via the titanium-catalyzed hydromagnesiation of alkenols", J. Organomet. Chem. 160:C8-C12.
Fielding & Fielding, 1995, "Molecular physiology of reverse cholesterol transport", J. Lipid Res. 36(2):211-28.
Fraser, et al., 1985, "Acidity measurements in THF. V. Heteroaromatic compounds containing 5-membered rings", Can J. Chem. 63:3505-09.
Garegg, et al., 1980, "Novel Reagent System for converting a Hydroxy-group into an Iodo-group in carbohydrates with inversion of Configuration", J.C.S. Perkin I 2866-2868.
Gearing, et al., 1993, "Interaction of the peroxisome-proliferator-activated receptor and retinoid X receptor", Proc. Natl. Acad. Sci. USA 90(4):14440-1444.
Gigg, et al., 1967, "The Preparation of Unsymmetrical Diglycerides", J. Chem. Soc., C. 431-434.
Gleiter, R. et al. "Synthesis and properties of 4,4,9,9-tetramethyl-1-oxa-cycloundecane-5,6,7,8-tetrone and 5,5,10,10-tetramethyl-1-oxa-cyclotridecane-6,7,8,9-tetrone," Chemistry—A European Journal (1996) vol. 2, No. 3, pp. 271-277.
Gleiter, R. et al., "Synthesis of 5,5,10,10-tetramethyl-1-oxacyclotridecane-6,7,8,9-tetrone—on the mechanism of the Rubotom reaction," Eur. J. Org. Chem. (1995) No. 9, pp. 1655-1661.
Green and Kehinde, 1975, "An established predispose cell line and its differentiation in culture II. Factors affecting the adipose conversion", Cell. 5(1):19-27.
Greene, T.W., 1999, "Protection for the Hydroxyl Group, Including 1,2-and 1,3-Diols", Protective Groups in Organic Synthesis.
Harris and Kletzien, 1994, "Localization of pioglitazone response element in the adipocyte fatty acid-binding protein gene", Mol Pharmacol. 45(3):439-45.
Hayden and Ma, 1992, "Molecular genetics of human lipoprotein lipase deficiency", Mol Cell Biochem. 113(2):171-6.
Heyman, et al., 1992, "9-cis retinoic acid is high affinity ligand for the retinoid X receptor", Cell 68(2):397-406.
Hidaka and Fidge, 1992, "Affinity purification of the hepatic high-density lipoprotein receptor identifies two acidic glycoproteins and enables further characterization of their binding properties", Biochem. J. 15(Pt1):161-7.
Hirano, et al., 1997, "Genetic cholesteryl ester transfer deficiency is extremely frequent in the Omagari area of Japan. Marked hyperalphalipoproteinema caused by CETP gene mutation is not associated with longevity", Arterioscler. Thromb. Vasc.Biol. 17(6):1053-1059.

Hoyer, et al., 1986, "Catalysis by acidic clay of the protective tetrahydropyranylation of alcohols and phenols", Synthesis 655-57.
Hudlicky, M., 1996, "Reduction of aldehydes and their derivatives", Reductions in Organic Chemistry, 2nd ed. pp. 137-139.
Hudlicky, M., 1996, "Reduction of esters and lactones of carboxylic acids", Reduction in Organic Chemistry 2nd ed. pp. 212-217.
International Search Report, International Application No. PCT/US2003/041411, dated Dec. 8, 2004 (12 pages).
Ishibashi, et al., 1993, "Hypercholesterolemia in low density lipoprotein receptor knockout mice and its reversal by adenovirus-mediated gene delivery", J. Clin. Invest. 92(2):883-93.
Ishibashi, et al., 1994, "Massive xanthomatosis and atherosclerosis in cholesterol-fed low density lipoprotein receptor-negative mice", J. Clin Invest. 93(5):1885-93.
Isseman and Green, 1990, "Activation of a member of the steroid hormone receptor superfamily by peroxisome proliferators", Nature 347(6294):645-650.
Iwai, et al, 1966, "Studies on acetylenic compounds. XLIV. Synthesis of 3-aminoisoxazoles and 3-hydroxyisoxazoles (3-Isoxazolones)", Chem. Pharm. Bull. 14:1277-88.
Jetter, R., "Long-chain alkanediols from Myricaria germanica leaf cuticular waxes," Phytochemistry, 55 (2), 2000, pp. 169-176.
Johnston, et al., 1988, "A new, mild heterogeneous catalyst for the tetrahydropyranylation of alcohols and phenols", Synthesis 393-4.
Katritzky, et al., 1993, "Generation and Reactions of $sp^2$-Carbanionic Centers in the Vicinity of Heterocyclic Nitrogen Atoms", Adv. Het. Chem. 56:155-303.
Keller and Wahli, 1993, "Peroxisome proliferator-activated receptors—A link between endocrinology and Nurition?" TEM, 4:291-295.
Keller, et al., 1993, "Fatty acids and retinoids control lipid metabolism through activation of peroxisome proliferator-activated receptor-retinoid X receptor heterodimers", Proc. Natl. Acad. Sci. USA 90(6):2160-2164.
Kessar, et al., 1997, "Lewis acid complexation of tertiary amines and related compounds: A strategy for a α-deprotonation and stereocontrol", Chem. Rev. 97:721-37.
Kletzein, et al., 1991, "Enhancement of adipocyte differentiation by an insulin-sensitizing agent", Mol Pharmacol 41(2):393-398.
Kliewer, et al., 1992, "Convergence of 9-cis retinoic acid and peroxisome proliferator signaling pathways through heterodimer formation of their receptors", Nature 27;358(6389):771-4.
Kurata, et al., 1998, "A candidate high density lipoprotein (HDL) receptor, HB2, with possible multiple functions shows sequence homology with adhesion molecules", J. Atherosclerosis and Thrombosis 4(3):112-7.
Kurz, et al., 1985, "Anomalous selectivities in methyl transfers to water: An explanation using free energy surfaces which model the effects of non-equilibrium solvation", Isr. J. Chem. 26:339-48.
Kurz, et al.. "Evidence for rate-determining solvation change in methyl transfer to water. Solvent dependence of $H_2O/D_2O$ kinetic isotope effects," J. Am. Chem. Soc. (1986) vol. 108, pp. 2960-2968.
Lagrost, et al., 1996, "Opposite effects of cholesteryl ester transfer protein and phospholipid transfer protein on the size distribution of plasma high density lipoproteins. Physiological relevance in alcoholic patients", J. Biol. Chem.271(32):19058-65.
Landshultz, et al., 1996, "Regulation of scavenger receptor, class B, type I, a high density lipoprotein receptor, in liver and steroidogenic tissues of the rat", J. Clin. Invest. 98(4):984-995.
Larock, 1989, Comprehensive Organic Transformations; Ch. 6, VCH: New York, pp. 446-448.
Lazarow and Fujiki, 1985, "Biogenesis of peroxisomes", Annu Rev Cell Biol. 1:489-530.
Levin, et al., 1992, "9-cis retinoic acid stereoisomer binds and activates the nuclear receptor RXR alpha", Nature 355(6358):359-61.
Ludwig, et al., 1989, "Rapid and efficient synthesis of nucleoside 5'-0-(1-thiotriphosphates), 5'triphosphates and 2',3'-Cyclophosphorothioates using 2-Chloro-4H-1,3,2-benzodioxaphosphorin-4-one", J. Org. Chem. 54:631-35.
Maddaford, et al., 1993, "A general asymmetric synthesis of (−)-alpha-Dimethylretrodendrin and its diastereomers", J. Org. Chem 58:4132-38.

(56) References Cited

OTHER PUBLICATIONS

March, J., 1992, Advanced Organic Chemistry: Reactions, Mechanisms, and Structure 4$^{th}$ ed., pp. 248-272, 1196-98, 437-438, 920-929.

Masamune, et al. "Tylonolide hemiacetal, the aglycone of tylosin, and its partial synthesis," *J. Am. Chem. Soc.* (1976) vol. 98, No. 24, pp. 7874-7875.

Masayuma, et al., 2000, "Regio-and diastereocontrol in carbonyl allylation by 1-halobut-2-enes with Tin(II) halides", J Org Chem. 65(2):494-8.

McCune et al., "Effect of Mevinolin on Cholesterol Metabolism in Obese and Lean Zucker Rats," *Biochemical Pharmacology* (1987) vol. 36, pp. 875-879. (abstract only).

Menger, et al., 1981, "Synthetically useful oxidations at solid sodium permanganate surfaces", Tetrahedron Lett. 22:1655-56.

Miyashita, et al., 1977, "Pyridinium .rho.-Toluenesulfonate. A mild and efficient catalyst for the tetrahydropyranylation of alcohols", J. Org. Chem 42:3772-74.

Moffet, et al., 1963, "2-(1-Pyrrolidyl)Propanol", Org. Synth. Collect 4:834-5.

Mulzer, 1995, Comprehensive Organic Functional Group Transformations Oxford 5 pp. 161.

Myers, et al., 1992, "Studies on the thermal generation and reactivity of a class of (.alpha., .pi.)-1,4-biradicals", J. Am. Chem. Soc. 114:9369-86.

Nagano H., et al., "Stereoselectivitiy in the formation and radical reduction of cyclic bromoacetals, key intermediates for the synthesis of delta-hydroxy-and epilson-hydroxy-alpha-methylcarboxylic acid esters", Tetrahedron Letters, 2003, pp. 6867-6870, vol. 44, No. 36.

Nan F, et al., "Dual Function Glutamate-Related Ligands: Discovery of a Novel, Potent Inhibitor of Glutamate Carboxypeptidase II Possessing mGluR3 Agonist Activity" Journal of Medicinal Chemistry 2000, 43:pp. 772-774.

Nemali, et al., 1988, "Comparison of constitutive and Inducible levels of expression of paroxisomal beta-oxidation and catalase genes in liver and extrahepatic tissues of rat", Cancer Res. 48(18):5316-24.

Nystrom, et al., 1947, "Reduction of Organic Compounds by Lithium Aluminum Hyride", J. Am. Chem. Soc. 69:1197-1199.

Nystrom, et al., 1949, "Lithium borohydride as a reducing agent", J. Am. Chem. 71:3245-47.

Ogata, et al., 1969, "Kinetics of the Baeyer-Villiger reaction of benzaldehydes with perbenzoic acid in aquoorganic solvents", J. Org. Chem. 34:3985-91.

Okamoto, et al., 1985, "Synthesis of Alkyl Dihydrogenphosphate by the Reaction of Alcohols and Silyl Polyphosphate", Bull Chem. Soc. Jpn. 58:3393-3394.

Olah, et al., 1979, "Transformations with Chlorotrimethylsilane/ Sodium Iodide, a Convenient In Situ Iodotrimethylsilane Reagent", J. Org. Chem 44:8, 1247-1251.

Olah, et al., 1984, "N-Formylmorpholine: A New and Effective Formylating Agent for the Preparation of Aldehydes and Dialkyl(1-Formylalkyl)phosphonates from Grignard or Organolithium Reagents", J. Org. Chem. 4.

Olah, et al., 1987, "Formylating Agents", Chem. Rev. 87:4, 671-686.

Oster, et al., 1983, "Generation and Reactions of the Dianion of 3-Hydroxy-5-methylisoxazole, a convenient β-keto Amide Synthon", J. Org Chem 48:4307-4311.

Parra, et al., 1992, "A case-control study of lipoprotein particles in two populations at contrasting risk for coronary heart disease. The ECTIM Study", Arterioscler Thromb. 12:701-707.

Pop, et al., 1997, "Allylic and Phenolic Phosphate Esters of Dexanabinol", Org. Prep. and Proc. Int. 29:341-347.

Ramirez, et al. "Phosphorylation by means of cyclic enediol phosphates," *Acc. Chem. Res.* (1978) vol. 11, pp. 239.

Raunio, et al., 1957, "Addition of Propargyl Acetal to Cyclohexanone in the Presence of Sodamide", J. Org. Chem 22:570.

Reaven, 1993, "Role of Insulin resistance in human disease (syndrome X): an expanded definition", Annu Rev Med. 44:121-31.

Reddy and Lalwani, 1983, "Carcinogenesis by hepatic peroxisome proliferators: evaluation of the risk of hypolipidemic drugs and industrial plasticizers to humans", Crit Rev Toxicol. 12(1):1-58.

Rigotti, et al., 1996, "Regulation by adrenocorticotropic hormone of the in vivo expression of scavenger receptor class B type I (SR-BI), a high density lipoprotein receptor, in steroidogenic cells of the murine adrenal", J. Biol. Chem. 1996, vol. 271(52):33545-9.

Robins and Fasulo, 1997, "High density lipoproteins, but not other lipoproteins, provide a vehicle for sterol transport to bile", J Clin Invest. 98(3):380-4.

Sam, et al., 1972, "Crown Polyether Chemistry, Potassium Permanganate Oxidations in Benzene", J. Am. Chem. Soc. 94:4024.

Saulnier, et al., 1982, "Generation and Reactions of 3-Lithio-1-(phenylsulfonyl)Indole", J. Org. Chem 47:757.

Schaper, U.A. (1980) "Die gemischte Guerbet-Reaktion zwischen cyclischen und acyclischen Alkoholen," *Fette, Seifen, Anstrichmittel, Industrieverlag von Hernhaussen kg*, 82 (11): 454-456.

Shirley, et al., 1995, "Metalation of pyrrole, 1-methylpyrrole, and 1-phenylpyrrole with n-Butyllithium", J. Org. Chem 20:225-31.

Sianesi, et al., 1971, "2.4-dihydro-1 H-2.1-, 3.4-Dihydro-2H-1.2-und. 3.4-Dihydro-1 H-2.3-benzothiazin-S.S-dioxid", Chem. Ber. 104:1880-91.

Silverman, The Organic Chemistry of Drug Design and Drug Interaction, 1992, pp. 15-22.

Skinner, et al., 1995, "Benzoylcyanamide from ethyl benzoylitioncarbomate", J. Am. Chem. Soc. 77:5440-42.

Smith, et al., 1957, "Nitrogen Compounds of the phosphoric and Phosphonic Acids, III, Preparation and Properties of Amides of Phenylphosphonic and Phenylphosphonothiolic Acids", J. Org. Chem. 22:265-267.

Song, et al., 1999, "Practical asymmetric synthesis of an endothelin receptor antagonist", J. Org. Chem. 64:9658-67.

Staels and Auwerx, 1998, "Regulation of apo A-I gene expression by fibrates", Atherosclerosis 137 Suppl:S19-23.

Stevens, et al., 1982, "Further studies on the utility of sodium hypochlorite in organic synthesis Selective oxidation of diols and direct conversion of aldehydes to esters," *Tetrahedron Lett.* 23:4647-4650.

Stowell, et al., 1995, "A new method for the phosphorylation of alcohols and phenols", Tetrahedron Lett. 36(11):1825-26.

Sundararaman, et al., 1978, "One step conversion of aldehydes to esters", Tetrahedron Lett. 19:1627-1628.

Sweeney, 1995, "Comprehensive Organic Functional Group Transformations", Oxford, vol. 2, pp. 104-109.

Taravel, et al., 1988, "Interglycosidic 13C-1H Coupling Constants", Tetrahedron Lett. 29:199-200.

Thums et al., "Epoxidation—a Consequence of Cell Damage," *Chemical Monthly*, 128 (4), 1997, pp. 411-420.

Tomroka, et al., 1995, "Catalytic Asymmetric Conjugate Addition of Grignard Reagents Mediated by Copper (I)-Chiral Bidentate Phosphine Complex", Tetrahedron Lett. 36:4275-4278.

Tontonoz, et al., 1994, "Adipocyte-specific transcription factor ARF6 is a heterodimeric complex of two nuclear hormone receptors, PPAR gamma and RXR alpha", Nucleic Acids Res. 22(5):5628-34.

Uhlmann, et al., 1986, "Chemical 5'-phosphorylation of oligonucleotides valuable in automated DNA synthesis", Tetrahedron Lett. 27:1023-26.

Ulrich, et al., 1995, "Cultured hepatocytes as investigational models for hepatic toxicity: practical applications in drug discovery and development", Toxicol Lett. 82/83:107-15.

Urata, et al., 1991, "Transition metal complex catalyzed carbonylation of organic halides in the presence of molecular sieves instead of base," *Tetrahedron Lett.* 32:36, 4733-36.

Vamecq and Draye, 1989, "Pathophysiology of peroxisomal beta-oxidation", Essays Biochem. 24:115-225.

Vippagunta, S. et al., "Crystalline Solids," *Advanced Drug Delivery Reviews* (2001) vol. 48, pp. 2-26. (abstract only).

Vogtle, et al., 1987, "Doubly Clamped Cope Systems", J. Org. Chem. 52:5560-5564.

(56) References Cited

OTHER PUBLICATIONS

Williams, et al., 1988, "Bromine as an oxidant for direct conversion of aldehydes to esters", Tetrahedron Lett. 29:5087-90.
Wilson, et al., 1982, "A novel, nonoxidative method for the conversion of aldehydes to esters", J. Org. Chem. 47:1360-61.
Wroblewski and Ladue, 1995, "Lactic dehydrogenase activity in blood", Proc. Soc. Exp. Biol. Med. 90:210-213.
Xu, et al., 1989, "The retinoblastoma susceptibility gene product: a characteristic pattern in normal cells and abnormal expression in malignant cells", Onocogene 4: 807-812.
Yamamoto, "Asymmetric synthesis of 5-and 6-membered lactones from cyclic substrates bearing a C2-chiral auxiliary", J. Org. Chem., 1991, pp. 1112-1119, vol. 35, No. 21.
Yanagisawa, et al., 1994, "Allylbarium Reagents: Unprecedented regio- and stereoselective allylation reactions of carbonyl compounds", J. Am. Chem. Soc. 116:6130-6141.
Yoshikawa, et al., 1983, "Catalytic Regioselective Dehydrogenation of Unsymmetrical alpha Omega-Diols Using Ruthenium Complexes", *Tetrahedron Lett.* 26:2677-2680.
Yoshikawa, et al., 1986, "Ruthenium Complex Catalyzed Regioselective Dehydrogenation of Unsymmetrical alpha Omega-Diols", *J. Org. Chem.* 51:2034.
Yu, et al., 1988, "A novel reagent for the synthesis of myo-inositol phosphates: N,N-diisopropyl dibenzyl phosphoramidite", Tetrahedron Lett. 29:979-82.
Yunker, et al., 1978, "Alpha-oxygenated fatty acids occurring as amides of 2-methylene beta-alanine in a marine sponge", Tetrahedron Lett. 47:4651-52.

\* cited by examiner

US 10,941,095 B2

HYDROXYL COMPOUNDS AND COMPOSITIONS FOR CHOLESTEROL MANAGEMENT AND RELATED USES

CROSS REFERENCE TO RELATED APPLICATIONS

This application is a continuation patent application under 35 U.S.C. § 120 of U.S. patent application Ser. No. 15/487,623, filed on Apr. 14, 2017, which application is a continuation patent application of U.S. patent application Ser. No. 14/674,028, filed on Mar. 31, 2015, now U.S. Pat. No. 9,624,152, issued on Apr. 18, 2017, which application is a continuation patent application of U.S. patent application Ser. No. 13/925,818, filed on Jun. 24, 2013, now U.S. Pat. No. 9,000,041, issued on Apr. 7, 2015, which application is a continuation patent application of U.S. patent application Ser. No. 13/470,825, filed on May 14, 2012, now U.S. Pat. No. 8,497,301, issued on Jul. 30, 2013, which application is a continuation patent application of U.S. patent application Ser. No. 12/870,184, filed on Aug. 27, 2010, now abandoned, which application is a divisional patent application of U.S. patent application Ser. No. 11/680,105, filed on Feb. 28, 2007, now U.S. Pat. No. 7,812,199, issued on Oct. 12, 2010, which application is a divisional patent application of U.S. patent application Ser. No. 10/743,470, filed on Dec. 23, 2003, now U.S. Pat. No. 7,335,799, issued on Feb. 26, 2008, which application claims priority to and the benefit of U.S. Provisional Patent Application No. 60/441,795, filed on Jan. 23, 2003; the contents of each of which are incorporated by reference herein in their entirety.

1. FIELD OF THE INVENTION

The invention relates to hydroxyl compounds and pharmaceutically acceptable salts, hydrates, solvates, and mixtures thereof; compositions comprising a hydroxyl compound or a pharmaceutically acceptable salt, hydrate, solvate, or mixtures thereof; and methods for treating or preventing a disease or disorder such as, but not limited to, aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), and a thrombotic disorder, which method comprise administering a hydroxyl compound or composition of the invention. The compounds of the invention can also treat or prevent inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism.

2. BACKGROUND OF THE INVENTION

Obesity, hyperlipidemia, and diabetes have been shown to play a causal role in atherosclerotic cardiovascular diseases, which currently account for a considerable proportion of morbidity in Western society. Further, one human disease, termed "Syndrome X" or "Metabolic Syndrome", is manifested by defective glucose metabolism (insulin resistance), elevated blood pressure (hypertension), and a blood lipid imbalance (dyslipidemia). See e.g. Reaven, 1993, *Annu. Rev. Med.* 44:121-131.

The evidence linking elevated serum cholesterol to coronary heart disease is overwhelming. Circulating cholesterol is carried by plasma lipoproteins, which are particles of complex lipid and protein composition that transport lipids in the blood. Low density lipoprotein (LDL) and high density lipoprotein (HDL) are the major cholesterol-carrier proteins. LDL is believed to be responsible for the delivery of cholesterol from the liver, where it is synthesized or obtained from dietary sources, to extrahepatic tissues in the body. The term "reverse cholesterol transport" describes the transport of cholesterol from extrahepatic tissues to the liver, where it is catabolized and eliminated. It is believed that plasma HDL particles play a major role in the reverse transport process, acting as scavengers of tissue cholesterol. HDL is also responsible for the removal of non-cholesterol lipid, oxidized cholesterol and other oxidized products from the bloodstream.

Atherosclerosis, for example, is a slowly progressive disease characterized by the accumulation of cholesterol within the arterial wall. Compelling evidence supports the belief that lipids deposited in atherosclerotic lesions are derived primarily from plasma apolipoprotein B (apo B)-containing lipoproteins, which include chylomicrons, CLDL, intermediate-density lipoproteins (IDL), and LDL. The apo B-containing lipoprotein, and in particular LDL, has popularly become known as the "bad" cholesterol. In contrast, HDL serum levels correlate inversely with coronary heart disease. Indeed, high serum levels of HDL are regarded as a negative risk factor. It is hypothesized that high levels of plasma HDL are not only protective against coronary artery disease, but may actually induce regression of atherosclerotic plaque (e.g., see Badimon et al., 1992, *Circulation* 86:(Suppl. III)86-94; Dansky and Fisher, 1999, *Circulation* 100:1762 3.). Thus, HDL has popularly become known as the "good" cholesterol.

2.1 Cholesterol Transport

The fat-transport system can be divided into two pathways: an exogenous one for cholesterol and triglycerides absorbed from the intestine and an endogenous one for cholesterol and triglycerides entering the bloodstream from the liver and other non-hepatic tissue.

In the exogenous pathway, dietary fats are packaged into lipoprotein particles called chylomicrons, which enter the bloodstream and deliver their triglycerides to adipose tissue for storage and to muscle for oxidation to supply energy. The remnant of the chylomicron, which contains cholesteryl esters, is removed from the circulation by a specific receptor found only on liver cells. This cholesterol then becomes available again for cellular metabolism or for recycling to extrahepatic tissues as plasma lipoproteins.

In the endogenous pathway, the liver secretes a large, very-low-density lipoprotein particle (VLDL) into the bloodstream. The core of VLDL consists mostly of triglycerides synthesized in the liver, with a smaller amount of cholesteryl esters either synthesized in the liver or recycled from chylomicrons. Two predominant proteins are displayed on the surface of VLDL, apolipoprotein B-100 (apo B-100) and apolipoprotein E (apo E), although other apolipoproteins are present, such as apolipoprotein CIII (apo CIII) and apolipoprotein CII (apo CII). When VLDL reaches the capillaries of adipose tissue or of muscle, its triglyceride is extracted. This results in the formation of a new kind of particle called intermediate-density lipoprotein (IDL) or VLDL remnant, decreased in size and enriched in cholesteryl esters relative to a VLDL, but retaining its two apoproteins.

In human beings, about half of the IDL particles are removed from the circulation quickly, generally within two to six hours of their formation. This is because IDL particles bind tightly to liver cells, which extract IDL cholesterol to make new VLDL and bile acids. The IDL not taken up by the liver is catabolized by the hepatic lipase, an enzyme bound to the proteoglycan on liver cells. Apo E dissociates from IDL as it is transformed to LDL. Apo B-100 is the sole protein of LDL.

Primarily, the liver takes up and degrades circulating cholesterol to bile acids, which are the end products of cholesterol metabolism. The uptake of cholesterol-containing particles is mediated by LDL receptors, which are present in high concentrations on hepatocytes. The LDL receptor binds both apo E and apo B-100 and is responsible for binding and removing both IDL and LDL from the circulation. In addition, remnant receptors are responsible for clearing chylomicrons and VLDL remnants (i.e., IDL). However, the affinity of apo E for the LDL receptor is greater than that of apo B-100. As a result, the LDL particles have a much longer circulating life span than IDL particles; LDL circulates for an average of two and a half days before binding to the LDL receptors in the liver and other tissues. High serum levels of LDL, the "bad" cholesterol, are positively associated with coronary heart disease. For example, in atherosclerosis, cholesterol derived from circulating LDL accumulates in the walls of arteries. This accumulation forms bulky plaques that inhibit the flow of blood until a clot eventually forms, obstructing an artery and causing a heart attack or stroke.

Ultimately, the amount of intracellular cholesterol liberated from the LDL controls cellular cholesterol metabolism. The accumulation of cellular cholesterol derived from VLDL and LDL controls three processes. First, it reduces the ability of the cell to make its own cholesterol by turning off the synthesis of HMGCoA reductase, a key enzyme in the cholesterol biosynthetic pathway. Second, the incoming LDL-derived cholesterol promotes storage of cholesterol by the action of cholesterol acyltransferase ("ACAT"), the cellular enzyme that converts cholesterol into cholesteryl esters that are deposited in storage droplets. Third, the accumulation of cholesterol within the cell drives a feedback mechanism that inhibits cellular synthesis of new LDL receptors. Cells, therefore, adjust their complement of LDL receptors so that enough cholesterol is brought in to meet their metabolic needs, without overloading (for a review, see Brown & Goldstein, in *The Pharmacological Basis Of Therapeutics*, 8th Ed., Goodman & Gilman, Pergamon Press, New York, 1990, Ch. 36, pp. 874-896).

High levels of apo B-containing lipoproteins can be trapped in the subendothelial space of an artery and undergo oxidation. The oxidized lipoprotein is recognized by scavenger receptors on macrophages. Binding of oxidized lipoprotein to the scavenger receptors can enrich the macrophages with cholesterol and cholesteryl esters independently of the LDL receptor. Macrophages can also produce cholesteryl esters by the action of ACAT. LDL can also be complexed to a high molecular weight glycoprotein called apolipoprotein (a), also known as apo(a), through a disulfide bridge. The LDL-apo(a) complex is known as Lipoprotein (a) or Lp(a). Elevated levels of Lp(a) are detrimental, having been associated with atherosclerosis, coronary heart disease, myocardial infarction, stroke, cerebral infarction, and restenosis following angioplasty.

2.2 Reverse Cholesterol Transport

Peripheral (non-hepatic) cells predominantly obtain their cholesterol from a combination of local synthesis and uptake of preformed sterol from VLDL and LDL. Cells expressing scavenger receptors, such as macrophages and smooth muscle cells, can also obtain cholesterol from oxidized apo B-containing lipoproteins. In contrast, reverse cholesterol transport (RCT) is the pathway by which peripheral cell cholesterol can be returned to the liver for recycling to extrahepatic tissues, hepatic storage, or excretion into the intestine in bile. The RCT pathway represents the only means of eliminating cholesterol from most extrahepatic tissues and is crucial to the maintenance of the structure and function of most cells in the body.

The enzyme in blood involved in the RCT pathway, lecithin:cholesterol acyltransferase (LCAT), converts cell-derived cholesterol to cholesteryl esters, which are sequestered in HDL destined for removal. LCAT is produced mainly in the liver and circulates in plasma associated with the HDL fraction. Cholesterol ester transfer protein (CETP) and another lipid transfer protein, phospholipid transfer protein (PLTP), contribute to further remodeling the circulating HDL population (see for example Bruce et al., 1998, *Annu. Rev. Nutr.* 0.8:297 330). PLTP supplies lecithin to HDL, and CETP can move cholesteryl esters made by LCAT to other lipoproteins, particularly apoB-containing lipoproteins, such as VLDL. HDL triglycerides can be catabolized by the extracellular hepatic triglyceride lipase, and lipoprotein cholesterol is removed by the liver via several mechanisms.

Each HDL particle contains at least one molecule, and usually two to four molecules, of apolipoprotein A I (apo A I). Apo A I is synthesized by the liver and small intestine as preproapolipoprotein, which is secreted as a proprotein that is rapidly cleaved to generate a mature polypeptide having 243 amino acid residues. Apo A I consists mainly of a 22 amino acid repeating segment, spaced with helix-breaking proline residues. Apo A I forms three types of stable structures with lipids: small, lipid-poor complexes referred to as pre-beta-1 HDL; flattened discoidal particles, referred to as pre-beta-2 HDL, which contain only polar lipids (e.g., phospholipid and cholesterol); and spherical particles containing both polar and nonpolar lipids, referred to as spherical or mature HDL (HDL3 and HDL2). Most HDL in the circulating population contains both apo A I and apo A II, a second major HDL protein. This apo A I- and apo A II-containing fraction is referred to herein as the AI/AII-HDL fraction of HDL. But the fraction of HDL containing only apo A I, referred to herein as the AI HDL fraction, appears to be more effective in RCT. Certain epidemiologic studies support the hypothesis that the AI-HDL fraction is antiartherogenic (Parra et al., 1992, *Arterioscler. Thromb.* 12:701-707; Decossin et al., 1997, *Eur. J. Clin. Invest.* 27:299-307).

Although the mechanism for cholesterol transfer from the cell surface is unknown, it is believed that the lipid-poor complex, pre-beta-1 HDL, is the preferred acceptor for cholesterol transferred from peripheral tissue involved in RCT. Cholesterol newly transferred to pre-beta-1 HDL from the cell surface rapidly appears in the discoidal pre-beta-2

HDL. PLTP may increase the rate of disc formation (Lagrost et al., 1996, *J. Biol. Chem.* 271:19058-19065), but data indicating a role for PLTP in RCT is lacking. LCAT reacts preferentially with discoidal and spherical HDL, transferring the 2-acyl group of lecithin or phosphatidylethanolamine to the free hydroxyl residue of fatty alcohols, particularly cholesterol, to generate cholesteryl esters (retained in the HDL) and lysolecithin. The LCAT reaction requires an apolipoprotein such as apo A I or apo A-IV as an activator. ApoA-I is one of the natural cofactors for LCAT. The conversion of cholesterol to its HDL-sequestered ester prevents re-entry of cholesterol into the cell, resulting in the ultimate removal of cellular cholesterol. Cholesteryl esters in the mature HDL particles of the AI-HDL fraction are removed by the liver and processed into bile more effectively than those derived from the AI/AII-HDL fraction. This may be due, in part, to the more effective binding of AI-HDL to the hepatocyte membrane. Several HDL receptors have been identified, the most well characterized of which is the scavenger receptor class B, type I (SR BI) (Acton et al., 1996, *Science* 271:518-520). The SR-BI is expressed most abundantly in steroidogenic tissues (e.g., the adrenals), and in the liver (Landshulz et al., 1996, *J. Clin. Invest.* 98:984-995; Rigotti et al., 1996, *J. Biol. Chem.* 271:33545-335449). Other proposed HDL receptors include HB1 and HB2 (Hidaka and Fidge, 1992, *Biochem J.* 15:161 7; Kurata et al., 1998, *J. Atherosclerosis and Thrombosis* 4:1127).

While there is a consensus that CETP is involved in the metabolism of VLDL- and LDL-derived lipids, its role in RCT remains controversial. However, changes in CETP activity or its acceptors, VLDL and LDL, play a role in "remodeling" the HDL population. For example, in the absence of CETP, the HDL becomes enlarged particles that are poorly removed from the circulation (for reviews on RCT and HDL, See Fielding & Fielding, 1995, *J. Lipid Res.* 36:211-228; Barrans et al., 1996, *Biochem. Biophys. Acta.* 1300:73-85; Hirano et al., 1997, *Arterioscler. Thromb. Vasc. Biol.* 17:1053-1059).

2.3 Reverse Transport of Other Lipids

HDL is not only involved in the reverse transport of cholesterol, but also plays a role in the reverse transport of other lipids, i.e., the transport of lipids from cells, organs, and tissues to the liver for catabolism and excretion. Such lipids include sphingomyelin, oxidized lipids, and lysophophatidylcholine. For example, Robins and Fasulo (1997, *J. Clin. Invest.* 99:380 384) have shown that HDL stimulates the transport of plant sterol by the liver into bile secretions.

2.4 Peroxisome Proliferator Activated Receptor Pathway

Peroxisome proliferators are a structurally diverse group of compounds that, when administered to rodents, elicit dramatic increases in the size and number of hepatic and renal peroxisomes, as well as concomitant increases in the capacity of peroxisomes to metabolize fatty acids via increased expression of the enzymes required for the β-oxidation cycle (Lazarow and Fujiki, 1985, *Ann. Rev. Cell Biol.* 1:489 530; Vamecq and Draye, 1989, *Essays Biochem.* 24:1115 225; and Nelali et al., 1988, *Cancer Res.* 48:5316 5324). Chemicals included in this group are the fibrate class of hypolipidemic drugs, herbicides, and phthalate plasticizers (Reddy and Lalwani, 1983, *Crit. Rev. Toxicol.* 12:1 58). Peroxisome proliferation can also be elicited by dietary or physiological factors, such as a high fat diet and cold acclimatization.

Insight into the mechanism whereby peroxisome proliferators exert their pleiotropic effects was provided by the identification of a member of the nuclear hormone receptor superfamily activated by these chemicals (Isseman and Green, 1990, *Nature* 347:645 650). This receptor, termed peroxisome proliferator activated receptor α (PPARα), was subsequently shown to be activated by a variety of medium and long chain fatty acids. PPARα activates transcription by binding to DNA sequence elements, termed peroxisome proliferator response elements (PPRE), in the form of a heterodimer with the retinoid X receptor (RXR). RXR is activated by 9-cis retinoic acid (see Kliewer et al., 1992, *Nature* 358:771 774; Gearing et al., 1993, *Proc. Natl. Acad. Sci. USA* 90:1440 1444, Keller et al., 1993, *Proc. Natl. Acad. Sci. USA* 90:2160 2164; Heyman et al., 1992, *Cell* 68:397 406, and Levin et al., 1992, *Nature* 355:359 361). Since the discovery of PPARα additional isoforms of PPAR have been identified, e.g., PPARβ, PPARγ and PPARδ, which have similar functions and are similarly regulated.

PPARs have been identified in the enhancers of a number of gene-encoding proteins that regulate lipid metabolism. These proteins include the three enzymes required for peroxisomal β-oxidation of fatty acids; apolipoprotein A-I; medium chain acyl-CoA dehydrogenase, a key enzyme in mitochondrial β-oxidation; and aP2, a lipid binding protein expressed exclusively in adipocytes (reviewed in Keller and Whali, 1993, *TEM*, 4:291 296; see also Staels and Auwerx, 1998, *Atherosclerosis* 137 Suppl:S19 23). The nature of the PPAR target genes coupled with the activation of PPARs by fatty acids and hypolipidemic drugs suggests a physiological role for the PPARs in lipid homeostasis.

Pioglitazone, an antidiabetic compound of the thiazolidinedione class, was reported to stimulate expression of a chimeric gene containing the enhancer/promoter of the lipid binding protein aP2 upstream of the chloroamphenicol acetyl transferase reporter gene (Harris and Kletzien, 1994, *Mol. PharmacoL.* 45:439 445). Deletion analysis led to the identification of an an approximately 30 bp region accounting for pioglitazone responsiveness. In an independent study, this 30 bp fragment was shown to contain a PPRE (Tontonoz et al., 1994, *Nucleic Acids Res.* 22:5628 5634). Taken together, these studies suggested the possibility that the thiazolidinediones modulate gene expression at the transcriptional level through interactions with a PPAR and reinforce the concept of the interrelatedness of glucose and lipid metabolism.

2.5 Current Cholesterol Management Therapies

In the past two decades or so, the segregation of cholesterolemic compounds into HDL and LDL regulators and recognition of the desirability of decreasing blood levels of the latter has led to the development of a number of drugs. However, many of these drugs have undesirable side effects and/or are contraindicated in certain patients, particularly when administered in combination with other drugs.

Bile-acid-binding resins are a class of drugs that interrupt the recycling of bile acids from the intestine to the liver. Examples of bile-acid-binding resins are cholestyramine (QUESTRAN LIGHT, Bristol-Myers Squibb), and colestipol hydrochloride (COLESTID, Pharmacia & Upjohn Company). When taken orally, these positively charged resins bind to negatively charged bile acids in the intestine. Because the resins cannot be absorbed from the intestine, they are excreted, carrying the bile acids with them. The use of such resins, however, at best only lowers serum cholesterol levels by about 20%. Moreover, their use is associated with gastrointestinal side-effects, including constipation and certain vitamin deficiencies. Moreover, since the resins bind to drugs, other oral medications must be taken at least one hour before or four to six hours subsequent to ingestion of the resin, complicating heart patients' drug regimens.

The statins are inhibitors of cholesterol synthesis. Sometimes, the statins are used in combination therapy with bile-acid-binding resins. Lovastatin (MEVACOR, Merck & Co., Inc.), a natural product derived from a strain of *Aspergillus*; pravastatin (PRAVACHOL, Bristol-Myers Squibb Co.); and atorvastatin (LIPITOR, Warner Lambert) block cholesterol synthesis by inhibiting HMGCoA reductase, the key enzyme involved in the cholesterol biosynthetic pathway. Lovastatin significantly reduces serum cholesterol and LDL-serum levels. However, serum HDL levels are only slightly increased following lovastatin administration. The mechanism of the LDL-lowering effect may involve both reduction of VLDL concentration and induction of cellular expression of LDL-receptor, leading to reduced production and/or increased catabolism of LDL. Side effects, including liver and kidney dysfiunction are associated with the use of these drugs.

Nicotinic acid, also known as niacin, is a water-soluble vitamin B-complex used as a dietary supplement and anti-hyperlipidemic agent. Niacin diminishes the production of VLDL and is effective at lowering LDL. It is used in combination with bile-acid-binding resins. Niacin can increase HDL when administered at therapeutically effective doses; however, its usefulness is limited by serious side effects.

Fibrates are a class of lipid-lowering drugs used to treat various forms of hyperlipidemia, elevated serun triglycerides, which may also be associated with hypercholesterolemria. Fibrates appear to reduce the VLDL fraction and modestly increase HDL; however, the effects of these drugs on serum cholesterol is variable. In the United States, fibrates have been approved for use as antilipidemic drugs, but have not received approval as hypercholesterolemia agents. For example, clofibrate (ATROMID-S, Wyeth-Ayerst Laboratories) is an antilipidemic agent that acts to lower serum triglycerides by reducing the VLDL fraction. Although ATROMID-S may reduce serum cholesterol levels in certain patient subpopulations, the biochemical response to the drug is variable, and is not always possible to predict which patients will obtain favorable results. ATROMID-S has not been shown to be effective for prevention of coronary heart disease. The chemically and pharmacologically related drug, gemfibrozil (LOPID, Parke-Davis), is a lipid regulating agent which moderately decreases serum triglycerides and VLDL cholesterol. LOPID also increases H-IDL cholesterol, particularly the HDL2 and HDL3 subfractions, as well as both the AI/AII-HDL fractions. However, the lipid response to LOPID is heterogeneous, especially among different patient populations. Moreover, while prevention of coronary heart disease was observed in male patients between the ages of 40 and 55 without history or symptoms of existing coronary heart disease, it is not clear to what extent these findings can be extrapolated to other patient populations (e.g., women, older and younger males). Indeed, no efficacy was observed in patients with established coronary heart disease. Serious side-effects are associated with the use of fibrates, including toxicity; malignancy, particularly malignancy of gastrointestinal cancer; gallbladder disease; and an increased incidence in non-coronary mortality. These drugs are not indicated for the treatment of patients with high LDL or low HDL as their only lipid abnormality.

Oral estrogen replacement therapy may be considered for moderate hypercholesterolemia in post-menopausal women. However, increases in HDL may be accompanied with an increase in triglycerides. Estrogen treatment is, of course, limited to a specific patient population, postmenopausal women, and is associated with serious side effects, including induction of malignant neoplasms; gall bladder disease; thromboembolic disease; hepatic adenoma; elevated blood pressure; glucose intolerance; and hypercalcemia.

Long chain carboxylic acids, particularly long chain $\alpha,\omega$-dicarboxylic acids with distinctive substitution patterns, and their simple derivatives and salts, have been disclosed for treating atherosclerosis, obesity, and diabetes (See, e.g., Bisgaier et al., 1998, *J. Lipid Res.* 39:17-30, and references cited therein; International Patent Publication WO 98/30530; U.S. Pat. No. 4,689,344; International Patent Publication WO 99/00116; and U.S. Pat. No. 5,756,344). However, some of these compounds, for example the $\alpha,\omega$-dicarboxylic acids substituted at their $\alpha,\alpha'$-carbons (U.S. Pat. No. 3,773,946), while having serum triglyceride and serum cholesterol-lowering activities, have no value for treatment of obesity and hypercholesterolemia (U.S. Pat. No. 4,689,344).

U.S. Pat. No. 4,689,344 discloses $\beta,\beta,\beta',\beta'$-tetrasubstituted-$\alpha,\omega$-alkanedioic acids that are optionally substituted at their $\alpha,\alpha,\alpha',\alpha'$-positions, and alleges that they are useful for treating obesity, hyperlipidernia, and diabetes. According to this reference, both triglycerides and cholesterol are lowered significantly by compounds such as 3,3,14,14-tetramethyl-hexadecane-1,16-dioic acid. U.S. Pat. No. 4,689,344 further discloses that the $\beta,\beta,\beta',\beta'$-tetramethyl-alkanediols of U.S. Pat. No. 3,930,024 also are not useful for treating hypercholesterolemia or obesity.

Other compounds are disclosed in U.S. Pat. No. 4,711, 896. In U.S. Pat. No. 5,756,544, $\alpha,\omega$-dicarboxylic acid-terminated dialkane ethers are disclosed to have activity in lowering certain plasma lipids, including Lp(a), triglycerides, VLDL-cholesterol, and LDL-cholesterol, in animals, and elevating others, such as HDL-cholesterol. The compounds are also stated to increase insulin sensitivity. In U.S. Pat. No. 4,613,593, phosphates of dolichol, a polyprenol isolated from swine liver, are stated to be useful in regenerating liver tissue, and in treating hyperuricuria, hyperlipemia, diabetes, and hepatic diseases in general.

U.S. Pat. No. 4,287,200 discloses azolidinedione derivatives with anti-diabetic, hypolipidemic, and anti-hypertensive properties. However, the administration of these compounds to patients can produce side effects such as bone marrow depression, and both liver and cardiac cytotoxicity. Further, the compounds disclosed by U.S. Pat. No. 4,287, 200 stimulate weight gain in obese patients.

It is clear that none of the commercially available cholesterol management drugs has a general utility in regulating lipid, lipoprotein, insulin and glucose levels in the blood. Thus, compounds that have one or more of these utilities are clearly needed. Further, there is a clear need to develop safer drugs that are efficacious at lowering serum cholesterol, increasing HDL serum levels, preventing coronary heart disease, and/or treating existing disease such as atherosclerosis, obesity, diabetes, and other diseases that are affected by lipid metabolism and/or lipid levels. There is also a clear need to develop drugs that may be used with other lipid-altering treatment regimens in a synergistic manner. There is still a further need to provide useful therapeutic agents whose solubility and Hydrophile/Lipophile Balance (HLB) can be readily varied.

Citation or identification of any reference in Section 2 of this application is not an admission that such reference is available as prior art to the present invention.

3. SUMMARY OF THE INVENTION

The invention encompasses hydroxyl compounds useful in treating various disorders.

The invention further encompasses pharmaceutical compositions comprising one or more compounds of the invention and a pharmaceutically acceptable vehicle, excipient, or diluent. A pharmaceutically acceptable vehicle can comprise a carrier, excipient, diluent, or a mixture thereof.

The invention encompasses a method for treating or preventing aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), and a thrombotic disorder, comprising administering to a patient in need of such treatment or prevention a therapeutically effective amount of a compound of the invention or a pharmaceutical composition comprising a compound of the invention and a pharmaceutically acceptable vehicle, excipient, or diluent.

The invention also encompasses a method for inhibiting hepatic fatty acid and sterol synthesis comprising administering to a patient in need thereof a therapeutically effective amount of a compound of the invention or a pharmaceutical composition comprising a compound of the invention and a pharmaceutically acceptable vehicle, excipient, or diluent.

The invention also encompasses a method of treating or preventing a disease or disorder that is capable of being treated or prevented by increasing HDL levels, which comprises administering to a patient in need of such treatment or prevention a therapeutically effective amount of a compound of the invention and a pharmaceutically acceptable vehicle, excipient, or diluent.

The invention also encompasses a method of treating or preventing a disease or disorder that is capable of being treated or prevented by lowering LDL levels, which comprises administering to such patient in need of such treatment or prevention a therapeutically effective amount of a compound of the invention and a pharmaceutically acceptable vehicle, excipient, or diluent.

The compounds of the invention favorably alter lipid metabolism in animal models of dyslipidemia at least in part by enhancing oxidation of fatty acids through the ACC/malonyl-CoA/CPT-I regulatory axis and therefore the invention also encompasses methods of treatment or prevention of metabolic syndrome disorders.

The invention further encompasses a method for reducing the fat content of meat in livestock comprising administering to livestock in need of such fat-content reduction a therapeutically effective amount of a compound of the invention or a pharmaceutical composition comprising a compound of the invention and a pharmaceutically acceptable vehicle, excipient, or diluent.

The invention encompasses a method for reducing the cholesterol content of a fowl egg comprising administering to a fowl species a therapeutically effective amount of a compound of the invention or a pharmaceutical composition comprising a compound of the invention and a pharmaceutically acceptable vehicle, excipient, or diluent.

The present invention may be understood more fully by reference to the detailed description and examples, which are intended to exemplify non-limiting embodiments of the invention.

4. DEFINITIONS AND ABBREVIATIONS

Apo(a): apolipoprotein(a)
Apo A-I: apolipoprotein A-I
Apo B: apolipoprotein B
Apo E: apolipoprotein E
FH: Familial hypercholesterolemia
FCH: Familial combined hyperlipidemia
GDM: Gestational diabetes mellitus
HDL: High density lipoprotein
IDL: Intermediate density lipoprotein
IDDM: Insulin dependent diabetes mellitus
LDH: Lactate dehdyrogenase
LDL: Low density lipoprotein
Lp(a): Lipoprotein (a)
MODY: Maturity onset diabetes of the young
NIDDM: Non-insulin dependent diabetes mellitus
PPAR: Peroxisome proliferator activated receptor
RXR: Retinoid X receptor
VLDL: Very low density lipoprotein As used herein, the phrase "compounds of the invention" means compounds disclosed herein. Particular compounds of the invention are compounds of formulas I, II, III, IV, V, VI, VII, VIII, IX and phanrnaceutically acceptable salts, hydrates, enantiomers, diastereomer, racemates or mixtures of stereoisomers thereof. Thus, "compound of the invention" collectively means compound of formulas I, II, III, IV, V, VI, VII, VIII, and IX and pharmaceutically acceptable salts, hydrates, enantiomers, diastereomer, racemates or mixtures of stereoisomers thereof. The compounds of the invention are identified herein by their chemical structure and/or chemical name. Where a compound is referred to by both a chemical structure and a chemical name, and the chemical structure and chemical name conflict, the chemical structure is to be accorded more weight.

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compounds' enantiomers and stereoisomers, that is, both the stereomerically pure form (e.g., geometrically pure, enantiomerically pure, or diastereomerically pure) and enantiomeric and stereoisomeric mixtures.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

A compound of the invention is considered optically active or enantiomerically pure (i.e., substantially the R-form or substantially the S-form) with respect to a chiral center when the compound is about 90% ee (enantiomeric excess) or greater, preferably, equal to or greater than 95% ee with respect to a particular chiral center. A compound of the invention is considered to be in enantiomerically-enriched form when the compound has an enantiomeric excess of greater than about 1% ee, preferably greater than about 5% ee, more preferably, greater than about 10% ee with respect to a particular chiral center. A compound of the invention is considered diastereomerically pure with respect to multiple chiral centers when the compound is about 90% de (diastereomeric excess) or greater, preferably, equal to or greater than 95% de with respect to a particular chiral center. A compound of the invention is considered to be in diastereomerically-enriched form when the compound has an diastereomeric excess of greater than about 1% de, preferably greater than about 5% de, more preferably, greater than about 10% de with respect to a particular chiral center. As used herein, a racemic mixture means about 50% of one enantiomer and about 50% of is corresponding enantiomer relative to all chiral centers in the molecule. Thus, the invention encompasses all enantiomerically-pure, enantiomerically-enriched, diastereomerically pure, diastereomerically enriched, and racemic mixtures of compounds of Formulas I through IX.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

The compounds of the invention are defined herein by their chemical structures and/or chemical names. Where a compound is referred to by both a chemical structure and a chemical name, and the chemical structure and chemical name conflict, the chemical structure is determinative of the compound's identity.

When administered to a patient, e.g., to an animal for veterinary use or for improvement of livestock, or to a human for clinical use, the compounds of the invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single hydroxy compound of the invention by weight of the isolate.

The phrase "pharmaceutically acceptable salt(s)," as used herein includes, but is not limited to, salts of acidic or basic groups that may be present in the compounds of the invention. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds of the invention that include an amino moiety also can form pharmaceutically acceptable salts with various amino acids, in addition to the acids mentioned above. Compounds of the invention that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, the term "hydrate" means a compound of the invention or a salt thereof, that further includes a stoichiometric or non-stoichiometric amount of water bound by non-covalent intermolecular forces. The term hydrate includes solvates, which are stoichiometric or non-stoichiometric amounts of a solvent bound by non-covalent intermolecular forces. Preferred solvents are volatile, non-toxic, and/or acceptable for administration to humans in trace amounts.

As used herein, the term "altering lipid metabolism" indicates an observable (measurable) change in at least one aspect of lipid metabolism, including but not limited to total blood lipid content, blood HDL cholesterol, blood LDL cholesterol, blood VLDL cholesterol, blood triglyceride, blood Lp(a), blood apo A-I, blood apo E and blood non-esterified fatty acids.

As used herein, the term "altering glucose metabolism" indicates an observable (measurable) change in at least one aspect of glucose metabolism, including but not limited to total blood glucose content, blood insulin, the blood insulin to blood glucose ratio, insulin sensitivity, and oxygen consumption.

As used herein, the term "alkyl group" means a saturated, monovalent unbranched or branched hydrocarbon chain. Examples of alkyl groups include, but are not limited to, $(C_1-C_6)$alkyl groups, such as methyl, ethyl, propyl, isopropyl, 2-methyl-1-propyl, 2 methyl 2-propyl, 2-methyl-1-butyl, 3-methyl-1-butyl, 2 methyl-3-butyl, 2,2 dimethyl 1-propyl, 2-methyl-1-pentyl, 3 methyl-1-pentyl, 4 methyl-pentyl, 2-methyl-2-pentyl, 3-methyl-2-pentyl, 4 methyl 2 pentyl, 2,2 dimethyl 1 butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein, the term an "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to $(C_2-C_6)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

As used herein, the term an "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_6)$alkynyl groups, such as ethynyl, propynyi, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein, the term an "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "$(C_6)$aryl".

As used herein, the term an "heteroaryl group" means a monocyclic- or polycyclic aromatic ring comprising carbon atoms, hydrogen atoms, and one or more heteroatoms, preferably 1 to 3 heteroatoms, independently selected from nitrogen, oxygen, and sulfur. Illustrative examples of heteroaryl groups include, but are not limited to, pyridinyl, pyridazinyl, pyrimidinyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thiophenyl, isoxazolyl, thiazolyl, furyl, phenyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "$(C_2-C_5)$heteroaryl".

As used herein, the term "cycloalkyl group" means a monocyclic or polycyclic saturated ring comprising carbon and hydrogen atoms and having no carbon-carbon multiple bonds. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. Preferably, the cycloalkyl group is a monocyclic ring or bicyclic ring.

As used herein, the term "heterocycloalkyl group" means a mnonocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and form 1 to 3 heteroatoms, referred to herein as $(C_1-C_6)$heterocycloalkyl.

As used herein, the terms "heterocyclic radical" or "heterocyclic ring" mean a heterocycloalkyl group or a heteroaryl group.

As used herein, the term "alkoxy group" means an —O-alkyl group, wherein alkyl is as defined above. An alkoxy group can be unsubstituted or substituted with one or two suitable substituents. Preferably, the alkyl chain of an alkyloxy group is from 1 to 6 carbon atoms in length, referred to herein as "$(C_1-C_6)$alkoxy".

As used herein, the term "aryloxy group" means an —O-aryl group, wherein aryl is as defined above. An aryloxy group can be unsubstituted or substituted with one or two suitable substituents. Preferably, the aryl ring of an aryloxy group is a monocyclic ring, wherein the ring comprises 6 carbon atoms, referred to herein as "$(C_6)$aryloxy".

As used herein, the term "benzyl" means —$CH_2$-phenyl.

As used herein, the term "phenyl" means —$C_6H_5$. A phenyl group can be unsubstituted or substituted with one or two suitable substituents, wherein the substituent replaces an H of the phenyl group. As used herein, "Ph," represents a phenyl group or a substituted phenyl group.

As used herein, the term "hydrocarbyl" group means a monovalent group selected from $(C_1-C_8)$alkyl, $(C_2-C_8)$alkenyl, and $(C_2-C_8)$alkynyl, optionally substituted with one or two suitable substituents. Preferably, the hydrocarbon chain of a hydrocarbyl group is from 1 to 6 carbon atoms in length, referred to herein as "$(C_1-C_6)$hydrocarbyl".

As used herein, a "carbonyl" group is a divalent group of the formula $C(O)$.

As used herein, the term "alkoxycarbonyl" group means a monovalent group of the formula —$C(O)$-alkoxy. Preferably, the hydrocarbon chain of an alkoxycarbonyl group is from 1 to 8 carbon atoms in length, referred to herein as a "lower alkoxycarbonyl" group.

As used herein, a "carbamaoyl" group means the radical —$C(O)N(R')_2$, wherein R' is chosen from the group consisting of hydrogen, alkyl, and aryl.

As used herein, "halogen" means fluorine, chlorine, bromine, or iodine.

Accordingly, the meaning of the terms "halo" and "Hal" encompass fluoro, chloro, bromo, and iodo.

As used herein, a "suitable substituent" means a group that does not nullify the synthetic or pharmaceutical utility of the compounds of the invention or the intermediates useful for preparing them. Examples of suitable substituents include, but are not limited to: $(C_1-C_8)$alkyl; $(C_1-C_8)$alkenyl; $(C_1-C_8)$alkynyl; $(C_6)$aryl; $(C_2-C_5)$heteroaryl; $(C_3-C_7)$cycloalkyl; $(C_1-C_8)$alkoxy; $(C_6)$aryloxy; —CN; —OH; oxo; halo, —$CO_2H$; —$NH_2$; —$NH((C_1-C_5)alkyl)$; —$N((C_1-C_8)alkyl)_2$; —$NH((C_6)aryl)$; —$N((C_6)aryl)_2$; —CHO; —$CO((C_1-C_8)alkyl)$; —$CO((C_6)aryl)$; —$CO_2((C_1-C_8)alkyl)$; and —$CO_2((C_6)aryl)$. One of skill in the art can readily choose a suitable substituent based on the stability and pharmacological and synthetic activity of the compound of the invention.

As used herein, a composition that is "substantially free" of a compound means that the composition contains less than about 20% by weight, more preferably less than about 10% by weight, even more preferably less than about 5% by weight, and most preferably less than about 3% by weight of the compound.

5. DETAILED DESCRIPTION OF THE INVENTION

The compounds of the invention are useful in medical applications for treating or preventing a variety of diseases and disorders such as, but not limited to, cardiovascular disease, stroke, and peripheral vascular disease; dyslipidemia; dyslipoproteinemia; a disorder of glucose metabolism; Alzheimer's Disease; Parkinson's Disease, diabetic nephropathy, diabetic retinopathy, insulin resistance, metabolic syndrome disorders (e.g., Syndrome X); a peroxisome proliferator activated receptor-associated disorder; septicemia; a thrombotic disorder; obesity; pancreatitis; hypertension; renal disease; cancer; inflammation; inflammatory muscle diseases, such as polymylagia rheumatica, polymyositis, and fibrositis; impotence; gastrointestinal disease; irritable bowel syndrome; inflanmmatory bowel disease;

inflammatory disorders, such as asthma, vasculitis, ulcerative colitis, Crohn's disease, Kawasaki disease, Wegener's granulomatosis, (RA), systemic lupus erythematosus (SLE), multiple sclerosis (MS), and autoimmune chronic hepatitis; arthritis, such as rheumatoid arthritis, juvenile rheumatoid arthritis, and osteoarthritis; osteoporosis, soft tissue rheumatism, such as tendonitis; bursitis; autoinunrune disease, such as systemic lupus and erythematosus; scleroderma; ankylosing spondylitis; gout; pseudogout; non-insulin dependent diabetes mellitus; polycystic ovarian disease; hyperlipidemias, such as familial hypercholesterolemia (FH), familial combined hyperlipidemia (FCH); lipoprotein lipase deficiencies, such as hypertriglyceridemia, hypoalphalipoproteinemia, and hypercholesterolemia; lipoprotein abnormalities associated with diabetes; lipoprotein abnormalities associated with obesity; and lipoprotein abnormalities associated with Alzheimer's Disease. The compounds and compositions of the invention are useful for treatment or prevention of high levels of blood triglycerides, high levels of low density lipoprotein cholesterol, high levels of apolipoprotein B, high levels of lipoprotein Lp(a) cholesterol, high levels of very low density lipoprotein cholesterol, high levels of fibrinogen, high levels of insulin, high levels of glucose, and low levels of high density lipoprotein cholesterol. The compounds and compositions of the invention also have utility for treatment of NIDDM without increasing weight gain. The compounds of the invention may also be used to reduce the fat content of meat in livestock and reduce the cholesterol content of eggs.

The invention provides novel compounds particularly useful for treating or preventing a variety of diseases and conditions, which include, but are not limited to aging, Alzheimer's Disease, cancer, cardiovascular disease, diabetic nephropathy, diabetic retinopathy, a disorder of glucose metabolism, dyslipidemia, dyslipoproteinemia, enhancing bile production, hypertension, impotence, inflammation, insulin resistance, lipid elimination in bile, modulating C reactive protein, obesity, oxysterol elimination in bile, pancreatitis, pancreatitius, Parkinson's disease, a peroxisome proliferator activated receptor-associated disorder, phospholipid elimination in bile, renal disease, septicemia, Syndrome X, and a thrombotic disorder.

The invention encompasses compounds of formula I:

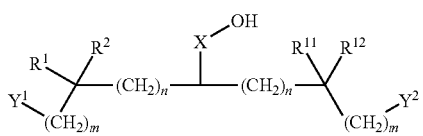

I or a pharmaceutically acceptable salt, hydrate, solvate or mixture thereof, wherein:
(a) each occurrence of m is independently an integer ranging from 0 to 5;
(b) each occurrence of n is independently an integer ranging from 3 to 7;
(c) X is $(CH_2)_z$ or Ph, wherein z is an integer from 0 to 4 and Ph is a 1,2-, 1,3-, or 1,4 substituted phenyl group;
(d) each occurrence of $R^1$, $R^2$, $R^{11}$, and $R^{12}$ is independently H, $(C_1-C_6)$alkyl, $(C_2-C_6)$alkenyl, $(C_2-C_6)$alkynyl, phenyl, or benzyl, wherein $R^1$, $R^2$, $R^{11}$, and $R^{12}$ are not each simultaneously H; and
(e) each occurrence of Y and $Y^2$ is independently $(C_1-C_6)$ alkyl, OH, COOH, $COOR^3$, $SO_3H$,

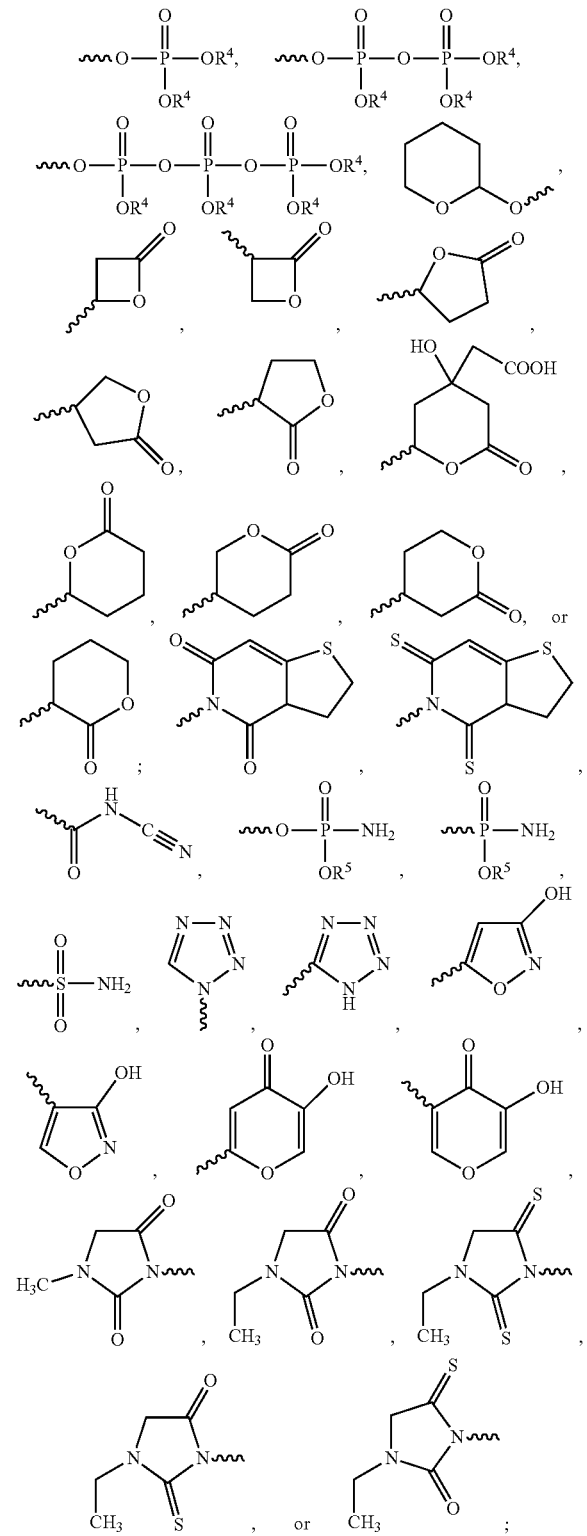

wherein:
(i) $Y^1$ and $Y^2$ are not each simultaneously $(C_1-C_6)$alkyl;
(ii) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups, (iii) each occurrence of $R^4$ is independently H, $(C_1-C_6)$alkyl, $(C_2-C_6)$alkenyl, or $(C_2-C_6)$alkynyl and is unsubstituted or substituted with one or two halo, OH, $C_1-C_6$ alkoxy, or phenyl groups; and (iv) each occurrence of $R^5$ is independently H, $(C_1-C_5)$alkyl, $(C_2-C_6)$alkenyl, or $(C_2-C_6)$alkynyl.

Preferably in formula I, each occurrence of $Y^1$ and $Y^2$ is independently OH, $COOR^3$, or COOH.

Other preferred compounds of formula I are those wherein m is 0.

Other preferred compounds of formula I are those wherein m is 1.

Other preferred compounds of formula I are those wherein n is 4.

Other preferred compounds of formula I are those wherein n is 5.

Other preferred compounds of formula I are those wherein z is 0.

Other preferred compounds of formula I are those wherein z is 1.

Other preferred compounds of formula I are those wherein $Y^1$ is $(C_1-C_6)$alkyl and $Y^2$ is OH.

Other preferred compounds of formula I are those wherein $Y^1$ is methyl and $Y^2$ is OH.

In another embodiment, the invention encompasses compounds of formula II:

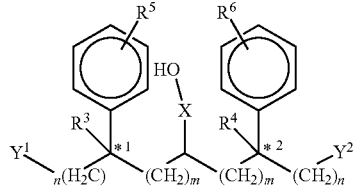

II or a pharmaceutically acceptable salt, hydrate, solvate, or mixture thereof, wherein:

(a) each occurrence of m is independently an integer ranging from 3 to 7;

(b) each occurrence of n is independently an integer ranging from 0 to 5;

(c) X is $(CH_2)_z$ or Ph, wherein z is an integer from 0 to 4 and Ph is a 1,2-, 1,3-, or 1,4 substituted phenyl group;

(d) each occurrence of $Y^1$ and $Y^2$ independently $(C_1-C_6)$ alkyl, OH, COOH, $COOR^7$, $SO_3H$,

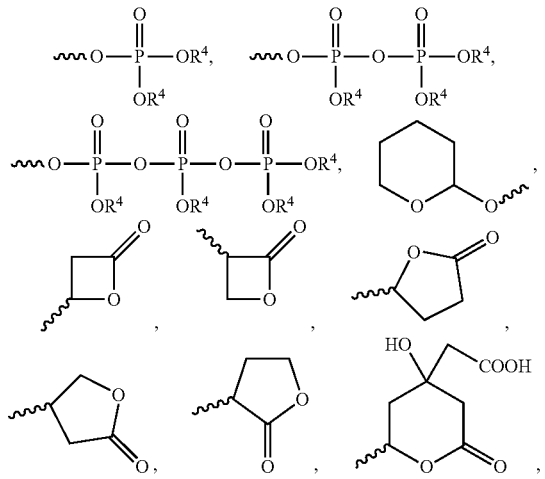

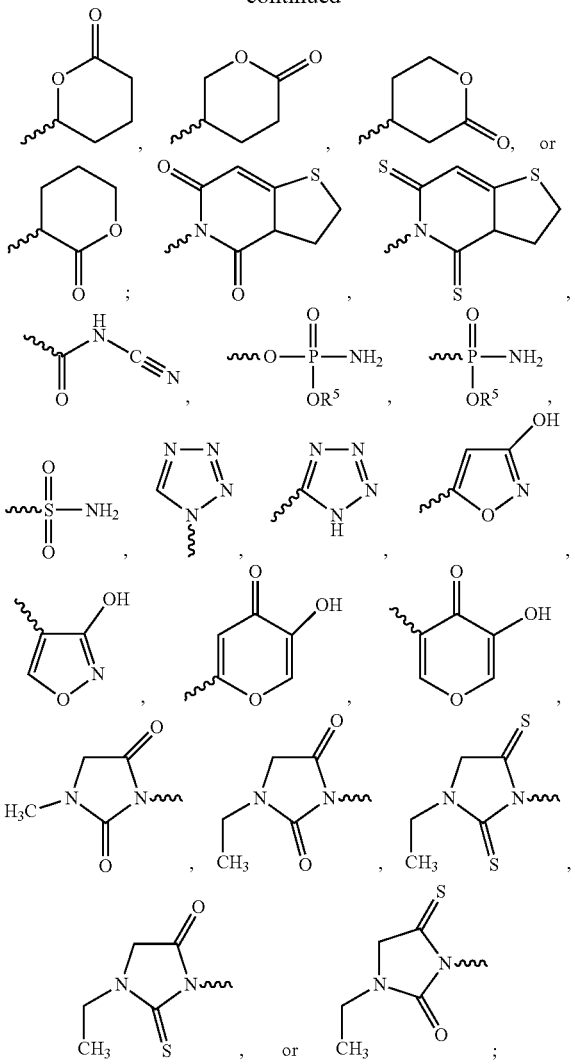

wherein:

(i) $R^7$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups;

(ii) each occurrence of $R^8$ is independently H, $(C_1-C_6)$alkyl, $(C_2-C_6)$alkenyl, or $(C_2-C_6)$alkynyl and is unsubstituted or substituted with one or two halo, OH, $C_1-C_6$ alkoxy, or phenyl groups, (iii) each occurrence of $R^9$ is independently H, $(C_1-C_6)$alkyl, $(C_2-C_6)$alkenyl, or $(C_2-C_6)$alkynyl;

(e) $R^3$ and $R^4$ are $(C_1-C_6)$alkyl, $(C_2-C_6)$alkenyl, $(C_2-C_6)$alkynyl, phenyl, or benzyl;

(f) R and $R^6$ are H, halogen, $(C_1-C_4)$alkyl, $(C_1-C_4)$alkoxy, $(C_2-C_6)$aryloxy, CN, or $NO_2$, $N(R^5)_2$ where $R^5$ is H, $(C_1-C_4)$ alkyl, phenyl, or benzyl;

(g) $C^{*1}$ and $C^{*2}$ represent independent chiral-carbon centers wherein each center may independently be R or S.

Exemplary compounds of formula II are those wherein each occurrence of $Y^1$ and $Y^2$ is independently OH, $COOR^7$, or COOH.

Other compounds of formula II are those wherein m is 4.

Other compounds of formula II are those wherein m is 5.

Other compounds of formula II are those wherein X is $(CH_2)$ and z is 0.

Other compounds of formula II are those wherein X is (CH$_2$) and z is 1.

Other compounds of formula II are those wherein Y$^1$ and/or Y$^2$ is C(O)OH or CH$_2$OH.

Other compounds of formula II are those wherein R$^3$ and R$^4$ are each independently (C$_1$-C$_6$) alkyl.

Other compounds of formula II are those wherein R$^3$ and R$^4$ are each methyl.

Other compounds of formula II are those wherein C* is of the stereochemical configuration R or substantially R.

Other compounds of formula II are those wherein C*$^1$ is of the stereochemical configuration S or substantially S.

Other compounds of formula II are those wherein C*$^2$ is of the stereochemical configuration R or substantially R.

Other compounds of formula II are those wherein C*$^2$ is of the stereochemical configuration S or substantially S.

In a particular embodiment, compounds of formula II are those wherein C*$^1$ C*$^2$ are of the stereochemical configuration (S$^1$, S$^2$) or substantially (S$^1$, S$^2$).

In another particular embodiment, compounds of formula II are those wherein C*$^1$ C*$^2$ are of the stereochemical configuration (S$^1$, R$^2$) or substantially (S$^1$, R$^2$).

In another particular embodiment, compounds of formula II are those wherein C*$^1$ C*$^2$ are of the stereochemical configuration (R$^1$, R$^2$) or substantially (R$^1$, R$^2$).

In another particular embodiment, compounds of formula II are those wherein C*$^1$ C*$^2$ are of the stereochemical configuration (R$^1$, S$^2$) or substantially (R$^1$, S$^2$).

In another embodiment, the invention encompasses compounds of formula

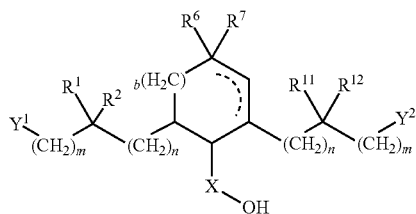

III or a pharmaceutically acceptable salt, hydrate, solvate, or mixture thereof, wherein
(a) each occurrence of R$^1$, R$^2$, R$^6$, R$^7$, R$^{11}$, or R$^{12}$ is independently hydrogen, (C$_1$-C$_6$)alkyl, (C$_2$-C$_6$)alkenyl, (C$_2$-C$_6$)alkynyl, phenyl, or benzyl;
(b) each occurrence of n is independently an integer ranging from 1 to 7;
(c) X is (CH$_2$) or Ph, wherein z is an integer from 0 to 4 and Ph is a 1,2-, 1,3-, or 1,4 substituted phenyl group;
(d) each occurrence of m is independently an integer ranging from 0 to 4;
(e) each occurrence of Y$^1$ and Y$^2$ is independently (C$_1$-C$_6$) alkyl, CH$_2$OH, C(O)OH, OC(O)R$^3$, C(O)OR$^3$, SO$_3$H,

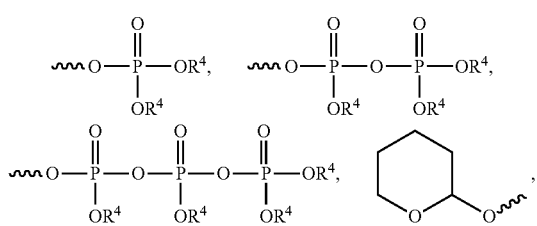

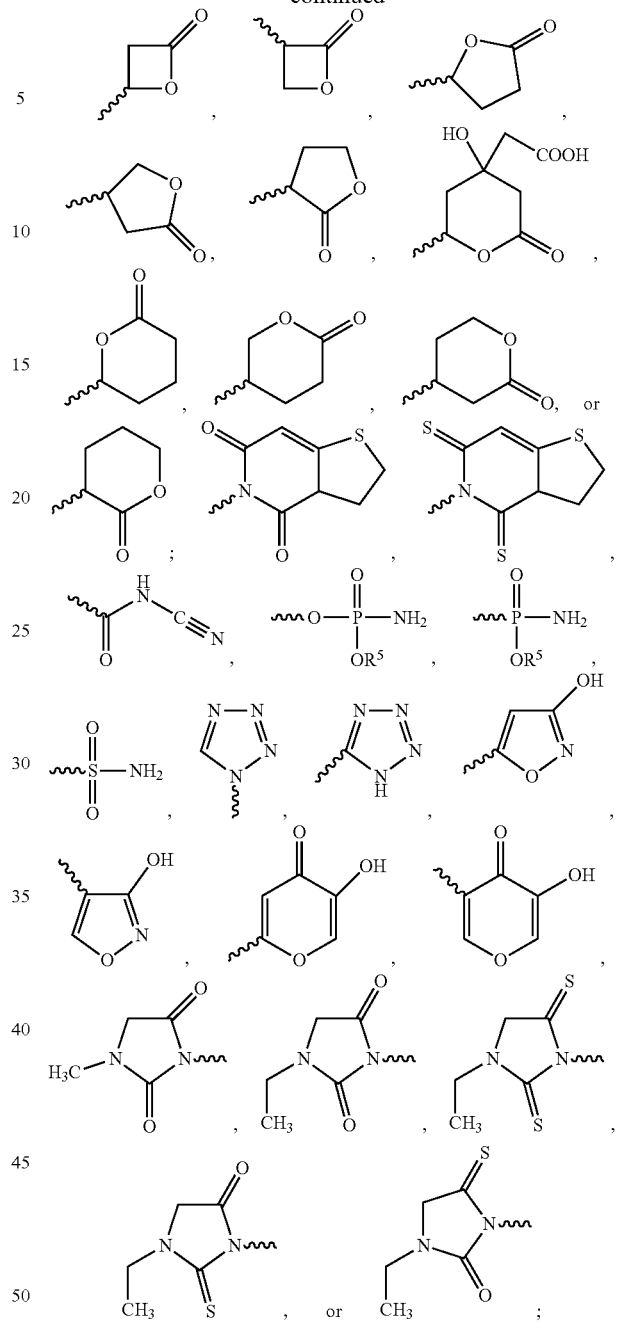

wherein:
(i) R$^3$ is (C$_1$-C$_6$)alkyl, (C$_2$-C$_6$)alkenyl, (C$_2$-C$_6$)alkynyl, phenyl, or benzyl and is unsubstituted or substituted with one or more halo, OH, (C$_1$-C$_6$)alkoxy, or phenyl groups,
(ii) each occurrence of R$^4$ is independently H, (C$_1$-C$_6$) alkyl, (C$_2$-C$_6$)alkenyl, or (C$_2$-C$_6$)alkynyl and is unsubstituted or substituted with one or two halo, OH, C$_1$-C$_6$ alkoxy, or phenyl groups;
(iii) each occurrence of R$^5$ is independently H, (C$_1$-C$_6$) alkyl, (C$_2$-C$_6$)alkenyl, or (C$_2$-C$_6$)alkynyl; and
(f) b is 0 or 1 and optionally the ring contains the presence of one or more additional carbon-carbon bonds that when present complete one or more carbon-carbon double bonds such that when b is 0 the maximum number of carbon-carbon bonds is two or when b is 1 the maximum number of carbon-carbon bonds is three.

In another embodiment, the invention encompasses compounds of formula IV:

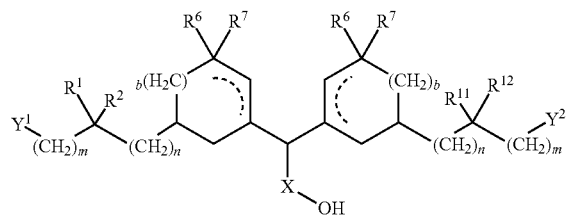

IV or a pharmaceutically acceptable salt, hydrate, solvate, or mixture thereof, wherein
(a) each occurrence of $R^1$, $R^2$, $R^6$, $R^7$, $R^{11}$, or $R^{12}$ is independently H, $(C_1-C_6)$alkyl, $(C_2-C_6)$alkenyl, $(C_2-C_6)$alkynyl, phenyl, or benzyl;
(b) each occurrence of n is independently an integer ranging from 1 to 7;
(c) X is $(CH_2)$ or Ph, wherein z is an integer from 0 to 4 and Ph is a 1,2-, 1,3-, or 1,4 substituted phenyl group;
(d) each occurrence of m is independently an integer ranging from 0 to 4;
(e) each occurrence of $Y^1$ and $Y^2$ is independently $(C_1-C_6)$ alkyl, $CH_2OH$, $C(O)OH$, $OC(O)R^3$, $C(O)OR^3$, $SO_3H$,

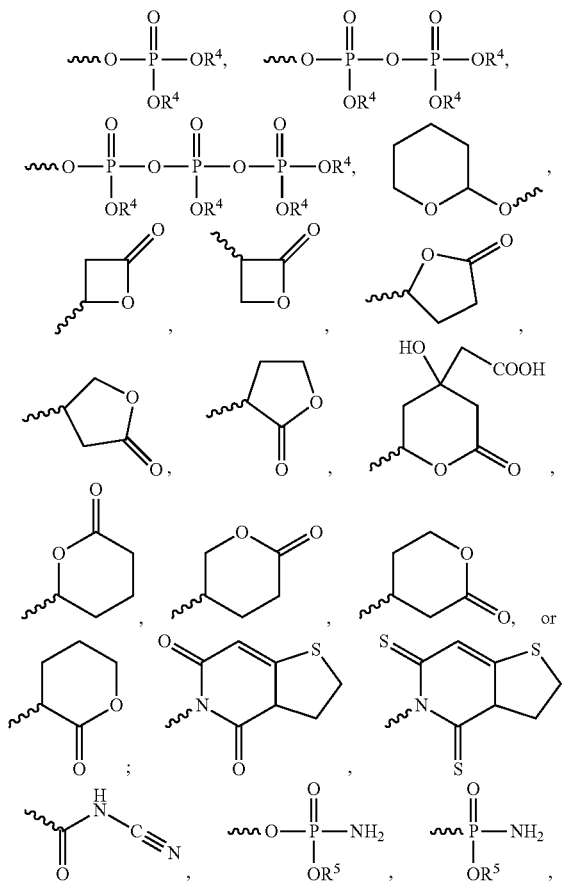

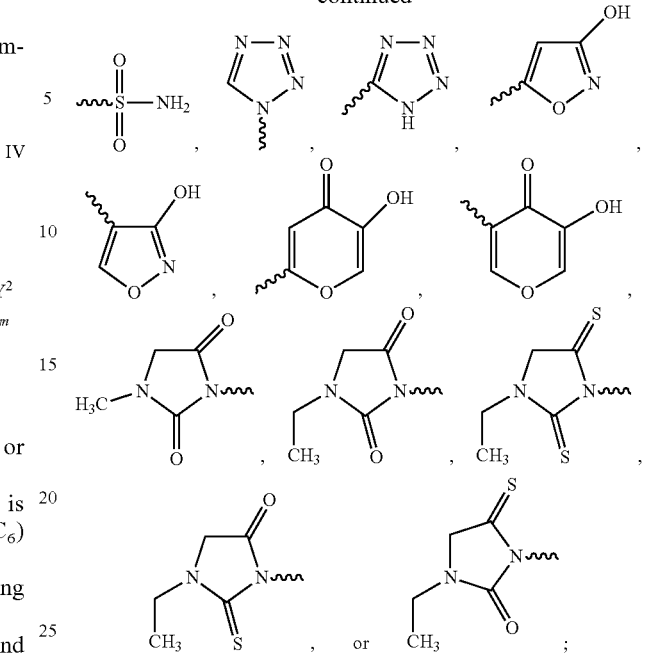

wherein:
(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^4$ is independently H, $(C_1-C_6)$alkyl, $(C_2-C_6)$alkenyl, or $(C_2-C_6)$alkynyl and is unsubstituted or substituted with one or two halo, OH, $C_1-C_6$ alkoxy, or phenyl groups;
(iii) each occurrence of $R^5$ is independently H, $(C_1-C_6)$alkyl, $(C_2-C_6)$alkenyl, or $(C_2-C_6)$alkynyl; and
(f) each occurrence of b is independently 0 or 1 and optionally each of the rings independently contains the presence of one or more additional carbon-carbon bonds that when present complete one or more carbon-carbon double bonds such that when b is 0 the maximum number of carbon-carbon bonds is two or when b is 1 the maximum number of carbon-carbon bonds is three.

In another embodiment, the invention encompasses compounds of formula V:

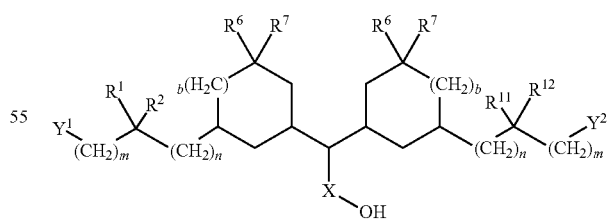

V or a pharmaceutically acceptable salt, hydrate, solvate, or mixture thereof, wherein
(a) each occurrence of $R^1$, $R^2$, $R^6$, $R^7$, $R^{11}$, or $R^{12}$ is independently hydrogen, $(C_1-C_6)$alkyl, $(C_2-C_6)$alkenyl, $(C_2-C_6)$alkynyl, phenyl, or benyl;
(b) each occurrence of n is independently an integer ranging from 1 to 7;

(c) X is $(CH_2)_z$ or Ph, wherein z is an integer from 0 to 4 and Ph is a 1,2-, 1,3-, or 1,4 substituted phenyl group;

(d) each occurrence of m is independently an integer ranging from 0 to 4;

(e) each occurrence of $Y^1$ and $Y^2$ is independently $(C_1-C_6)$ alkyl, $CH_2OH$, $C(O)OH$, $OC(O)R^3$, $C(O)OR^3$, $SO_3H$,

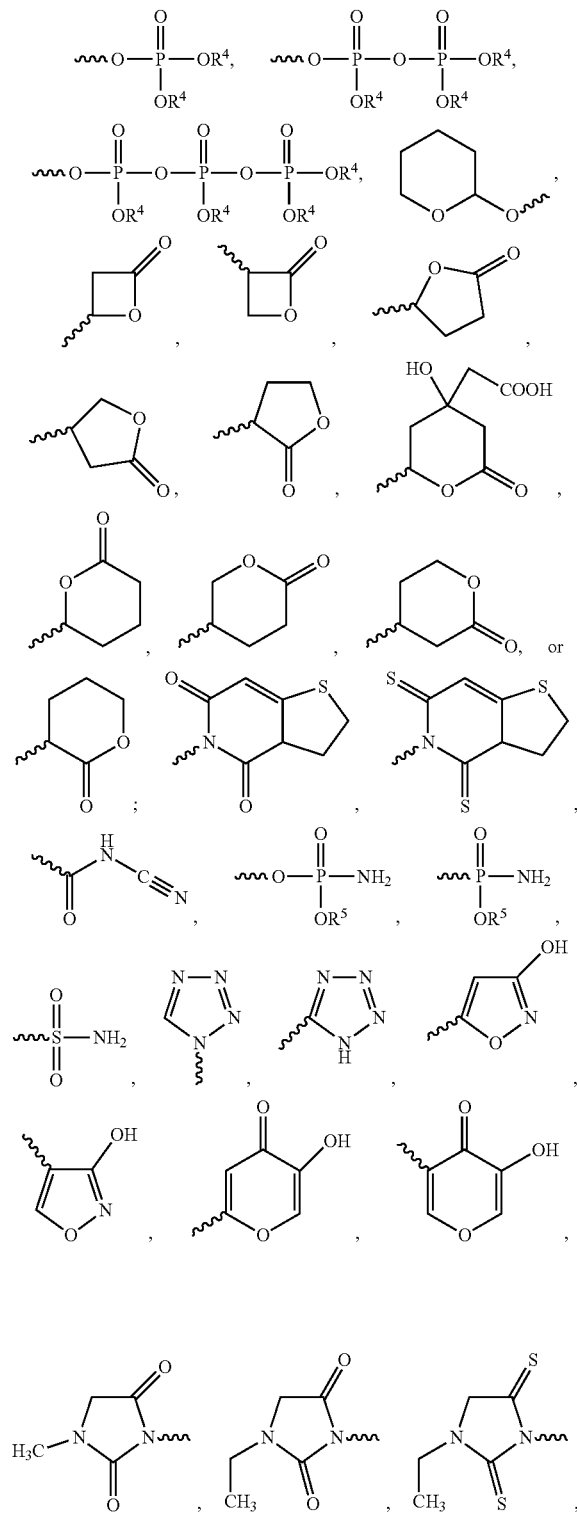

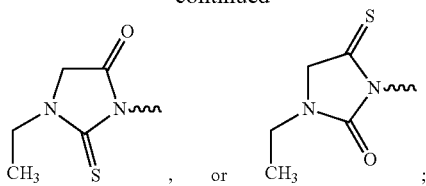

wherein:
(i) $R^3$ is $(C_1-C_6)$alkyl, $(C_2-C_6)$alkenyl, $(C_2-C_6)$alkyl, phenyl, or benzyl and is unsubstituted or substituted with one or more halo, OH, $(C_1-C_6)$alkoxy, or phenyl groups, (ii) each occurrence of $R^4$ is independently H, $(C_1-C_6)$alkyl, $(C_1-C_6)$alkenyl, or $(C_2-C_6)$alkynyl and is unsubstituted or substituted with one or two halo, OH, $C_1-C_6$ alkoxy, or phenyl groups;

(iii) each occurrence of $R^5$ is independently H, $(C_1-C_6)$alkyl, $(C_2-C_6)$alkenyl, or $(C_2-C_6)$alkynyl; and (f) b is 0 or 1 and optionally the ring contains one or more carbon-carbon bonds that when present complete one or more carbon-carbon double bonds.

In another embodiment, the invention encompasses compounds of the formula VI:

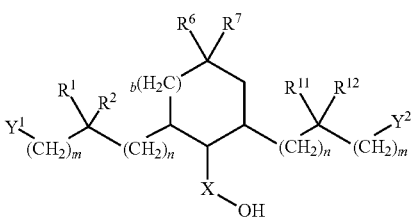

VI or a pharmaceutically acceptable salt, hydrate, solvate, or mixture thereof, wherein:

(a) each occurrence of $R^1$, $R^2$, $R^6$, $R^7$, $R^{11}$, or $R^{12}$ is independently hydrogen, $(C_1-C_6)$alkyl, $(C_2-C_6)$alkenyl, $(C_2-C_6)$alkynyl, phenyl, or benzyl;

(b) each occurrence of n is independently an integer ranging from 1 to 7;

(c) X is $(CH_2)_z$ or Ph, wherein z is an integer from 0 to 4 and Ph is a 1,2-, 1,3-, or 1,4 substituted phenyl group;

(d) each occurrence of m is independently an integer ranging from 0 to 4;

(e) each occurrence of $Y^1$ and $Y^2$ is independently $(C_1-C_6)$ alkyl, $CH_2OH$, $C(O)OH$, $OC(O)R^3$, $C(O)OR^3$, $SO_3H$,

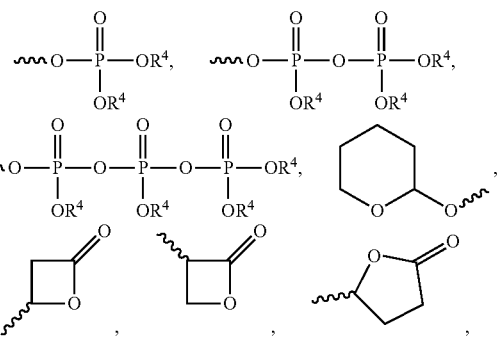

-continued

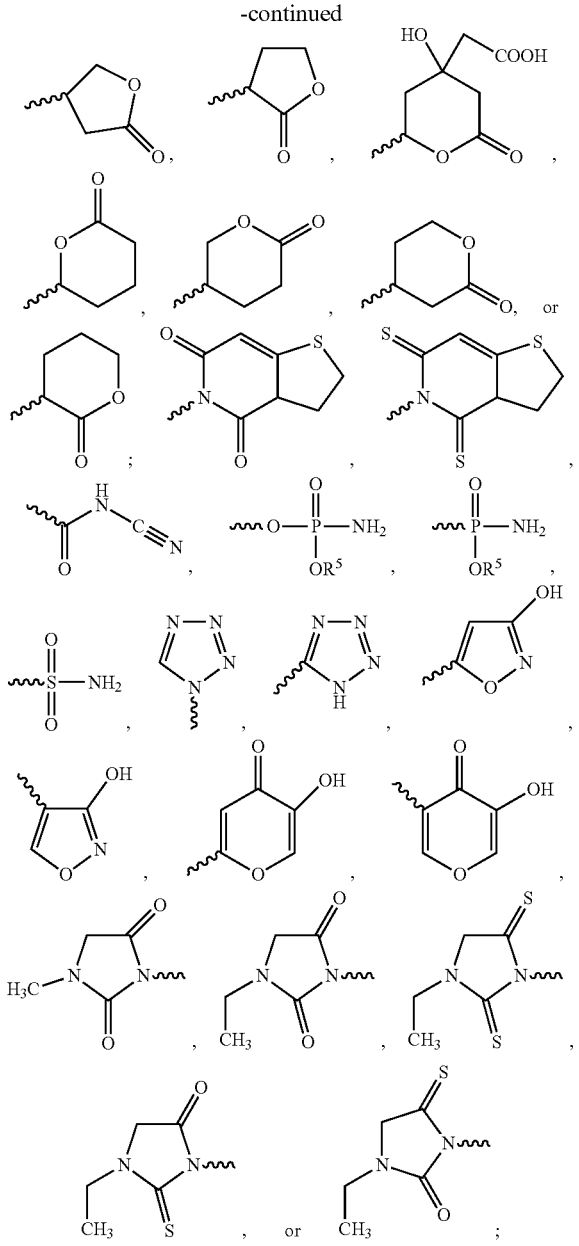

wherein:
(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of R is independently H, $(C_1-C_6)$ alkyl, $(C_2-C_6)$alkenyl, or $(C_2-C_6)$alkynyl and is unsubstituted or substituted with one or two halo, OH, $C_1-C_6$ alkoxy, or phenyl groups; and
(iii) each occurrence of $R^5$ is independently H, $(C_1-C_6)$ alkyl, $(C_2-C_6)$alkenyl, or $(C_2-C_6)$alkynyl; and
(f) b is 0 or 1 and optionally the ring contains one or more carbon-carbon bonds that when present complete one or more carbon-carbon double bonds.

In another embodiment, the invention encompasses compounds of the formula VII:

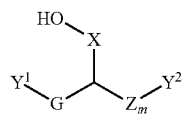

VII or a pharmaceutically acceptable salt, hydrate, solvate, or mixture thereof, wherein
(a) Z is $CH_2$, CH=CH, or phenyl, where each occurrence of m is independently an integer ranging from 1 to 9, but when Z is phenyl then its associated m is 1;
(b) G is $(CH_2)_x$, where x is 1, 2, 3, or 4, $CH_2CH$=$CHCH_2$, CH=CH, $CH_2$-phenyl-$CH_2$, or phenyl;
(c) each occurrence of $Y^1$ and $Y^2$ is independently L, V, $C(R^1)(R^2)$—$(CH_2)$c-$C(R^3)(R^4)$—$(CH_2)$n-Y, or $C(R^1)$ $(R^2)$—$(CH_2)$c-V where c is 1 or 2 and n is an integer ranging from 0 to 4; when G is $(CH_2)_x$, where x is 1, 2, 3, or 4, $W^2$ is $CH_3$;
(d) each occurrence of R' or $R^2$ is independently $(C_1-C_6)$ alkyl, $(C_2-C_6)$alkenyl, $(C_2-C_6)$alkynyl, phenyl, or benzyl or when one or both of $Y^1$ and $Y^2$ is $C(R^1)(R^2)$—$(CH_2)$ c-$C(R^3)(R^4)$—$(CH_2)$n-W, then $R^1$ and $R^2$ can both be H to form a methylene group;
(e) $R^3$ is H, $(C_1-C_6)$alkyl, $(C_2-C_6)$alkenyl, $(C_2-C_6)$alkynyl, $(C_1-C_6)$alkoxy, phenyl, benzyl, Cl, Br, CN, $NO_2$, or $CF_3$;
(f) $R^4$ is OH, $(C_1-C_6)$alkyl, $(C_2-C_6)$alkenyl, $(C_2-C_6)$alkynyl, $(C_1-C_6)$alkoxy, phenyl, benzyl, Cl, Br, CN, $NO_2$, or $CF_3$;
(g) L is $C(R^1)(R^2)$—$(CH_2)$n-W;
(h) V is:

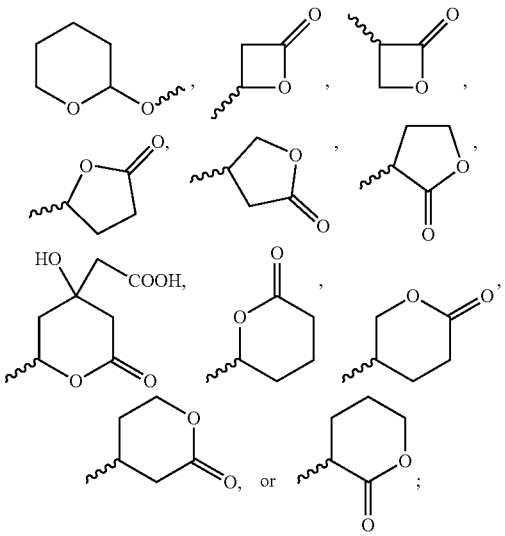

(i) each occurrence of W is independently OH, COOH, CHO, $COOR^5$, $SO_3H$,

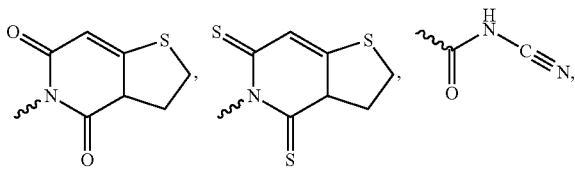

-continued

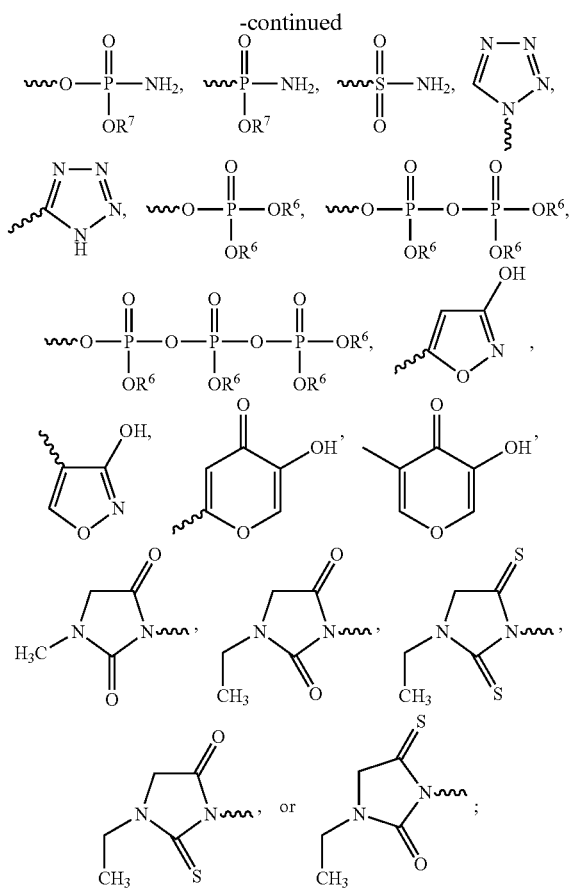

wherein
(i) $R^3$ is $(C_1\text{-}C_6)$alkyl, $(C_2\text{-}C_6)$alkenyl, $(C_2\text{-}C_6)$alkynyl, phenyl, or benzyl and is unsubstituted or substituted with one or more halo, OH, $(C_1\text{-}C_6)$alkoxy, or phenyl groups,
(ii) each occurrence of $R^6$ is independently H, $(C_1\text{-}C_6)$alkyl, $(C_2\text{-}C_6)$alkenyl, or $(C_2\text{-}C_6)$alkynyl and is unsubstituted or substituted with one or two halo, OH, $(C_1\text{-}C_6)$ alkoxy, or phenyl groups;
(iii) each occurrence of $R^7$ is independently H, $(C_1\text{-}C_6)$alkyl, $(C_2\text{-}C_6)$alkenyl, or $(C_2\text{-}C_6)$alkynyl; and
(j) X is $(CH_2)_z$ or PH, wherein z is an integer from 0 to 4.

In a particular embodiment, the invention encompasses compounds of the formula VIII:

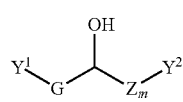

VIII or a pharmaceutically acceptable salt, hydrate, solvate, or mixture thereof, wherein
(a) Z is $CH_2$, CH=CH, or phenyl, where each occurrence of m is independently an integer ranging from 1 to 9, but when Z is phenyl then its associated m is 1;
(b) G is $(CH_2)_x$, where x is 1, 2, 3, or 4, $CH_2CH$=$CHCH_2$, CH=CH, $CH_2$-phenyl-$CH_2$, or phenyl;
(c) each occurrence of $Y^1$ and $Y^2$ is independently L, V, $C(R^1)(R^2)$—$(CH_2)c$-$C(R^3)(R^4)$—$(CH_2)n$-Y, or $C(R^1)$ $(R^2)$—$(CH_2)c$-V where c is 1 or 2 and n is an integer ranging from 0 to 4; when G is $(CH_2)_x$, where x is 1, 2, 3, or 4, $W^2$ is $CH_3$;
(d) each occurrence of $R^1$ or $R^2$ is independently $(C_1\text{-}C_6)$ alkyl, $(C_2\text{-}C_6)$alkenyl, $(C_2\text{-}C_6)$alkynyl, phenyl, or benzyl or when one or both of $Y^1$ and $Y^2$ is $C(R^1)(R^2)$—$(CH_2)$ c-$C(R^3)(R^4)$—$(CH_2)n$-W, then $R^1$ and $R^2$ can both be H to form a methylene group;
(e) $R^3$ is H, $(C_1\text{-}C_6)$alkyl, $(C_2\text{-}C_6)$alkenyl, $(C_2\text{-}C_6)$alkynyl, $(C_1\text{-}C_6)$alkoxy, phenyl, benzyl, Cl, Br, CN, $NO_2$, or $CF_3$;
(f) $R^4$ is OH, $(C_1\text{-}C_6)$alkyl, $(C_2\text{-}C_6)$alkenyl, $(C_2\text{-}C_6)$alkynyl, $(C_1\text{-}C_6)$alkoxy, phenyl, benzyl, Cl, Br, CN, $NO_2$, or $CF_3$;
(g) L is $C(R^1)(R^2)$—$(CH_2)n$-W;
(h) V is:

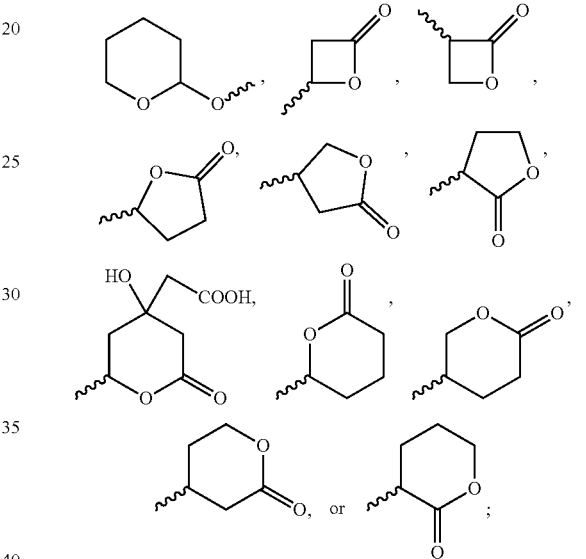

(i) each occurrence of W is independently OH, COOH, CHO, COOR, $SO_3H$,

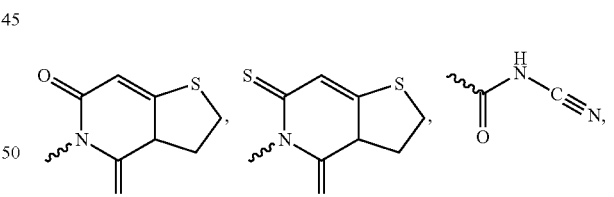

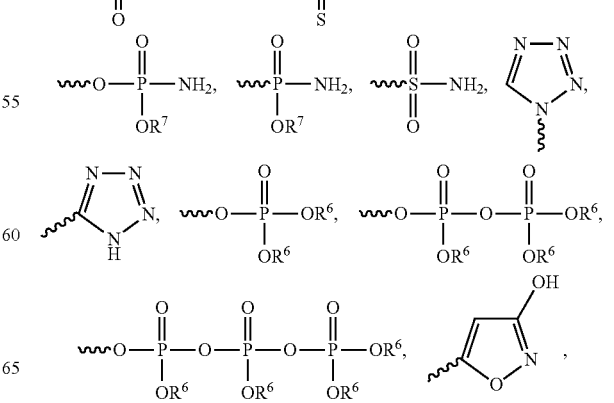

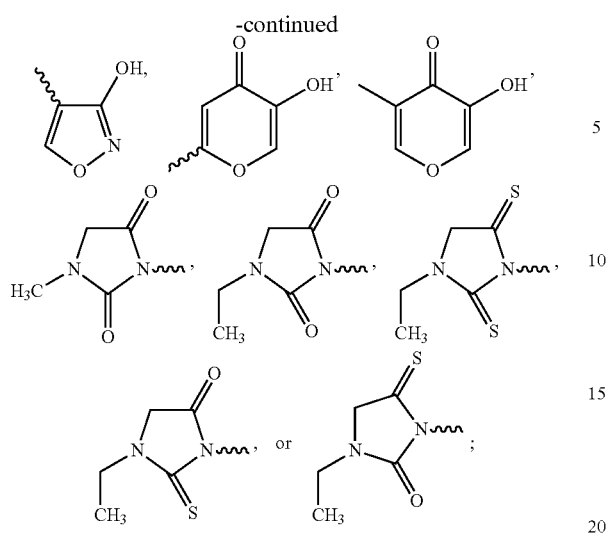

wherein:
  (i) $R^5$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
  (ii) each occurrence of $R^6$ is independently H, $(C_1-C_6)$ alkyl, $(C_2-C_6)$alkenyl, or $(C_2-C_6)$alkynyl and is unsubstituted or substituted with one or two halo, OH, $(C_1-C_6)$ alkoxy, or phenyl groups; and
  (iii) each occurrence of $R^7$ is independently H, $(C_1-C_6)$ alkyl, $(C_2-C_6)$alkenyl, or $(C_2-C_6)$alkynyl.

In another particular embodiment, the invention encompasses compounds of formula IX:

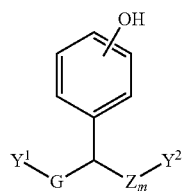

IX or a pharmaceutically acceptable salt, hydrate, solvate, or mixture thereof, wherein
  (a) Z is $CH_2$, $CH=CH$, or phenyl, where each occurrence of m is independently an integer ranging from 1 to 9, but when Z is phenyl then its associated m is 1;
  (b) G is $(CH_2)_x$, where x is 1, 2, 3, or 4, $CH_2CH=CHCH_2$, $CH=CH$, $CH_2$-phenyl-$CH_2$, or phenyl;
  (c) each occurrence of $Y^1$ and $Y^2$ is independently L, V, $C(R^1)(R^2)$—$(CH_2)c$-$C(R^3)(R^4)$—$(CH_2)n$-Y, or $C(R^1)(R^2)$—$(CH_2)c$-V where c is 1 or 2 and n is an integer ranging from 0 to 4; when G is $(CH_2)_x$, where x is 1, 2, 3, or 4, $W^2$ is $CH_3$;
  (d) each occurrence of R' or $R^2$ is independently $(C_1-C_6)$ alkyl, $(C_2-C_6)$alkenyl, $(C_2-C_6)$alkynyl, phenyl, or benzyl or when one or both of $Y^1$ and $Y^2$ is $C(R^1)(R^2)$—$(CH_2)$ c-$C(R^3)(R^4)$—$(CH_2)n$-W, then $R^1$ and $R^2$ can both be H to form a methylene group;
  (e) $R^3$ is H, $(C_1-C_6)$alkyl, $(C_2-C_6)$alkenyl, $(C_2-C_6)$alkynyl, $(C_1-C_6)$alkoxy, phenyl, benzyl, Cl, Br, CN, $NO_2$, or $CF_3$;
  (f) $R^4$ is OH, $(C_1-C_6)$alkyl, $(C_2-C_6)$alkenyl, $(C_2-C_6)$alkynyl, $(C_1-C_6)$alkoxy, phenyl, benzyl, Cl, Br, CN, $NO_2$, or $CF_3$;
  (g) L is $C(R^1)(R^2)$—$(CH_2)n$-W;
  (h) V is:

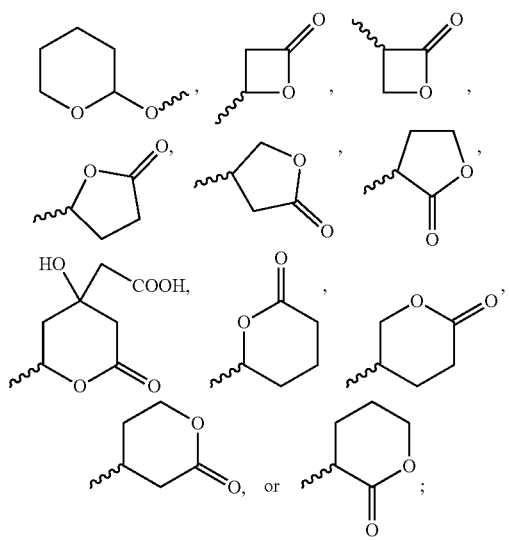

(i) each occurrence of W is independently OH, COOH, CHO, $COOR^5$, $SO_3H$,

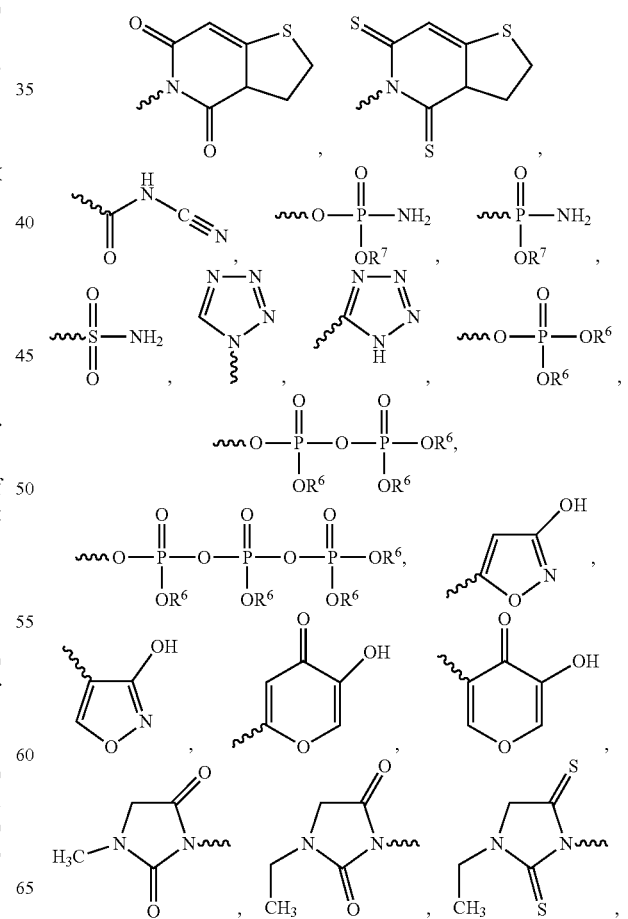

-continued

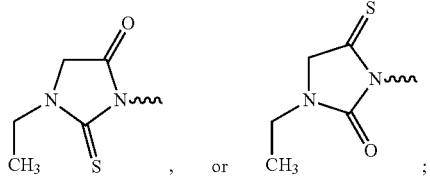

wherein:
(i) $R^5$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^6$ is independently H, $(C_1-C_6)$ alkyl, $(C_2-C_6)$alkenyl, or $(C_2-C_6)$alkynyl and is unsubstituted or substituted with one or two halo, OH, $(C_1-C_6)$ alkoxy, or phenyl groups; and
(iii) each occurrence of $R^7$ is independently H, $(C_1-C_6)$ alkyl, $(C_2-C_6)$alkenyl, or $(C_2-C_6)$alkynyl.

The present invention further provides pharmaceutical compositions comprising one or more compounds of the invention. Particular pharmaceutical compositions further comprise pharmaceutically acceptable vehicle, which can comprise a carrier, excipient, diluent, or a mixture thereof.

The present invention provides a method for treating or preventing aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, pancreatitius, Parkinson's disease, a peroxisome proliferator activated receptor-associated disorder, phospholipid elimination in bile, renal disease, septicemia, metabolic syndrome disorders (e.g., Syndrome X), and a thrombotic disorder, comprising administering to a patient in need of such treatment or prevention a therapeutically effective amount of a compound of the invention.

The present invention further provides a method for reducing the fat content of meat in livestock comprising administering to livestock in need of such fat-content reduction a therapeutically effective amount of a compound of the invention or a pharmaceutical composition.

The present invention provides a method for reducing the cholesterol content of a fowl egg comprising administering to a fowl species a therapeutically effective amount of a compound of the invention.

The compounds of the invention are particularly useful when incorporated in a pharmaceutical composition comprising a carrier, excipient, diluent, or a mixture thereof. However, a compound of the invention need not be administered with excipients or diluents and can be delivered in a gel cap or drug delivery device.

In certain embodiments of the invention, a compound of the invention is administered in combination with another therapeutic agent. The other therapeutic agent provides additive or synergistic value relative to the administration of a compound of the invention alone. Examples of other therapeutic agents include, but are not limited to, a lovastatin; a thiazolidinedione or fibrate; a bile-acid-binding-resin; a niacin; an anti-obesity drug; a hormone; a tyrophostine; a sulfonylurea-based drug; a biguanide; an a-glucosidase inhibitor; an apolipoprotein A-I agonist; apolipoprotein E; a cardiovascular drug; an HDL-raising drug; an HDL enhancer; or a regulator of the apolipoprotein A-I, apolipoprotein A-IV and/or apolipoprotein genes.

Illustrative examples of compounds of the invention are encompassed by formulas I-IX and include those shown below, and pharmaceutically acceptable salts, hydrates, enantiomers, diastereomers, and geometric isomers thereof:

Compound 1

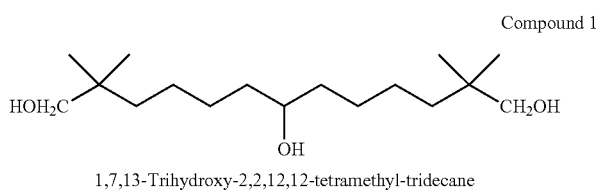

1,7,13-Trihydroxy-2,2,12,12-tetramethyl-tridecane

Compound 2

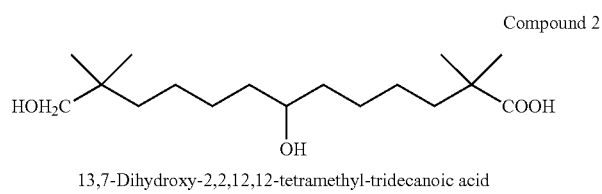

13,7-Dihydroxy-2,2,12,12-tetramethyl-tridecanoic acid

Compound 3

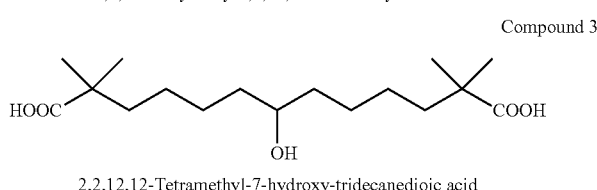

2,2,12,12-Tetramethyl-7-hydroxy-tridecanedioic acid

Compound 4

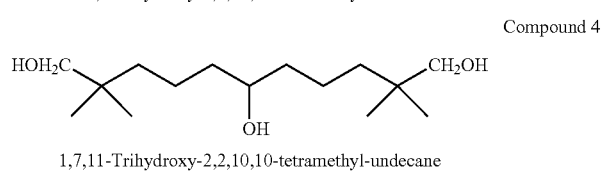

1,7,11-Trihydroxy-2,2,10,10-tetramethyl-undecane

Compound 5

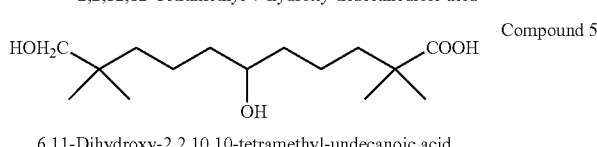

6,11-Dihydroxy-2,2,10,10-tetramethyl-undecanoic acid

Compound 6

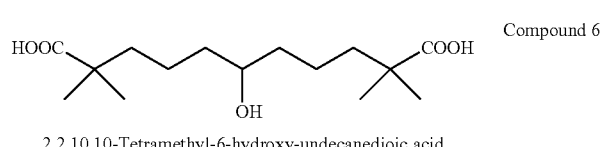

2,2,10,10-Tetramethyl-6-hydroxy-undecanedioic acid

Compound 7

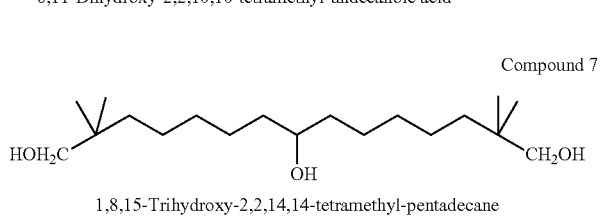

1,8,15-Trihydroxy-2,2,14,14-tetramethyl-pentadecane

Compound 8

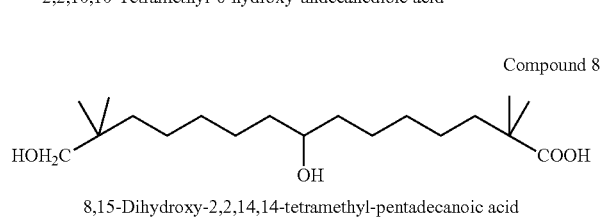

8,15-Dihydroxy-2,2,14,14-tetramethyl-pentadecanoic acid

-continued

Compound 9

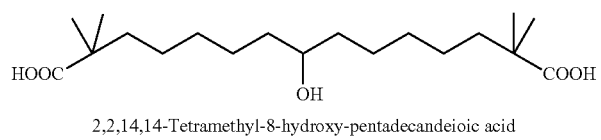

2,2,14,14-Tetramethyl-8-hydroxy-pentadecandeioic acid

Compound 10

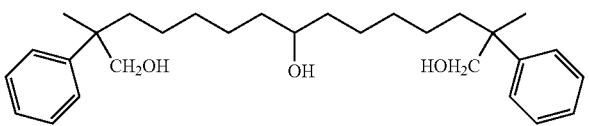

1,8,15-Trihydroxy-2,14-dimethyl-2,14-diphenyl-pentadecane

Compound 11

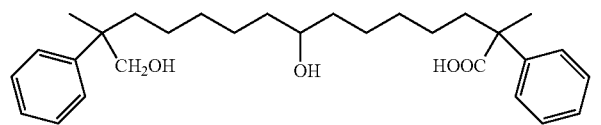

8,15-Dihydroxy-2,14-dimethyl-2,14-diphenyl-pentadecanoic acid

Compound 12

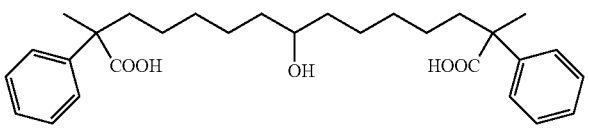

2,14-Dimethyl-8-hydroxy-2,14-diphenyl-pentadecanedioic acid

Compound 13

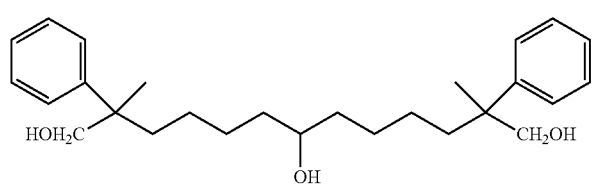

1,7,13-Trihydroxy-2,12-dimethyl-2,12-diphenyl-tridecane

Compound 14

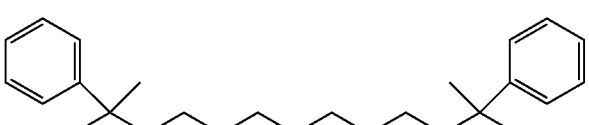

7,13-Dihydroxy-2,12-dimethyl-2,12-diphenyl-tridecanoic acid

Compound 15

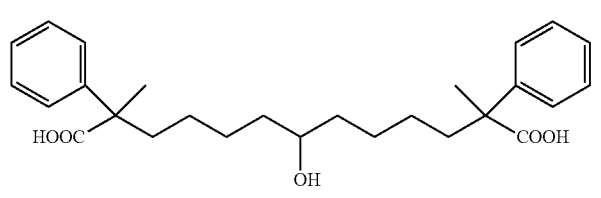

2,12-Dimethyl-7-hydoxy-2,12-diphenyl-tridecanedioic acid

Compound 16

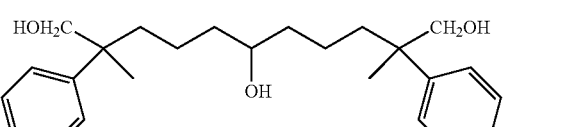

1,6,11-Trihydroxy-2,10-dimethyl-2,10-diphenyl-undecane

Compound 17

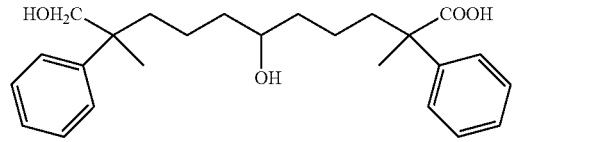

6,11-Dihydroxy-2,10-dimethyl-2,10-diphenyl-undecanoic acid

Compound 18

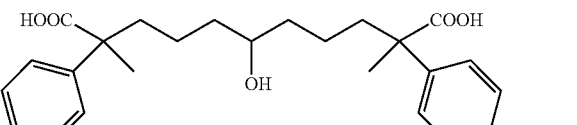

2,10-dimethyl-6-hydroxy-2,10-diphenyl-undecanedioic acid

Compound 19

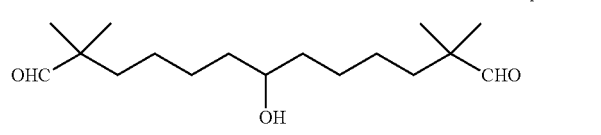

2,2,12,12-Tetramethyl-7-hydroxy-tridecanedial

Compound 20

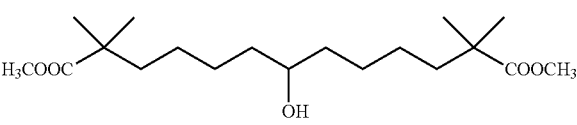

2,2,12,12-Tetramethyl-7-hydroxy-tridecanedioic acid dimethyl ester

Compound 21

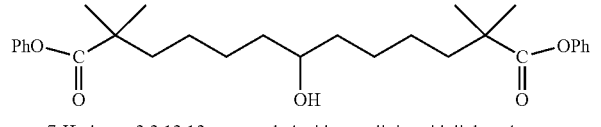

7-Hydroxy-2,2,12,12-tetramethyl-tridecanedioic acid diphenyl ester

Compound 22

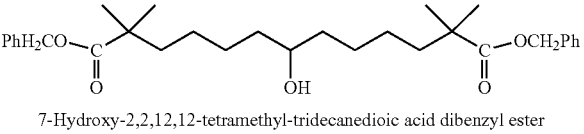

7-Hydroxy-2,2,12,12-tetramethyl-tridecanedioic acid dibenzyl ester

Compound 23

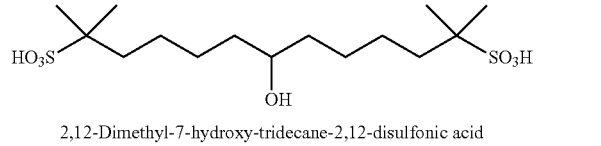

2,12-Dimethyl-7-hydroxy-tridecane-2,12-disulfonic acid

Compound 24

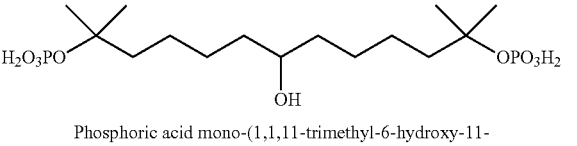

Phosphoric acid mono-(1,1,11-trimethyl-6-hydroxy-11-phosphonooxy-dodecyl)ester

Compound 25

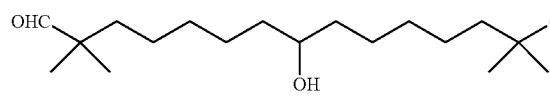

2,2,14,14-Tetramethyl-8-hydroxy-pentadecanedial

Compound 26

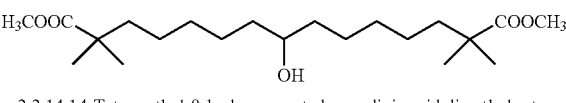

2,2,14,14-Tetramethyl-8-hydroxy-pentadecanedioic acid dimethyl ester

Compound 27

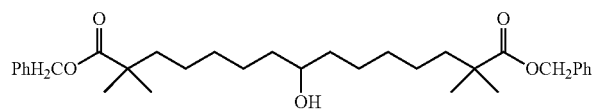

8-Hydroxy-2,2,14,14-tetramethyl-pentadecanedioic acid dibenzyl ester

Compound 28

8-Hydroxy-2,2,14,14-tetramethyl-pentadecanedioic acid diphenyl ester

Compound 29

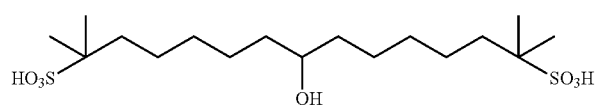

2,14-Dimethyl-8-hydroxy-pentadecane-2,14-disulfonic acid

Compound 30

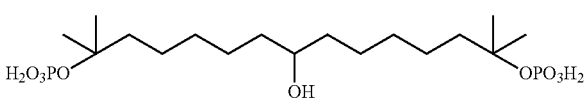

Phosphoric acid mono-(1,1,13-trimethyl-7-hydroxy-13-phosphonooxy-tetradecyl)ester Compound 31

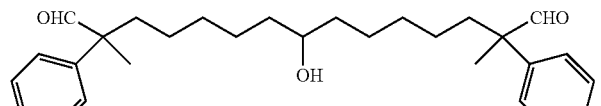

8-Hydroxy-2,14-dimethyl-2,14-diphenyl-pentadecanedial

Compound 32

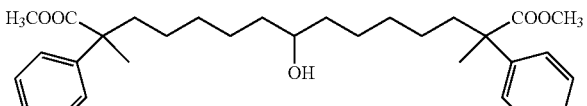

2,14-Dimethyl-8-hydroxy-2,14-diphenyl-pentadecanedioic acid dimethyl ester

Compound 33

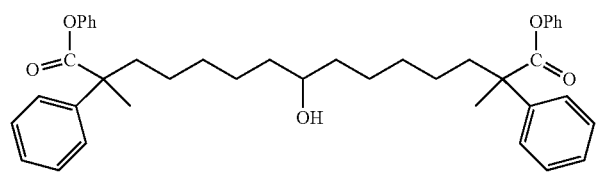

8-Hydroxy-2,14-dimethyl-2,14-diphenyl-pentadecanedioic acid diphenyl ester

Compound 34

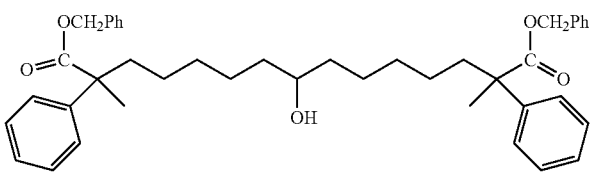

8-Hydroxy-2,14-dimethyl-2,14-diphenyl-pentadecanedioic acid dibenzyl ester

Compound 35

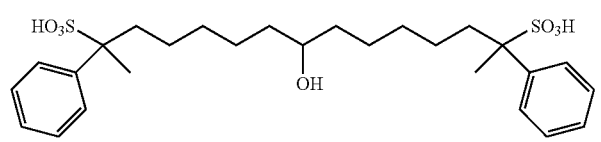

8-Hydroxy-2,14-diphenyl-pentadecane-2,14-disulfonic acid

Compound 36

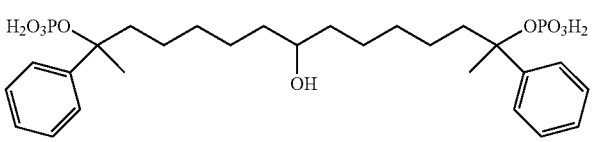

Phosphoric acid mono-(1-methyl-7-hydroxy-1,13-diphenyl-13-phosphonooxy-tetradecyl)ester Compound 37

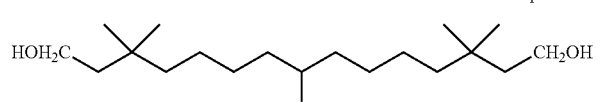

1,8,15-Trihydroxy-3,3,13,13-tetramethyl-pentadecane

Compound 38

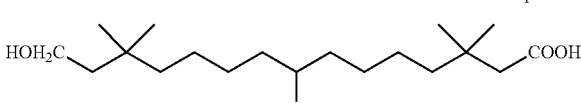

8,15-Dihydroxy-3,3,13,13-tetramethyl-pentadecanoic acid

Compound 39

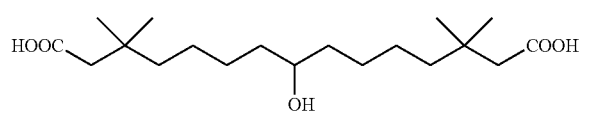

8-Hydroxy-3,3,13,13-tetramethyl-pentadecanedioic acid

Compound 40

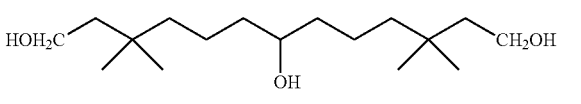

1,7,13-Trihydroxy-3,3,11,11-tetramethyl-tridecane

-continued

Compound 41

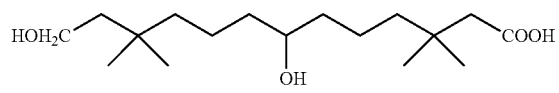

7,13-Dihydroxy-3,3,11,11-tetramethyl-tridecanoic acid

Compound 42

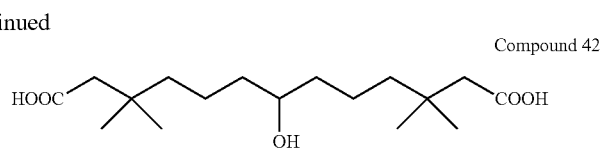

3,3,11,11-Tetramethyl-7-hydroxy-tridecanedioic acid

Compound 43

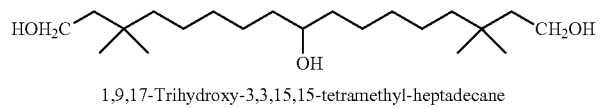

1,9,17-Trihydroxy-3,3,15,15-tetramethyl-heptadecane

Compound 44

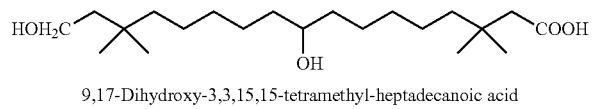

9,17-Dihydroxy-3,3,15,15-tetramethyl-heptadecanoic acid

Compound 45

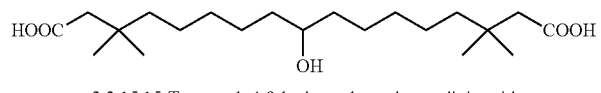

3,3,15,15-Tetramethyl-9-hydroxy-heptadecanedioic acid

Compound 46

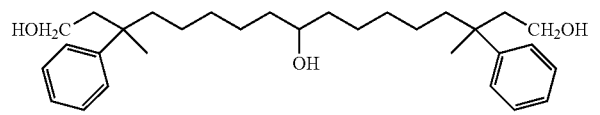

1,9,17-Trihydroxy-3,15-dimethyl-3,15-diphenyl-heptadecane

Compound 47

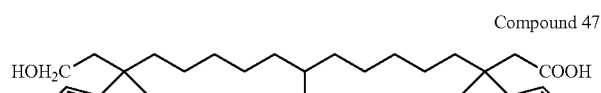

9,17-Dihydroxy-3,15-dimethyl-3,15-diphenyl-heptadecanoic acid

Compound 48

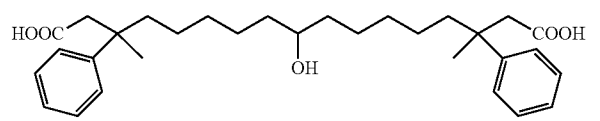

3,15-Dimethyl-9-hydroxy-3,15-diphenyl-heptadecanedioic acid

Compound 49

1,8,15-Trihydroxy-3,13-dimethyl-3,13-diphenyl-pentadecane

Compound 50

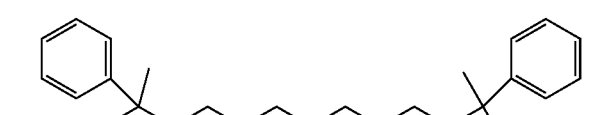

8,15-Trihydroxy-3,13-dimethyl-3,13-diphenyl-pentadecanoic acid

Compound 51

3,13-Dimethyl-8-hydroxy-3,13-diphenyl-pentadecanedioic acid

Compound 52

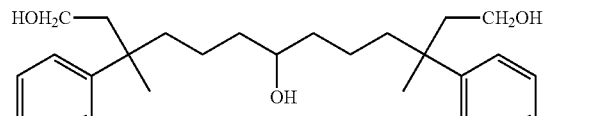

1,7,13-Trihydroxy-3,11-dimethyl-3,11-diphenyl-tridecane

Compound 53

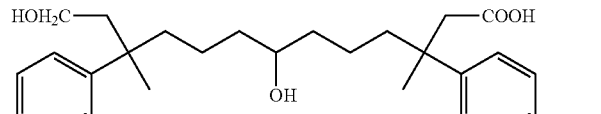

7,13-Dihydroxy-3,11-dimethyl-3,11-diphenyl-tridecanoic acid

Compound 54

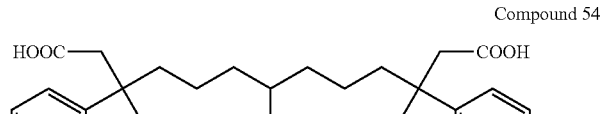

3,11-Dimethyl-7-hydroxy-3,11-diphenyl-tridecanedioic acid

Compound 55

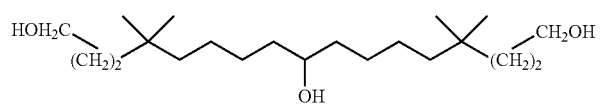

1,9,17-Trihydroxy-4,4,14,14-tetramethyl-heptadecane

Compound 56

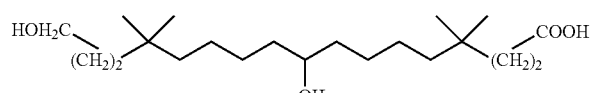

9,17-Dihydroxy-4,4,14,14-tetramethyl-heptadecanoic acid

Compound 57

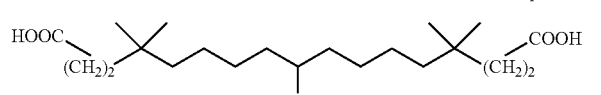

4,4,14,14-Tetramethyl-heptadecan-9-hydroxy-1,17-decarboxylic acid

Compound 58

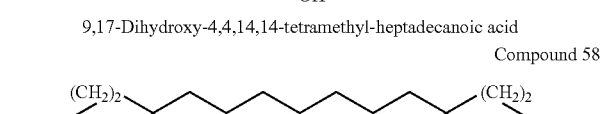

4,4,14,14-Tetramethyl-heptadecan-9-hydroxy-1,17-decarboxylic acid

-continued

Compound 59

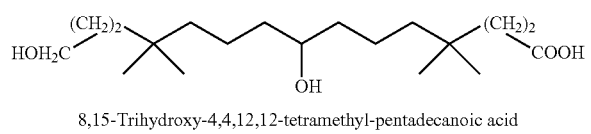

8,15-Trihydroxy-4,4,12,12-tetramethyl-pentadecanoic acid

Compound 60

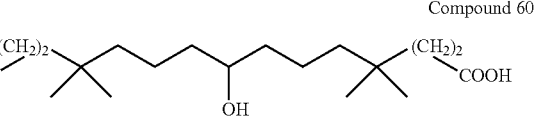

4,4,12,12-Tetramethyl-8-hydroxy-pentadecanedioic acid

Compound 61

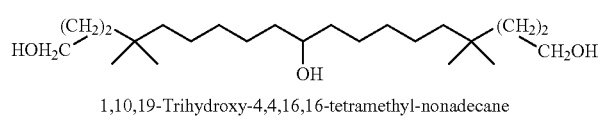

1,10,19-Trihydroxy-4,4,16,16-tetramethyl-nonadecane

Compound 62

1,19-Dihydroxy-4,4,16,16-tetramethyl-nonadecanoic acid

Compound 63

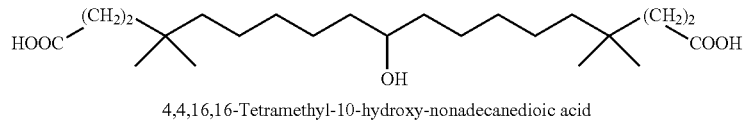

4,4,16,16-Tetramethyl-10-hydroxy-nonadecanedioic acid

Compound 64

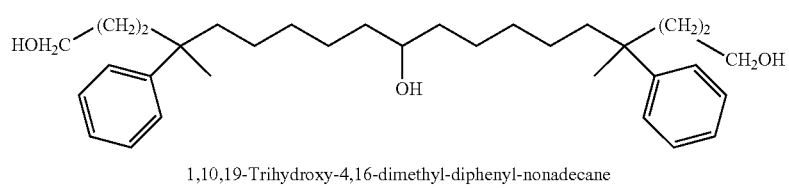

1,10,19-Trihydroxy-4,16-dimethyl-diphenyl-nonadecane

Compound 65

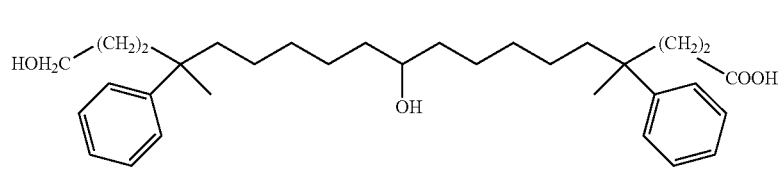

10,19-Hydroxy-4,16-dimethyl-4,16-diphenyl-nonadecanoic acid

Compound 66

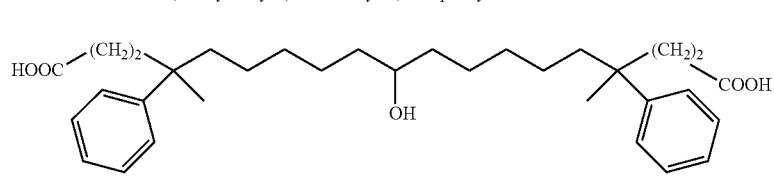

10,19-Hydroxy-4,16-dimethyl-4,16-diphenyl-nonadecanoic acid

Compound 67

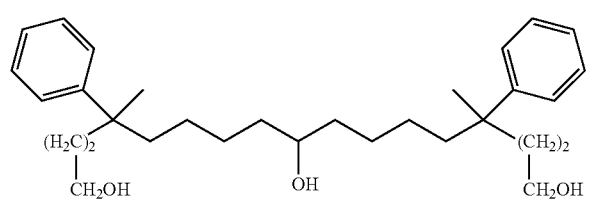

1,9,17-Trihydroxy-4,14-dimethyl-4,14-diphenyl-heptadecane

Compound 68

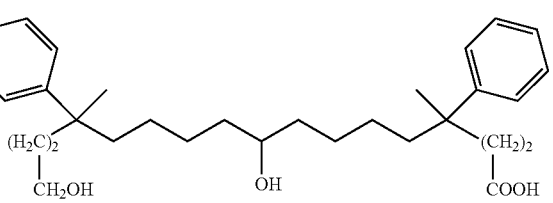

9,17-Dihydroxy-4,14-dimethyl-4,14-diphenyl-heptadecanoic acid

Compound 69

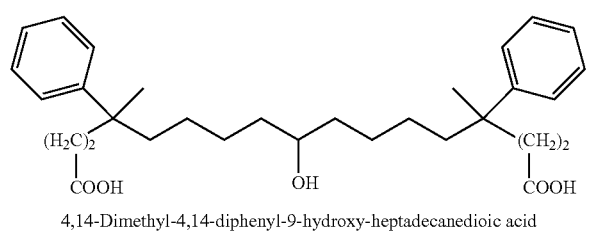

4,14-Dimethyl-4,14-diphenyl-9-hydroxy-heptadecanedioic acid

Compound 70

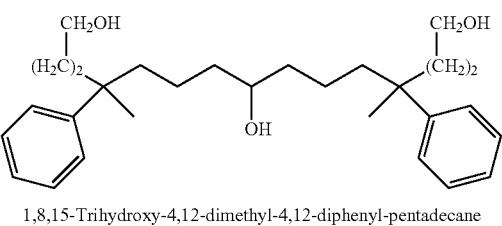

1,8,15-Trihydroxy-4,12-dimethyl-4,12-diphenyl-pentadecane

Compound 71

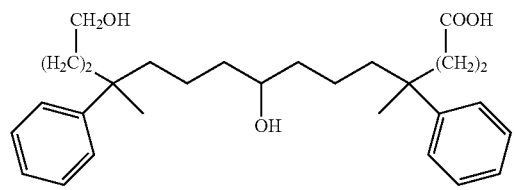

8,15-Dihydroxy-4,12-dimethyl-4,12-diphenyl-pentadecanoic acid

Compound 72

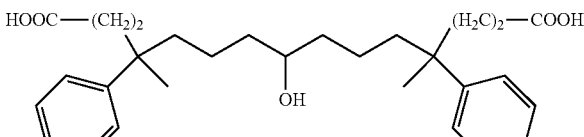

4,12-Dimethyl-8-hydroxy-4,12-diphenyl-pentadecanedioic acid

Compound 73

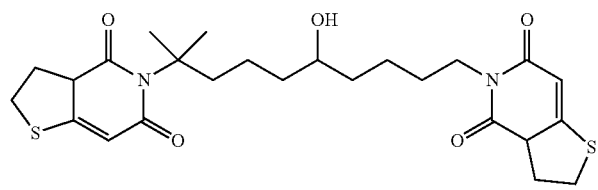

2-10-Bis-(4,6-dioxo-2,3,3a,6-tetrahydro-4H-thieno[3,2-c]pyridin-5-yl)-2,10-dimethyl-6-hydoxy-undecane Compound 74

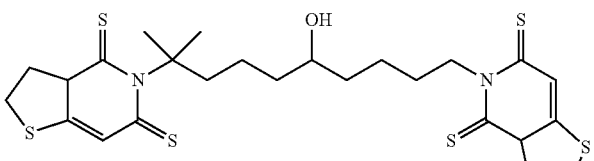

2-10-Bis-(4,6-dithioxo-2,3,3a,6-tetrahydro-4H-thieno[3,2-c]pyridin-5-yl)-2,10-dimethyl-6-hydoxy-undecane Compound 75

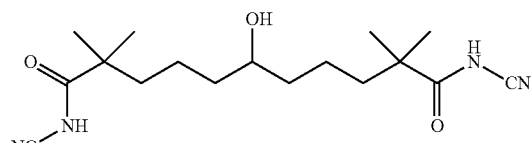

2,2,10,10-Tetramethyl-6-hydroxy-undecandioic acid dicyanimide

Compound 76

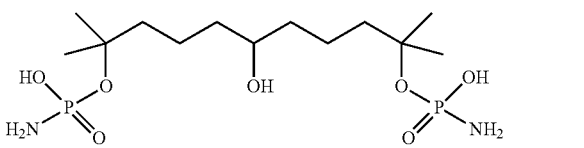

Phosphoramidic acid mono-[9-(amino-hydroxy-phosphoryloxy)-1,1,9-trimethyl-5-hydroxy-decyl]ester Compound 77

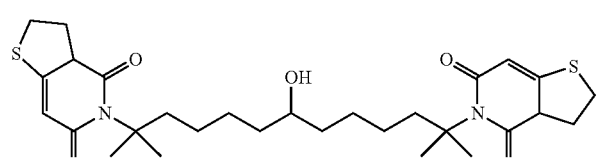

2-12-Bis-(4,6-dithioxo-2,3,3a,6-tetrahydro-4H-thieno[3,2-c]pyridin-5-yl)-2,10-dimethyl-6-hydoxy-undecane Compound 78

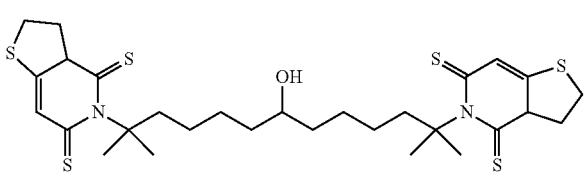

2-12-Bis-(4,6-dithioxo-2,3,3a,6-tetrahydro-4H-thieno[3,2-c]pyridin-5-yl)-2,10-dimethyl-6-hydoxy-undecane Compound 79

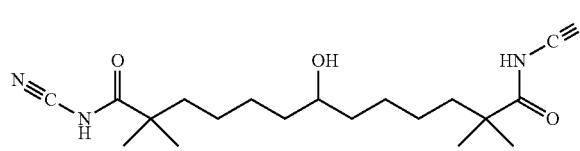

2,2,10,10-Tetramethyl-6-hydroxy-tridecandioic acid dicyanimide

Compound 80

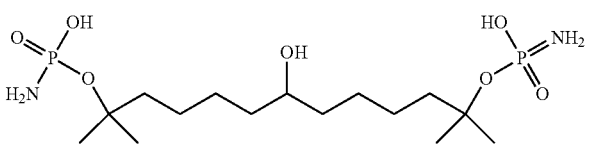

Phosphoramidic acid mono-[11=(amino-hydroxy-phosphoryloxy)-1,1,11-trimethyl-7-hydroxy-dodecyl]ester Compound 81

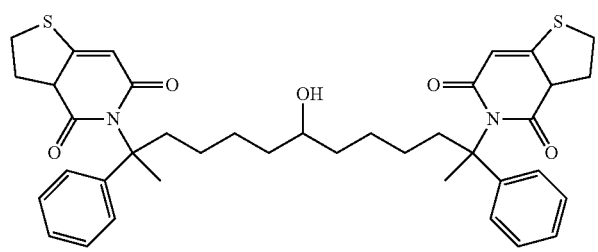

2-12-Bis-(4,6-dioxo-2,3,3a,6-tetrahydro-4H-thieno[3,2-c]pyridin-5-yl)-2,12-diphenyl-7-hydroxy-tridecane Compound 82

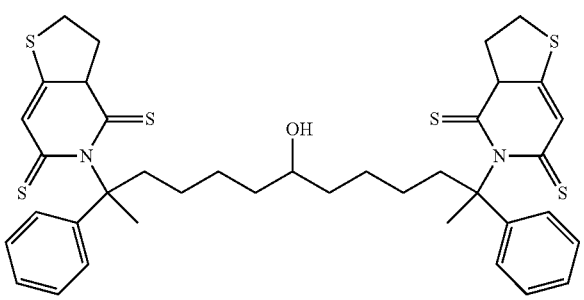

2-12-Bis-(4,6-dioxo-2,3,3a,6-tetrahydro-4H-thieno[3,2-c]pyridin-5-yl)-2,12-diphenyl-7-hydroxy-tridecane -continued Compound 83

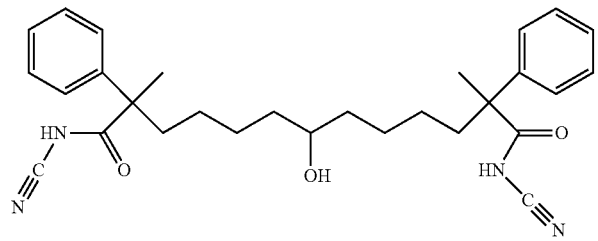

2,12-Dimethyl-2,12-diphenyl-7-hydroxy-tridecandioic acid dicyanimide

Compound 84

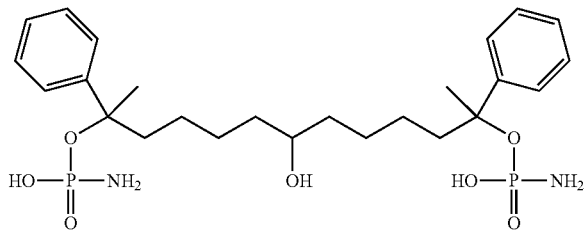

Phosphoramidic acid mono-[11-(amino-hydroxy-phosphoryloxy)-1-methyl-6-hydroxy-1,11-diphenyl-dodecyl]ester Compound 85

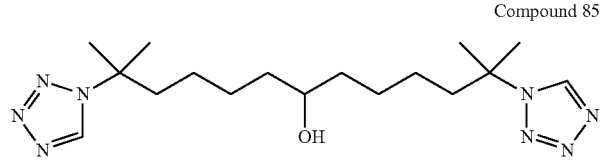

2,12-Dimethyl-2,12-bis-tetrazol-1-yl-7-hydroxy-tridecane

Compound 86

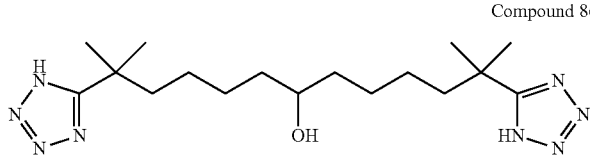

2,12-Dimethyl-2,12-bis-(1H-tetrazol-5-yl)-7-hydroxy-tridecane

Compound 87

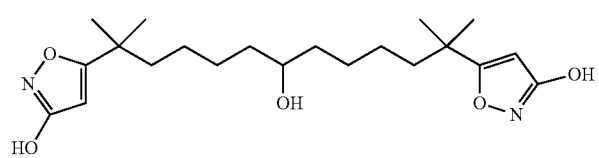

2,12-Bis-(3-hydroxy-isoxazol-5-yl)-2,12-dimethyl-7-hydroxy-tridecane

Compound 88

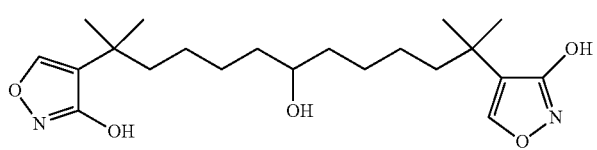

2,12-Bis-(3-hydroxy-isoxazol-4-yl)-2,12-dimethyl-7-hydroxy-tridecane

Compound 89

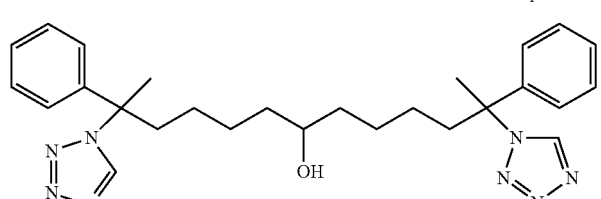

2,12-Bis(tetrazol-1-yl)-2,12-diphenyl-7-hydroxy-tridecane

Compound 90

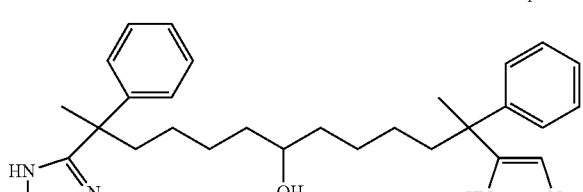

2,12-Diphenyl-2,12-bis-(1H-tetrazol-5-yl)-7-hydroxy-tridecane

Compound 91

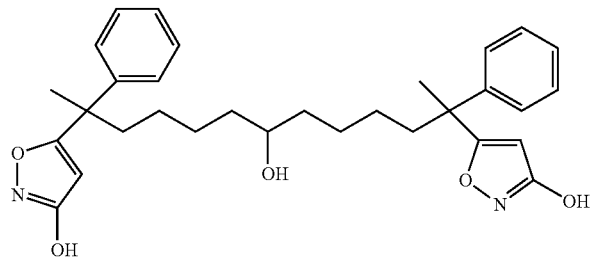

2,12-Bis-(3-hydroxy-isoxazol-5-yl)-2,12-diphenyl-7-hydroxy-tridecane

Compound 92

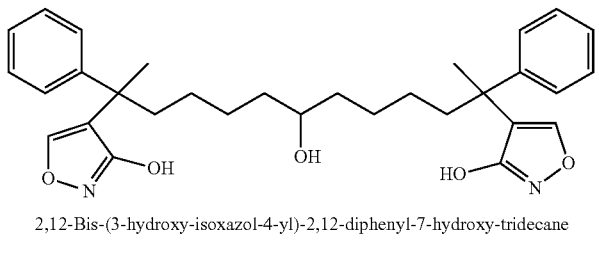

2,12-Bis-(3-hydroxy-isoxazol-4-yl)-2,12-diphenyl-7-hydroxy-tridecane

Compound 93

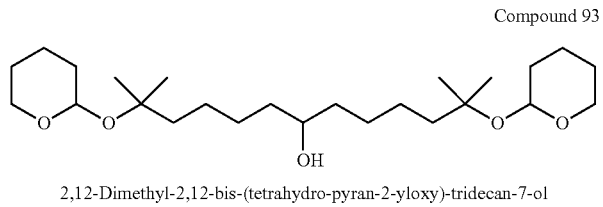

2,12-Dimethyl-2,12-bis-(tetrahydro-pyran-2-yloxy)-tridecan-7-ol

Compound 94

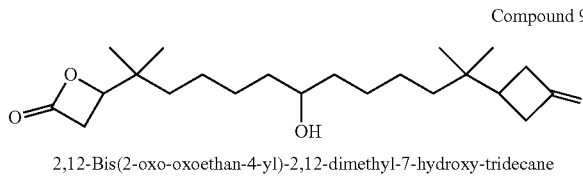

2,12-Bis(2-oxo-oxoethan-4-yl)-2,12-dimethyl-7-hydroxy-tridecane

Compound 95

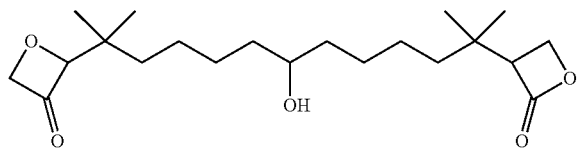

2,12-Bis(2-oxo-oxoethan-3-yl)-2,12-dimethyl-7-hydroxy-tridecane

Compound 96

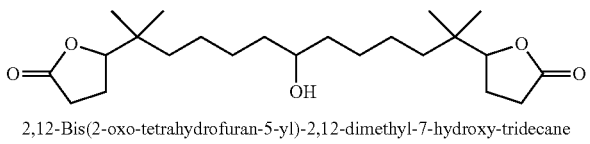

2,12-Bis(2-oxo-tetrahydrofuran-5-yl)-2,12-dimethyl-7-hydroxy-tridecane

Compound 97

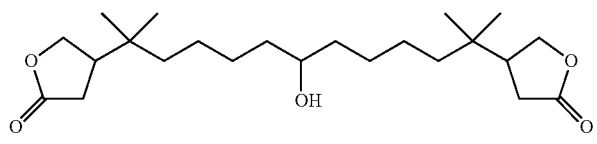

2,12-Bis(2-oxo-tetrahydrofuran-4-yl)-2,12-dimethyl-7-hydroxy-tridecane

Compound 98

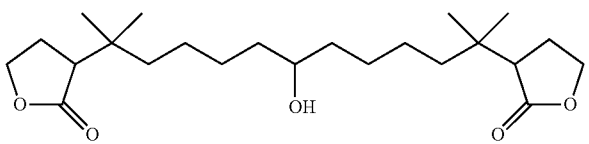

2,12-Bis(2-oxo-tetrahydrofuran-3-yl)-2,12-dimethyl-7-hydroxy-tridecane

Compound 99

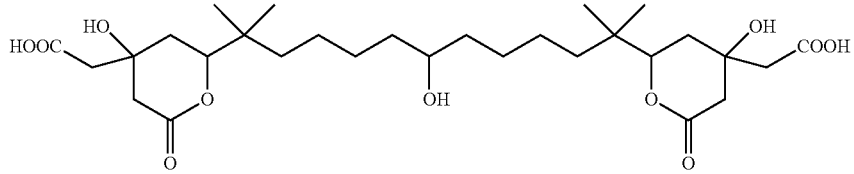

{2-[9-(4-Carboxymethyl-4-hydroxy-6-oxo-tetrahydro-pyran-2-yl)1,1,9-trimethyl-5-hydroxy-decyl]-4-hydroxy-6-oxo-tetrahydro-pyran-4-yl}-cetic acid Compound 100

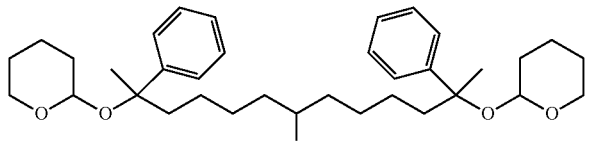

2,12-Diphenyl-2,12-bis(tetrahydro-pyran-2-yloxy)-7-hydroxy-tridecane

Compound 101

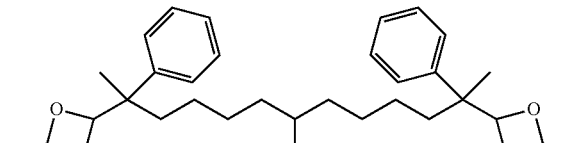

2,12-Bis(2-oxo-oxoethan-4-yl)-2,12-diphenyl-7-hydroxy-tridecane

Compound 102

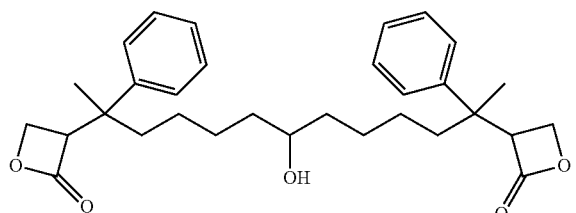

2,12-Bis(2-oxo-oxoethan-3-yl)-2,12-diphenyl-7-hydroxy-tridecane

Compound 103

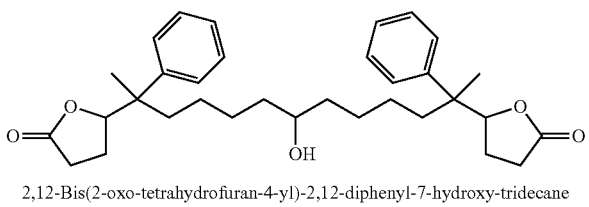

2,12-Bis(2-oxo-tetrahydrofuran-4-yl)-2,12-diphenyl-7-hydroxy-tridecane

Compound 104

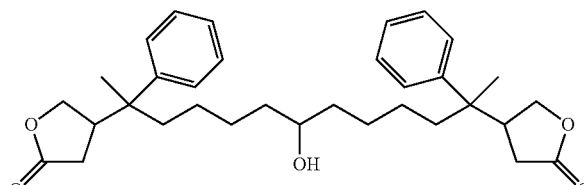

2,12-Bis(2-oxo-tetrahydrofuran-4-yl)-2,12-diphenyl-7-hydroxy-tridecane

Compound 105

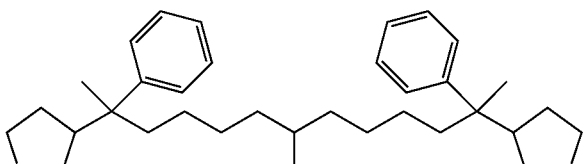

2,12-Bis(2-oxo-tetrahydrofuran-3-yl)-2,12-diphenyl-7-hydroxy-tridecane

-continued

Compound 106

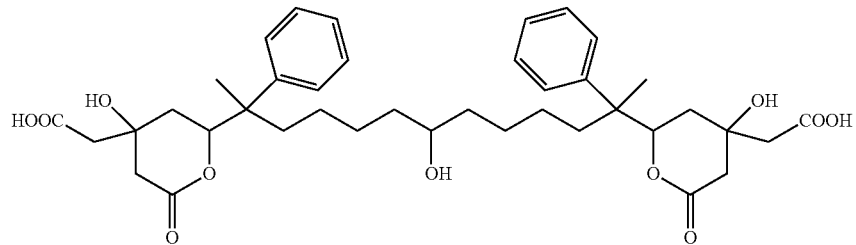

{2-[11-(4-Crboxymethyl-4-hydroxy-6-oxo-tetrahydro-pyran-2-yl)-1-methyl-6-hydroxy-1,11-diphenyl-dodecyl]-4-hydroxy-6-oxo-tetrahydro-pyran-4-yl}-acetic acid Compound 107

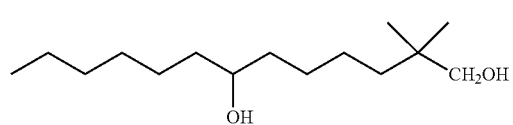

2,2-Dimethyl-tridecane-1,7-diol

Compound 108

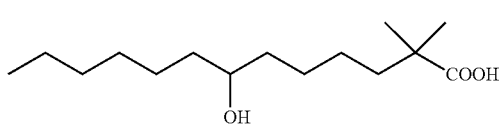

7-Hydroxy-2,2-dimethyl-tridecanoic acid

Compound 109

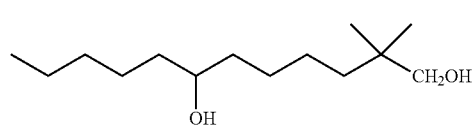

2,2-Dimethyl-dodecane-1,7-diol

Compound 110

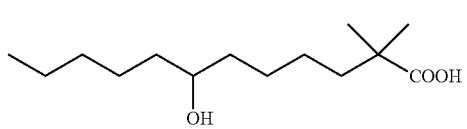

7-Hydroxy-2,2-dimethyl-dodecanoic acid

Compound 111

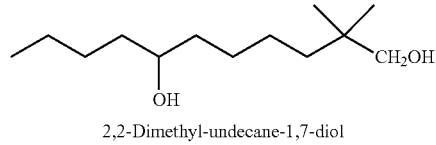

2,2-Dimethyl-undecane-1,7-diol

Compound 112

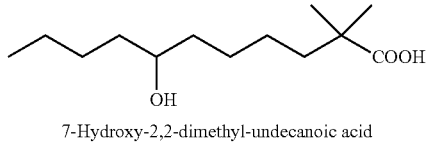

7-Hydroxy-2,2-dimethyl-undecanoic acid

Compound 113

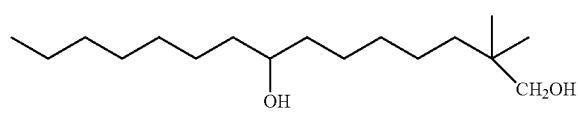

2,2-Dimethyl-pentadecane-1,8-diol

Compound 114

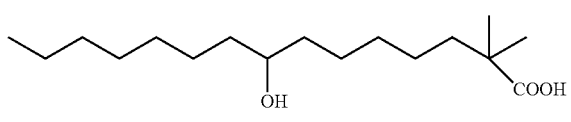

8-Hydroxy-2,2-dimethyl-pentadecanoic acid

Compound 115

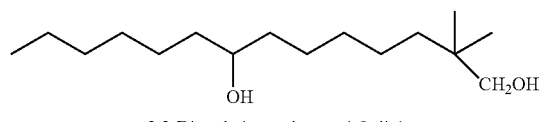

2,2-Dimethyl-tetradecane-1,8-diol

Compound 116

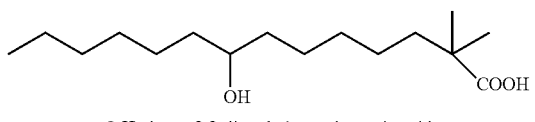

8-Hydroxy-2,2-dimethyl-tetradecanoic acid

Compound 117

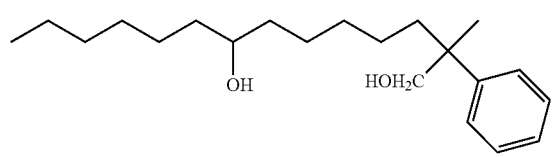

2-Methyl-2-phenyl-tetradecane-1,8-diol

Compound 118

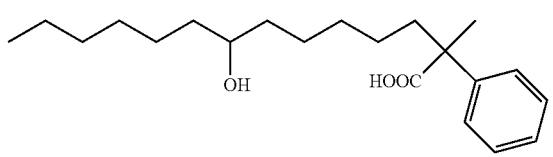

8-Hydroxy-2-methyl-2-phenyl-tetradecanoic acid

Compound 119

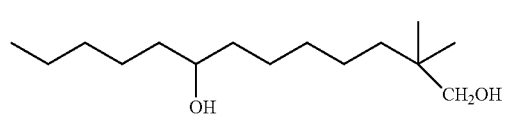

2,2-Dimethyl-tridecane-1,8-diol

Compound 120

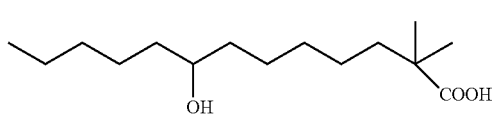

8-Hydroxy-2,2-dimethyl-tridecanoic acid

Compound 121

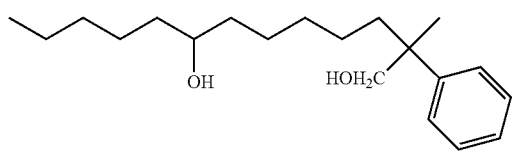

2-Methyl-2-phenyl-tridecane-1,8-diol

Compound 122

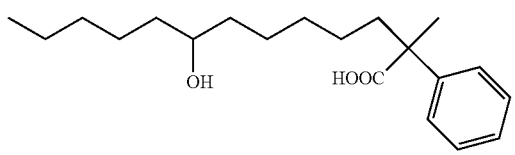

8-Hydroxy-2-methyl-2-phenyl-tridecanoic acid

Compound 123

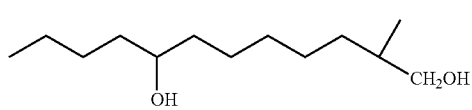

2,2-Dimethyl-dodecane-1,8-diol

Compound 124

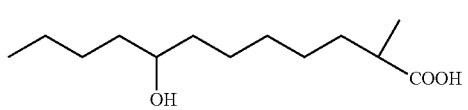

8-Hydroxy-2,2-dimethyl

Compound 125

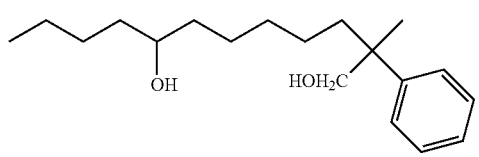

2-Methyl-2-phenyl-dodecane-1,8-diol

Compound 126

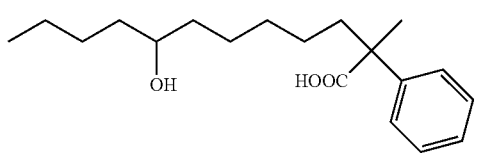

8-Hydroxy-2-methyl-2-phenyl-dodecanoic acid

Compound 127

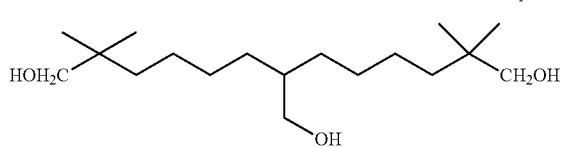

7-Hydroxymethyl-2,2,12,12-tetramethyl-tridecane-1,13-diol

Compound 128

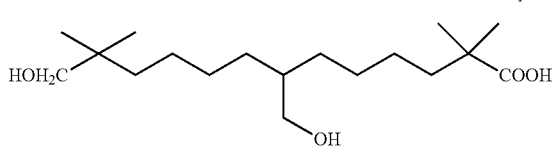

13-Hydroxy-7-hydroxymethyl-2,2,12,12-tetramethyl-tridecanoic acid

Compound 129

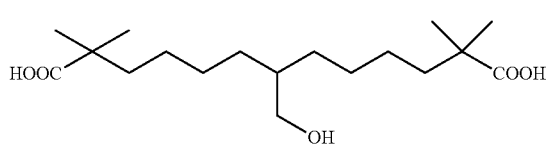

7-Hydroxymethyl-2,2,12,12-tetramethyl-tridecanedioic acid

Compound 130

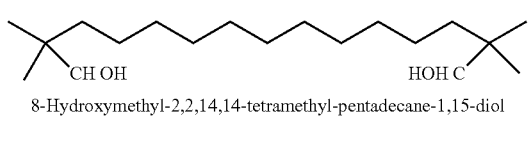

8-Hydroxymethyl-2,2,14,14-tetramethyl-pentadecane-1,15-diol

Compound 131

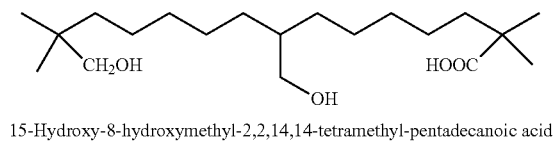

15-Hydroxy-8-hydroxymethyl-2,2,14,14-tetramethyl-pentadecanoic acid

Compound 132

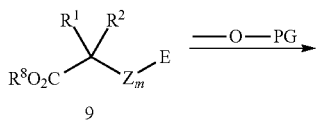

8-Hydroxymethyl-2,2,14,14-tetramethyl-pentadecedioic acid

5.1 Synthesis of the Compounds of the Invention

The compounds of the invention can be obtained via the synthetic methodology illustrated in Schemes 1-20. Starting materials useful for preparing the compounds of the invention and intermediates thereof, are commercially available or can be prepared from commercially available materials using known synthetic methods and reagents.

Scheme 1: Synthesis of Compounds of Formula X

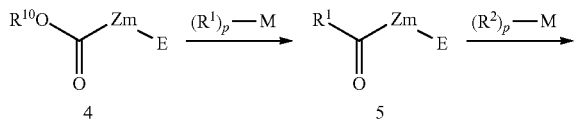

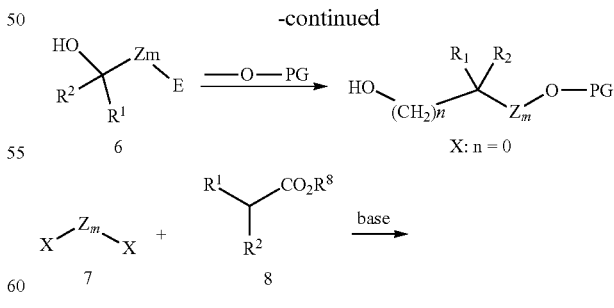

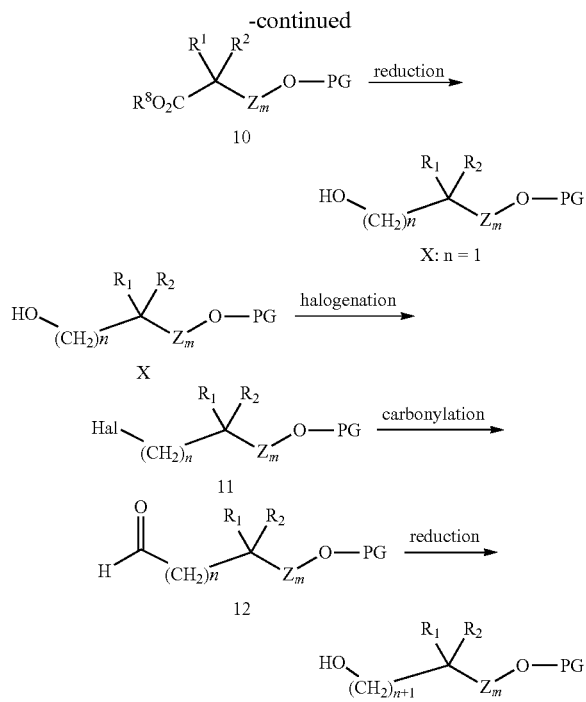

X, wherein n is an integer ranging from 2 to 5

Scheme 1 illustrates the synthesis of mono-protected diols of the formula X, wherein n is an integer ranging from 0 to 4 and $R^1$ and $R^2$ are as defined herein, and E is a leaving group as defined herein. Scheme 1 first outlines the synthesis of mono-protected diols X, wherein n is 0, where esters 4 are successively reacted with a first $((R^1)_p\text{-M})$ then a second $((R^2)_p\text{-M})$ organometallic reagent providing hydroxys 5 and alcohols 6, respectively. M is a metal group and p is the metal's valency value (e.g., the valency of Li is 1 and that of Zn is 2). Suitable metals include, but are not limited to, Zn, Na, Li, and —Mg-Hal, wherein Hal is a halide selected from iodo, bromo, or chloro. Preferably, M is —Mg-Hal, in which case the organometallic reagents, $(R^1)_p$—Mg-Hal and $(R^2)_p$—Mg-Hal, are known in the art as a Grignard reagents. Esters 4 are available commercially (e.g., Aldrich Chemical Co., Milwaukee, Wis.) or can be prepared by well-known synthetic methods, for example, via esterification of the appropriate 5-halovaleric acid (commercially available, e.g., Aldrich Chemical Co., Milwaukee, Wis.). Both $(R^1)_p$-M and $(R^2)_p$-M are available conmmercially (e.g., Aldrich Chemical Co., Milwaukee, Wis.) or can be prepared by well-known methods (see e.g., Kharasch et al., *Grignard Reactions of Non-Metallic Substances*; Prentice-Hall, Englewood Cliffs, N.J., pp. 138-528 (1954) and Hartley; Patai, *The Chemistry of the Metal-Carbon Bond*, Vol. 4, Wiley: New York, pp. 159-306 and pp. 162-175 (1989), both citations are hereby expressly incorporated herein by reference). The reaction of a first $((R^1)_p\text{-M})$ then a second $((R^2)_p\text{-M})$ organometallic reagent with esters 4 can be performed using the general procedures referenced in March, J. *Advanced Organic Chemistry; Reactions Mechanisms, and Structure*, 4th ed., 1992, pp. 920-929 and Eicher, Patai, *The Chemistry of the Carbonyl Group*, pt. 1, pp. 621-693; Wiley: New York, (1966), hereby expressly incorporated herein by reference. For example, the synthetic procedure described in Comins et al., 1981, *Tetrahedron Lett.* 22:1085, hereby expressly incorporated herein by reference, can be used. As one example, the reaction can be performed by adding an organic solution of $(R^1)_p$-M (about 0.5 to about 1 equivalents) to a stirred, cooled (about 0° C. to about −80° C.) solution comprising esters 4, under an inert atmosphere (e.g., nitrogen) to give a reaction mixture comprising ketones 5. Preferably, $(R^1)_p$-M is added at a rate such that the reaction-mixture temperature remains within about one to two degrees of the initial reaction-mixture temperature. The progress of the reaction can be followed by using an appropriate analytical method, such as thin-layer chromatography or high-performance-liquid chromatography. Next, an organic solution of $(R^1)_p$-M (about 0.5 to about 1 equivalent) is added to the reaction mixture comprising ketones 5 in the same manner used to add $(R^1)_p$-M. After the reaction providing alcohols 6 is substantially complete, the reaction mixture can be quenched and the product can be isolated by workup. Suitable solvents for obtaining alcohols 6 include, but are not limited to, dichloromethane, diethyl ether, tetrahydrofuran, benzene, toluene, xylene, hydrocarbon solvents (e.g., pentane, hexane, and heptane), and mixtures thereof. Preferably, the organic solvent is diethyl ether or tetrahydrofuran. Next, alcohols 6 are converted to mono-protected diols X, wherein n is 0, using the well-known Williamson ether synthesis. This involves reacting alcohols 6 with —O—PG, wherein —PG is a hydroxy-protecting group. For a general discussion of the Williamson ether synthesis, See March, 3. *Advanced Organic Chemistry; Reactions Mechanisms, and Structure*, 4th ed., 1992, pp. 386-387, and for a list of procedures and reagents useful in the Williamson ether synthesis, See, for example, Larock *Comprehensive Organic Transformations*; VCH: New York, 1989, pp. 446-448, both of which references are incorporated herein by reference. As used herein, the term "hydroxy-protecting group" means a group that is reversibly attached to a hydroxy moiety that renders the hydroxy moiety unreactive during a subsequent reaction(s) and that can be selectively cleaved to regenerate the hydroxy moiety once its protecting purpose has been served. Examples of hydroxy-protecting groups are found in Greene, T. W., *Protective Groups in Organic Synthesis*, 3rd edition 17-237 (1999), hereby expressly incorporated herein by reference. Preferably, the hydroxy-protecting group is stable in a basic reaction medium, but can be cleaved by acid. Examples of suitable base-stable acid-labile hydroxy-protecting groups suitable for use with the invention include, but are not limited to, ethers, such as methyl, methoxy methyl, methylthiomethyl, methoxyethoxymetoxymethyl, bis(2-chloroethoxy)methyl, tetrahydropyranyl, tetrahydrothiopyranyl, tetrahyrofuranyl, tetrahydrothiofuranyl, 1-ethoxyethyl, 1-methyl-1-methoxyethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, and triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably —PG is methoxymethyl ($CH_3OCH_2$—). Reaction of alcohols 6 with —O—PG under the conditions of the Williamson ether synthesis involves adding a base to a stirred organic solution comprising HO—PG (e.g, methoxymethanol), maintained at a constant temperature within the range of about 0° C. to about 80° C., preferably at about room temperature. Preferably, the base is added at a rate such that the reaction-mixture temperature remains within about one to two degrees of the initial reaction-mixture temperature. The base can be added as an organic solution or in undiluted form. Preferably, the base will have a base strength sufficient to deprotonate a proton, wherein the proton has a $pK_a$ of greater than about 15, preferably greater than about 20. As is well known in the art, the $pK_a$ is a measure of the acidity of an acid H-A, according to the equation $pK_a = -\log K_a$, wherein $K_a$ is the equilibrium constant for the proton transfer. The acidity of an acid H-A is proportional to the stability of its conjugate base -A. For tables listing $pK_a$ values for various organic acids and a discussion on $pK_a$ measurement, see March, J. *Advanced Organic Chemistry; Reactions Mechanisms, and Structure*, 4th ed., 1992, pp. 248-272, incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. The preferred base is lithium diisopropylamide. Solvents suitable for reacting alcohols 6 with —OPG include, but are not limited, to dimethyl sulfoxide, dichloromethane, ethers, and mixtures thereof, preferably tetrahydrofuran. After addition of the base, the reaction mixture can be adjusted to within a temperature range of about 0° C. to about room temperature and alcohols 6 can be added, preferably at a rate such that the reaction-mixture temperature remains within about one to two degrees of the initial reaction-mixture temperature. Alcohols 6 can be diluted in an organic solvent or added in their undiluted form. The resulting reaction mixture is stirred until the reaction is substantially complete as determined by using an appropriate analytical method, preferably by gas chromatography, then the mono-protected diols X can be isolated by workup and purification.

Next, Scheme 1 outlines a method usefill for synthesizing mono-protected diols X, wherein n is 1. First, compounds 7, wherein E is a suitable leaving group, are reacted with compounds 8, wherein $R^1$ and $R^2$ are as defined above and $R^8$ is H, $(C_1-C_6)$alkyl or $(C_6)$aryl, providing compounds 9. Suitable leaving groups are well known in the art, for example, but not limited to halides, such as chloride, bromide, and iodide; aryl- or alkylsulfonyloxy, substituted arylsulfonyloxy (e.g., tosyloxy or mesyloxy); substituted alkylsulfonyloxy (e.g., haloalkylsulfonyloxy); $(C_6)$aryloxy or substituted $(C_6)$aryloxy; and acyloxy groups. Compounds 7 are available commercially (e.g., Aldrich Chemical Co., Milwaukee, Wis.) or can be prepared by well-known methods such as halogenation or sulfonation of butanediol. Compounds 8 are also available commercially (e.g., Aldrich Chemical Co., Milwaukee, Wis.) or by well-known methods, such as those listed in Larock *Comprehensive Organic Transformations*; Wiley-VCH: New York, 1999, pp. 1754-1755 and 1765. A review on alkylation of esters of type 8 is given by J. Mulzer in *Comprehensive Organic Functional Transformations*, Pergamon, Oxford 1995, pp. 148-151 and exemplary synthetic procedures for reacting compounds 7 with compounds 8 are described in U.S. Pat. No. 5,648,387, column 6 and Ackerly, et al., *J. Med. Chem.* 1995, pp. 1608, all of which citations are hereby expressly incorporated herein by reference. The reaction requires the presence of a suitable base. Preferably, a suitable base will have a $pK_a$ of greater than about 25, more preferably greater than about 30. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; hydride bases such as sodium hydride and potassium hydride. Metal amide bases, such as lithium diisopropylamide are preferred. Preferably, to react compounds 7 with compounds 8, a solution of about 1 to about 2 equivalents of a suitable base is added to a stirred solution comprising esters 8 and a suitable organic solvent, under an inert atmosphere, the solution maintained at a constant temperature within the range of about -95° C. to about room temperature, preferably at about -78° C. to about -20° C. Preferably, the base is diluted in a suitable organic solvent before addition. Preferably, the base is added at a rate of about 1.5 moles per hour. Organic solvents suitable for the reaction of compounds 7 with the compounds 8 include, but are not limited to, dichloromethane, diethyl ether, tetrahydrofuran, dimethylformamide, dimethyl sulfoxide, benzene, toluene, xylene, hydrocarbon solvents (e.g., pentane, hexane, and heptane), and mixtures thereof. After addition of the base, the reaction mixture is allowed to stir for about 1 to about 2 hours, and a compound 7, preferably dissolved in a suitable organic solvent, is added, preferably at a rate such that the reaction-mixture temperature remains within about one to two degrees of the initial reaction-mixture temperature. After addition of compounds 7, the reaction-mixture temperature can be adjusted to within a temperature range of about -20° C. to about room temperature, preferably to about room temperature, and the reaction mixture is allowed to stir until the reaction is substantially complete as determined by using an appropriated analytical method, preferably thin-layer chromatography or high-performance liquid chromatography. Then the reaction mixture is quenched and compounds 9, wherein n is 1 can be isolated by workup. Compounds 10 are then synthesized by reacting compounds 9 with —O—PG according to the protocol described above for reacting alcohols 6 with —O—PG. Next, compounds 10 can be converted to mono-protected diols X, wherein n is 1, by reduction of the ester group of compounds 10 to an alcohol group with a suitable reducing agent. A wide variety of reagents are available for reduction of such esters to alcohols, e.g., see M. Hudlicky, *Reductions in Organic Chemistry*, 2nd ed., 1996 pp. 212-217, hereby expressly incorporated herein by reference. Preferably, the reduction is effected with a hydride type reducing agent, for example, lithium aluminum hydride, lithium borohydride, lithium triethyl borohydride, diisobutylaluminum hydride, lithium triethoxyaluminum hydride, or sodium bis(2-methoxy)aluminum hydride. For exemplary procedures for reducing esters to alcohols, see Nystrom et al., 1947, *J. Am. Chem. Soc.* 69:1197; and Moffet et al., 1963, *Org. Synth., Collect.* 834(4), lithium aluminum hydride; Brown et al., 1965, *J. Am. Chem. Soc.* 87:5614, lithium triethoxyaluminum hydride; Cerny et al., 1969, *Collect. Czech. Chem. Commun.* 34:1025, sodium bis(2-methoxy)aluminum hydride; Nystrom et al., 1949, *J. Am. Chem.* 71:245, lithium borohydride; and Brown et al., 1980, 1 *Org. Chem.* 45: 1, lithium triethyl borohydride, all of which citations are hereby expressly incorporated herein by reference. Preferably, the reduction is conducted by adding an organic solution of compounds 10 to a stirred mixture comprising a reducing agent, preferably lithium aluminum hydride, and an organic solvent. During the addition, the reaction mixture is maintained at a constant temperature within the range of about −20° C. to about 80° C., preferably at about room temperature. Organic solvents suitable for reacting 9 with —OPG include, but are not limited to, dichloromethane, diethyl ether, tetrahydrofuran or mixtures thereof, preferably tetrahydrofuran. After the addition, the reaction mixture is stirred at a constant temperature within the range of about room temperature to about 60° C., until the reaction is substantially complete as determined by using an appropriate analytical method, preferably thin-layer chromatography or high-performance-liquid chromatography. Then the reaction mixture can be quenched and mono-protected diols X, wherein n is 1, can be isolated by workup and purification.

Scheme 1 next illustrates a three step synthetic sequence for homologating mono-protected diols X comprising: (a) halogenation (converting —CH$_2$OH to —CH$_2$-Hal); (b) carbonylation (replacing -Hal with —CHO); and (c) reduction (converting —CHO to —CH$_2$OH), wherein a reaction sequence of (a), (b), and (c) increases the value of n by 1. In step (a) protected halo-alcohols 11, wherein Hal is a halide selected from the group of chloro, bromo, or iodo, preferably iodo, can be prepared by halogenating mono-protected diols X, by using well-known methods (for a discussion of various methods for conversion of alcohols to halides see March, J. *Advanced Organic Chemistry; Reactions Mechanisms, and Structure*, 4th ed., 1992, pp. 431-433, hereby expressly incorporated herein by reference). For example, protected iodo-alcohols 11 can be synthesized starting from mono-protected diols X by treatment with Ph$_3$/I$_2$/imidazole (Garegg et al., 1980, 19, *J.C.S Perkin* 12866); 1,2-dipheneylene phosphorochloridite/I$_2$ (Corey et al., 1967, *J. Org. Chem.* 82:4160); or preferably with Me$_3$SiCl/NaI (Olah et al., 1979, *J. Org. Chem.* 44:8, 1247), all of which citations are hereby expressly incorporated herein by reference. Step (b); carbonylation of alkyl halides, such as protected halo-alcohols 11, is reviewed in Olah et al., 1987, *Chem Rev,* 87:4, 671; and March, J., *Advanced Organic Chemistry; Reactions Mechanisms, and Structure*, 4th ed., 1992, pp. 483-484, both of which are hereby expressly incorporated herein by reference). Protected halo-alcohols 11 can be carbonylated with Li(BF$_3$.Et$_2$O)/HCONMe$_2$ using the procedure described in Maddaford et al., 1993, *J. Org. Chem.* 58:4132; Becker et al., 1982, *J. Org. Chem.* 3297; or Myers et al., 1992, *J. Am. Chem. Soc.* 114:9369 or, alternatively, with an organometallic/N-formylmorpholine using the procedure described in Olah et al., 1984, *J. Org. Chem.* 49:3856 or Vogtle et al., 1987, *J. Org. Chem.* 52:5560, all of which citations are hereby expressly incorporated herein by reference. The method described in Olah et al., 1984, *J. Org. Chem.* 49:3856 is preferred. Reduction step (c) useful for synthesizing mono-protected diols X from aldehydes 12, can be accomplished by well-known methods in the art for reduction of aldehydes to the corresponding alcohols (for a discussion see M. Hudlicky, *Reductions in Organic Chemistry*, 2nd ed., 1996 pp 137-139), for example, by catalytic hydrogenation (see e.g., Carothers, 1949, *J. Am. Chem. Soc.* 46:1675) or, preferably by reacting aldehydes 12 with a hydride reducing agent, such as lithium aluminum hydride, lithium borohydride, sodium borohydride (see e.g., the procedures described in Chalkin et al., 1949, *J. Am. Chem. Soc.* 71:3245; Nystrom et al., 1947, *J. Am. Chem. Soc.* 69:1197; and Nystrom et al, 1949, *J. Am. Chem.* 71:3245, all of which are hereby expressly incorporated herein by reference). Reduction with lithium aluminum hydride is preferred.

Scheme 2: Synthesis of Compounds of Formula 12a, which correspond to Compounds W$^{(1)(2)}$—Z$_m$—OH, Wherein W$^{(1)(2)}$ is C(R$^1$)(R$^2$)—Y

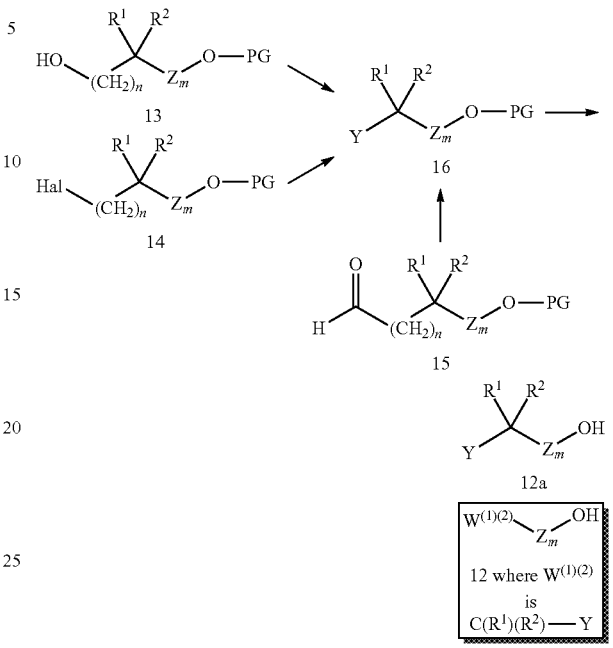

Scheme 2 outlines the method for the synthesis of protected alcohols 12a wherein Y, R$^1$, R$^2$, Z, and m are defined as above. Protected alcohols 12a correspond to compounds of the formula W$^{(1)(2)}$-Zm-OPG, wherein W$^{(1)(2)}$ is C(R$^1$)(R$^2$)—Y.

Protected alcohols 16, wherein Y comprises a —C(O)OH group, can be synthesized by oxidizing mono-protected diols X with an agent suitable for oxidizing a primary alcohol to a carboxylic acid (for a discussion see M. Hudlicky, *Oxidations in Organic Chemistry*, ACS Monograph 186, 1990, pp. 127-130, hereby expressly incorporated herein by reference). Suitable oxidizing agents include, but are not limited to, pyridinium dichromate (Corey et al., 1979, *Tetrahedron Lett.* 399); manganese dioxide (Ahrens et al., 1967, *J. Heterocycl. Chem.* 4:625); sodium permanganate monohydrate (Menger et al., 1981, *Tetrahedron Lett.* 22:1655); and potassium permanganate (Sam et al, 1972, *J. Am. Chem. Soc.* 94:4024), all of which citations are hereby expressly incorporated herein by reference. The preferred oxidizing reagent is pyridinium dichromate. In an alternative synthetic procedure, protected alcohols 16, wherein Y comprises a —C(O)O— group, can be synthesized by treatment of protected halo-alcohols 15, wherein X is iodo, with CO or CO$_2$, as described in Bailey et al., 1990, *J. Org. Chem.* 55:5404 and Yanagisawa et al, 1994, *J. Am. Chem. Soc.* 116:6130, the two of which citations are hereby expressly incorporated herein by reference. Protected alcohols 16, wherein Y comprises —C(O)OR$^5$, wherein R$^5$ is as defined above, can be synthesized by oxidation of mono-protected diols X in the presence of R$^5$OH (see generally, March, *J. Advanced Organic Chemistry; Reactions Mechanisms, and Structure*, 4th ed., 1992, p. 1196). An exemplary procedure for such an oxidation is described in Stevens et al., 1982, *Tetrahedron Lett.* 23:4647 (HOCl); Sundarararan et al., 1978, *Tetrahedron Lett.* 1627 (O$_3$/KOH); Wilson et al, 1982, *J. Org. Chem.* 47:1360 (t-BuOOH/Et$_3$N); and Williams et al., 1988, *Tetrahedron Lett.* 29:5087 (Br$_2$), the four of which citations are hereby expressly incorporated herein by reference. Preferably, protected alcohols 16, wherein Y comprises a —C(O)OR$^5$ group are synthesized from the corresponding carboxylic acid (i.e., 16, wherein Y comprises —C(O)OH) by esterification with R$^5$OH (e.g., see March, J., *Advanced Organic Chemistry; Reactions Mechanisms, and Structure*, 4th ed., 1992, p. 393-394, hereby expressly incorporated herein by reference). In another alternative synthesis, protected alcohols 16, wherein Y comprises —C(O)OR$^5$, can be prepared from protected halo-alcohols 14 by carbonylation with transition metal complexes (see e.g., March, J. *Advanced Organic Chemistry; Reactions Mechanisms, and Structure*, 4th ed., 1992, p. 484-486; Urata et al., 1991, *Tetrahedron Lett.* 32:36, 4733); and Ogata et al., 1969, *J. Org. Chem.* 3985, the three of which citations are hereby expressly incorporated herein by reference).

Protected alcohols 16, wherein Y comprises —OC(O)R$^5$, wherein R$^5$ is as defined above, can be prepared by acylation of mono-protected diols X with a carboxylate equivalent such as an acyl halide (i.e., R$^5$C(O)-Hal, wherein Hal is iodo, bromo, or chloro, see e.g., March, J. *Advanced Organic Chemistry; Reactions Mechanisms, and Structure*, 4th ed., 1992, p. 392 and *Org. Synth. Coll.* Vol. III, Wiley, N Y, pp. 142, 144, 167, and 187 (1955)) or an anhydride (i.e., R$^5$C(O)—O—(O)CR$^5$, see e.g., March, J. *Advanced Organic Chemistry; Reactions Mechanisms, and Structure*, 4th ed., 1992, p. 392-393 and *Org. Synth. Coll.* Vol. III, Wiley, N Y, pp. 11, 127, 141, 169, 237, 281, 428, 432, 690, and 833 (1955), all of which citations are hereby expressly incorporated herein by reference). Preferably, the reaction is conducted by adding a base to a solution comprising mono-protected diols X, a carboxylate equivalent, and an organic solvent, which solution is preferably maintained at a constant temperature within the range of 0° C. to about room temperature. Solvents suitable for reacting mono-protected diols X with a carboxylate equivalent include, but are not limited to, dichloromethane, toluene, and ether, preferably dichloromethane. Suitable bases include, but are not limited to, hydroxide sources, such as sodium hydroxide, potassium hydroxide, sodium carbonate, or potassium carbonate; or an amine such as triethylamine, pyridine, or dimethylaminopyridine, amines are preferred. The progress of the reaction can be followed by using an appropriate analytical technique, such as thin layer chromatography or high performance liquid chromatography and when substantially complete, the product can be isolated by workup and purified if desired.

Protected alcohols 16, wherein Y comprises one of the following phosphate ester groups

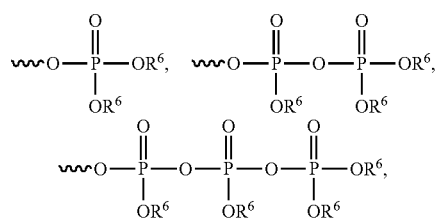

wherein R$^6$ is defined as above, can be prepared by phosphorylation of mono-protected diols X according to well-known methods (for a general reviews, see Corbridge *Phosphorus: An Outline of its Chemistry, Biochemistry, and Uses*, Studies in Inorganic Chemistry, 3rd ed., pp. 357-395 (1985); Ramirez et al., 1978, *Acc. Chem. Res.* 11:239; and Kalckare *Biological Phosphorylations*, Prentice-Hall, New York (1969); J. B. Sweeny in *Comprehensive Organic Functional Group Transformations*, A. R. Katritzky, O. Meth-Cohn and C. W. Rees, Eds. Pergamon: Oxford, 1995, vol 2, pp. 104-109, the four of which are hereby expressly incorporated herein by reference). Protected alcohols 16 wherein Y comprises a monophosphate group of the formula:

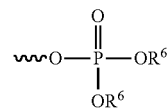

wherein R$^6$ is defined as above, can be prepared by treatment of mono-protected diol X with phosphorous oxychloride in a suitable solvent, such as xylene or toluene, at a constant temperature within the range of about 100° C. to about 150° C. for about 2 hours to about 24 hours. After the reaction is deemed substantially complete, by using an appropriate analytical method, the reaction mixture is hydrolyzed with R$^6$—OH. Suitable procedures are referenced in Houben-Weyl, Methoden der Organische Chemie, Georg Thieme Verlag Stuttgart 1964, vol. XII/2, pp. 143-210 and 872-879, hereby expressly incorporated herein by reference. Alternatively, when both R$^6$ are hydrogen, can be synthesized by reacting mono-protected diols X with silyl polyphosphate (Okamoto et al, 1.985, *Bull Chem. Soc. Jpn.* 58:3393, hereby expressly incorporated herein by reference) or by hydrogenolysis of their benzyl or phenyl esters (Chen et al., 1998, *J. Org. Chem.* 63:6511, hereby expressly incorporated herein by reference). In another alternative procedure, when R$^6$ is (C$_1$-C$_8$)alkyl, (C$_2$_C$_6$)alkenyl, or (C$_2$-C$_6$)alkynyl, the monophosphate esters can be prepared by reacting mono-protected diols X with appropriately substituted phophoramidites followed by oxidation of the intermediate with m-chloroperbenzoic acid (Yu et al., 1988, *Tetrahedron Lett.* 29:979, hereby expressly incorporated herein by reference) or by reacting mono-protected diols X with dialkyl or diaryl substituted phosphorochloridates (Pop, et al, 1997, *Org. Prep. and Proc. Imt.* 29:341, hereby expressly incorporated herein by reference). The phosphoramidites are commercially available (e.g., Aldrich Chemical Co., Milwaukee, Wis.) or readily prepared according to literature procedures (see e.g., Uhlmann et at 1986, *Tetrahedron Lett.* 27:1023 and Tanaka et al., 1988, *Tetrahedron Lett.* 29:199, both of which are hereby expressly incorporated herein by reference). The phosphorochloridates are also commercially available (e.g., Aldrich Chemical Co., Milwaukee, Wis.) or prepared according to literature methods (e.g., Gajda et al, 1995, *Synthesis* 25:4099. In still another alternative synthesis, protected alcohols 16, wherein Y comprises a monophosphate group and R$^6$ is alkyl or aryl, can be prepared by reacting IP+(OR$^6$)$_3$ with mono-protected diols X according to the procedure described in Stowell et al., 1995, *Tetrahedron Lett.* 36:11, 1825 or by alkylation of protected halo alcohols 14 with the appropriate dialkyl or diaryl phosphates (see e.g., Okamoto, 1985, *Bull Cher. Soc. Jpn.* 58:3393, hereby expressly incorporated herein by reference).

Protected alcohols 16 wherein Y comprises a diphosphate group of the formula

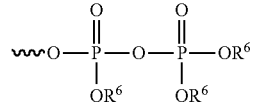

wherein R⁶ is defined as above, can be synthesized by reacting the above-discussed monophosphates of the formula:

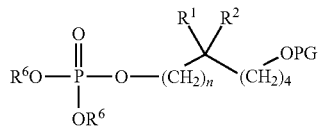

with a phosphate of the formula

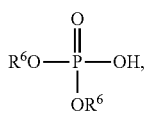

(commercially available, e.g., Aldrich Chemical Co., Milwaukee, Wis.), in the presence of carbodiimide such as dicyclohexylcarbodiimide, as described in Houben-Weyl, *Methoden der Organische Chemie*, Georg Thieme Verlag Stuttgart 1964, vol. XII/2, pp. 881-885. In the same fashion, protected alcohols 16, wherein Y comprises a triphosphate group of the formula:

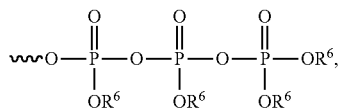

can be synthesized by reacting the above-discussed diphosphate protected alcohols, of the formula:

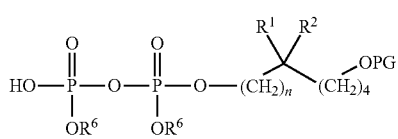

with a phosphate of the formula:

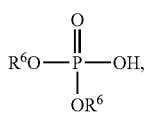

as described above. Alternatively, when R⁶ is H, protected alcohols 16 wherein Y comprises the triphosphate group, can be prepared by reacting mono-protected diols X with salicyl phosphorochloridite and then pyrophosphate and subsequent cleavage of the adduct thus obtained with iodine in pyridine as described in Ludwig et al., 1989, *J. Org. Chem.* 54:631, hereby expressly incorporated herein by reference.

Protected alcohols 1.6, wherein Y is —SO₃H or a heterocyclic group selected from the group consisting of:

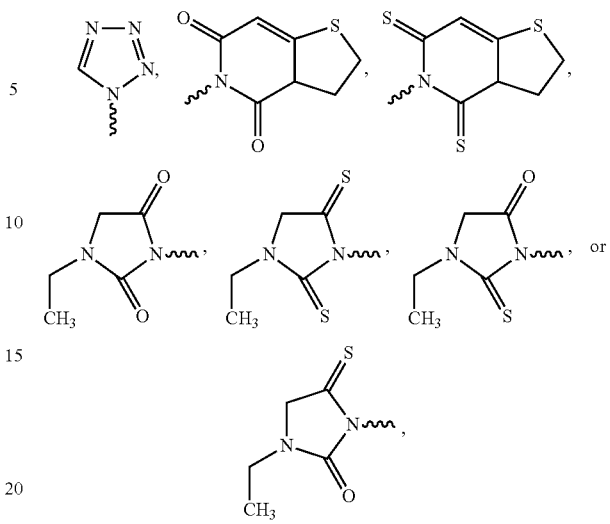

can be prepared by halide displacement from protected halo-alcohols 14. Thus, when Y is —SO₃H, protected alcohols 16 can by synthesized by reacting protected halo-alcohols 14 with sodium sulfite as described in Gilbert *Sulfonation and Related Reactions*; Wiley: New York, 1965, pp. 136-148 and pp. 161-163; *Org. Synth. Coll.* Vol. II, Wiley, N Y, 558, 564 (1943); and *Org. Synth. Coll.* Vol. IV, Wiley, N Y, 529 (1963), all three of which are hereby expressly incorporated herein by reference. When Y is one of the above-mentioned heterocycles, protected alcohols 16 can be prepared by reacting protected halo-alcohols 14 with the corresponding heterocycle in the presence of a base. The heterocycles are available commercially (e.g., Aldrich Chemical Co., Milwaukee, Wis.) or prepared by well-known synthetic methods (see the procedures described in Ware, 1950, *Chem. Rev.* 46:403-470, hereby expressly incorporated herein by reference). Preferably, the reaction is conducted by stirring a mixture comprising 14, the heterocycle, and a solvent at a constant temperature within the range of about room temperature to about 100° C., preferably within the range of about 50° C. to about 70° C. for about 10 to about 48 hours. Suitable bases include hydroxide bases such as sodium hydroxide, potassium hydroxide, sodium carbonate, or potassium carbonate. Preferably, the solvent used in forming protected alcohols 16 is selected from dimethylformamide; formamide; dimethyl sulfoxide; alcohols, such as methanol or ethanol; and mixtures thereof. The progress of the reaction can be followed by using an appropriate analytical technique, such as thin layer chromatography or high performance liquid chromatography and when substantially complete, the product can be isolated by workup and purified if desired.

Protected alcohols 16, wherein Y is a heteroaryl ring selected from

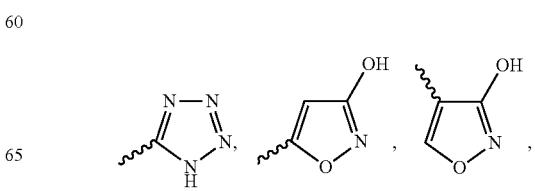

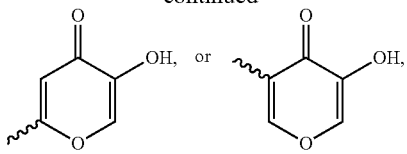

can be prepared by metallating the suitable heteroaryl ring then reacting the resulting metallated heteroaryl ring with protected halo-alcohols 14 (for a review, see Katritzky *Handbook of Heterocyclic Chemistry*, Pergamon Press: Oxford 1985). The heteroaryl rings are available commercially or prepared by well-known synthetic methods (see e.g., Joule et al., *Heterocyclic Chemistry*, 3rd ed., 1995; De Sarlo et al., 1971, *J. Chem. Soc.* (C) 86; Oster et al., 1983, *J. Org. Chem.* 48:4307; Iwai et al., 1966, *Chem. Pharm. Bull.* 14:1277; and U.S. Pat. No. 3,152,148, all of which citations are hereby expressly incorporated herein by reference). As used herein, the term "metallating" means the forming of a carbon-metal bond, which bond may be substantially ionic in character. Metallation can be accomplished by adding about 2 equivalents of strong organometallic base, preferably with a $pK_a$ of about 25 or more, more preferably with a $pK_a$ of greater than about 35, to a mixture comprising a suitable organic solvent and the heterocycle. Two equivalents of base are required: one equivalent of the base deprotonates the —OH group or the —NH group, and the second equivalent metallates the heteroaryl ring. Alternatively, the hydroxy group of the heteroaryl ring can be protected with a base-stable, acid-labile protecting group as described in Greene, T. W., *Protective Groups in Organic Synthesis*, 3rd edition 17-237 (1999), hereby expressly incorporated herein by reference. Where the hydroxy group is protected, only one equivalent of base is required. Examples of suitable base-stable, acid-labile hydroxyl-protecting groups, include but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahyrofuranyl, tetrahydrothiofuranyl, 1-ethoxyethyl, 1-methyl-1-methoxyethyl, t-butyl, allyl, benzyl, o-nitrobenzyl, triphenylmethyl, α-naphthyldiphenylmethyl, p-methoxyphenyldipheylmethyl, 9-(9-phenyl-1 0-oxo)anthranyl, trimethylsilyl, isopropyldimethylsilyl, t-butyldimethylsilyl, t-butyldiphenylsilyl, tribenzylsilyl, triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably, the $pK_a$ of the base is higher than the $pK_a$ of the proton of the heterocycle to be deprotonated. For a listing of $pK_a$s for various heteroaryl rings, see Fraser et al., 1985, *Can. J. Chem.* 63:3505, hereby expressly incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. If desired, the organometallic base can be activated with a complexing agent, such as N,N,N',N'-tetramethylethylenediamine or hexamethylphosphoramide (1970, *J. Am.* *Chem. Soc.* 92:4664, hereby expressly incorporated herein by reference). Solvents suitable for synthesizing protected alcohols 16, wherein Y is a heteroaryl ring include, but are not limited to, diethyl ether; tetrahydrofuran; and hydrocarbons, such as pentane. Generally, metallation occurs alpha to the heteroatom due to the inductive effect of the heteroatom, however, modification of conditions, such as the identity of the base and solvents, order of reagent addition, reagent addition times, and reaction and addition temperatures can be modified by one of skill in the art to achieve the desired metallation position (see e.g., Joule et al., *Heterocyclic Chemistry*, 3rd ed., 1995, pp. 30-42, hereby expressly incorporated herein by reference) Alternatively, the position of metallation can be controlled by use of a halogenated heteroaryl group, wherein the halogen is located on the position of the heteroaryl ring where metallation is desired (see e.g., Joule et al., *Heterocyclic Chemistry*, 3rd ed., 1995, p. 33 and Saulnier et al., 1982, *J. Org. Chem.* 47:757, the two of which citations are hereby expressly incorporated herein by reference). Halogenated heteroaryl groups are available commercially (e.g., Aldrich Chemical Co., Milwaukee, Wis.) or can be prepared by well-known synthetic methods (see e.g., Joule et al., *Heterocyclic Chemistry*, 3rd ed., 1995, pp. 78, 85, 122, 193, 234, 261, 280, 308, hereby expressly incorporated herein by reference). After metallation, the reaction mixture comprising the metallated heteroaryl ring is adjusted to within a temperature range of about 0° C. to about room temperature and protected halo-alcohols 14 (diluted with a solvent or in undiluted form) are added, preferably at a rate such that the reaction-mixture temperature remains within about one to two degrees of the initial reaction-mixture temperature. After addition of protected halo-alcohols 14, the reaction mixture is stirred at a constant temperature within the range of about room temperature and about the solvent's boiling temperature and the reaction's progress can be monitored by the appropriate analytical technique, preferably thin-layer chromatography or high-performance liquid chromatography. After the reaction is substantially complete, protected alcohols 16 can be isolated by workup and purification. It is to be understood that conditions, such as the identity of protected halo-alcohol 14, the base, solvents, orders of reagent addition, times, and temperatures, can be modified by one of skill in the art to optimize the yield and selectivity. Exemplary procedures that can be used in such a transformation are described in Shirley et al., 1995, *J. Org. Chem.* 20:225; Chadwick et al., 1979, *J Chem. Soc., Perkin Trans.* 1 2845; Rewcastle, 1993, *Adv. Het. Chem.* 56:208; Katritzky et al., 1993, *Adv. Het. Chem.* 56:155; and Kessar et al., 1997, *Chem. Rev.* 97:721. When Y is

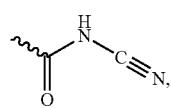

protected alcohols 16 can be prepared from their corresponding carboxylic acid derivatives (16, wherein Y is —CO$_2$H) as described in Belletire et a, 1988, *Synthetic Commun.* 18:2063 or from the corresponding acylchlorides (16, wherein Y is —CO-halo) as described in Skinner et al., 1995, *J. Am. Chem. Soc.* 77:5440, both citations are hereby expressly incorporated herein by reference. The acylhalides can be prepared from the carboxylic acids by well known procedures such as those described in March, J., *Advanced*

Organic Chemistry; Reactions Mechanisms, and Structure, 4th ed., 1992, pp. 437-438, hereby expressly incorporated herein by reference. When Y is

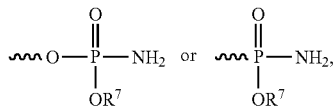

wherein $R^7$ is as defined above, protected alcohols 16 can be prepared by first reacting protected halo-alcohols 15 with a trialkyl phosphite according to the procedure described in Kosolapoff, 1951, *Org. React.* 6:273 followed by reacting the derived phosphonic diester with ammonia according to the procedure described in Smith et al., 1957, *J. Org. Chem.* 22:265, hereby expressly incorporated herein by reference. When Y is

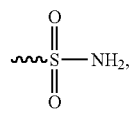

protected alcohols 16 can be prepared by reacting their sulphonic acid derivatives (i.e., 16, wherein Y is —SO$_3$H) with ammonia as described in Sianesi et al., 1971, *Chem. Ber.* 104:1880 and Campagna et al., 1994, *Farmaco, Ed. Sci.* 49:653, both of which citations are hereby expressly incorporated herein by reference).

As further illustrated in Scheme 2, protected alcohols 16 can be deprotected providing alcohols 20a. The deprotection method depends on the identity of the alcohol-protecting group, see e.g., the procedures listed in Greene, T. W., *Protective Groups in Organic Synthesis*, 3rd edition 17-237 (1999), particularly see pages 48-49, hereby expressly incorporated herein by reference. One of skill in the art will readily be able to choose the appropriate deprotection procedure. When the alcohol is protected as an ether function (e.g., methoxymethyl ether), the alcohol is preferably deprotected with aqueous or alcoholic acid. Suitable deprotection reagents include, but are not limited to, aqueous hydrochloric acid, p-toluenesulfonic acid in methanol, pyridinium-p-toluenesulfonate in ethanol, Amberlyst H-15 in methanol, boric acid in ethylene-glycol-monoethylether, acetic acid in a water-tetrahydrofuran mixture, aqueous hydrochloric acid is preferred. Examples of such procedures are described, respectively, in Bernady et al., 1979, *J. Org. Chem.* 44:1438; Miyashita et al., 1977, *J. Org. Chem.* 42:3772; Johnston et al., 1988, *Synthesis* 393; Bongini et al., 1979, *Synthesis* 618; and Hoyer et al., 1986, *Synthesis* 655; Gigg et al., 1967, *J. Chem. Soc. C*, 431; and Corey et al., 1978, *J. Am. Chem. Soc.* 100:1942, all of which are hereby expressly incorporated herein by reference.

Scheme 3: Synthesis of Compounds of Formula 13a, which correspond to $W^{(1)(2)}$—$Z_m$—OH, Wherein $W^{(1)(2)}$ is a Lactone Group

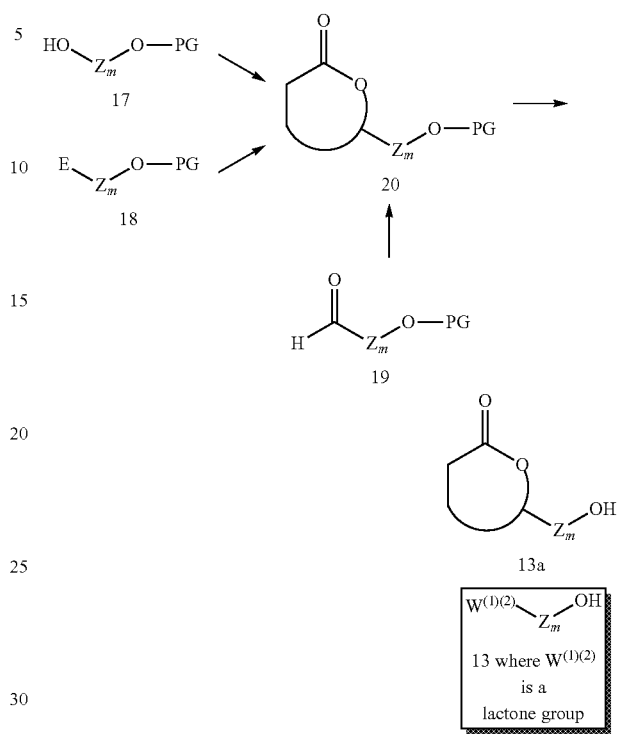

Scheme 3 depicts the synthesis of protected lactone alcohols 20 and lactone alcohols 13a. Compounds 20 and 13a correspond to compounds of the formula $W^{(1)(2)}$-Zm-OPG and $W^{(1)(2)}$ $Z_m$-OH respectively, wherein $W^{(1)(2)}$ is a lactone group selected from:

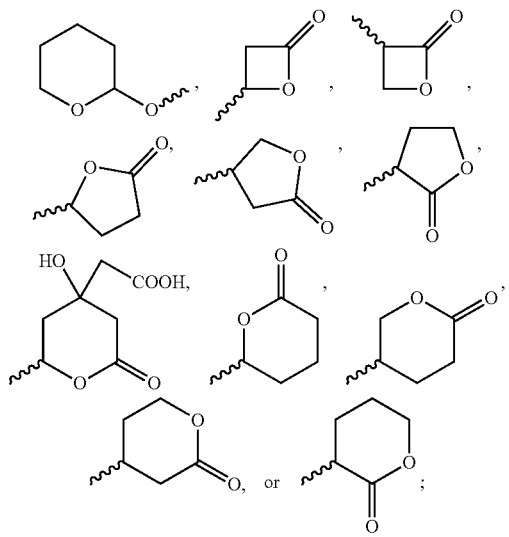

Protected lactone alcohols 20 can be prepared from compounds of the formula 17, 18, or 19 by using well-known condensation reactions and variations of the Michael reaction. Methods for the synthesis of lactones are disclosed in Multzer in *Comprehensive Organic Functional Group Transformations*, A. R. Katritzky, O. Meth-Cohn and C. W.

Rees, Eds. Pergamon: Oxford, 1995, vol 5, pp, 161-173, hereby expressly incorporated herein by reference. Monoprotected diols 19, electrophilic protected alcohols 18, and aldehydes 19 are readily available ether commercially (e.g., Aldrich Chemical Co., Milwaukee, Wis.) or by well known synthetic procedures.

When $W^{(1)(2)}$ is a beta-lactone group of the formula:

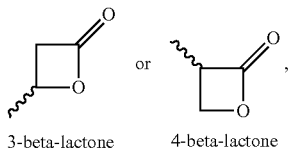

3-beta-lactone    4-beta-lactone protected lactone alcohols 20 can be prepared from aldehydes 19 and electrophilic protected alcohols 18, respectively, by a one-pot-addition-lactonization according to the procedure of Masamune et al., 1976, *J. Am. Chem. Soc.* 98:7874 and Danheiser et al., 1991. *J. Org. Chem.* 56:1176, both of which are hereby expressly incorporated herein by reference. This one-pot-addition-lactonization methodology has been reviewed by Multzer in *Comprehensive Organic Functional Group Transformations*, A. R. Katritzky, O. Meth-Cohn and C. W. Rees, Eds. Pergamon: Oxford, 1995, vol 5, pp. 161, hereby expressly incorporated herein by reference When $W^{(1)(2)}$ is a gamma- or delta-lactone group of the formula:

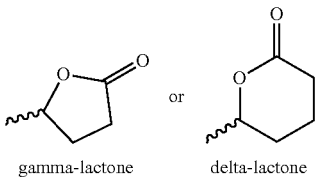

gamma-lactone    delta-lactone protected lactone alcohols 20 can be prepared from aldehydes 19 according to well known synthetic methodology. For example, the methodology described in Masuyama et al., 2000, *J. Org. Chem.* 65:494; Eisch et al., 1978, *J. Organo. Met. Chem.* C8 160; Eaton et al., 1947, *J. Org. Chem.* 37:1947; Yunker et al., 1978, *Tetrahedron Lett.* 4651; Bhanot et al., 1977, *J Org. Chem.* 42:1623; Ehlinger et al., 1980, *J. Am. Chem. Soc.* 102:5004; and Raunio et al., 1957, *J. Org. Chem.* 22:570, all of which citations are hereby expressly incorporated herein by reference. For instance, as described in Masuyama et al., 2000, *J. Org. Chem.* 65:494, aldehydes 19 can be treated with about 1 equivalent of a strong organometallic base, preferably with a $pK_a$ of about 25 or more, more preferably with a $pK_a$ of greater than about 35, in a suitable organic solvent to give a reaction mixture. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium ainide, potassium amide, lithium tetramethylpiperidide, lithium diisopropylamide, lithium diethylamide, lithium dicyclohexylamide, sodium hexanethyidisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. The reaction-mixture temperature is adjusted to within the range of about 0° C. to about 100° C., preferably about room temperature to about 50° C., and a halide of the formula:

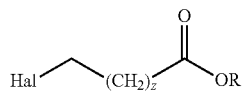

wherein z is 1 or 2 (diluted with a solvent or in undiluted form) is added. The reaction mixture is stirred for a period of about 2 hours to about 48 hours, preferably about 5 to about 10 hours, during which time the reaction's progress can be followed by using an appropriate analytical technique, such as thin layer chromatography or high performance liquid chromatography. When the reaction is deemed substantially complete, protected lactone alcohols 20 can be isolated by workup and purified if desired. When $W^{(1)(2)}$ is a gamma- or delta-lactone group of the formula:

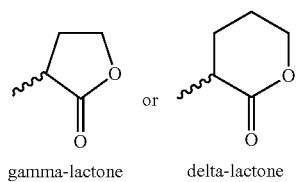

gamma-lactone    delta-lactone protected lactone alcohols 20 can be synthesized by deprotonating the corresponding lactone with a strong base providing the lactone enolate and reacting the enolate with electrophilic protected alcohols 20 (for a detailed discussion of enolate formation of active methylene compounds such as lactones, see *House Modern Synthetic Reactions*; W. A. Benjamin, Inc. Philippines 1972 pp. 492-570, and for a discussion of reaction of lactone enolates with electrophiles such as carbonyl compounds, see March, J. *Advanced Organic Chemistry; Reactions Mechanisms, and Structure*, 4th ed., 1992, pp. 944-945, both of which are hereby expressly incorporated herein by reference). Lactone-enolate formation can be accomplished by adding about 1 equivalent of a strong organometallic base, preferably with a $pK_a$ of about 25 or more, more preferably with a $pK_a$ of greater than about 35, to a mixture comprising a suitable organic solvent and the lactone. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Solvents suitable for lactone-enolate formation include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols 18 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, protected lactone alcohols 20 can be isolated by workup and purified if desired. When W$^{(1)(2)}$ is a lactone group of the formula:

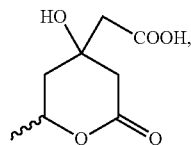

protected lactone alcohols 20 can be prepared from aldehydes 19 according to the procedure described in U.S. Pat. No. 4,622,338, hereby expressly incorporated herein by reference.

When W$^{(1)(2)}$ is a gamma- or delta-lactone group of the formula:

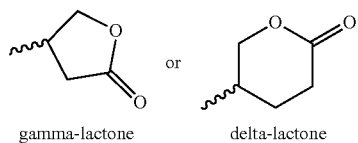

gamma-lactone    delta-lactone protected lactone alcohols 20 can be prepared according to a three step sequence. The first step comprises base-mediated reaction of electrophilic protected alcohols 18 with succinic acid esters (i.e., R$^9$O$_2$CCH$_2$CH$_2$CO$_2$R$^9$, wherein R$^9$ is alkyl) or glutaric acid esters (i.e., R$^9$O$_2$CCH$_2$CH$_2$C$_2$CHCO$_2$R$^9$, wherein R$^9$ is alkyl) providing a diester intermediate of the formula 21:

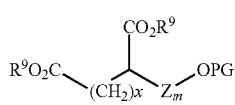

wherein x is 1 or 2 depending on whether the gamma or delta lactone group is desired. The reaction can be performed by adding about 1 equivalent of a strong organometallic base, preferably with a pK$_a$ of about 25 or more, more preferably with a pK$_a$ of greater than about 35, to a mixture comprising a suitable organic solvent and the succinic or glutaric acid ester. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. After enolate formation, the reaction-mixture temperature is adjusted to within the range of about −78° C. to about room temperature, preferably about −50° C.

to about 0° C., and electrophilic protected alcohols 18 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, the diester intermediate be isolated by workup and purified if desired. In the second step, the intermediate diester can be reduced, with a hydride reducing agent, to yield a diol of the formula 22:

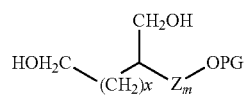

The reduction can be performed according to the procedures referenced in March, J. *Advanced Organic Chemistry, Reactions Mechanisms, and Structure,* 4th ed., 1992, p. 1214, hereby expressly incorporated herein by reference). Suitable reducing agents include, but are not limited to, lithium aluminum hydride, diisobutylaluminum hydride, sodium borohydride, and lithium borohydride). In the third step, the diol can be oxidatively cyclized with RuH$_2$(PPh$_3$)$_4$ to the product protected lactone alcohols 20 according to the procedure of Yoshikawa et al., 1986, *J. Org. Chem.* 51:2034 and Yoshikawa et al., 1983, *Tetrahedron Lett.* 26:2677, both of which citations are hereby expressly incorporated herein by reference. When W$^{(1)(2)}$ is a lactone group of the formula:

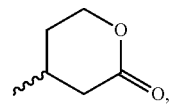

protected lactone alcohols 20 can be synthesized by reacting the Grignard salts of electrophilic protected alcohols 18, where E is a halide, with 5,6-dihydro-2H-pyran-2-one, commercially available (e.g., Aldrich Chemical Co., Milwaukee, Wis.), in the presence of catalytic amounts of a 1-dimethylaminoacetyl)pyrolidine-2yl)methyl-diarylphosphine-copper (1) iodide complex as described in Tomioka et al., 1995, *Tetrahedron Lett.* 36:4275, hereby expressly incorporated herein by reference.

Scheme 4: Synthesis of Compounds of Formula 14

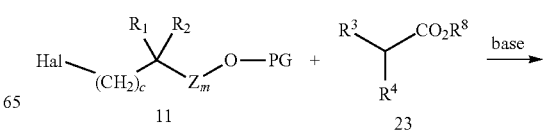

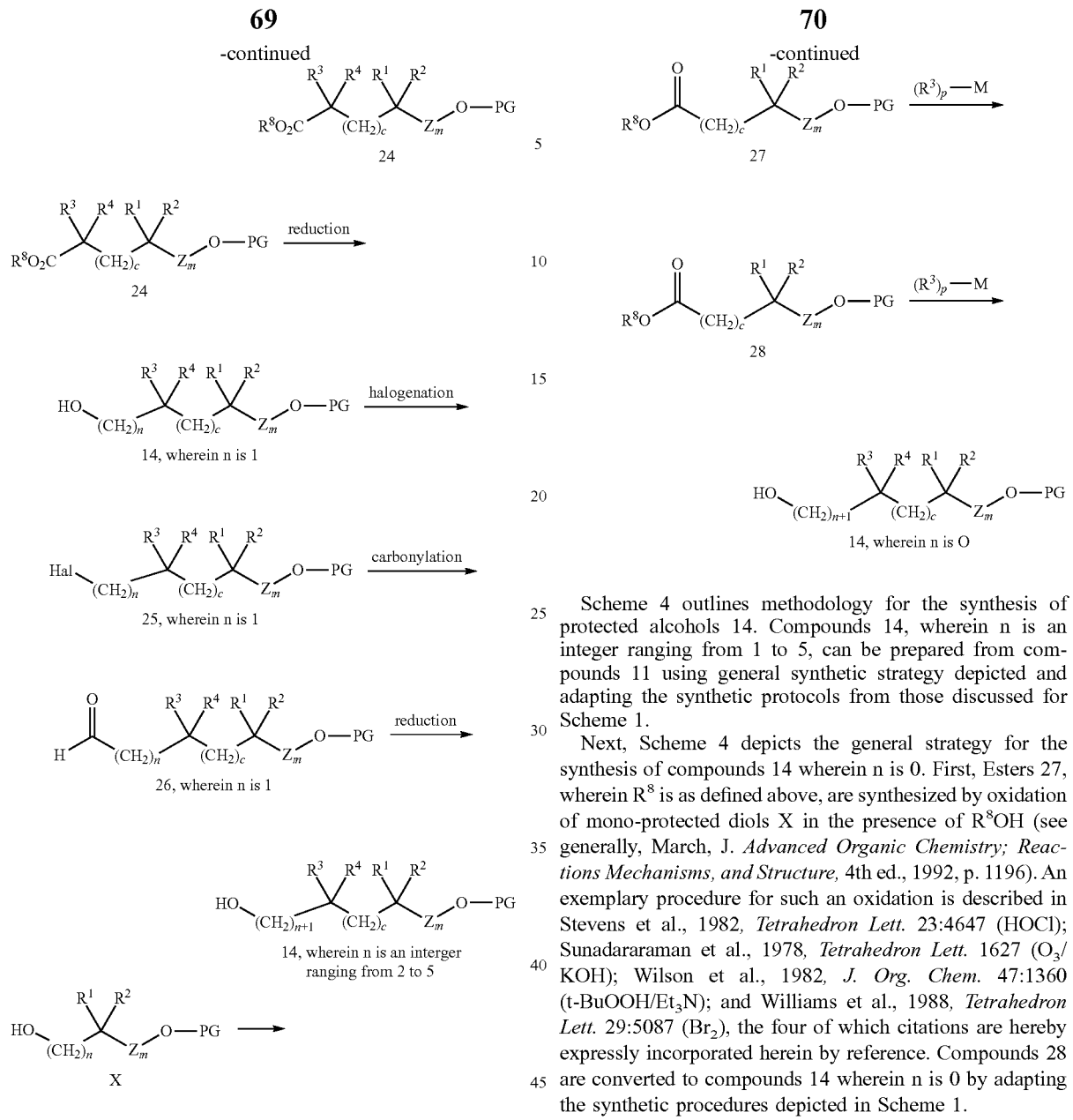

Scheme 4 outlines methodology for the synthesis of protected alcohols 14. Compounds 14, wherein n is an integer ranging from 1 to 5, can be prepared from compounds 11 using general synthetic strategy depicted and adapting the synthetic protocols from those discussed for Scheme 1.

Next, Scheme 4 depicts the general strategy for the synthesis of compounds 14 wherein n is 0. First, Esters 27, wherein $R^8$ is as defined above, are synthesized by oxidation of mono-protected diols X in the presence of $R^8OH$ (see generally, March, J. *Advanced Organic Chemistry; Reactions Mechanisms, and Structure*, 4th ed., 1992, p. 1196). An exemplary procedure for such an oxidation is described in Stevens et al., 1982, *Tetrahedron Lett.* 23:4647 (HOCl); Sunadararaman et al., 1978, *Tetrahedron Lett.* 1627 ($O_3$/KOH); Wilson et al., 1982, *J. Org. Chem.* 47:1360 (t-BuOOH/$Et_3N$); and Williams et al., 1988, *Tetrahedron Lett.* 29:5087 ($Br_2$), the four of which citations are hereby expressly incorporated herein by reference. Compounds 28 are converted to compounds 14 wherein n is 0 by adapting the synthetic procedures depicted in Scheme 1.

Scheme 5: Synthesis of Compounds of Formula 15a, which correspond to compounds $W^{(1)(2)}—Z_m—OH$, Where $W^{(1)(2)}$ is $C(R^1)R^2)—(CH_2)_c—C(R^3)(R^4)—Y$

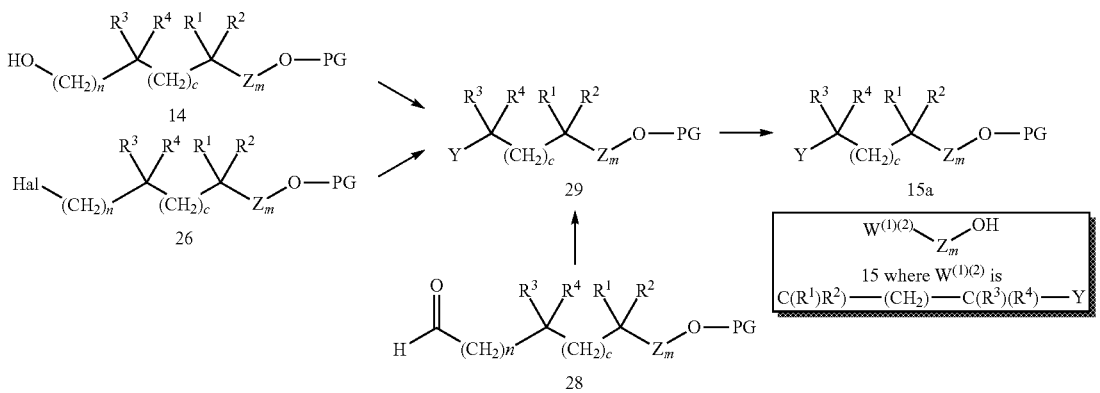

Scheme 5 outlines methodology for the synthesis of protected alcohols 29 and alcohols 15a, which correspond to $W^{(1)(2)}\text{-}Z_m\text{-}OPG$ and $W^{(1)(2)}\text{-}Z_m\text{-}OH$, respectively, wherein $W^{(1)(2)}$ is $C(R^1)(R^2)$—$(CH_2)_cC(R^3)(R^4)$—Y. The synthesis of starting materials 14, 26, and 28 are depicted in Scheme 4 and the synthetic methods and procedures can be adapted from those described for Scheme 2.

-continued

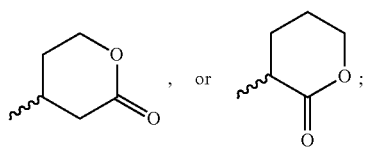

Scheme 6: Synthesis of Compounds of Formula 16, which correspond to compounds $W^{(1)(2)}$—$Z_m$—OH, Wherein $W^{(1)(2)}$ is $C(R^1)(R^2)(CH_2)_c$—V where V is a Lactone Group

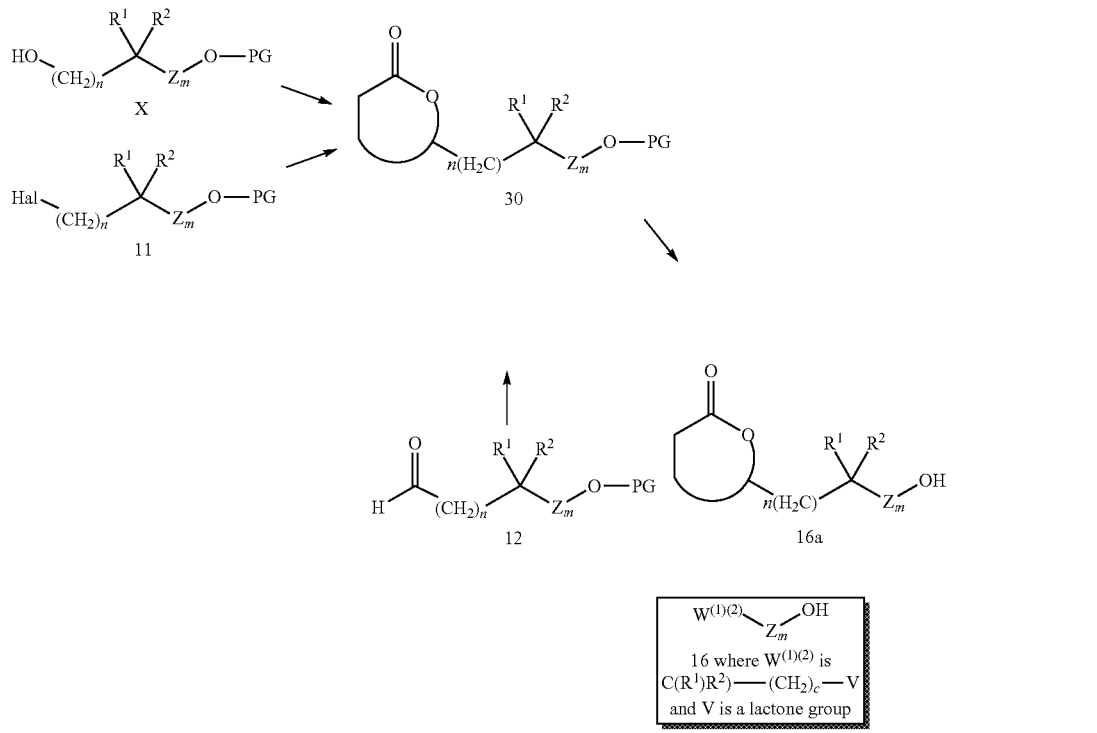

Scheme 6 depicts the synthesis of protected lactone alcohols 30 and lactone alcohols 16a. Compounds 30 and 16a correspond to compounds of the formula, which correspond to compounds $W^{(1)(2)}\text{-}Z_m\text{-}OH$, wherein $W^{(1)(2)}$ is $C(R^1)(R^2)(CH_2)_c\text{-}V$ and V is a Group selected from:

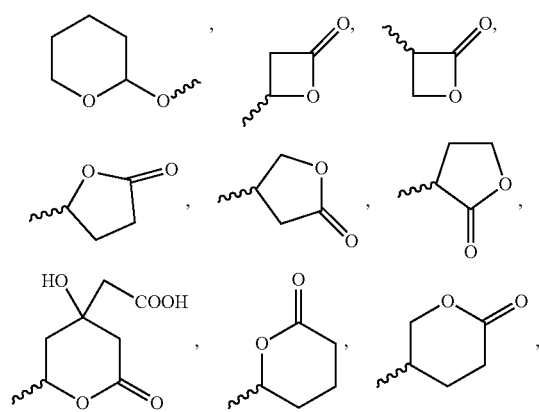

As shown in Scheme 6, protected lactone alcohols 30 and lactone alcohols 16a can be synthesized from compounds of the formula X, 11, or 12 by adaptation of the methods and procedures discussed above for Scheme 3.

Scheme 7: Conversion of Alcohols 18 to Halides 18e

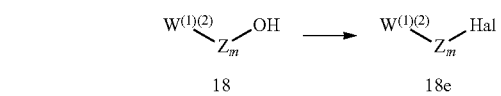

Scheme 7 depicts the synthesis of halides 18e. Halides 18 can be synthesized by a variety of methods. One method involves conversion of the alcohol to a leaving group such as a sulfonic ester, such as, for example, tosylate, brosylate, mesylate, or nosylate. This intermediate is then treated with a source of $X^-$, wherein $X^-$ is $I^-$, $Br^-$, or $Cl^-$ in a solvent such as THF or ether. A general method for converting vinyl and phenyl alcohols to thiols involves initially converting the alcohol to a leaving group (e.g., a tosylate) then treating with a halide nucleophile.

Scheme 8: Synthesis of Compounds of Formula I

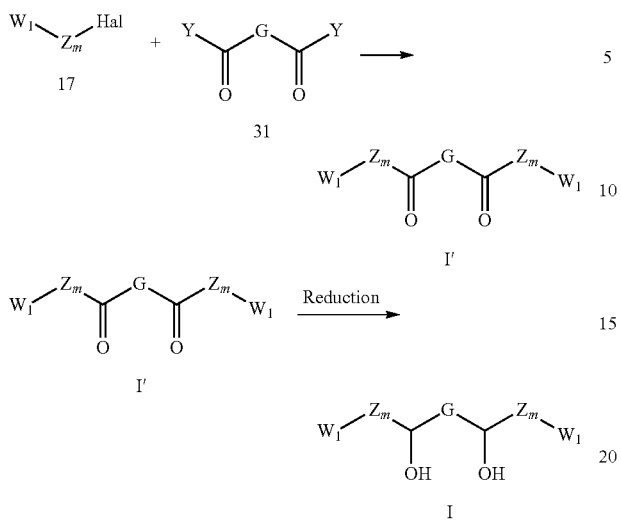

Scheme 8 outlines the synthesis of compounds 1. In the first step, compounds 1 are synthesized by reacting compounds 17 (compounds X 11, 12, 13, 14, 15, and 16 are encompassed by 17) with compounds 31 under the conditions suitable for the formation of compounds I'. The conditions and methods discussed in Scheme 1 above for the synthesis of mono-protected diols X from alcohols 6 can be adapted for the synthesis of compounds 17. Compounds 31, wherein Y is a suitable leaving group as defined above, preferably an anhydride, an ester, or an amide group, are readily obtained commercially (e.g., Aldrich Chemical Co. Milwaukee Wis.) or by well known synthetic methods. Compounds I' are obtained by reacting compounds 31 with compounds 17 under the conditions suitable for alkyl-deacyloxy substitution. (For a review, See Kharasch; Reinmuth, *Grignard Reactions of Nonmetallic Substances*; Prentice Hall: Englewood Cliffs, N J, 1954, pp. 561-562 and 846-908). In a preferred procedure, the conversion of anhydrides, carboxylic esters, or amides to ketones can be accomplished with organometallic compounds. In a particular procedure, anhydrides and carboxylic esters give ketones when treated using inverse addition of Grignard reagents at low temperature with a solvent in the presence of iHMPA. See Newman, *J. Org. Chem.* 1948, 13, 592; Huet; Empotz; Jubier *Tetrahedron* 1973, 29, 479; and Larock, *Comprehensive Organic Transformations*; VCH: New York, 1989, pp. 685-686, 693-700. Ketones can also be prepare by the treatment of thioamides with organolithium compounds (alkyl or aryl). See Tominaga; Kohra; Hosomi *Tetrahedron Lett.* 1987, 28, 1529. Moreover, alkyllithium compounds have been used to give ketones from carboxylic esters. See Petrov; Kaplan; Tsir *J. Gen. Chem. USSR* 1962, 32, 691. The reaction must be carried out in a high-boiling solvent such as toluene. Di-substituted amides also can be used to synthesize ketones. See Evans J. Chem. Soc. 1956, 4691; and Wakefield *Organolithium Methods*; Academic Press: New York, 1988, pp. 82-88. Finally, compounds I' are reduced using methods known to those of ordinary skill in the art to afford diol I. See *Comprehensive Organic Transformations*; VCH: New York, 1989. It is readily recognized that the diol compound I are stereoisomeric and can therefore exist as enantiomers and diastereomers. Separation of the stereoisomers (i.e., enantiomers or diastereomers) can be achieved by methods known in the art, for example, conversion to a chiral salt and crystallization, chiral chromatography, or chiral HPLC.

Scheme 9: Synthesis of Compounds 37

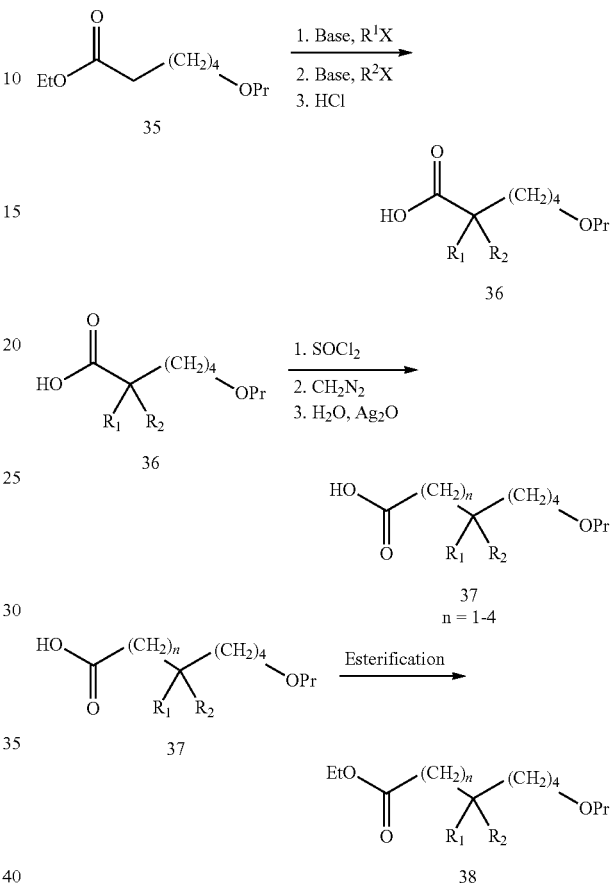

Scheme 9 illustrates the alpha disubstitution of an ester containing a terminal protected hydroxyl moiety. Compounds that contain strong electron withdrawing groups are easily converted to the corresponding enolates. These enolate ions can readily attack an electrophile resulting in alpha substitution. For a review see *Some Modern Methods of Organic Synthesis*, 3$^{rd}$ Ed.; Cambridge University Press: Cambridge, 1986, pp. 1-26, incorporated herein by reference. Typical procedures are described in Juaristi et al., *J. Org. Chem.*, 56, 1623 (1991) and Julie et al., *Tetrahedron*, 41, 3717 (1985). The reaction is successful for primary and secondary alkyl, allyic, and benzylic. The use of polar aprotic solvents, e.g., dimethylformamide or dimethylsulfoxide, are preferred. Phase transfer catalysts can also be used. See Tundo et al. *J. Chem. Soc., Perkin Trans.* 1, 1987, 2159, which is hereby expressly incorporated herein by reference.

The conversion to a carboxylic acid with an additional carbon is achieved by treating an acyl halide with diazomethane to generate an intermediate diazo ketone, which in the presence of water and silver oxide rearranges through a ketene intermediate to a carboxylic acid with an additional carbon aton 37. If the reaction is done in an alcohol instead of water an ester is recovered. See *Vogel's Textbook of Practical Chemistry*, Longman: London, 1978, pp. 483;

Meier et al. *Angew. Chem. Int. Ed. Eng.* 1975, 14, 32-43, which are incorporated herein by reference. Alternatively, the carboxylic acid can be esterified by known techniques. The reaction can be repeated to generate methylene groups adjacent to the carboxylic acid, sized from the corresponding carboxylic acid (i.e., 42, wherein Y comprises —C(O)OH) by esterification with $R^5OH$ (e.g., see March, J., *Advanced Organic Chemistry; Reactions Mechanisms, and Structure*, 4th ed., Wiley, New York, 1992, p. 393-394, incorporated herein by reference).

Scheme 10: Synthesis of Compounds of Formula 42a which correspond to Compounds $W^{(1)(2)}$—(CH$_2$)$_4$—OH, wherein $W^{(1)(2)}$ is $C(R^1)(R^2)(CH_2)_n Y$

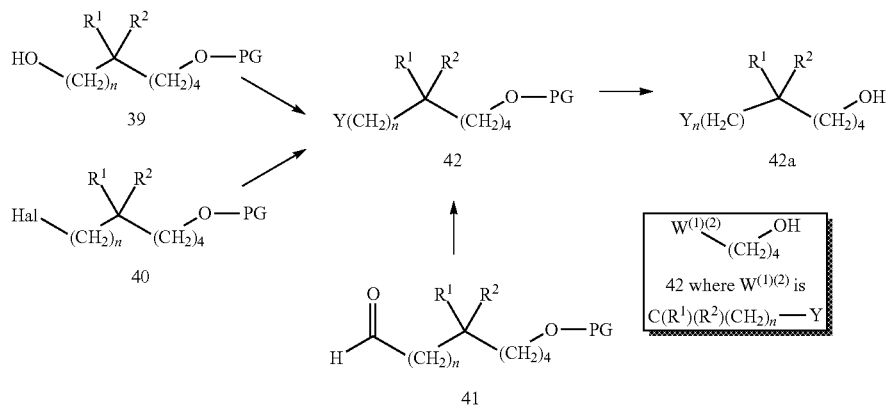

Scheme 10 outlines methodology for the synthesis of protected alcohols 42a wherein Y, $R^1$, $R^2$, Z. and m are defined as above. Protected alcohols 42a correspond to compounds of the formula $W^{(1)(2)}$-Zm-OPG, wherein $W^{(1)(2)}$ is $C(R^1)(R^2)$—Y.

Protected alcohols 42, wherein Y comprises a —C(O)OH group, can be synthesized by oxidizing mono-protected diols 39 with an agent suitable for oxidizing a primary alcohol to a carboxylic acid. (M. Hudlicky, *Oxidations in Organic Chemistry*, ACS Monograph 186, 1990, pp. 127-130, incorporated herein by reference). Suitable oxidizing agents include, but are not limited to, pyridinium dichromate (Corey et al., 1979, *Tetrahedron Lett.* 399); manganese dioxide (Ahrens et al., 1967, *J. Heterocycl. Chem.* 4:625); sodium permanganate monohydrate (Menger et al., 1981. *Tetrahedron Lett* 22:1655); and potassium permanganate (Sam et al., 1972, *J. Am. Chem. Soc.* 94:4024), all of which citations are hereby expressly incorporated herein by reference. The preferred oxidizing reagent is pyridinium dichromate. In an alternative synthetic procedure, protected alcohols 42, wherein Y comprises a —C(O)OH group, can be synthesized by treatment of protected halo-alcohols 40, wherein X is iodo, with CO or $CO_2$, as described in Bailey et al., 1990, *J. Org. Chem.* 55:5404 and Yanagisawa et al., 1994, *J. Am. Chem. Soc.* 116:6130, the two of which citations are hereby expressly incorporated herein by reference. Protected alcohols 42, wherein Y comprises —C(O)OR$^5$, wherein $R^5$ is as defined above, can be synthesized by oxidation of mono-protected diols 39 in the presence of RSOH (see generally, March, J. *Advanced Organic Chemistry; Reactions Mechanisms, and Structure*, 4th ed., 1992, p. 1196). An exemplary procedure for such an oxidation is described in Stevens et al., 1982, *Tetrahedron Lett.* 23:4647 (HOCl); Sundararaman et al., 1978, *Tetrahedron Lett.* 1627 ($O_3$/KOH); Wilson et al., 1982, *J. Org. Chem.* 47:1360 (t-BuOOHEt$_3$N); and Williams et al., 1988, *Tetrahedron Lett.* 29:5087 (Br$_2$), the four of which citations are incorporated herein by reference. Preferably, protected alcohols 42, wherein Y comprises a —C(O)OR$^5$ group are synthe- In another alternative synthesis, protected alcohols 42, wherein Y comprises —C(O)OR$^5$, can be prepared from protected halo-alcohols 40 by carbonylation with transition metal complexes (see e.g., March, J. *Advanced Organic Chemistry; Reactions Mechanisms, and Structure*, 4th ed., Wiley, New York, 1992, p. 484-486; Urata et al., 1991, *Tetrahedron Lett.* 32:36, 4733); and Ogata et al., 1969, *J. Org. Chem.* 3985, the three of which citations are hereby expressly incorporated herein by reference).

Protected alcohols 42, wherein Y comprises —OC(O)R$^5$, wherein $R^5$ is as defined above, can be prepared by acylation of mono-protected diols 39 with a carboxylate equivalent such as an acyl halide (i.e., $R^5$C(O)-Hal, wherein Hal is iodo, bromo, or chloro, see e.g., March, J. *Advanced Organic Chemistry; Reactions Mechanisms, and Structure*, 4th ed., Wiley, New York, 1992, p. 392 and *Org. Synth. Coll.* Vol. II, Wiley, N Y, pp. 142, 144, 167, and 187 (1955)) or an anhydride (i.e., $R^5$C(O)—O—(O)CR$^5$, see e.g., March, J. *Advanced Organic Chemistry Reactions Mechanisms, and Structure*, 4th ed., 1992, p. 392-393 and *Org. Synth. Coll.* Vol. III, Wiley, N Y, pp. 11, 127, 141, 169, 237, 281, 428, 432, 690, and 833 (1955)), all of which citations are incorporated herein by reference). Preferably, the reaction is conducted by adding a base to a solution comprising mono-protected diols 39, a carboxylate equivalent, and an organic solvent, which solution is preferably maintained at a constant temperature within the range of 0° C. to about room temperature. Solvents suitable for reacting mono-protected diols 39 with a carboxylate equivalent include, but are not limited to, dichloromethane, toluene, and ether, preferably dichloromethane. Suitable bases include, but are not limited to, hydroxide sources, such as sodium hydroxide, potassium hydroxide, sodium carbonate, or potassium carbonate; or an amine such as triethylamine, pyridine, or dimethylaminopyridine. The progress of the reaction can be followed by using an appropriate analytical technique, such as thin layer chromatography or high performance liquid chromatography and when substantially complete, the product can be isolated by workup and purified if desired.

Protected alcohols 42, wherein Y comprises one of the following phosphate ester groups

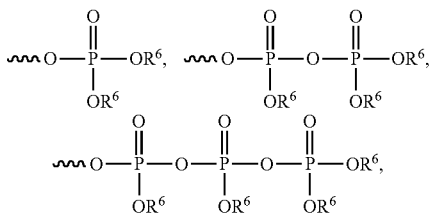

wherein $R^6$ is defined as above, can be prepared by phosphorylation of mono-protected diols X according to well-known methods (for general reviews, see Corbridge *Phosphorus: An Outline of its Chemistry, Biochemistry, and Uses*, Studies in Inorganic Chemistry, 3rd ed., pp. 357-395 (1985); Ramirez et al., 1978, *Acc. Chem. Res.* 11:239; and Kalckare *Biological Phosphorylations*, Prentice-Hall, New York (1969); J. B. Sweeny in *Comprehensive Organic Functional Group Transformations*, A. R. Katritzky, O. Meth-Cohn and C. W. Rees, Eds. Pergamon: Oxford, 1995, vol 2, pp. 104-109, the four of which are hereby expressly incorporated herein by reference). Protected alcohols 42 wherein Y comprises a monophosphate group of the formula:

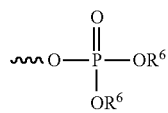

wherein $R^6$ is defined as above, can be prepared by treatment of mono-protected diol 39 with phosphorous oxychloride in a suitable solvent, such as xylene or toluene, at a constant temperature within the range of about 100° C. to about 150° C. for about 2 hours to about 24 hours. After the reaction is deemed substantially complete, by using an appropriate analytical method, the reaction mixture is hydrolyzed with $R^6$—OH. Suitable procedures are referenced in Houben-Weyl, Methoden der Organische Chemie, Georg Thieme Verlag Stuttgart: 1964, vol. XII/2, pp. 143-210 and 872-879, incorporated herein by reference. Alternatively, when both $R^6$ are hydrogen, can be synthesized by reacting mono-protected diols X with silyl polyphosphate (Okamoto et al., 1985, *Bull Chem. Soc. Jpn.* 58:3393, hereby expressly incorporated herein by reference) or by hydrogenolysis of their benzyl or phenyl esters (Chen et al., 1998, *J. Org. Chem.* 63:6511, incorporated herein by reference). In another alternative procedure, when $R^6$ is ($C_1$-$C_6$)alkyl, ($C_2$-$C_6$)alkenyl, or ($C_2$-$C_6$)alkynyl, the monophosphate esters can be prepared by reacting mono-protected diols 39 with appropriately substituted phophoramidites followed by oxidation of the intermediate with m-chloroperbenzoic acid (Yu et al., 1988, *Tetrahedron Lett.* 29:979, incorporated herein by reference) or by reacting mono-protected diols 39 with dialkyl or diaryl substituted phosphorochloridates (Pop, et al, 1997, *Org. Prep. and Proc. Int.* 29:341, incorporated herein by reference). The phosphoramidites are commercially available (e.g., Aldrich Chemical Co., Milwaukee, Wis.) or readily prepared according to literature procedures (see e.g., Uhlmann et al. 1986, *Tetrahedron Lett.* 27:1023 and Tanaka et al., 1988, *Tetrahedron Lett.* 29:199, both of which are incorporated herein by reference). The phosphorochloridates are also commercially available (e.g., Aldrich Chemical Co., Milwaukee, Wis.) or prepared according to literature methods (e.g., Gajda et al, 1995, *Synthesis* 25:4099. In still another alternative synthesis, protected alcohols 42, wherein Y comprises a monophosphate group and $R^6$ is alkyl or aryl, can be prepared by reacting IP$^+$ ($OR^6$)$_3$ with mono-protected diols 39 according to the procedure described in Stowell et al., 1995, *Tetrahedron Lett.* 36:11, 1825 or by alkylation of protected halo alcohols 40 with the appropriate dialkyl or diaryl phosphates (see e.g., Okamoto, 1985, *Bull Chem. Soc. Jpn.* 58:3393, incorporated herein by reference).

Protected alcohols 42 wherein Y comprises a diphosphate group of the formula

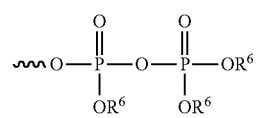

wherein $R^6$ is defined as above, can be synthesized by reacting the above-discussed monophosphates of the formula:

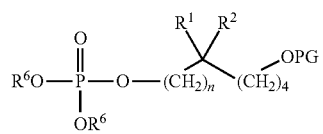

with a phosphate of the formula

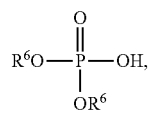

(commercially available, e.g., Aldrich Chemical Co., Milwaukee, Wis.), in the presence of carbodiimide such as dicyclohexylcarbodiimide, as described in Houben-Weyl, *Methoden der Organische Chemie*, Georg Thieme Verlag Stuttgart 1964, vol. XII/2, pp. 881-885. In the same fashion, protected alcohols 42, wherein Y comprises a triphosphate group of the formula:

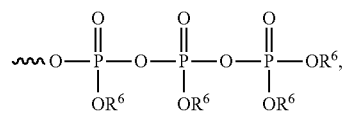

can be synthesized by reacting the above-discussed diphosphate-protected alcohols, of the formula:

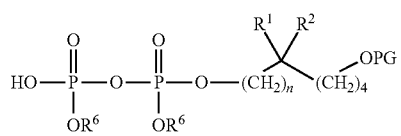

with a phosphate of the formula:

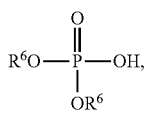

as described above. Alternatively, when $R^6$ is H, protected alcohols 42 wherein Y comprises the triphosphate group, can be prepared by reacting mono-protected diols 39 with salicyl phosphorochloridite and then pyrophosphate and subsequent cleavage of the adduct thus obtained with iodine in pyridine as described in Ludwig et al., 1989, *J. Org. Chem.* 54:631, incorporated herein by reference.

Protected alcohols 42, wherein Y is —SO$_3$H or a heterocyclic group selected from the group consisting of:

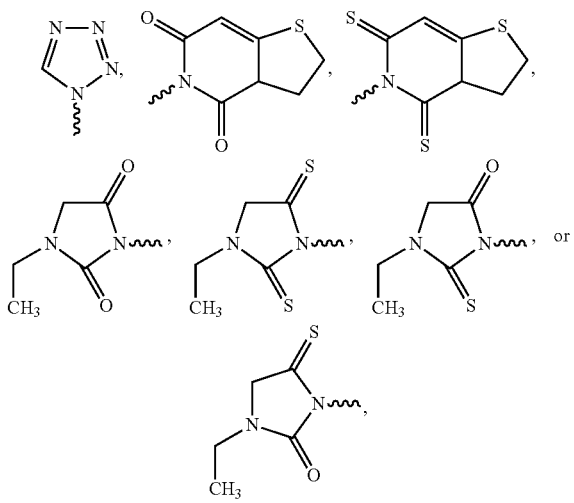

can be prepared by halide displacement from protected halo-alcohols 40. Thus, when Y is —SO$_3$H, protected alcohols 42 can by synthesized by reacting protected halo-alcohols 40 with sodium sulfite as described in Gilbert *Sulfonation and Related Reactions*; Wiley: New York, 1965, pp. 136-148 and pp. 161-163; *Org. Synth. Coll.* Vol. II, Wiley, N Y, 558, 564 (1943); and *Org. Synth. Coll.* Vol. IV, Wiley, N Y, 529 (1963), all three of which are incorporated herein by reference. When Y is one of the above-mentioned heterocycles, protected alcohols 42 can be prepared by reacting protected halo-alcohols 40 with the corresponding heterocycle in the presence of a base. The heterocycles are available commercially (e.g., Aldrich Chemical Co., Milwaukee, Wis.) or prepared by well-known synthetic methods (see the procedures described in Ware, 1950, *Chem. Rev.* 46:403-470, incorporated herein by reference). Preferably, the reaction is conducted by stirring a mixture comprising 40, the heterocycle, and a solvent at a constant temperature within the range of about room temperature to about 100° C., preferably within the range of about 50° C. to about 70° C. for about 10 to about 48 hours. Suitable bases include hydroxide bases such as sodium hydroxide, potassium hydroxide, sodium carbonate, or potassium carbonate. Preferably, the solvent used in forming protected alcohols 42 is selected from dimethylformamide; formamide; dimethyl sulfoxide; alcohols, such as methanol or ethanol; and mixtures thereof. The progress of the reaction can be followed by using an appropriate analytical technique, such as thin layer chromatography or high performance liquid chromatography and when substantially complete, the product can be isolated by workup and purified if desired.

Protected alcohols 42, wherein Y is a heteroaryl ring selected from

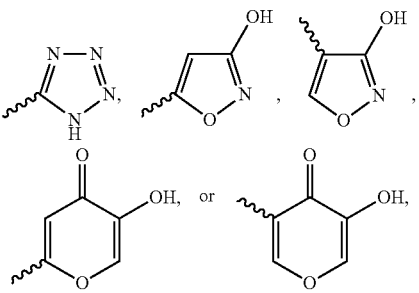

can be prepared by metallating the suitable heteroaryl ring then reacting the resulting metallated heteroaryl ring with protected halo-alcohols 40 (for a review, see Katritzky *Handbook of Heterocyclic Chemistry*, Pergamon Press: Oxford 1985). The heteroaryl rings are available commercially or prepared by well-known synthetic methods (see e.g., Joule et al., *Heterocyclic Chemistry*, 3rd ed., 1995; De Sarlo et al., 1971, *J. Chem. Soc.* (C) 86; Oster et al., 1983, *J. Org. Chem.* 48:4307; Iwai et al., 1966, *Chem. Pharm. Bull.* 14:1277; and U.S. Pat. No. 3,152,148, all of which citations are incorporated herein by reference). As used herein, the term "metallating" means the forming of a carbon-metal bond, which bond may be substantially ionic in character. Metallation can be accomplished by adding about 2 equivalents of strong organometallic base, preferably with a pK$_a$ of about 25 or more, more preferably with a pK$_a$ of greater than about 35, to a mixture comprising a suitable organic solvent and the heterocycle. Two equivalents of base are required: one equivalent of the base deprotonates the —OH group or the —NH group, and the second equivalent metallates the heteroaryl ring. Alternatively, the hydroxy group of the heteroaryl ring can be protected with a base-stable, acid-labile protecting group as described in Greene, T. W., *Protective Groups in Organic Synthesis*, 3rd edition 17-237 (1999), hereby expressly incorporated herein by reference. Where the hydroxy group is protected, only one equivalent of base is required. Examples of suitable base-stable, acid-labile hydroxyl-protecting groups, include but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahyrofuranyl, tetrahydrothiofuranyl, 1-ethoxyethyl, 1-methyl-1-methoxyethyl, t-butyl, allyl, benzyl, o-nitrobenzyl, triphenylmethyl, ca-naphthyldiphenylmethyl, p-methoxyphenyldiphnyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably, the pK$_a$ of the base is higher than the pK$_a$ of the proton of the heterocycle to be deprotonated. For a listing of pK$_a$s for various heteroaryl rings, see Fraser et al., 1985, *Can. J. Chem.* 63:3505, incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. If desired, the organometallic base can be activated with a complexing agent, such as N,N,N',N'-tetramethylethylenediamine or hexamethylphosphoramide (1970, *J. Am. Chem. Soc.* 92:4664, hereby expressly incorporated herein by reference). Solvents suitable for synthesizing protected alcohols 42, wherein Y is a heteroaryl ring include, but are not limited to, diethyl ether; tetrahydrofuran; and hydrocarbons, such as pentane. Generally, metallation occurs alpha to the heteroatom due to the inductive effect of the heteroatom, however, modification of conditions, such as the identity of the base and solvents, order of reagent addition, reagent addition times, and reaction and addition temperatures can be modified by one of skill in the art to achieve the desired metallation position (see e.g., Joule et al., *Heterocyclic Chemistry*, 3rd ed., 1995, pp. 30-42, hereby expressly incorporated herein by reference) Alternatively, the position of metallation can be controlled by use of a halogenated heteroaryl group, wherein the halogen is located on the position of the heteroaryl ring where metallation is desired (see e.g., Joule et al., *Heterocyclic Chemistry*, 3rd ed., 1995, p. 33 and Saulnier et al., 1982, *J. Org. Chem.* 47:757, the two of which citations are hereby expressly incorporated herein by reference). Halogenated heteroaryl groups are available commercially (e.g., Aldrich Chemical Co., Milwaukee, Wis.) or can be prepared by well-known synthetic methods (see e.g., Joule et al., *Heterocyclic Chemistry*, 3rd ed., 1995, pp. 78, 85, 122, 193, 234, 261, 280, 308, hereby expressly incorporated herein by reference). After metallation, the reaction mixture comprising the metallated heteroaryl ring is adjusted to within a temperature range of about 0° C. to about room temperature and protected halo-alcohols 40 (diluted with a solvent or in undiluted form) are added, preferably at a rate such that the reaction-mixture temperature remains within about one to two degrees of the initial reaction-mixture temperature. After addition of protected halo-alcohols 40, the reaction mixture is stirred at a constant temperature within the range of about room temperature and about the solvent's boiling temperature and the reaction's progress can be monitored by the appropriate analytical technique, preferably thin-layer chromatography or high-performance liquid chromatography. After the reaction is substantially complete, protected alcohols 42 can be isolated by workup and purification. It is to be understood that conditions, such as the identity of protected halo-alcohol 40, the base, solvents, orders of reagent addition, times, and temperatures, can be modified by one of skill in the art to optimize the yield and selectivity. Exemplary procedures that can be used in such a transformation are described in Shirley et al., 1995, *J. Org. Chem.* 20:225; Chadwick et al., 1979, *J Chem. Soc., Perkin Trans.* 1 2845; Rewcastle, 1993, *Adv. Het. Chem.* 56:208; Katritzky et al., 1993, *Adv. Het. Chem.* 56:155; and Kessar et al., 1997, *Chem. Rev.* 97:721. When Y is

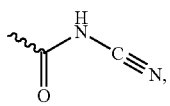

protected alcohols 42 can be prepared from their corresponding carboxylic acid derivatives (42, wherein Y is —CO₂H) as described in Belletire et al, 1988, *Synthetic Commun.* 18:2063 or from the corresponding acylchlorides (42, wherein Y is —CO-halo) as described in Skinner et al., 1995, *J. Am. Chem. Soc.* 77:5440, both citations are incorporated herein by reference. The acylhalides can be prepared from the carboxylic acids by well known procedures such as those described in March, J., *Advanced Organic Chemistry; Reactions Mechanisms, and Structure*, 4th ed., 1992, pp. 437-438, hereby expressly incorporated herein by reference. When Y is

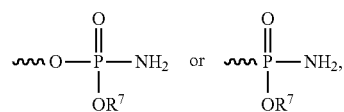

wherein $R^7$ is as defined above, protected alcohols 42 can be prepared by first reacting protected halo-alcohols 40 with a trialkyl phosphite according to the procedure described in Kosolapoff, 1951, *Org. React.* 6:273 followed by reacting the derived phosphonic diester with ammonia according to the procedure described in Smith et al., 1957, *J. Org. Chem.* 22:265, incorporated herein by reference. When Y is

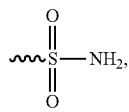

protected alcohols 42 can be prepared by reacting their sulphonic acid derivatives (i.e., 42, wherein Y is —SO₃H) with ammonia as described in Sianesi et al., 1971, *Chem. Ber.* 104:1880 and Campagna et al., 1994, *Farmaco, Ed. Sci.* 49:653, both of which citations are incorpoprated herein by reference).

As further illustrated in Scheme 10, protected alcohols 42 can be deprotected providing alcohols 42a. The deprotection method depends on the identity of the alcohol-protecting group, see e.g., the procedures listed in Greene, T. W., *Protective Groups in Organic Synthesis*, 3rd edition 17-237 (1999), particularly see pages 48-49, incorporated herein by reference. One of skill in the art will readily be able to choose the appropriate deprotection procedure. When the alcohol is protected as an ether function (e.g., methoxymethyl ether), the alcohol is preferably deprotected with aqueous or alcoholic acid. Suitable deprotection reagents include, but are not limited to, aqueous hydrochloric acid, p-toluenesulfonic acid in methanol, pyridinium-p-toluenesulfonate in ethanol, Amberlyst H-15 in methanol, boric acid in ethylene-glycol-monoethylether, acetic acid in a water-tetrahydrofuran mixture, aqueous hydrochloric acid is preferred. Examples of such procedures are described, respectively, in Bernady et al., 1979, *J. Org. Chem.* 44:1438; Miyashita et al., 1977, *J. Org. Chem.* 42:3772; Johnston et al., 1988, *Synthesis* 393; Bongini et al., 1979, *Synthesis* 618: and Hoyer et al., 1986, *Synthesis* 655; Gigg et al., 1967, *J. Chem. Soc. C*, 431; and Corey et al., 1978, *J. Am. Chem. Soc.* 100:1942, all of which are incorporated herein by reference.

Scheme 11: Synthesis of Compounds of Formula 46 which correspond to Compounds $W^{(1)(2)}$—$(CH_2)_4$—OH, wherein $W^{(1)(2)}$ is $C(R^1)(R^2)(CH_2)_4$-Lactone

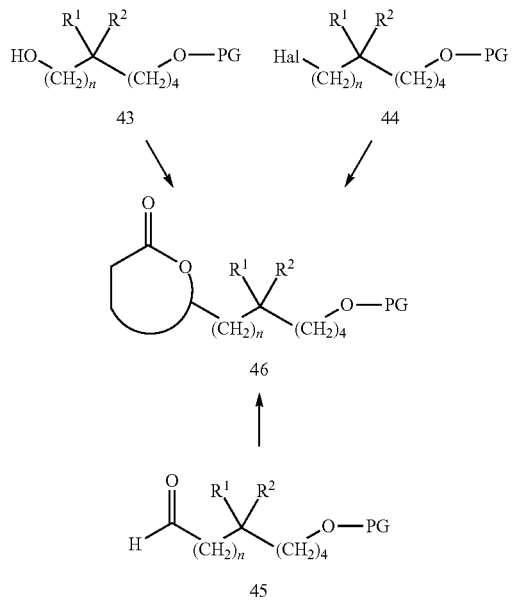

Scheme 11 depicts the synthesis of protected lactone alcohols 46 and lactone. Compound 46 corresponds to compounds of the formula $W^{(1)(2)}$-Zm-OPG and, wherein $W^{(1)(2)}$ is a lactone group selected from:

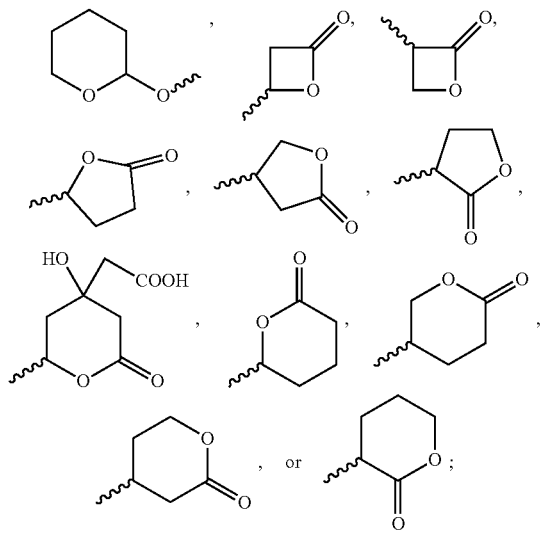

Protected lactone alcohols 46 can be prepared from compounds of the formula 43, 44, or 45 by using well-known condensation reactions and variations of the Michael reaction. Methods for the synthesis of lactones are disclosed in Multzer in *Comprehensive Organic Functional Group Transformations*, A. R. Katritzky, O. Meth-Cohn and C. W. Rees, Eds. Pergamon: Oxford, 1995, vol 5, pp. 161-173, incorporated herein by reference. Mono-protected diols 43, electrophilic protected alcohols 44, and aldehydes 45 are readily available either commercially (e.g., Aldrich Chemical Co., Milwaukee, Wis.) or can be prepared by well known synthetic procedures.

When $W^{(1)(2)}$ is a beta-lactone group of the formula:

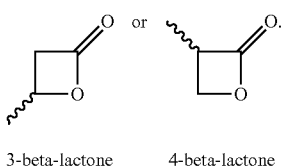

3-beta-lactone    4-beta-lactone protected lactone alcohols 46 can be prepared from aldehydes 45 and electrophilic protected alcohols 44, respectively, by a one-pot-addition-lactonization according to the procedure of Masamune et al., 1976, *J. Am. Chem. Soc.* 98:7874 and Danheiser et al., 1991, *J. Org. Chem.* 56:1176, both of which are incorporated herein by reference. This one-pot-addition-lactonization methodology has been reviewed by Multzer in *Comprehensive Organic Functional Group Transformations*, A. R. Katritzky, O. Meth-Cohn and C. W. Rees, Eds. Pergamnon: Oxford, 1995, vol 5, pp. 161, incorporated herein by reference When $W^{(1)(2)}$ is a gamma- or delta-lactone group of the formula:

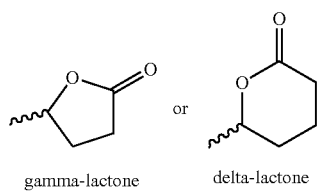

gamma-lactone    delta-lactone protected lactone alcohols 46 can be prepared from aldehydes 45 according to well known synthetic methodology. For example, the methodology described in Masuyama et al., 2000, *J. Org. Chem.* 65:494; Eisch et al., 1978, *J. Organomet. Chem.* C8 160; Eaton et al., 1947, *J. Org. Chem.* 37:1947; Yunker et al., 1978, *Tetrahedron Lett.* 4651; Bhanot et al., 1977, *J. Org. Chem.* 42:1623; Ehlinger et al., 1980, *J. Am. Chem. Soc.* 102:5004; and Raunio et al., 1957, *J. Org. Chem.* 22:570, all of which citations are incorporated herein by reference. For instance, as described in Masuyama et al., 2000, *J. Org. Chem.* 65:494, aldehydes 45 can be treated with about 1 equivalent of a strong organometallic base, preferably with a $pK_a$ of about 25 or more, more preferably with a $pK_a$ of greater than about 35, in a suitable organic solvent to give a reaction mixture. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. The reaction-mixture temperature is adjusted to within the range of about 0° C. to about 100° C., preferably about room temperature to about 50° C., and a halide of the formula:

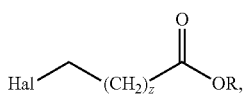

wherein z is 1 or 2 (diluted with a solvent or in undiluted form) is added. The reaction mixture is stirred for a period of about 2 hours to about 48 hours, preferably about 5 to about 10 hours, during which time the reaction's progress can be followed by using an appropriate analytical technique, such as thin layer chromatography or high performance liquid chromatography. When the reaction is deemed substantially complete, protected lactone alcohols 46 can be isolated by workup and purified if desired. When $W^{(1)(2)}$ is a gamma- or delta-lactone group of the formula:

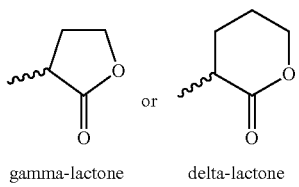

gamma-lactone    delta-lactone protected lactone alcohols 46 can be synthesized by deprotonating the corresponding lactone with a strong base providing the lactone enolate and reacting the enolate with electrophilic protected alcohols 44 (for a detailed discussion of enolate formation of active methylene compounds such as lactones, see House *Modern Synthetic Reactions*; W. A. Benjamin, Inc. Philippines 1972 pp. 492-570, and for a discussion of reaction of lactone enolates with electrophiles such as carbonyl compounds, see March, J. *Advanced Organic Chemistry; Reactions Mechanisms, and Structure*, 4th ed., 1992, pp. 944-945, both of which are incorporated herein by reference). Lactone-enolate formation can be accomplished by adding about 1 equivalent of a strong organometallic base, preferably with a $pK_a$ of about 25 or more, more preferably with a $pK_a$ of greater than about 35, to a mixture comprising a suitable organic solvent and the lactone. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Solvents suitable for lactone-enolate formation include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols 44 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, protected lactone alcohols 46 can be isolated by workup and purified if desired. When $W^{(1)(2)}$ is a lactone group group of the formula:

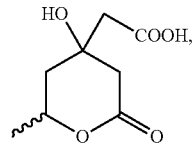

protected lactone alcohols 46 can be prepared from aldehydes 45 according to the procedure described in U.S. Pat. No. 4,622,338, hereby expressly incorporated herein by reference.

When $W^{(1)(2)}$ is a gamma- or delta-lactone group of the formula:

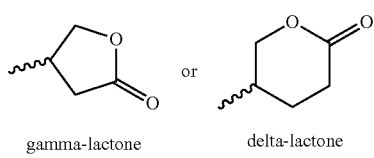

gamma-lactone    delta-lactone protected lactone alcohols 46 can be prepared according to a three step sequence. The first step comprises base-mediated reaction of electrophilic protected alcohols 44 with succinic acid esters (i.e., $R^9O_2CCH_2CH_2CO_2R^9$, wherein $R^9$ is alkyl) or glutaric acid esters (i.e., $R^9O_2CCH_2CH_2CH_2CO_2R^9$, wherein $R^9$ is alkyl) providing a diester intermediate of the formula 44i:

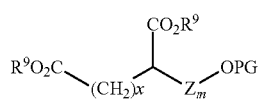

wherein x is 1 or 2 depending on whether the gamma or delta lactone group is desired. The reaction can be performed by adding about 1 equivalent of a strong organometallic base, preferably with a $pK_a$ of about 25 or more, more preferably with a $pK_a$ of greater than about 35, to a mixture comprising a suitable organic solvent and the succinic or glutaric acid ester. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols 44 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, the diester intermediate can be isolated by work-up and purified if desired. In the second step, the intermediate diester can be reduced, with a hydride reducing agent, to yield a diol:

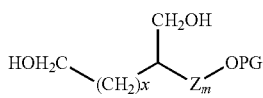

The reduction can be performed according to the procedures referenced in March, J. *Advanced Organic Chemistry; Reactions Mechanisms, and Structure*, 4th ed., 1992, p. 1214, incorporated herein by reference. Suitable reducing agents include, but are not limited to, lithium aluminum hydride, diisobutyl aluminum hydride, sodium borohydride, and lithium borohydride). In the third step, the diol can be oxidatively cyclized with RuH$_2$(PPh$_3$)$_4$ to the product protected lactone alcohols 46 according to the procedure of Yoshikawa et al., 1986, *J. Org. Chem.* 51:2034 and Yoshikawa et al., 1983, *Tetrahedron Lett.* 26:2677, both of which citations are incorporated herein by reference. When W$^{(1)(2)}$ is a lactone group of the formula:

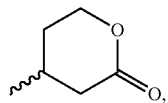

protected lactone alcohols 46 can be synthesized by reacting the Grignard salts of electrophilic protected alcohols 44, where E is a halide, with 5,6-dihydro-2H-pyran-2-one, commercially available (e.g., Aldrich Chemical Co., Milwaukee, Wis.), in the presence of catalytic amounts of a 1-dimethylaminoacetyl)pyrolidine-2yl)methyl-diarylphosphine-copper (I) iodide complex as described in Tomioka et al., 1995, *Tetrahedron Lett.* 36:4275, incorporated herein by reference.

Scheme 12: Synthesis of Compounds of Formula II

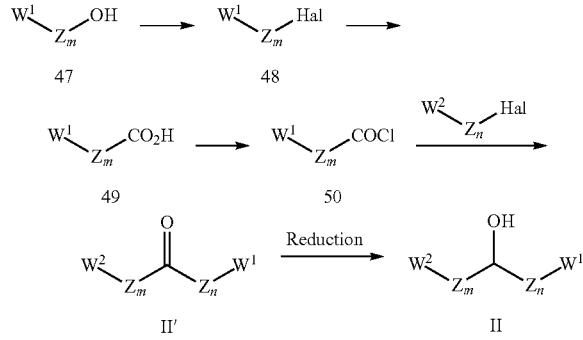

Scheme 12 illustrates the synthesis of alcohol 11. The alcohol 47 is initially converted to a halogen 48. See Larock, *Comprehensive Organic Transformations*, VCH: New York, 1989, pp. 360-362; all references disclosed therein are incorporated herein by reference. The halide 48 is then converted to a carboxylic acid 49 with subsequent conversion to a acyl halide 50. See Larock, *Comprehensive Organic Transformations*, VCH: New York, 1989, pp. 850-851, 855-856, 859-860, 977, 980, and 985; all references disclosed therein are incorporated herein by reference. The acyl halide 50 is then coupled with the halide to afford compound II'. See Rappoport, *The Chemistry of the Functional Groups, Supp. D*, pt. 2; Wiley: New York, 1983; House, *Modern Synthetic Reactions*, 2$^{nd}$ Ed. Benjamin: New York, 1972, pp. 691-694, 734-765, which are incorporated herein by reference. Finally, compounds II' are reduced using methods known to those of ordinary skill in the art to afford alcohol II. See Larock, *Comprehensive Organic Transformations*; VCH: New York, 1989.

In a typical procedure, the ketone II' is dissolved in an organic solvent such as, but not limited to, toluene, xylene, diethyl ether, t-butyl methyl ether, diglyme, methanol, ethanol, dichloromethane, chloroform, dichloroethane, preferably diethyl ether, and it is then treated with a reducing agent such as, but not limited to, lithium aluminum hydride, sodium borohydride, lithium borohydride, preferably sodium borohydride. When the reaction is complete, as determined by an analytical method such as HPLC, gas chromatography, thin layer chromatography, or NMR, the mixture is subjected to work-up. The compound thus obtained can be purified by various purification methods known in the field, such as chromatography or recrystallization. It is readily recognized that the alcohol compound II can exist as enantiomers. Separation of the stereoisomers (i.e., enantiomers) can be achieved by methods known in the art, for example, conversion to a chiral salt and crystallization, chiral chromatography, or chiral HPLC.

Scheme 13: Synthesis of Compounds III

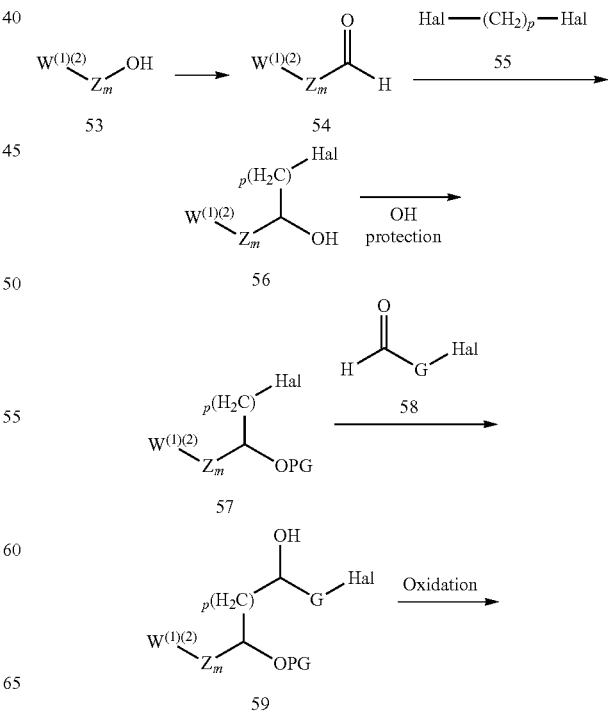

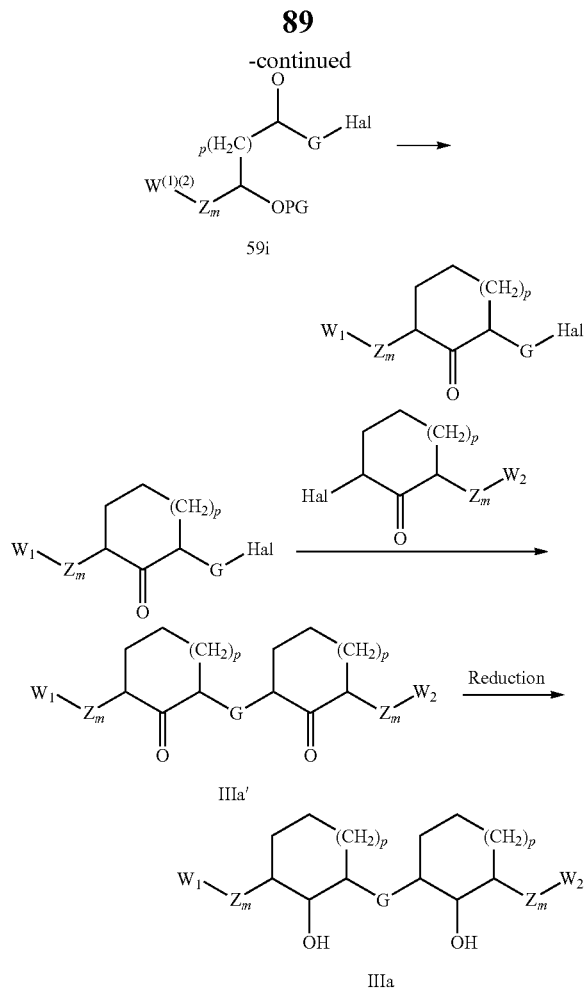

Scheme 13 depicts the synthesis of compounds IIIa, that is, compounds III where a double bond is not present in the ring. In the first step, compounds 53, prepared as discussed in Schemes 1 to 6 above, can be converted to compounds 54 by standard oxidation of the primary alcohol to an aldehyde group. Such oxidations are described in M. Hudlicky, *Oxidations in Organic Chemistry*, ACS Monograph 186, 1990, pp. 114-127, hereby expressly incorporated herein by reference. In the next step Grignard reaction of 54 with 55 followed by standard OH protection gives 57. Compounds 55 are commercially available (e.g., from Aldrich Chemical Co. Milwaukee, Wis.) or can be readily prepared by standard synthetic methodology. For exemplary procedures for Grignard reactions see March, J. *Advanced Organic Chemistry; Reactions Mechanisms, and Structure,* 4th ed., 1992, pp. 920-929, incorporated herein by reference. Similarly, in the next step, the Grignard salt of 57 is condensed with 58 to provide 59. Next 59 is oxidized and then cyclized to 60. When p is one, exemplary cyclization procedures are found in Friedrichsen, W. in *Comprehensive Heterocyclic Chemistry II*; Katritzky, A. R.; Rees, W. C.; Scriven, E. F. V. Eds.; Pergamon Press: Oxford, 1996; Vol. 2, p 351, and *Comprehensive Heterocyclic Chemistry*; Katritzky, A. R.; Rees, W. C. Eds.; Pergamon Press: Oxford, 1986; Vol. 3. When p is 0, cyclization procedures are found in Hepworth, J. D. in *Comprehensive Heterocyclic Chemistry II*; Katritzky, A. R.; Rees, W. C.; Scriven, E. F. V. Eds.; Pergamon Press: Oxford, 1996; Vol. 5, p 351 and *Comprehensive Heterocyclic Chemistry*; Katritzky, A. R.; Rees, W. C. Eds.; Pergamon Press:

Oxford, 1986; Vol. 3, all of which citations are hereby expressly incorporated herein by reference.

The hydroxy ketone is subjected to cyclization, as described in the above Hepworth, J. D. in *Comprehensive Heterocyclic Chemistry II*; Katritzky, A. R.; Rees, W. C.; Scriven, E. F. V. Eds.; Pergamon Press: Oxford, 1996; Vol. 5, p 386. For compounds III where $W^{(1)(2)}$ is $HO(CH_2)_n$—$R^1R^2$: The hydroxy group is first deprotected as described in Greene, T. W., *Protective Groups in Organic Synthesis,* 3rd edition (1999). For other structures, where Y is a group such as an acid, aldehydes, etc., protection is needed (acids as esters, preferably pivaloyl, aldehydes as silyl derivatives such as TIPS, stable in both basic and acidic conditions). When $W^{(1)(2)}$ is a lactone it can be introduced as discussed in Scheme 3 above. The compounds are then coupled to afford compound of the formula IIIa.

The reactions are performed under similar conditions for substituted cyclic compounds. After the formation of the monocyclic compounds, they are reacted in situ with electrophiles (e.g., MeI) at temperatures between −40° C. to +60° C., for a reaction time of 1 hr to 5 days. In addition, double bonds can be selectively added or reduced or otherwise manipulated by well known synthetic methods to give compounds III having one or two selectively-placed double bonds (i.e., the double bond(s) can be positioned in the desired location within the ring), for example, the methods disclosed in March, J. *Advanced Organic Chemistry; Reactions Mechanisms, and Structure,* 4th ed., 1992, pp. 771-780, incorporated herein by reference. Finally, compounds IIIa are reduced using methods known to those of ordinary skill in the art to afford alcohol IIIa. See *Comprehensive Organic Transformations*; VCH: New York, 1989. It is readily recognized that the alcohol compound IIIa is stereoisomeric and can therefore exist as enantiomers and diastereomer. Separation of the stereoisomers (i.e., enantiomers or diastereomers) can be achieved by methods known in the art, for example, conversion to a chiral salt and crystallization, chiral chromatography, or chiral HPLC.

Scheme 14: Synthesis of Compounds IV

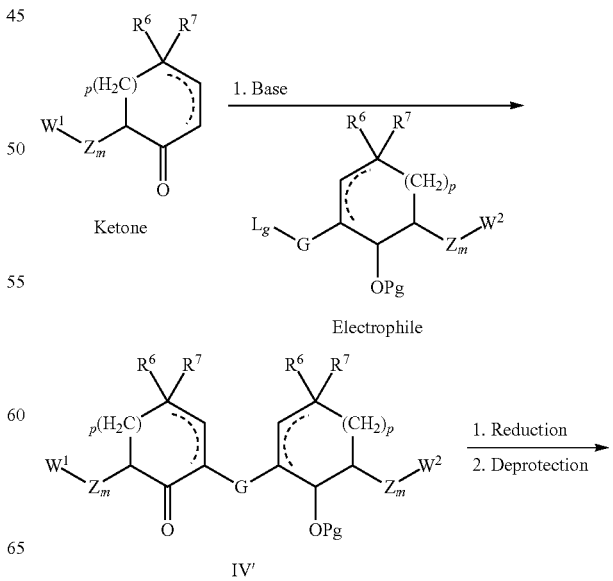

-continued

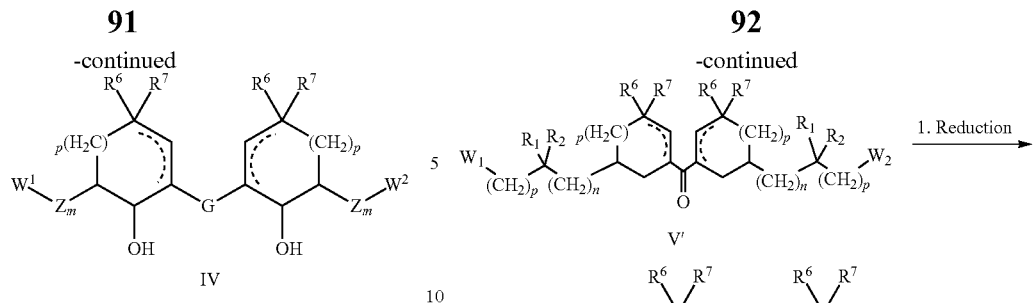

Scheme 14 depicts the synthesis of compounds IV. In the first step, ketone compounds can be converted to compounds IV' by treating with a strong base (e.g., LiHMDS, LDA) to generate the kinetic enolate followed by addition of the electrophile. In the next step, the ketone moiety of compound IV' is reduced using standard methods known to those of ordinary skill in the art. For exemplary procedures for Grignard reaction see March, J. *Advanced Organic Chemistry; Reactions Mechanisms, and Structure*, 4th ed., 1992, incorporated herein by reference. See also *Comprehensive Heterocyclic Chemistry II*; Katritzky, A. R.; Rees, W. C.; Scriven, E. F. V. Eds.; Pergamon Press. Oxford, 1996; Vol. 2, and *Comprehensive Heterocyclic Chemistry*; Katritzky, A. R.; Rees, W. C. Eds.; Pergamon Press: Oxford, 1986; Vol. 3. Press: Oxford, 1996; Vol. 5.

It is readily recognized that the diol compound IV is stereoisomeric and can therefore exist as enantiomers and diastereomers. Separation of the stereoisomers (i.e., enantiomers or diastereomers) can be achieved by methods known in the art, for example, conversion to a chiral salt and crystallization, chiral chromatography, or chiral HPLC.

Scheme 15: Synthesis of Compounds V

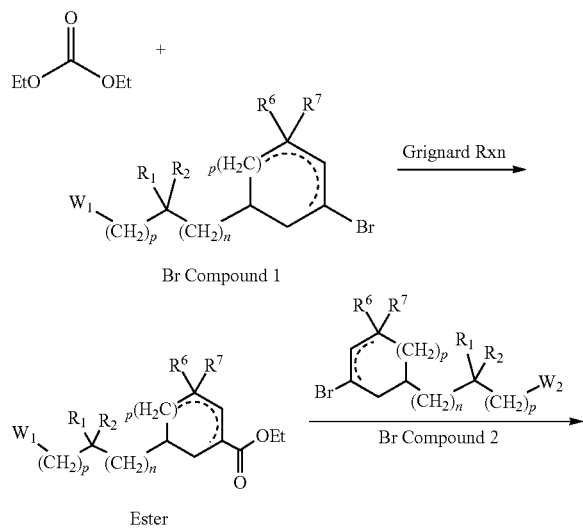

Scheme 15 depicts the synthesis of compounds IV. In the first step, compounds of the type Br-compound 1, undergoes a Grignard reaction with diethylorthoformate to give the ester compound. For exemplary procedures for Grignard reaction see March, J. *Advanced Organic Chemistry; Reactions Mechanisms, and Structure*, 4th ed., 1992, pp. 920-929, incorporated herein by reference. Similarly, in the next step, the Grignard salt of Br-compound 2 is condensed with the ester compound to provide ketone V'.

The ketone is then reduced under standard conditions known in the art to afford compound V, for example, the methods disclosed in *Organikum, Organisch-Chemisches Grundpraktikum*, VEB Deutscher Verlag der Wissenschaften, Berlin, 1984, p. 616; March, J. *Advanced Organic Chemistry; Reactions Mechanisms, and Structure*, 4th ed., 1992, and Larock *Comprehensive Organic Transformations*; VCH: New York, 1989, each of which are incorporated herein by reference. It is readily recognized that the alcohol compound is stereoisomeric and can therefore exist as enantiomers and diastereomer. Separation of the stereoisomers (i.e., enantiomers or diastereomers) can be achieved by methods known in the art, for example, conversion to a chiral salt and crystallization, chiral chromatography, or chiral HPLC. In a typical procedure, the alcohol compounds are dissolved in the appropriate solvent, such as methanol, ethanol, isopropanol, preferably isopropanol, and is treated with a reducing agent, preferably sodium borohydride at temperatures between about −20° C. and solvent reflux, preferably at about −5° C. to about 10° C. When the reaction is considered complete by an analytical method such as HPLC, GC, TLC, or NMR, the reaction is subject to work-up known in the art.

Scheme 16

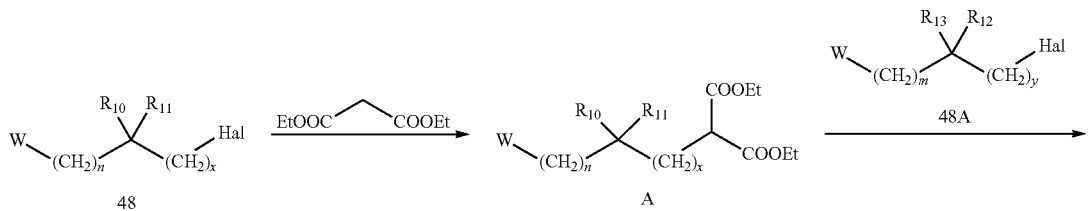

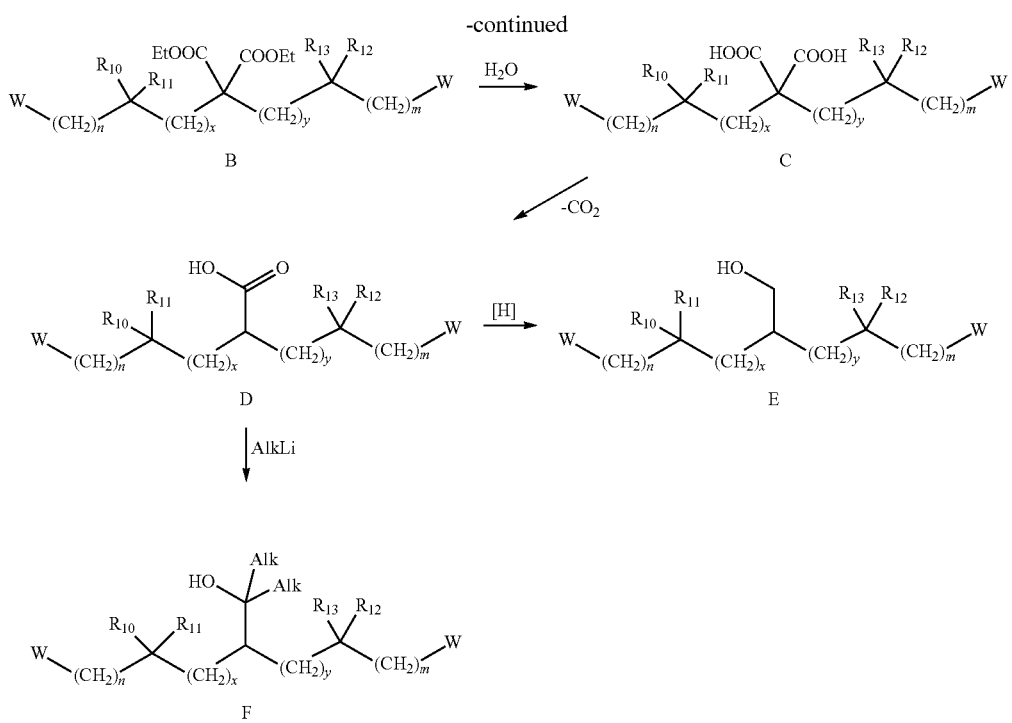

Halides 48 (prepared as described in Dasseux and Oniciu, U.S. Pat. No. 6,410,802, 2002) are treated with diethyl malonate anion (obtained from diethyl malonate and a dehydration agent such as sodium hydride, sodium or potassium methoxide, ethoxide or t-butoxide) in an anhydrous solvent such as DMSO, alcohol (methanol, ethanol or t-butanol) or a hydrocarbon (heptane, xylene, toluene) or an ether (THF, diethyl ether), preferably sodium hydride in DMSO, at room temperature or at temperatures up to the reflux of the solvent, for two hours up to 72 hours. The reaction is monitored by usual analytical methods such as tlc, GC and HPLC, and it is stopped when no significant change of the reaction mixture is seen by one of these methods. The reaction is performed sequentially when an unsymmetrical derivative is desired. Intermediates of type A are prepared as described above by using 1 to 1.2 equivalents of dehydrating agent and halide 48; in order to afford compounds of type B, when this reaction is deemed complete by one of the analytical methods mentioned above, a second mole of dehydrating agent is added followed by 1 to 1.2 equivalents of the second halide 48A. This type of compounds may be purified by column chromatography or by HPLC, or use as crude in the next step. The ester moieties in intermediate B thus obtained are hydrolysed by usual methods such as basic hydrolysis, to afford diacids of type C that could be either purified by usual methods, e.g. column chromatography or preparative HPLC, or decarboxilated as crude. The decarboxilation is performed either neat at temperatures from 150 to 220° C., or in a solvent. Monoacid D thus obtained is finally reduced more commonly with metals and proton donors or with reducing agents such as lithium aluminum hydride in ether or tetrahydrofuran to give the desired compounds of type E. Symmetrical derivatives may be prepared similarly, by using 2.2 to 3 equivalents halide 48, when intermediate B is formed directly. If intermediate D is treated with an alkyl lithium alcohol F is then obtained.

Scheme 17: Synthesis of 7-hydroxymethyl-2,2,12,12-tetramethyl-tridecane-1,13-diol

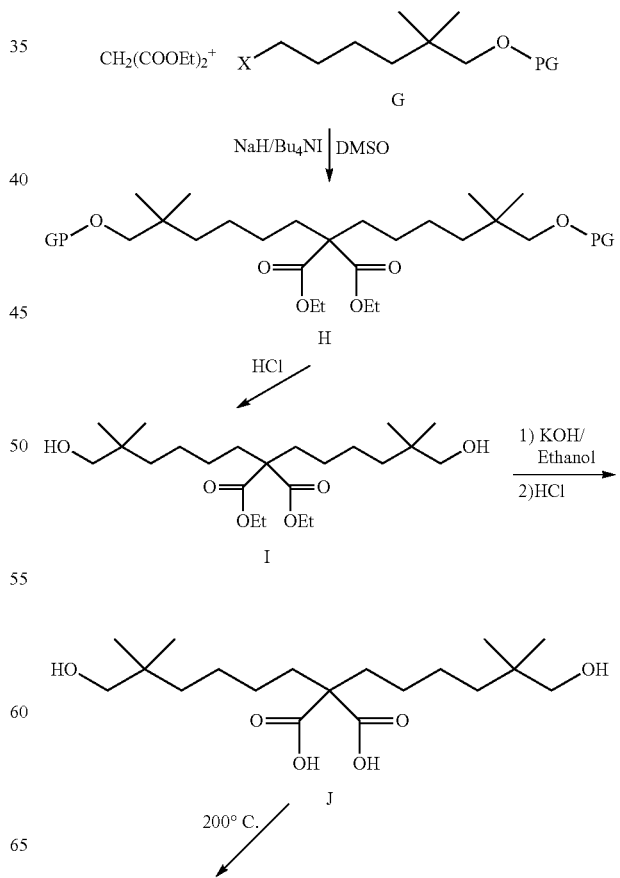

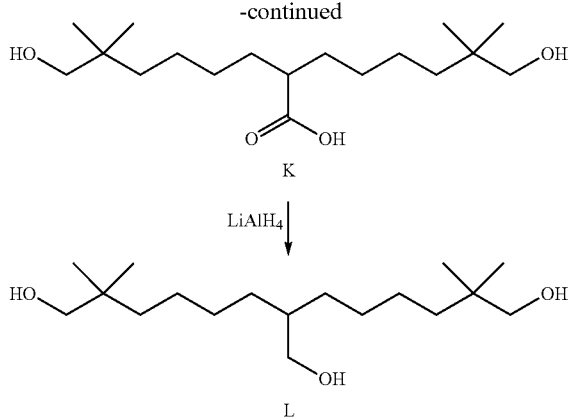

K

LiAlH₄ ↓

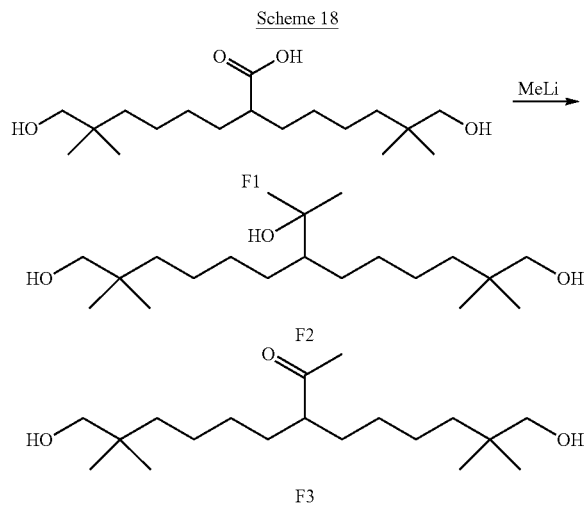

Diethyl malonate and G were treated with NaH/Bu4NI in anhydrous DMSO (as described in Possel, O.; van Leusen, A. M. Tetrahedron Lett. 1977, 18, 4229-4232; Kurosawa, K.; Suenaga, M.; Inazu, T.; Yoshino, T. Tetrahedron Lett. 1982, 23, 5335-5338) at room temperature for 16 h to afford H (99%, crude); this intermediate was hydrolysed in acid conditions (e.g. hydrochloric acid) to give intermediate 1 (for a general description of the method see Vogel's Practical Organic Chemistry, 4th Edition, Longman Inc.: New York 1978, pp. 494). Subsequent hydrolysis of the ester groups in the presence of potassium hydroxide affords intermediate J [for a general method see Vogel's Practical Organic Chemistry, 4th Edition, Longman Inc.: New York 1978, pp 491). Decarboxylation of the above compound is accomplished by heating neat at 200° C. to yield the monoacid intermediate K that is reduced by LiAlH4 in tetrahydrofuran to the target compound L.

Scheme 18

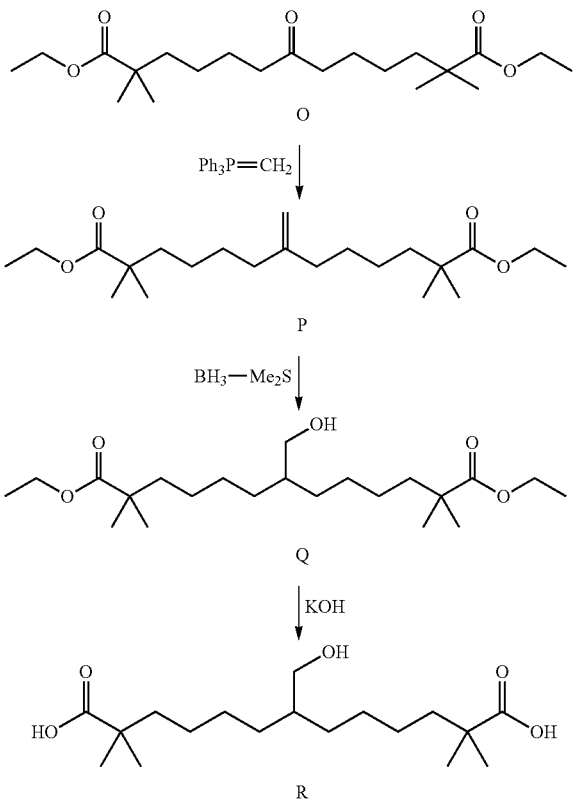

The intermediate F1 synthesized as described above was reacted with methyl lithium to give 7-(1-hydroxy-1-methylethyl)-2,2,12,12-tetramethyl-tridecane-1,13-diol (F2) together with F3. The two compounds were separated by column chromatography.

Compounds of type E are also obtained as described in Scheme 19 by treating the ketones of type M with a Wittig reagent, followed by an anti-Markovnikov addition of water to the marginal double bond thus created or by hydroboration with a Brown reagent.

Scheme 20 presents an example for the above method in the synthesis of 7-hydroxymethyl-2,2,12,12-tetramethyl-tridecanedioic acid (R).

Scheme 19

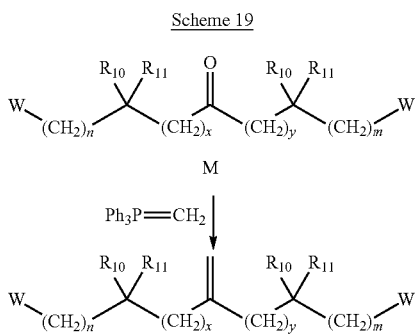

M

Ph₃P=CH₂ ↓

N

BH₃—Me₂S ↓

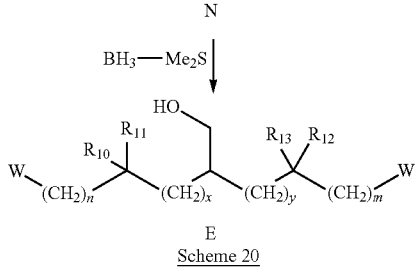

E

Scheme 20

2,2,12,12-Tetramethyl-7-oxo-tridecanedioic acid diethyl ester O (Dasseux and Oniciu, U.S. patent application Ser. No. 09/976,938, Oct. 11, 2001 was treated with Wittig reagent (methyltriphenylphosphonium iodide and phenyllithium) [Leopold, E. J. Organic Syntheses Collective Volume VII, Wiley: New York 1986, pp 258.] to produce P. Compound Q was prepared by treatment of compound P with BH$_3$-Me$_2$S [Dalko, P. I.; Langlois, Y. J. Org. Chem. 1998, 63, 8107]. Other selective hydroboration method for the preparation of primary alcohol Q is performed by treating the alkene with disiamylborane (prepared from diborane and 2-methyl-2-butene in THF at −30° C.) in THF, as reported in Leopold, E. J. Organic Syntheses Collective Volume VII, Wiley: New York 1986, pp 258. Hydrolysis of Q by treatment with KOH in ethanol gave the final compound R [Vogel's Practical Organic Chemistry, 4th Edition, Longman Inc.: New York 1978, pp 492].

5.2 Therapeutic Uses of Compounds or Compositions of the Invention

In accordance with the invention, a compound of the invention or a composition of the invention, comprising a compound of the invention and a pharmaceutically acceptable vehicle, is administered to a patient, preferably a human, with or at risk of aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumaticaifibrositis; infection and arthritis, juvenile rheumatoid arthritis, tendonitis, bursitis and other soft tissue rheumatism. In one embodiment, "treatment" or "treating" refers to an amelioration of a disease or disorder, or at least one discernible symptom thereof. In another embodiment, "treatment" or "treating" refers to inhibiting the progression of a disease or disorder, either physically, e.g., stabilization of a discernible symptom, physiologically, e.g., stabilization of a physical parameter, or both.

In certain embodiments, the compounds of the invention or the compositions of the invention are administered to a patient, preferably a human, as a preventative measure against such diseases. As used herein, "prevention" or "preventing" refers to a reduction of the risk of acquiring a given disease or disorder. In a preferred mode of the embodiment, the compositions of the present invention are administered as a preventative measure to a patient, preferably a human having a genetic predisposition to a aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumaticafibrositis; infection and arthritis, juvenile rheumatoid arthritis, tendonitis, bursitis and other soft tissue rheumatism. Examples of such genetic predispositions include but are not limited to the ε4 allele of apolipoprotein E, which increases the likelihood of Alzheimer's Disease; a loss of function or null mutation in the lipoprotein lipase gene coding region or promoter (e.g., mutations in the coding regions resulting in the substitutions D9N and N291 S; for a review of genetic mutations in the lipoprotein lipase gene that increase the risk of cardiovascular diseases, dyslipidemias and dyslipoproteinemias, see Hayden and Ma, 1992, Mol. Cell Biochem. 113:171-176); and familial combined hyperlipidemia and familial hypercholesterolemia.

In another preferred mode of the embodiment, the compounds of the invention or compositions of the invention are administered as a preventative measure to a patient having a non-genetic predisposition to a aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisorne proliferator activated receptor-associated disorder, phospholipid elimination in bile, renal disease, septicemia, metabolic syndrome disorders (e.g., Syndrome X), a thrombotic disorder, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. Examples of such non-genetic predispositions include but are not limited to cardiac bypass surgery and percutaneous transluminal coronary angioplasty, which often lead to restenosis, an accelerated form of atherosclerosis; diabetes in women, which often leads to polycystic ovarian disease; and cardiovascular disease, which often leads to impotence. Accordingly, the compositions of the invention may be used for the prevention of one disease or disorder and concurrently treating another (e.g., prevention of polycystic ovarian disease while treating diabetes; prevention of impotence while treating a cardiovascular disease).

5.2.1 Treatment of Cardiovascular Diseases

The present invention provides methods for the treatment or prevention of a cardiovascular disease, comprising administering to a patient a therapeutically effective amount of a compound or a composition comprising a compound of the invention and a pharmaceutically acceptable vehicle. As used herein, the term "cardiovascular diseases" refers to diseases of the heart and circulatory system. These diseases are often associated with dyslipoproteinemias and/or dyslipidemias. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity;

peripheral vascular disease; coronary heart disease; myocardial infarction; cerebral infarction and restenosis.

5.2.2 Treatment of Dyslipidemias

The present invention provides methods for the treatment or prevention of a dyslipidemia comprising administering to a patient a therapeutically effective amount of a compound or a composition comprising a compound of the invention and a pharmaceutically acceptable vehicle.

As used herein, the term "dyslipidemias" refers to disorders that lead to or are manifested by aberrant levels of circulating lipids. To the extent that levels of lipids in the blood are too high, the compositions of the invention are administered to a patient to restore normal levels. Normal levels of lipids are reported in medical treatises known to those of skill in the art. For example, recommended blood levels of LDL, HDL, free triglycerides and others parameters relating to lipid metabolism can be found at the web site of the American Heart Association and that of the National Cholesterol Education Program of the National Heart, Lung and Blood Institute (http://wwvw.amnericanheart.org/cholesterol/about_level.html and http://www.nhlbi.nih.gov/health/public/heart/chol/hbc_what.html, respectively). At the present time, the recommended level of HDL cholesterol in the blood is above 35 mg/dL; the recommended level of LDL cholesterol in the blood is below 130 mg/dL; the recommended LDL:HDL cholesterol ratio in the blood is below 5:1, ideally 3.5:1; and the recommended level of free triglycerides in the blood is less than 200 mg/dL.

Dyslipidemias which the compositions of the present invention are useful for preventing or treating include but are not limited to hyperlipidemia and low blood levels of high density lipoprotein (HDL) cholesterol. In certain embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of urea bodies (e.g. β-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, e.g., reducing LDL in the blood of a patient, reducing free triglycerides in the blood of a patient, increasing the ratio of HDL to LDL in the blood of a patient, and inhibiting saponified and/or non-saponified fatty acid synthesis, said methods comprising administering to the patient a compound or a composition comprising a compound of the invention in an amount effective alter lipid metabolism.

5.2.3 Treatment of Dysliporoteinemias

The present invention provides methods for the treatment or prevention of a dyslipoproteinemia comprising administering to a patient a therapeutically effective amount of a compound or a composition comprising a compound of the invention and a pharmaceutically acceptable vehicle.

As used herein, the term "dyslipoproteinemias" refers to disorders that lead to or are manifested by aberrant levels of circulating lipoproteins. To the extent that levels of lipoproteins in the blood are too high, the compositions of the invention are administered to a patient to restore normal levels. Conversely, to the extent that levels of lipoproteins in the blood are too low, the compositions of the invention are administered to a patient to restore normal levels. Normal levels of lipoproteins are reported in medical treatises known to those of skill in the art.

Dyslipoproteinemias which the compositions of the present invention are useful for preventing or treating include but are not limited to high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes; lipoprotein abnormalities associated with obesity; lipoprotein abnormalities associated with Alzheimer's Disease; and familial combined hyperlipidemia.

The present invention further provides methods for reducing apo C-II levels in the blood of a patient; reducing apo C-III levels in the blood of a patient; elevating the levels of HDL associated proteins, including but not limited to apo A-I, apo A-II, apo A-IV and apo E in the blood of a patient; elevating the levels of apo E in the blood of a patient, and promoting clearance of triglycerides from the blood of a patient, said methods comprising administering to the patient a compound or a composition comprising a compound of the invention in an amount effective to bring about said reduction, elevation or promotion, respectively.

5.2.4 Treatment of Glucose Metabolism Disorders

The present invention provides methods for the treatment or prevention of a glucose metabolism disorder, comprising administering to a patient a therapeutically effective amount of a compound or a composition comprising a compound of the invention and a pharmaceutically acceptable vehicle. As used herein, the term "glucose metabolism disorders" refers to disorders that lead to or are manifested by aberrant glucose storage and/or utilization. To the extent that indicia of glucose metabolism (i.e., blood insulin, blood glucose) are too high, the compositions of the invention are administered to a patient to restore normal levels. Conversely, to the extent that indicia of glucose metabolism are too low, the compositions of the invention are administered to a patient to restore normal levels. Normal indicia of glucose metabolism are reported in medical treatises known to those of skill in the art.

Glucose metabolism disorders which the compositions of the present invention are useful for preventing or treating include but are not limited to impaired glucose tolerance; insulin resistance; insulin resistance related breast, colon or prostate cancer; diabetes, including but not limited to non-insulin dependent diabetes mellitus (NIDDM), insulin dependent diabetes mellitus (IDDM), gestational diabetes mellitus (GDM), and maturity onset diabetes of the young (MODY); pancreatitis; hypertension; polycystic ovarian disease; and high levels of blood insulin and/or glucose.

The present invention further provides methods for altering glucose metabolism in a patient, for example to increase insulin sensitivity and/or oxygen consumption of a patient, said methods comprising administering to the patient a compound or a composition comprising a compound of the invention in an amount effective to alter glucose metabolism.

5.2.5 Treatment of PPAR-Associated Disorders

The present invention provides methods for the treatment or prevention of a PPAR-associated disorder, comprising administering to a patient a therapeutically effective amount of a compound or a composition comprising a compound of the invention and a pharmaceutically acceptable vehicle. As used herein, "treatment or prevention of PPAR associated disorders" encompasses treatment or prevention of rheumatoid arthritis; multiple sclerosis; psoriasis; inflammatory bowel diseases; breast; colon or prostate cancer; low levels of blood HDL; low levels of blood, lymph and/or cerebrospinal fluid apo E; low blood, lymph and/or cerebrospinal fluid levels of apo A-I; high levels of blood VLDL; high levels of blood LDL; high levels of blood triglyceride; high levels of blood apo B; high levels of blood apo C-III and reduced ratio of post-heparin hepatic lipase to lipoprotein lipase activity. HDL may be elevated in lymph and/or cerebral fluid.

5.2.6 Treatment of Renal Diseases

The present invention provides methods for the treatment or prevention of a renal disease, comprising administering to a patient a therapeutically effective amount of a compound or a composition comprising a compound of the invention and a pharmaceutically acceptable vehicle. Renal diseases that can be treated by the compounds of the present invention include glomerular diseases (including but not limited to acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (including but not limited to acute tubular necrosis and acute renal failure, polycystic renal disease-medullary sponge kidney, medullary cystic disease, nephrogenic diabetes, and renal tubular acidosis), tubulointerstitial diseases (including but not limited to pyelonephritis, drug and toxin induced tubulointerstitial nephritis, hypercalcemic nephropathy, and hypokalemic nephropathy) acute and rapidly progressive renal failure, chronic renal failure, nephrolithiasis, or tumors (including but not limited to renal cell carcinoma and nephroblastoma). In a most preferred embodiment, renal diseases that are treated by the compounds of the present invention are vascular diseases, including but not limited to hypertension, nephrosclerosis, microangiopathic hemolytic anemia, atheroembolic renal disease, diffuse cortical necrosis, and renal infarcts.

5.2.7 Treatment of Cancer

The present invention provides methods for the treatment or prevention of cancer, comprising administering to a patient a therapeutically effective amount of a compound or a composition comprising a compound of the invention and a pharmaceutically acceptable vehicle. Types of cancer that can be treated using a Compound of the Invention include, but are not limited to, those listed in Table 2.

TABLE 2

| Solid tumors, including but not limited to |
|---|
| fibrosarcoma |
| myxosarcoma |
| liposarcoma |
| chondrosarcoma |
| osteogenic sarcoma |
| chordoma |
| angiosarcoma |
| endotheliosarcoma |
| lymphangiosarcoma |
| lymphangioendotheliosarcoma |
| synovioma |
| mesothelioma |
| Ewing's tumor |
| leiomyosarcoma |
| rhabdomyosarcoma |
| colon cancer |
| colorectal cancer |
| kidney cancer |
| pancreatic cancer |
| bone cancer |
| breast cancer |
| ovarian cancer |
| prostate cancer |
| esophogeal cancer |
| stomach cancer |
| oral cancer |
| nasal cancer |
| throat cancer |
| squamous cell carcinoma |
| basal cell carcinoma |
| adenocarcinoma |
| sweat gland carcinoma |
| sebaceous gland carcinoma |
| papillary carcinoma |
| papillary adenocarcinomas |
| cystadenocarcinoma |
| medullary carcinoma |
| bronchogenic carcinoma |
| renal cell carcinoma |
| hepatoma |
| bile duct carcinoma |
| choriocarcinoma |
| seminoma |
| embryonal carcinoma |
| Wilms' tumor |
| cervical cancer |
| uterine cancer |
| testicular cancer |
| small cell lung carcinoma |
| bladder carcinoma |
| lung cancer |
| epithelial carcinoma |
| glioma |
| glioblastoma multiforme |
| astrocytoma |
| medulloblastoma |
| craniopharyngioma |
| ependymoma |
| pinealoma |
| hemangioblastoma |
| acoustic neuroma |
| oligodendroglioma |
| meningioma |
| skin cancer |
| melanoma |
| neuroblastoma |
| retinoblastoma |
| Blood-borne cancers, including but not limited to: |
| acute lymphoblastic B-cell leukemia |
| acute lymphoblastic T-cell leukemia |
| acute myeloblastic leukemia "AML" |
| acute promyelocytic leukemia "APL" |
| acute monoblastic leukemia |
| acute erythroleukemic leukemia |
| acute megakaryoblastic leukemia |
| acute myelomonocytic leukemia |
| acute nonlymphocytic leukemia |
| acute undifferentiated leukemia |
| chronic myelocytic leukemia "CML" |
| chronic lymphocytic leukemia "CLL" |
| hairy cell leukemia |

TABLE 2-continued multiple myeloma
Acute and chronic leukemias
Lymphoblastic
myelogenous
lymphocytic
myelocytic leukemias
Lymphomas:
Hodgkin's disease
non-Hodgkin's Lymphoma
Multiple myeloma
Waldenström's macroglobulinemia
Heavy chain disease
Polycythemia vera Cancer, including, but not limited to, a tumor, metastasis, or any disease or disorder characterized by uncontrolled cell growth, can be treated or prevented by administration of a Compound of the Invention.

5.2.8 Treatment of Other Diseases

The present invention provides methods for the treatment or prevention of Alzheimer's Disease, Syndrome X, septicemia, thrombotic disorders, obesity, pancreatitis, hypertension, inflammation, and impotence, comprising administering to a patient a therapeutically effective amount of a compound or a composition comprising a compound of the invention and a pharmaceutically acceptable vehicle.

As used herein, "treatment or prevention of Alzheimer's Disease" encompasses treatment or prevention of lipoprotein abnormalities associated with Alzheimer's Disease.

As used herein, "treatment or prevention of Syndrome X or Metabolic Syndrome" encompasses treatment or prevention of a symptom thereof, including but not limited to impaired glucose tolerance, hypertension and dyslipidemia/dyslipoproteinemia.

As used herein, "treatment or prevention of septicemia" encompasses treatment or prevention of septic shock.

As used herein, "treatment or prevention of thrombotic disorders" encompasses treatment or prevention of high blood levels of fibrinogen and promotion of fibrinolysis.

In addition to treating or preventing obesity, the compositions of the invention can be administered to an individual to promote weight reduction of the individual.

As used herein, "treatment or prevention of diabetic nephropathy" encompasses treating or preventing kidney disease that develops as a result of diabetes mellitus (DM). Diabetes mellitus is a disorder in which the body is unable to metabolize carbohydrates (e.g., food starches, sugars, cellulose) properly. The disease is characterized by excessive amounts of sugar in the blood (hyperglycemia) and urine; inadequate production and/or utilization of insulin; and by thirst, hunger, and loss of weight. Thus, the compounds of the invention can also be used to treat or prevent diabetes mellitus.

As used herein, "treatment or prevention of diabetic retinopathy" encompasses treating or preventing complications of diabetes that lead to or cause blindness. Diabetic retinopathy occurs when diabetes damages the tiny blood vessels inside the retina, the light-sensitive tissue at the back of the eye.

As used herein, "treatment or prevention of impotence" includes treating or preventing erectile dysfunction, which encompasses the repeated inability to get or keep an erection firm enough for sexual intercourse. The word "impotence" may also be used to describe other problems that interfere with sexual intercourse and reproduction, such as lack of sexual desire and problems with ejaculation or orgasm. The term "treatment or prevention of impotence includes, but is not limited to impotence that results as a result of damage to nerves, arteries, smooth muscles, and fibrous tissues, or as a result of disease, such as, but not limited to, diabetes, kidney disease, chronic alcoholism, multiple sclerosis, atherosclerosis, vascular disease, and neurologic disease.

As used herein, "treatment or prevention of hypertension" encompasses treating or preventing blood flow through the vessels at a greater than normal force, which strains the heart; harms the arteries; and increases the risk of heart attack, stroke, and kidney problems. The term hypertension includes, but is not limited to, cardiovascular disease, essential hypertension, hyperpiesia, hyperpiesis, malignant hypertension, secondary hypertension, or white-coat hypertension.

As used herein, "treatment or prevention of inflammation" encompasses treating or preventing inflammation diseases including, but not limited to, chronic inflammatory disorders of the joints including arthritis, e.g., rheumatoid arthritis and osteoarthritis; respiratory distress syndrome, inflammatory bowel diseases such as ileitis, ulcerative colitis and Crohn's disease; and inflammatory lung disorders such as asthma and chronic obstructive airway disease, inflammatory disorders of the eye such as corneal dystrophy, trachoma, onchocerciasis, uveitis, sympathetic ophthalmitis, and endophthalmitis; inflammatory disorders of the gum, e.g., periodontitis and gingivitis; tuberculosis; leprosy; inflammatory diseases of the kidney including glomerulonephritis and nephrosis; inflammatory disorders of the skin including acne, scierodermatitis, psoriasis, eczema, photoaging and wrinkles; inflammatory diseases of the central nervous system, including AIDS-related neurodegeneration, stroke, neurotrauma, Alzheimer's disease, encephalomyelitis and viral or autoimmune encephalitis; autoinmmnune diseases including immune-complex vasculitis, systemic lupus and erythematodes; systemic lupus erythematosus (SLE); and inflammatory diseases of the heart such as cardiomyopathy.

5.3 Combination Therapy

In certain embodiments of the present invention, the compounds and compositions of the invention can be used in combination therapy with at least one other therapeutic agent. The compound of the invention and the therapeutic agent can act additively or, more preferably, synergistically. In a preferred embodiment, a composition or a composition comprising a compound of the invention is administered concurrently with the administration of another therapeutic agent, which can be part of the same composition as the compound of the invention or a different composition. In another embodiment, a compound or a composition comprising a compound of the invention is administered prior or subsequent to administration of another therapeutic agent. As many of the disorders for which the compounds and compositions of the invention are useful in treating are chronic disorders, in one embodiment combination therapy involves alternating between administering a compound or a composition comprising a compound of the invention and a composition comprising another therapeutic agent, e.g., to minimize the toxicity associated with a particular drug. The duration of administration of each drug or therapeutic agent can be, e.g., one month, three months, six months, or a year. In certain embodiments, when a composition of the invention is administered concurrently with another therapeutic agent that potentially produces adverse side effects including but not limited to toxicity, the therapeutic agent can advantageously be administered at a dose that falls below the threshold at which the adverse side is elicited.

The present compositions can be administered together with a statin. Statins for use in combination with the compounds and compositions of the invention include but are not limited to atorvastatin, pravastatin, fluvastatin, lovastatin, simvastatin, and cerivastatin.

The present compositions can also be administered together with a PPAR agonist, for example a thiazolidinedione or a fibrate. Thiazolidinediones for use in combination with the compounds and compositions of the invention include but are not limited to 5 ((4 (2 (methyl 2 pyridinylamino)ethoxy)phenyl)methyl) 2,4 thiazolidinedione, troglitazone, pioglitazone, ciglitazone, WAY 120,744, englitazone, AD 5075; darglitazone, and rosiglitazone. Fibrates for use in combination with the compounds and compositions of the invention include but are not limited to gemrfibrozil, fenofibrate, clofibrate, or ciprofibrate. As mentioned previously, a therapeutically effective amount of a fibrate or thiazolidinedione often has toxic side effects. Accordingly, in a preferred embodiment of the present invention, when a composition of the invention is administered in combination with a PPAR agonist, the dosage of the PPAR agonist is below that which is accompanied by toxic side effects.

The present compositions can also be administered together with a bile acid binding resin. Bile acid binding resins for use in combination with the compounds and compositions of the invention include but are not limited to cholestyramine and colestipol hydrochloride. The present compositions can also be administered together with niacin or nicotinic acid. The present compositions can also be administered together with a RXR agonist. RXR agonists for use in combination with the compounds of the invention include but are not limited to LG 100268, LGD 1069, 9-cis retinoic acid, 2 (1 (3,5,5,8,8 pentamethyl 5,6,7,8 tetrahydro 2 naphthyl) cyclopropyl) pyridine 5 carboxylic acid, or 4 ((3,5,5,8,8 pentamethyl 5,6,7,8 tetrahydro 2 naphthyl)2 carbonyl) benzoic acid. The present compositions can also be administered together with an anti-obesity drug. Anti-obesity drugs for use in combination with the compounds of the invention include but are not limited to β-adrenergic receptor agonists, preferably β-3 receptor agonists, fenfluramine, dexfenfluramine, sibutramine, bupropion, fluoxetine, and phentermine. The present compositions can also be administered together with a hormone. Hormones for use in combination with the compounds of the invention include but are not limited to thyroid hormone, estrogen and insulin. Preferred insulins include but are not limited to injectable insulin, transdermal insulin, inhaled insulin, or any combination thereof. As an alternative to insulin, an insulin derivative, secretagogue, sensitizer or mimetic may be used. Insulin secretagogues for use in combination with the compounds of the invention include but are not limited to forskolin, dibutryl cAMP or isobutylmethylxanthine (IBMX).

The present compositions can also be administered together with a phosphodiesterase type 5 ("PDE5") inhibitor to treat or prevent disorders, such as but not limited to, impotence. In a particular, embodiment the combination is a synergistic combination of a composition of the invention and a PDE5 inhibitor.

The present compositions can also be administered together with a tyrophostine or an analog thereof. Tyrophostines for use in combination with the compounds of the invention include but are not limited to tryophostine 51.

The present compositions can also be administered together with sulfonylurea-based drugs. Sulfonylurea-based drugs for use in combination with the compounds of the invention include, but are not limited to, glisoxepid, glyburide, acetohexamide, chlorpropamide, glibornuride, tolbutamide, tolazamide, glipizide, gliclazide, gliquidone, glyhexamide, phenbutanide, and tolcyclamide. The present compositions can also be administered together with a biguanide. Biguanides for use in combination with the compounds of the invention include but are not limited to metformin, phenformin and buformin.

The present compositions can also be administered together with an a-glucosidase inhibitor. α-glucosidase inhibitors for use in combination with the compounds of the invention include but are not limited to acarbose and miglitol.

The present compositions can also be administered together with an apo A-I agonist. In one embodiment, the apo A-I agonist is the Milano form of apo A-I (apo A-IM). In a preferred mode of the embodiment, the apo A-IM for administration in conjunction with the compounds of the invention is produced by the method of U.S. Pat. No. 5,721,114 to Abrahamsen. In a more preferred embodiment, the apo A-I agonist is a peptide agonist. In a preferred mode of the embodiment, the apo A-I peptide agonist for administration in conjunction with the compounds of the invention is a peptide of U.S. Pat. No. 6,004,925 or 6,037,323 to Dasseux.

The present compositions can also be administered together with apolipoprotein E (apo E). In a preferred mode of the embodiment, the apoE for administration in conjunction with the compounds of the invention is produced by the method of U.S. Pat. No. 5,834,596 to Ageland.

In yet other embodiments, the present compositions can be administered together with an H-IDL-raising drug; an HDL enhancer; or a regulator of the apolipoprotein A-I, apolipoprotein A-IV and/or apolipoprotein genes.

In one embodiment, the other therapeutic agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethyiperazine, thioproperazine and tropisetron.

In another embodiment, the other therapeutic agent can be an hematopoietic colony stimulating factor. Suitable hematopoietic colony stimulating factors include, but are not limited to, filgrastim, sargramostim, molgramostim and erythropoietin alfa.

In still another embodiment, the other therapeutic agent can be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketopen, ketoprofen, indomethacin, ketorolac, meclofenamate, mefanamic acid, naburnetone, naproxen, piroxicari and sulindac.

5.3.1 Combination Therapy of Cardiovascular Diseases

The present compositions can be administered together with a known cardiovascular drug. Cardiovascular drugs for use in combination with the compounds of the invention to prevent or treat cardiovascular diseases include but are not limited to peripheral antiadrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., amrinone, milrinone, enoximone, fenoximone, imazodan, sulmrazole), antidysrhythmnic drugs, calcium entry blockers, ranitine, bosentan, and rezulin.

5.3.2 Combination Therapy of Cancer

The present invention includes methods for treating cancer, comprising administering to an animal in need thereof an effective amount of a Compound of the Invention and another therapeutic agent that is an anti-cancer agent. Suitable anticancer agents include, but are not limited to, those listed in Table 3.

TABLE 3

| Alkylating agents | |
|---|---|
| Nitrogen mustards: | Cyclophosphamide |
|  | Ifosfamide |
|  | trofosfamide |
|  | Chlorambucil |
|  | Treos |
| Nitrosoureas: | carbustine (BCNU) |
|  | Lomustine (CCNU) |
| Alkylsulphonates | Busulfan |
|  | Treosulfan |
| Triazenes: | Dacarbazine |
| Platinum containing compounds: | Cisplatin |
|  | carboplatin |
| Plant Alkaloids | |
| Vinca alkaloids: | Vicristine |
|  | Vinblastine |
|  | Vindesine |
|  | Vinorelbine |
| Taxoids: | paclitaxel |
|  | Docetaxol |
| DNA Topoisomerase Inhibitors | |
| Epipodophyllins: | Etoposide |
|  | Teniposide |
|  | Topotecan |
|  | 9-aminocamptothecin |
|  | camptothecin |
|  | crisnatol |
| mitomycins: | Mitomycin C |
| Anti-metabolites | |
| Anti-folates: | |
| DHFR inhibitors: | METHOTREXATE |
|  | Trimetrexate |
| IMP dehydrogenase Inhibitors: | Mycophenolic acid |
|  | Tiazofurin |
|  | Ribavirin |
|  | EICAR |
| Ribonucleotide reductase Inhibitors: | Hydroxyurea |
|  | deferoxamine |

TABLE 3-continued

| Pyrimidine analogs: | |
|---|---|
| Uracil analogs | 5-Fluorouracil |
|  | Floxuridine |
|  | Doxifluridine |
|  | Ratitrexed |
| Cytosine analogs | cytarabine (ara C) |
|  | Cytosine arabinoside |
|  | fludarabine |
| Purine analogs: | mercaptopurine |
|  | Thioguanine |
| Hormonal therapies: | |
| Receptor antagonists: | |
| Anti-estrogen | Tamoxifen |
|  | Raloxifene |
|  | megestrol |
|  | goscrclin |
|  | Leuprolide acetate |
| LHRH agonists: | flutamide |
|  | bicalutamide |
| Retinoids/Deltoids | |
| Vitamin D3 analogs: | EB 1089 |
|  | CB 1093 |
|  | KH 1060 |
| Photodynamic therapies: | vertoporfin (BPD-MA) |
|  | Phthalocyanine |
|  | photosensitizer Pc4 |
|  | Demethoxy-hypocrellin A |
|  | (2BA-2-DMHA) |
| Cytokines: | Interferon-α |
|  | Interferon-γ |
|  | Tumor necrosis factor |
| Others: | |
| Isoprenylation inhibitors: | Lovastatin |
| Dopaminergic neurotoxins: | 1-methyl-4-phenylpyridinium ion |
| Cell cycle inhibitors: | staurosporine |
| Actinomycines: | Actinomycin D |
|  | Dactinomycin |
| Bleomycins: | bleomycin A2 |
|  | Bleomycin B2 |
|  | Peplomycin |
| Anthracyclines: | daunorubicin |
|  | Doxorubicin (adriamycin) |
|  | Idarubicin |
|  | Epirubicin |
|  | Pirarubicin |
|  | Zorubicin |
|  | Mitoxantrone |
| MDR inhibitors | verapamil |
| $Ca^{2+}$ ATPase inhibitors: | thapsigargin |

In a specific embodiment, a composition of the invention further comprises one or more chemotherapeutic agents and/or is administered concurrently with radiation therapy. In another specific embodiment, chemotherapy or radiation therapy is administered prior or subsequent to administration of a present composition, preferably at least an hour, five hours, 12 hours, a day, a week, a month, more preferably several months (e.g., up to three months), subsequent to administration of a composition of the invention.

In other embodiments, the invention provides methods for treating or preventing cancer, comprising administering to an animal in need thereof an effective amount of a Compound of the Invention and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Compounds of the Invention can be administered to an animal that has also undergone surgery as treatment for the cancer.

In one embodiment, the additional method of treatment is radiation therapy.

In a specific embodiment, the Compound of the Invention is administered concurrently with the chemotherapeutic agent or with radiation therapy. In another specific embodiment, the chemotherapeutic agent or radiation therapy is administered prior or subsequent to administration of a Compound of the Invention, preferably at least an hour, five hours, 12 hours, a day, a week, a month, more preferably several months (e.g., up to three months), prior or subsequent to administration of a Compound of the Invention.

A chemotherapeutic agent can be administered over a series of sessions, any one or a combination of the chemotherapeutic agents listed in Table 3 can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, the invention provides methods of treatment of cancer with a Compound of the Invention as an alternative to chemotherapy or radiation therapy where the chemotherapy or the radiation therapy has proven or can prove too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

The Compounds of the Invention can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the patient's remaining bone-marrow cell population is then eradicated via the administration of a high dose of a Compound of the Invention with or without accompanying high dose radiation therapy, and the stem cell graft is infused back into the animal. Supportive care is then provided while bone marrow function is restored and the animal recovers.

5.4 Surgical Uses

Cardiovascular diseases such as atherosclerosis often require surgical procedures such as angioplasty. Angioplasty is often accompanied by the placement of a reinforcing a metallic tube shaped structure known as a "stent" into a damaged coronary artery. For more serious conditions, open heart surgery such as coronary bypass surgery may be required. These surgical procedures entail using invasive surgical devices and/or implants, and are associated with a high risk of restenosis and thrombosis. Accordingly, the compounds and compositions of the invention may be used as coatings on surgical devices (e.g., catheters) and implants (e.g., stents) to reduce the risk of restenosis and thrombosis associated with invasive procedures used in the treatment of cardiovascular diseases.

5.5 Veterinary and Livestock Uses

A composition of the invention can be administered to a non-human animal for a veterinary use for treating or preventing a disease or disorder disclosed herein.

In a specific embodiment, the non-human animal is a household pet. In another specific embodiment, the non-human animal is a livestock animal. In a preferred embodiment, the non-human animal is a mammal, most preferably a cow, horse, sheep, pig, cat, dog, mouse, rat, rabbit, or guinea pig. In another preferred embodiment, the non-human animal is a fowl species, most preferably a chicken, turkey, duck, goose, or quail.

In addition to veterinary uses, the compounds and compositions of the invention can be used to reduce the fat content of livestock to produce leaner meats. Alternatively, the compounds and compositions of the invention can be used to reduce the cholesterol content of eggs by administering the compounds to a chicken, quail, or duck hen. For non-human animal uses, the compounds and compositions of the invention can be administered via the animals' feed or orally as a drench composition.

5.6 Therapeutic/Prophylactic Administration and Compositions

Due to the activity of the compounds and compositions of the invention, they are useful in veterinary and human medicine. As described above, the compounds and compositions of the invention are useful for the treatment or prevention of aging, Alzheimer's Disease, cancer, cardiovascular disease, diabetic nephropathy, diabetic retinopathy, a disorder of glucose metabolism, dyslipidernia, dyslipoproteinemia, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, enhancing bile production, enhancing reverse lipid transport, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism.

The invention provides methods of treatment and prophylaxis by administration to a patient of a therapeutically effective amount of a compound or a composition comprising a compound of the invention. The patient is an animal, including, but not limited, to an animal such a cow, horse, sheep, pig, chicken, turkey, quail, cat, dog, mouse, rat, rabbit, guinea pig, etc., and is more preferably a mammal, and most preferably a human.

The compounds and compositions of the invention, are preferably administered orally. The compounds and compositions of the invention may also be administered by any other convenient route, for example, by intravenous infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

In certain embodiments, for example, for the treatment of Alzheimer's Disease, it may be desirable to introduce one or more compounds of the invention into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds and compositions of the invention can be delivered in a vesicle, in particular a liposome (see Langer, 1990, Science 249:1527 1533; Treat et al., in Liposomes in the Therapy of Infectious Disease and Cancer, Lopez-Berestein and Fidler (eds.), Liss, New York, pp. 353 365 (1989); Lopez Berestein, ibid., pp. 317 327; see generally ibid.).

In yet another embodiment, the compounds and compositions of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of the target area to be treated, e.g., the liver, thus requiring only a fraction of the systemic dose (see, e.g., Goodson, in Medical Applications of Controlled Release, supra, vol. 2, pp. 115 138 (1984)). Other controlled-release systems discussed in the review by Langer, 1990, Science 249:1527 1533) may be used.

The present compositions will contain a therapeutically effective amount of a compound of the invention, optionally more than one compound of the invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds and compositions of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin.

In a preferred embodiment, the compounds and compositions of the invention are formulated in accordance with routine procedures as a pharmaceutical composition adapted for intravenous administration to human beings. Typically, compounds and compositions of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by intravenous infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compounds and compositions of the invention for oral delivery may be in the form of tablets, lozenges, aqueous or oily suspensions, granules, powders, emulsions, capsules, syrups, or elixirs. Compounds and compositions of the invention for oral delivery can also be formulated in foods and food mixes. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds and compositions of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 2000 milligrams of a compound of the invention per kilogram body weight. In specific preferred embodiments of the invention, the oral dose is 0.01 milligram to 1000 milligrams per kilogram body weight, more preferably 0.1 milligram to 100 milligrams per kilogram body weight, more preferably 0.5 milligram to 25 milligrams per kilogram body weight, and yet more preferably 1 milligram to 10 milligrams per kilogram body weight. In a most preferred embodiment, the oral dose is 5 milligrams of a compound of the invention per kilogram body weight. The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

Suitable dosage ranges for intravenous (i.v.) administration are 0.01 milligram to 1000 milligrams per kilogram body weight, 0.1 milligram to 350 milligrams per kilogram body weight, and 1 milligram to 100 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. In another embodiment, the kit comprises a compound of the invention and another lipid-mediating compound, including but not limited to a statin, a thiazolidinedione, or a fibrate.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for lowering fatty acid synthesis. The compounds and compositions of the invention may also be demonstrated to be effective and safe using animal model systems.

Other methods will be known to the skilled artisan and are within the scope of the invention.

The following examples are provided by way of illustration and not limitation.

6. SYNTHETIC EXAMPLES

6.1 2,2,12,12-Tetramethyltridecane-1,7,13-triol

Under nitrogen atmosphere, to a suspension of lithium borohydride (2.65 g, 122 mmol) in dichloromethane (60 mL) was added methanol (4.0 g, 125 mmol) dropwise at room temperature over 30 min. The reaction mixture was heated at reflux and 2,2,12,12-tetramethyl-7-oxo-tridecane-dioic acid diethyl ester (10.0 g, 27 mmol) was introduced. Heating at reflux temperature was continued overnight. The reaction mixture was cooled to room temperature and hydrolyzed with saturated ammonium chloride solution (100 mL). The layers were separated and the aqueous layer was extracted with dichloromethane (3×50 mL). The combined organic layers were washed with 2 N hydrochloric acid (100 mL) and saturated sodium chloride solution (100 mL), dried over anhydrous sodium sulfate and concentrated in vacuo to afford the crude product. The crude compound was purified by chromatography on silica (hexanes:ethyl acetate=40:60) to yield the pure product (5.8 g, 74%) as a white solid. M.p.: 72-74° C. $^1$H NMR (300 MHz, CDCl$_3$/TMS): δ (ppm): 3.58 (br. m, 1H), 3.30 (s, 4H), 1.80-1.64 (m, 3H), 1.56-1.15 (m, 16H), 0.86 (s, 12H). $^{13}$C NMR (75 MHz, CDCl$_3$/TMS): δ (ppm): 71.87, 71.72, 38.71, 37.46, 35.11, 26.66, 24.18, 24.05, 23.97. HRMS (LSIMS, gly): Calcd. for C$_{17}$H$_{37}$O$_3$ (MH+): 289.2743, found: 289.2756. HPLC: 90.6% purity.

6.2 2,2-Bis[5,5-dimethyl-6-(tetrahydropyran-2-yloxy)-hexyl]malonic Acid Diethyl Ester Under nitrogen atmosphere, to a solution of 2-(6-bromo-2,2-dimethylhexyloxy)-tetrahydropyran (17.6 g, 60 mmol) and diethyl malonate (4.8 g, 30 mmol) in anhydrous dimethyl sulfoxide (145 mL) was added sodium hydride (60% dispersion in mineral oil, 2.9 g, 72 mmol) under cooling with a water bath. Tetra-n-butylammonium iodide (2.1 g, 3.6 mmol) was added and the mixture was stirred for 16 hi at room temperature. The reaction mixture was carefully hydrolyzed with water (140 mL) under cooling with a water bath. The mixture was extracted with diethyl ether (3'60 mL). The combined organic layers were washed with water (4×50 mL) and brine (50 mL), dried over sodium sulfate, and concentrated in vacuo, affording 2,2-bis[5,5-dimethyl-6-(tetrahydropyran-2-yloxy)-hexyl]malonic acid diethyl ester (17.3 g, 82%) as an oil. $^1$H NMR (300 MHz, CDCl$_3$/TMS): δ (ppm): 4.41 (t, 2H, J=3.1 Hz), 4.01 (q, 4H, J=7.0 Hz), 3.82-3.70 (m, 2H), 3.50-3.30 (m, 4H), 2.87 (d, 2H, J=9.1 Hz), 1.80-1.35 (m, 16H), 1.30-0.95 (m, 18H), 0.88-0.74 (min, 12H). $^{13}$C NMR (75 MHz, CDCl$_3$/TMS): δ (ppm): 172.0, 99.1, 76.6, 61.9, 60.9, 57.6, 39.2, 34.3, 32.3, 30.7, 25.7, 25.0, 24.6, 24.6, 24.3, 19.5, 14.2.

6.3 2,2-Bis(6-hydroxy-5,5-dimethylhexyl)malonic Acid Diethyl Ester

A solution of 2,2-bis[5,5-dimethyl-6-(tetrahydropyran-2-yloxy)-hexyl]malonic acid diethyl ester (2.92 g, 5.0 mmol) in concentrated hydrochloric acid (2.4 mL) and water (1.6 mL) was heated at reflux for 1 h. Ethanol (8.2 mL) was added and the reaction mixture was heated at reflux for 3 h. The reaction mixture was diluted with water (20 mL) and extracted with diethyl ether (3×20 mL). The combined organic layers were washed with water (20 mL) and brine (20 mL), dried over sodium sulfate, and concentrated in vacuo to afford 2,2-bis(6-hydroxy-5,5-dimethylhexyl)malonic acid diethyl ester (1.74 g, 84%) as an oil. $^1$H NMR (300 MHz, CDCl$_3$/TMS): δ (ppm): 4.13 (q, 4H, J=7.2 Hz), 3.25 (s, 4H), 2.42 (s, 2H), 1.90-1.75 (m, 4H), 1.30-1.12 (m, 18H), 0.84 (s, 12H). 13C NMR (75 MHz, CDCl$_3$/TMS): δ (ppm): 172.0, 71.7, 60.9, 57.4, 38.2, 34.9, 32.1, 24.8, 24.0, 23.7, 14.0. HRMS (LSIMS, gly): Calcd. for C$_{23}$H$_{45}$O$_6$ (MH+): 417.3216, found: 417.3210.

6.4 2,2-Bis(6-hydroxy-5,5-dimethyl)hexyl)malonic Acid

To a stirred solution of potassium hydroxide (4.83 g, 75 mmol) in water (4.2 mL) and ethanol (15 mL) was added 2,2-bis(6-hydroxy-5,5-dimethylhexyl)malonic acid diethyl ester (15.0 g). The reaction mixture was heated at reflux for 14 h. The ethanol was removed under reduced pressure and the aqueous solution was extracted with chloroform (2×50 mL). The aqueous layer was acidified with hydrochloric acid to pH 1 and extracted with diethyl ether (3×50 mL). The ethereal phases were dried over magnesium sulfate and concentrated in vacuo to yield 2,2-bis(6-hydroxy-5,5-dimethylhexyl)malonic acid (7.8 g, 82%) as a yellow solid. M.P.: 178-180° C. $^1$H NMR (300 MHz, CD$_3$OD/TMS): δ (ppm): 4.86 (s br., 4H), 3.22 (s, 4H), 1.9-1.8 (m, 4H), 1.36-1.10 (m, 12H), 0.84 (s, 12H). $^{13}$C NMR (75 MHz, CD$_3$OD/TMS): δ (ppm): 176.0, 72.0, 58.7, 39.8, 36.0, 34.1, 26.5, 25.5, 24.5. HRMS (LSIMS, gly): Calcd. for C$_{19}$H$_{37}$O$_6$ (MH+): 361.2590, found: 361.2582.

6.5 8-Hydroxy-2-(6-hydroxy-5,5-dimethylhexyl)-7,7-dimethyloctanoic Acid

Using an oil-bath, 2,2-bis(6-hydroxy-5,5-dimethylhexyl) malonic acid was heated to 200° C. for 30 min until the effervescence ceased. The product (4.04 g, 98%) was obtained as an oil. $^1$H NMR (300 MHz, CD$_3$OD/TMS): δ (ppm): 4.88 (s br., 3H), 3.22 (s, 4H), 2.29 (m, 1H), 1.70-1.40 (m, 4H), 1.4-1.1 (m, 12H), 0.84 (s, 12H). $^{13}$C NMR (75 MHz, CD$_3$OD/TMS): δ (ppm): 180.5, 72.1, 47.1, 39.9, 36.0, 33.8, 29.7, 25.0, 24.6. HRMS (LSIMS, gly): Calcd. for C$_{18}$H$_{37}$O$_4$ (MH+): 317.2692, found: 317.2689.

6.6 7-Hydroxymethyl-2,2,12,12-tetramethyltridecane-1,13-diol

Under nitrogen atmosphere, to a solution of lithium aluminum hydride (1.09 g, 28.8 mmol) in anhydrous THF (100 mL) was added dropwise a solution of 8-hydroxy-2-(6-hydroxy-5,5-dimethylhexyl)-7,7-dimethyloctanoic acid (3.64 g, 11.5 mmol) in THF (40 mL) at room temperature. The reaction mixture was heated at reflux for 5 h and kept at room temperature overnight. Water (100 mL) was added carefully to the reaction mixture under cooling with a water bath. The pH was adjusted to 1 with 2 N hydrochloric acid. The product was extracted with diethyl ether (3×60 mL). The combined organic layers were washed with water (2×50 mL) and brine (50 mL). The ethereal solution was dried over sodium sulfate and concentrated in vacuo to furnish the crude product (3.2 g), which was purified by chromatography on silica (hexanes:ethyl acetate=50:50) to yield 7-hydroxymethyl-2,2,12,12-tetramethyltridecane-1,13-diol (3.0 g, 86%) as a yellow oil. $^1$H NMR (300 MHz, CD$_3$OD/TMS): δ (ppm): 4.88 (s, 3H), 3.44 (d, 2H, J=4.8 Hz), 3.23 (s, 4H), 1.5-1.1 (m, 17H), 0.85 (s, 12H). $^{13}$C NMR (75 MHz, CD$_3$OD/TMS): δ (ppm): 72.0, 65.7, 41.7, 40.0, 36.0, 32.2, 29.0, 25.4, 24.7, 24.6. HRMS (LSIMS, gly): Calcd. for C$_{18}$H$_{39}$O$_3$ (MH+): 303.2899, found 303.2901. HPLC: 94.6% purity.

6.7 7-Hydroxy-2,2,12,12-tetramethyltridecanedioic Acid Diethyl Ester

7-Oxo-2,2,12,12-tetramethyltridecanedioic acid diethyl ester (9.2 g, 25 mmol) was dissolved in methanol (200 mL) and the solution was cooled in an ice-water bath. Sodium borohydride (0.95 g, 25 mmol) was added. After 2 hi, another portion of sodium borohydride (0.95 g, 25 mmol) was added and stirring was continued for 2 h. The reaction mixture was hydrolyzed with water (200 mL). The aqueous solution was extracted with dichloromethane (3×150 mL). The combined organic layers were dried over magnesium sulfate and concentrated in vacuo to give the product (8.5 g, 92%) as an oil. $^1$H NMR (300 MHz, CDCl$_3$/TMS): δ (ppm): 4.11 (q, 4H, J=7.0 Hz), 3.60-3.50 (m, 1H), 1.66-1.32 (m, 11H), 1.24 (pseudo-t, 12H, J=7.0 Hz), 1.15 (s, 12H). $^{13}$C NMR (75 MHz, CDCl$_3$/TMS): δ (ppm): 178.0, 71.7, 60.1, 42.1, 40.6, 37.3, 26.0, 25.1, 24.9, 14.2. HRMS (LSIMS, nba): Calcd. for C$_{21}$H$_{41}$O$_3$ (MH+): 373.2954, found: 373.2936. HPLC: 88.90% purity.

6.8 7-Hydroxy-2,2,12,12-tetramethyltridecanedioic Acid

To a homogeneous solution of potassium hydroxide (3.45 g, 61 mmol) in water (3.3 mL) and ethanol (11.1 mL) was added 7-hydroxy-2,2,12,12-tetramethyltridecanedioic acid diethyl ester (8.2 g, 22 mmol) and the mixture was heated at reflux for 4 h. The mixture was concentrated in vacuo and the residue was extracted with diethyl ether (3×50 mL). The water layer was acidified with concentrated hydrochloric acid (6 mL) to pH 1. The product was extracted with diethyl ether (3'100 mL). The combined organic layers were dried over sodium sulfate and concentrated in vacuo. The crude product was purified by column chromatography (silica, dichloromethane:methanol=90:10) to give the pure product (6.6 g, 95%) as a colorless oil. $^1$H NMR (300 MHz, CDCl$_3$/TMS): δ (ppm): 8.10 (br., 3H), 3.58 (br., 1H), 1.62-1.22 (m, 16H), 1.18 (s, 12H). $^{13}$C NMR (75 MHz, CDCl$_3$/TMS): δ (ppm): 184.3, 71.8, 42.1, 40.5, 36.9, 25.9, 25.0, 24.9. HRMS (LSIMS, gly): Calcd. for C$_{17}$H$_{33}$O$_5$ (MH+): 317.2328; found 317.2330. HPLC: 90.4% purity.

6.9
2,2,12,12-Tetramethyl-7-methylene-tridecanedioic Acid diethyl Ester

Under nitrogen atmosphere, a solution of phenyllithium (in diethyl ether:cyclohexane=30:70, 7.06 mL, 1.8 M, 12.7 mmol) was added dropwise over 10 min to a solution of methyltriphenylphosphonium iodide (5.52 g, 13.3 mmol) in anhydrous THF (40 mL) at room temperature. The reaction mixture was stirred at room temperature for 30 mm, before 2,2,12,12-tetramethyl-7-oxo-tridecanedioic acid diethyl ester (4.5 g, 12.2 mmol) was added and the reaction mixture was stirred for 5 h at 50 □C. The resulting light-orange mixture was quenched by adding methanol (0.3 mL), and most of the solvent was removed on a rotary evaporator. The residue was purified by chromatography on silica (hexanes: ethyl acetate=95:5) to furnish the product (2.1 g, 47%) as an oil. $^1$H NMR (300 MHz, CDCl$_3$/TMS): δ (ppm): 4.67 (s, 2H), 4.10 (q, 4H, J=7.3 Hz), 1.97 (t, 4H, J=7.6 Hz), 1.6-1.3 (m, 8H), 1.30-1.15 (m, 10H), 1.15 (s, 12H). $^{13}$C NMR (75 MHz, CDCl$_3$/TMS): δ (ppm): 178.0, 149.6, 108.6, 60.1, 42.1, 40.6, 35.8, 28.2, 25.1, 24.7, 14.2. HRMS (LSIMS, nba): Calcd. for C$_{22}$H$_{41}$O$_4$ (MH+): 369.3004, found 369.3009.

6.10
7-Hydromethyl-2,2,12,12-tetramethyltridecanedioic Acid diethyl Ester Into a stirred solution of 2,2,12,12-tetramethyl-7-methylene-tridecanedioic acid diethyl ester (3.7 g, 10 mmol) in anhydrous THF (50 mL) was added borane-methyl sulfide complex (2.0 M in THF, 6 mL, 12 mmol) at room temperature and the solution was stirred for 6 h under argon atmosphere. Hydrogen peroxide (50 wt. % solution in water, 9 mL, 144 mmol) and an aqueous solution of sodium hydroxide (30 mL, 2.5 M, 75 mmol) were slowly introduced at 0-5° C. The reaction mixture was stirred for an additional h at room temperature and then extracted with dichloromethane (3×100 mL). The combined organic layers were dried over sodium sulfate, filtered, evaporated, and purified by column chromatography on silica (hexanes:ethyl acetate=95:5, then 90:10) to furnish the product (2.9 g, 77%) as an oil. $^1$H NMR (300 MHz, CDCl$_3$/TMS): δ (ppm): 4.11 (q, 4H, J=7.0 Hz), 3.51 (d, 2H, J=5.4 Hz), 1.60-1.16 (m, 18H), 1.25 (t, 6H, J=7.0 Hz), 1.15 (s, 12H). $^{13}$C NMR (75 MHz, CDCl$_3$/TMS): δ (ppm): 178.0, 65.3, 60.1, 42.0, 40.6, 40.4, 30.7, 27.2, 25.4, 25.1, 14.2. HRMS (LSIMS, nba): Calcd. for C$_{22}$H$_{43}$O. (MH+): 387.3110, found 387.3108.

6.11 7-Hydroxymethyl-2,2,12,12-tetramethyltridecanedioic Acid

To a homogeneous solution of potassium hydroxide (1.18 g, 21 mmol) in water (1.12 mL) and ethanol (3.8 mL) was added 7-hydroxymethyl-2,2,12,12-tetramethyltridecanedioic acid diethyl ester (2.9 g, 7.5 mmol) and the reaction mixture was heated at reflux for 4 h. The mixture was concentrated in vacuo, cooled to room temperature, and the residue was extracted with diethyl ether (2×50 mL). The pH of the aqueous layer was adjusted to 1 by addition of hydrochloric acid. The product was extracted with diethyl ether (3×50 mL). The combined organic layers were dried over sodium sulfate and concentrated in vacuo to afford the crude product which was purified by column chromatography on silica (hexanes:ethyl acetate=60:40) to yield 7-hydroxymethyl-2,2,12,12-tetramethyltridecanedioic acid (2.0 g, 81%) as an oil. $^1$H NMR (300 MHz, CDCl$_3$/TMS): δ (ppm): 7.64 (br., 3H), 3.50 (d, 2H, J=4.4 Hz), 1.60-1.20 (m, 17H), 1.16 (s, 12H). $^{13}$C NMR (75 MHz, CDCl$_3$/TMS): δ (ppm): 184.3, 65.2, 42.1, 40.5, 40.1, 30.6, 27.1, 25.2, 25.0. HRMS (LSIMS, nba): Calcd. for C$_{18}$H$_{35}$O$_5$ (MH+): 331.2484, found 331.2484.

6.12 7-(1-Hydroxy-1-methylethyl)-2,2,12,12-tetramethyltridecane-1,3-diol

A solution of 8-hydroxy-2-(6-hydroxy-5,5-dimethylhexyl)-7,7-dimethyloctanoic acid (1.0 g, 3.16 mmol) in THF (40 mL) was cooled in an ice-water bath and methyl lithium (1.4 M in diethyl ether, 27 mL, 37.8 mmol) was added in one portion. The reaction mixture was stirred for 2 h at 0° C., then poured into dilute hydrochloric acid (5 mL concentrated hydrochloric acid/60 mL water). The organic layer was separated and the aqueous layer was extracted with diethyl ether (2×50 mL). The combined organic layers were dried over sodium sulfate and concentrated in vacuo to get the crude product (1.0 g). The crude product was purified by column chromatography on silica (hexanes; ethyl acetate=80:20, then 50:50) to give 7-(1-hydroxy-1-methylethyl)-2,2,12,12-tetramethyltridecane-1,13-diol (0.40 g, 38%) as a white solid (together with 7-acetyl-2,2,12,12-tetramethyltridecan-1,13-diol, 0.41 g, 41%). M.p.: 72-74° C. H NMR (300 MHz, CDCl$_3$/TMS): δ (ppm): 3.24 (s, 4H), 2.59 (br., 3H), 1.55-0.95 (min, 23H), 0.81 (s, 12H). $^{13}$C NMR (75 MHz, CDCl$_3$/TMS): δ (ppm): 74.0, 71.5, 49.6, 38.4, 34.9, 31.2, 30.3, 27.1, 24.3, 23.9, 23.8. FIRMS (LSIMS, gly): Calcd. for C$_{20}$H$_{43}$O$_3$ (MH+): 331.3212, found: 331.3205. HPLC: 96.4% purity.

6.13 7-Bromo-2,2-dimethylheptanoic Acid Ethyl Ester

Under argon atmosphere and cooling with an ice-bath, a solution of lithium diisopropylamide in THF (1.7 L, 2.0 M, 3.4 mol) was slowly dropped into a solution of 1,5-dibromopentane (950 g, 4.0 mol) and ethyl isobutyrate (396 g, 3.4 mol) in THF (5 L) while keeping the temperature below +5° C. The reaction mixture was stirred at room temperature for 20 h and quenched by slow addition of saturated ammonium chloride solution (3 L). The resulting solution was divided into three 4-L portions. Each portion was diluted with saturated ammonium chloride solution (5 L) and extracted with ethyl acetate (2×2 L). Each 4-L portion of ethyl acetate was washed with saturated sodium chloride solution (2 L), 1 N hydrochloric acid (2 L), saturated sodium chloride solution (2 L), saturated sodium bicarbonate solution (2 L), and saturated sodium chloride solution (2 L). The three separate ethyl acetate layers were combined into a single 12-L, portion, dried over magnesium sulfate, and concentrated in vacuo to give the crude material (1.7 L) which was purified by vacuum distillation. Two fractions were obtained: the first boiling at 88-104° C./0.6 torr (184.2 g), the second at 105-120° C./1.4 torr (409.6 g) for a total yield of 60%. $^1$H NMR (300 MHz, CDCl$_3$/TMS): δ (ppm): 4.11

(q, 2H, J=7.2 Hz), 3.39 (t, 2H, J=6.8 Hz), 1.85 (m, 2H), 1.56-1.35 (m, 4H), 1.24 (t, 3H, J=7.2 Hz), 1.31-1.19 (m, 2H), 1.16 (s, 6H). $^{13}$C NMR (75 MHz, CDCl$_3$/TMS): δ (ppm): 177.9, 60.2, 42.1, 40.5, 33.8, 32.6, 28.6, 25.2, 24.2, 14.3. HRMS (EI, pos): Calcd. for C$_{11}$H$_{22}$BrO$_2$ (MH+): 265.0803, found: 265.0810.

6.14 7-Bromo-2,2-dimethylheptan-1-ol

Under Ar atmosphere, to a stirred suspension solution of LiBH4 (5.55 g, 95%, 0.24 mol) in dichloromethane (80 mL) was added dropwise methanol (9.8 mL, 0.24 mol), keeping a gentle reflux while hydrogen gas was formed. The mixture was stirred for 30 min at 45° C. To this solution was added dropwise a solution of 7-bromo-2,2-dimethylheptanoic acid ethyl ester (43 g, 0.15 mol) in dichloromethane (120 mL) at such a rate as to maintain a gentle reflux. The reaction mixture was heated at reflux for 20 h, cooled to room temperature and carefully hydrolyzed with 6 N hydrochloric acid (30 mL) and saturated ammonium chloride solution (360 mL). The aqueous layer was extracted with dichloromethane (3×50 mL). The combined organic layers were washed with water (2 □ 100 mL) and dried over anhydrous MgSO4. The reaction mixture was evaporated to yield crude 7-bromo-2,2-dimethylheptan-1-ol (36.2 g, 88%) as a colorless, viscous oil. 1H NMR (300 MHz, CDCl$_3$/TMS): δ (ppm): 3.41 (t, 2H, J=6.9 Hz), 3.30 (br. s, 2H), 1.90-1.84 (m, 3H), 1.42-1.22 (m, 6), 0.86 (s, 6H). $^{13}$C NMR (75 MHz, CDCl$_3$/TMS): δ (ppm): 71.9, 38.6, 35.1, 34.1, 32.9, 29.2, 24.0, 23.2. HRMS (LSIMS, nba): Calcd. for C$_9$H$_{18}$Br (MH+–H$_2$O): 205.0592, found: 205.0563.

6.15 2-(7-Bromo-2,2-dimethylheptyloxy)-tetrahydropyran

To a solution of 7-bromo-2,2-dimethylheptan-1-ol (36.0 g, 133.0 mmol) in dichloromethane (60 mL) was added p-toluenesulfonic acid (0.28 g, 1.3 mmol) and 3,4-dihydro-2H-pyran (18.54 g, 213 mmol) at 5-10° C. under cooling with an ice-water bath. The mixture was stirred and allowed to warm to room temperature overnight. The reaction solution was filtered through neutral alumina (200 g), which was rinsed with dichloromethane (500 mL). Concentration of the solvent gave the crude product as a brown oil, which was subjected to column chromatography on silica gel (240 g) using hexanes; ethyl acetate (50:1) as eluent to yield 2-(7-bromo-2,2-dimethylheptyloxy)-tetrahydropyran as a colorless oil (23.0 g, 48%). $^1$H NMR (300 MHz, CDCl$_3$/TMS): δ (ppm): 4.54 (t, 1H, J=3.0 Hz), 3.84 (m, 1H), 3.51-3.39 (m, 4H), 2.98 (d, 1H, J=9.3 Hz), 1.89-1.80 (m, 3H), 1.70-1.40 (m, 7H), 1.29-1.22 (m, 4H), 0.89 (s, 6H). $^{13}$C NMR (75 MHz, CDCl$_3$/TMS): δ (ppm): 99.3, 76.6, 62.1, 39.3, 34.3, 34.2, 33.0, 30.8, 29.2, 25.7, 24.7, 23.2, 19.6. HRMS (LSIMS, nba): Calcd. for C$_{14}$H$_{27}$BrO$_2$: 307.1272, found: 307.1245.

6.16 8-Oxo-2,2,14,14-tetramethylpentadecane-1,15-diol

Under nitrogen atmosphere, to a solution of 2-(7-bromo-2,2-dimethylheptyloxy)-tetrahydropyran (26.0 g, 39.4 mmol), tetra-n-butylammonium iodide (3.0 g, 8.1 mmol) and p-toluenesulfonyl methyl isocyanide (7.80 g, 39.4 mmol) in anhydrous DMSO (200 mL) was added sodium hydride (3.80 g, 20.5 mmol, 60% dispersion in mineral oil) in portions at 5-10° C. The reaction mixture was stirred at room temperature for 20 h and quenched with ice-water (400 mL). The product was extracted with diethyl ether (3□100 mL). The combined organic layers were washed with water (200 mL) and saturated sodium chloride solution (2×200 mL), dried over MgSO4, and concentrated in vacuo to get crude 2-[8-isocyano-2,2,14,14-tetramethyl-15-(tetrahydropyran-2-yloxy)-8-(toluene-4-sulfonyl)-pentadecyloxy]-tetrahydropyran (28.2 g) as an orange oil, which was used without purification. A solution of this crude product (28.0 g) and 48% sulfuric acid (46 g, from 12 mL of concentrated sulfuric acid and 24 mL of water) in methanol (115 mL) was stirred for 80 min at room temperature. The solution was diluted with ice-water (120 mL). The aqueous layer was extracted with dichloromethane (3×100 mL). The combined organic layers were washed with saturated Na$_2$CO$_3$ solution (2×150 mL) and saturated NaCl solution (150 mL). The organic solution was dried over MgSO4 and concentrated in vacuo. The residue was purified by column chromatography (silica gel, hexanes:ethyl acetate=2:1) to give 8-oxo-2,2,14,14-tetramethylpentadecane-1,15-diol (9.97 g, 80% over two steps) as a colorless oil. $^1$H NMR (300 MHz, CDCl$_3$/TMS): δ (ppm): 3.30 (s, 4H), 2.39 (t, 4H, J=7.2 Hz), 2.07 (br. s, 2H), 1.60-1.55 (m, 4H), 1.28-1.17 (m, 12H), 0.85 (s, 12H). $^{13}$C NMR (75 MHz, CDCl$_3$/TMS): δ (ppm): 212.0, 72.0, 43.0, 38.6, 35.2, 30.3, 24.0, 23.8. FIRMS (LSIMS, gly): Calcd. for C$_{19}$H$_{39}$O$_3$ (MH+): 315.2899, found: 315.2886. HPLC: 94.7% purity.

6.17 2,2,14,14-Tetramethylpentadecane-1,8,15-triol

Under nitrogen atmosphere, a solution of 8-oxo-2,2,14,14-tetramethylpentadecane-1,15-diol (0.9 g, 2.5 mmol) in iso-propanol (10 mL) was added dropwise to a stirred suspension of sodium borohydride (0.1 g, 2.7 mmol) in iso-propanol (10 mL) at room temperature. The reaction progress was monitored by thin layer chromatography (silica, hexanes:ethyl acetate=1:1). Additional sodium borohydride was added after each hour (0.36 g, 10 mmol, six times). The reaction mixture was stirred for additional 20 h, hydrolyzed with water (10 mL), acidified with 1 N hydrochloric acid (25 mL) to pH 1, and extracted with dichloromethane (4×15 mL). The combined organic phases were washed with saturated sodium chloride solution (15 mL), dried over magnesium sulfate, and concentrated in vacuo to furnish the crude product (1.0 g) as a white solid in oil, which was purified by column chromatography (silica; hexanes, then hexanes; ethyl acetate=2:1 to 1:2) to give the pure product (0.35 g, 43%) as nice white crystals. M.p.: 71-75° C. $^1$H NMR (300 MHz, CD$_3$COCD$_3$/CD$_3$OD/TMS): δ (ppm): 4.32-4.03 (m, 3H), 3.52 (s, 1H), 3.22 (s, 4H), 1.63-1.20 (m, 20H), 0.83 (s, 12H). $^{13}$C NMR (75 MHz, CD$_3$COCD$_3$/CD$_3$OD/TMS): δ (ppm): 72.0, 71.7, 39.8, 38.4, 35.8, 31.8, 26.7, 24.8, 24.6. HRMS (LSIMS, gly): Calcd. for C$_{19}$H$_{41}$O$_3$ (MH+): 317.3056, found: 317.3026. HPLC: 97.1% purity.

6.18 2,2,14,14-Tetramethyl-8-oxo-pentadecanedioic Acid diethyl Ester

Under Ar atmosphere, to a solution of 7-bromo-2,2-dimethylheptanoic acid ethyl ester (26.50 g, 100 mmol), tetra-n-butylammonium iodide (3.69 g, 10 mmol) and p-toluenesulfonyl methyl isocyanide (9.80 g, 50 mmol) in anhydrous DMSO (300 mL) was added sodium hydride (4.80 g, 20.5 mmol, 60% dispersion in mineral oil) at 5-10° C. The reaction mixture was stirred at room temperature for 20 h and quenched with ice-water (300 mL). The product was extracted with dichloromethane (3 □100 mL). The combined organic layers were washed with water (200 mL), half-saturated NaCl solution (2'200 mL), and saturated NaCl solution (200 mL), dried over MgSO4, and concentrated in vacuo to get the crude 8-isocyano-2,2,14,14-tetramethyl-8-(toluene-4-sulfonyl)-pentadecanedioic acid diethyl ester (36.8 g) as an orange oil, which was used in the next step without purification. To a solution of this crude product (36.8 g) in dichloromethane (450 mL) was added concentrated hydrochloric acid (110 mL) and the mixture was stirred at room temperature for 1 h. The solution was diluted with water (400 mL) and the aqueous layer was extracted with dichloromethane (200 mL). The combined organic layers were washed with saturated NaHCO$_3$ solution (2×150 mL) and saturated NaCl solution (150 mL). The organic solution was dried over Na$_2$SO$_4$ and concentrated in vacuo. The residue was subjected to column chromatography (silica gel, hexanes:ethyl acetate=11:1) to give 2,2,14,14-tetramethyl-8-oxo-pentadecanedioic acid diethyl ester (12.20 g, 66% over two steps) as a colorless oil. $^1$H NMR (300 MHz, CDCl$_3$/TMS): δ (ppm): 4.11 (q, 4H, J=6.9 Hz), 2.37 (t, 4H, J=7.5 Hz), 1.58-1.47 (m, 8H), 1.35-1.10 (m, 8H), 1.24 (t, 6H, J=7.2 Hz), 1.15 (s, 12H). $^{13}$C NMR (75 MHz, CDCl3/TMS): δ (ppm): 211.6, 178.3, 60.5, 43.1, 42.5, 40.9, 30.1, 25.5, 25.1, 24.1, 14.7. HRMS (LSIMS, nba): Calcd. for C$_{23}$H$_{43}$O$_5$ (MH+): 399.3110, found: 399.3129.

6.19 8-Oxo-2,2,14,14-tetramethylpentadecanedioic Acid

A solution of KOH (25 g) in water (50 mL) was added to a solution of 2,2,14,14-tetramethyl-8-oxo-pentadecanedioic acid diethyl ester (10.69 g, 155 mmol) in ethanol (400 mL), then heated at reflux for 4 h. After cooling, the solution was evaporated to a volume of ca. 50 mL and diluted with water (800 mL). The organic impurities were removed by extracting with dichloromethane (2×200 mL). The aqueous layer was acidified to pH 2 with concentrated hydrochloric acid (50 mL) and extracted with methyl tert.-butyl ether (MTBE, 3×200 mL). The combined organic layers were dried over magnesium sulfate and concentrated in vacuo to give the crude product (9.51 g) as an oil. Crystallization from hexanes/MTBE (50 mL: 25 mL) afforded 8-oxo-2,2,14,14-tetramethylpentadecanedioic acid (6.92 g, 79%) as waxy, white crystals. M.p.: 83-84° C.

$^1$H NMR (300 MHz, CDCl$_3$/TMS): δ (ppm): 12.03 (s, 2H), 2.37 (t, 4H, J=7.3 Hz), 1.52-1.34 (m, 8H), 1.28-1.10 (m, 8H), 1.06 (s, 12H$_1$-1). $^{13}$C NMR (75 MHz, CDCl$_3$/TMS): δ (ppm): 210.5, 178.8, 41.7, 41.2, 29.1, 25.0, 24.4, 23.1. HRMS (LSIMS, gly): Calcd. for C$_{19}$H$_{35}$O$_5$ (MH+): 343.2484, found: 343.2485.

6.20 8-Hydroxy-2,214,14-tetramethylpentadcanedioic Acid

Under nitrogen atmosphere, sodium borohydride (0.06 g, 1.6 mmol) was added to a stirred solution of 8-oxo-2,2,14,14-tetramethylpentadecanedioic acid (1.18 g, 3.4 mmol) in methanol (50 mL) at 0° C. The reaction progress was monitored by thin layer chromatography (silica; hexanes: ethyl acetate=50:50). Additional sodium borohydride was added after 1 h (0.48 g, 13 mmol). After 8 h, the reaction mixture was hydrolyzed with water (50 mL) and acidified with concentrated hydrochloric acid (3 mL) to pH 1. The solution was diluted with water (50 mL) and extracted with dichloromethane (4×25 mL). The combined organic layers were washed with saturated sodium chloride solution (2×30 mL), dried over magnesium sulfate, concentrated in vacuo, and dried in high vacuo to give 8-hydroxy-2,2,14,14-tetramethylpentadecanedioic acid (0.7 g, 60%) as a very viscous oil.

$^1$H NMR (300 MHz, CDCl$_3$/TMS): S (ppm): 7.42 (br. s, 3H), 3.59 (br. s, 1H), 1.65-1.00 (m, 20H), 1.18 (s, 12H). $^{13}$C NMR (75 MHz, CDCl$_3$/TMS): δ (ppm): 184.5, 71.8, 42.1, 40.5, 37.0, 29.8, 25.2, 25.1, 24.9, 24.8. HRMS (FAB): Calcd. for C$_{19}$H$_{37}$O$_5$ (MH+): 345.2635, found: 345.2646. HPLC: 83.8% purity.

6.21 7-Isocyano-2,2-dimethyl-7-(toluene-4-sulfonyl)-heptanoic Acid Ethyl Ester Under nitrogen atmosphere, to a solution of ethyl 6-bromo-2,2-dimethylhexanoate (Ackerley, N. J. Med. Chem. 1995, 38, 1608-1628) (36.60 g, 140 mmol), tetra-n-butylammonium iodide (4.23 g, 11 mmol) and p-toluenesulfonyl methyl isocyanide (27.56 g, 140 mmol) in anhydrous DMSO (500 mL) was added sodium hydride (5.80 g, 146 mmol, 60% dispersion in mineral oil) at 5-10° C. The reaction mixture was stirred at room temperature for 20 h. The cooled solution was carefully quenched by addition of ice-water (1000 mL). The product was extracted with dichloromethane (3×150 mL). The combined organic layers were washed with water (200 mL) and saturated NaCl solution (2×200 mL), dried over MgSO4, and concentrated in vacuo to obtain the crude product mixture (40.9 g) as orange oil. The crude product (10.22 g) was subjected to column chromatography on silica gel eluting with hexanes/ethyl acetate (10:1) to give 7-isocyano-2,2-dimethyl-7-(toluene-4-sulfonyl)-heptanoic acid ethyl ester (2.05 g, 15%) as a pale yellow oil and 7-isocyano-2,2,12,12-tetramethyl-7-(toluene-4-sulfonyl)-tridecanedioic acid diethyl ester (1.60 g, 8%) as a colorless oil, together with a mixture of both (2.50 g, 7-isocyano-2,2-dimethyl-7-(toluene-4-sulfonyl)-heptanoic acid ethyl ester: 7-isocyano-2,2,12,12-tetramethyl-7-(toluene-4-sulfonyl)-tridecanedioic acid diethyl ester=90:10). $^1$H NMR (300 MHz, CDCl$_3$/TMS): δ (ppm): 7.86 (d, 2H, J=8.1 Hz), 7.43 (d, 2H, J=8.1 Hz), 4.48 (dd, 1H, J=7.2, 3.6 Hz), 4.11 (q, 2H, J=7.2 Hz), 2.49 (s, 3H), 2.21-2.16 (m, 1H), 1.90-1.78 (m, 1H), 1.56-1.50 (m, 4H), 1.25 (t, 5H, J=7.2 Hz), 1.16 (s, 6H). $^{13}$C NMR (75 MHz, CDCl$_3$/TMS): δ (ppm): 177.8, 165.0, 146.7, 131.3, 130.3, 130.2, 72.9, 60.5, 42.2, 40.2, 28.3, 25.8, 25.3, 25.2, 24.2, 21.9, 14.4. HRMS (LSIMS, nba): Calcd. for C$_{19}$H$_{28}$NO$_4$S (MH+): 366.1739, found: 366.1746.

6.22 Ethyl 12-hydroxy-22,11,11-tetramethyl-7-oxo-dodecaoate

Under nitrogen atmosphere, to a solution of 7-isocyano-2,2-dimethyl-7-(toluene-4-sulfonyl)-heptanoic acid ethyl ester (1.72 g, 4.71 mmol), tetra-n-butylammonium iodide (0.17 g, 0.47 mmol) and 2-(5-bromo-2,2-dimethylpentyl)-tetrahydropyran (1.45 g, 4.95 mmol) in anhydrous DMSO (20 mL) was added sodium hydride (0.20 g, 4.75 mmol, 60% dispersion in mineral oil) at 5-10° C. The reaction mixture was stirred for 20 h at room temperature, and the cooled solution was carefully quenched by addition of ice-water (1000 mL). The product was extracted with dichloromethane (3×15 mL). The combined organic layers were washed with water (40 mL) and saturated sodium chloride solution (2'20 mL), dried over MgSO4, and concentrated in vacuo to obtain the crude intermediate (3.50 g) as a brown oil. This intermediate was dissolved in 48% aqueous sulfuric acid (6 mL) and methanol (12 mL), stirred 100 min at room temperature, and diluted with water (50 mL). The product was extracted with dichloromethane (3×15 mL). The combined organic layers were washed with water (100 mL) and saturated NaCl solution (100 mL), dried over MgSO4, and concentrated in vacuo to obtain crude ethyl 12-hydroxy-2,2,11,11-tetramethyl-7-oxo-dodecanoate (2.70 g) as a yellow oil. The crude product (2.5 g) was subjected to column chromatography on silica gel eluting with hexanes/ethyl acetate (4:1, then 3:1) to give the pure product (0.82 g, 55%) as a pale yellow oil. $^1$H NMR (300 MHz, CDCl$_3$/TMS): δ (ppm): 4.14-4.03 (m, 2H), 3.31 (br. s, 2H), 2.42 (br. s, 1H), 2.39 (m, 4H), 1.54-1.48 (m, 6H), 1.24-1.18 (m, 7H), 1.14 (s, 6H), 0.86 (s, 6H). $^{13}$C NMR (75 MHz, CDCl$_3$/TMS): δ (ppm): 211.7, 178.0, 71.2, 60.3, 43.2, 42.7, 42.1, 40.4, 37.9, 35.1, 25.2, 24.6, 24.2, 24.1, 18.0, 14.3. HRMS (LSIMS, gly): Calcd. for $C_{18}H_{35}O_4$ (MH+): 315.2535, found: 315.2541.

6.23 2,2,11,11-Tetramethyl-7-oxo-dodecanedioic Acid 1-ethyl Ester

A mixture of ethyl 12-hydroxy-2,2,11,11-tetramethyl-7-oxo-dodecanoate (3.26 g, 10 mmol) and pyridinium dichromate (14.0 g, 36 mmol) in DMF (45 mL) was stirred at room temperature for 46 h. The solution was diluted with 48% aqueous sulfuric acid (30 mL) and water (300 mL). The product was extracted with ethyl acetate (5×100 mL). The combined organic layers were washed with saturated NaCl solution (5×100 mL), dried over MgSO4, and concentrated to give the crude product (3.19 g) as a green oil. The crude product (3.1 g) was subjected to column chromatography on silica gel eluting with hexanes/ethyl acetate (3:1, then 2:1) to give pure 2,2,11,11-tetramethyl-7-oxo-dodecanedioic acid 1-ethyl ester (2.69 g, 82%) as a pale yellow oil. $^1$H NMR (300 MHz, CDCl$_3$/TMS): δ (ppm): 11.30 (br. s, 1H), 4.10 (q, 2H, J=7.2 Hz), 2.39 (t, 4H, J=7.2 Hz), 1.56-1.48 (m, 8H), 1.24 (t, 5H, J=7.2 Hz), 1.20 (s, 6H), 1.15 (s, 6H). $^{13}$C NMR (75 MHz, CDCl$_3$/TMS): δ (ppm): 210.9, 184.4, 178.1, 60.4, 43.1, 42.7, 42.2, 40.5, 39.8, 25.3, 25.0, 24.7, 24.3, 19.3, 14.4. HRMS (LSIMS, gly): Calcd. for $C_8H_{33}O_5$ (MH+): 329.2328, found: 329.2330.

6.24 2,2,11,11-Tetramethyl-6-oxo-dodecanedioic Acid

A solution of 2,2,11,11-tetramethyl-7-oxo-dodecanedioic acid 1-ethyl ester (2.5 g, 7.2 mmol) and potassium hydroxide (1.8 g, 27.3 mmol) in water (3 mL) and ethanol (8 mL) was heated at reflux for 4 h. Ethanol was evaporated under reduced pressure and the residue was dissolved in water (10 mL). The solution was extracted with diethyl ether (50 mL) and then acidified with 6 N hydrochloric acid to pH 1. The product was extracted with diethyl ether (4×40 mL). The combined organic layers were washed with saturated NaCl solution (2×100 mL), dried over MgSO4, and concentrated in vacuo to give the crude product (2.17 g) as a white solid. The crude product (2.05 g) was recrystallized from diethyl ether/hexanes (30 mL/10 mL) to obtain pure 2,2,11,11-tetramethyl-6-oxo-dodecanedioic acid (1.94 g, 88%) as white needles. M.p.: 72-73° C. H NMR (300 MHz, CDCl$_3$/TMS): δ ppm): 11.67 (br. s, 2H), 2.41 (m, 4H), 1.60-1.52 (m, 8H), 1.29-1.24 (m, 2H), 1.20 (s, 6H), 1.18 (s, 6H). $^{13}$C NMR (75 MHz, CDCl$_3$/TMS): δ (ppm): 211.2, 185.1, 184.9, 43.9, 42.7, 42.2, 40.3, 39.8, 25.1, 25.0, 24.7, 24.2, 19.3. HRMS (LSIMS, gly): Calcd. for $C_{16}H_{29}O_5$ (MH+): 301,2015, found: 301.2023. HPLC: 95.8% purity.

6.25 2,2,11,11-Tetramethyl-6-hydroxy-dodecanedioic Acid

To a solution of 2,2,11,11-tetramethyl-6-oxo-dodecanedioic acid (0.51 g, 1.5 mmol) in methanol (20 mL) was added sodium borohydride (0.60 g, 15.5 mmol) in portions at 0° C. The mixture was stirred for 20 h, the methanol was evaporated, and the residue was carefully dissolved in 2 N hydrochloric acid (20 mL). The solution was extracted with dichloromethane (4×15 mL) and the aqueous layer acidified with 6 N hydrochloric acid to pH 1. The product was extracted with diethyl ether (4×40 mL). The combined organic layers were washed with saturated sodium chloride solution (2×100 mL), dried over magnesium sulfate, and concentrated to give the crude product (0.52 g) as a white solid. The crude product (0.51 g) was subjected to column chromatography on silica gel eluting with hexanes/ethyl acetate (2:1) to give pure 2,2,11,11-tetramethyl-6-hydroxy-dodecanedioic acid (0.42 g, 91%) as a colorless oil. $^1$H NMR (300 MHz, CDCl$_3$/TMS): S (ppm): 9.07 (br, s, 3H), 3.53 (i, 1H), 1.47-1.44 (m, 4H), 1.35 (m, 6H), 1.23-1.22 (m, 4H), 1.11 (s, 6H), 1.10 (s, 6H). $^{13}$C NMR (75 MHz, CDCl$_3$/TMS): δ (ppm): 184.4, 184.3, 71.9, 42.2, 40.6, 40.5, 37.6, 37.1, 26.1, 25.1, 21.2. HRMS (LSIMS, gly): Calcd. for $C_{16}H_{31}O_5$ (MH+): 303.2171, found: 303.2157. HPLC: 86.3% purity.

6.26 1-Ethyl 14-hydroxy-2,2,13,13-tetramethyl-7-oxo-tetradecanoate

Under nitrogen atmosphere, to a solution of crude 7-isocyano-2,2-dimethyl-7-(toluene-4-sulfonyl)-heptanoic acid ethyl ester (prepared as described above, but without chromatographic purification, 1.72 g, 4.71 mmol), tetra-n-butylammonium iodide (0.17 g, 0.47 mmol) and 2-(7-bromo-2,2-dimethylheptyl)-tetrahydropyran (1.45 g, 4.95 mmol) in anhydrous DMSO (20 mL) was added sodium hydride (0.20 g, 4.75 mmol, 60% dispersion in mineral oil) at 5-10° C. The reaction mixture was stirred at room temperature for 20 h and the cooled solution was carefully quenched by addition of ice-water (1000 mL). The product was extracted with dichloromethane (3×15 mL). The combined organic layers were washed with water (40 mL) and saturated NaCl solution (2×20 mL), dried over MgSO4, and concentrated in vacuo to obtain the crude intermediate (3.50 g) as a brown oil. This intermediate was dissolved in 48% aqueous sulfuric acid (6 mL) and methanol (12 mL). The mixture was stirred for 100 min and diluted with water (50 mL). The product was extracted with dichloromethane (3×15 mL). The combined organic layers were washed with water (100 mL) and saturated NaCl solution (100 mL), dried over MgSO4, and concentrated in vacuo to obtain the crude product (2.70 g) as a yellow oil. The crude product (2.5 g) was subjected to column chromatography on silica gel eluting with hexanes/ethyl acetate (4:1, then 3:1) to give pure 1-ethyl 14-hydroxy-2,2,13,13-tetramethyl-7-oxo-tetradecanoate (0.82 g, 55%) as a pale yellow oil. $^1$H NMR (300 MHz, CDCl$_3$/TMS): δ (ppm): 4.10 (q, 2H, J=6.9 Hz), 3.30 (br. s, 2H), 2.39 (t, 4H, J=6.9 Hz), 1.98 (br. s, 1H), 1.56-1.48 (m, 6H), 1.27-1.18 (m, 11H), 1.14 (s, 6H), 0.85 (s, 6H). $^{13}$C NMR (75 MHz, CDCl$_3$/TMS): δ (ppm): 211.5, 178.0, 71.9, 60.3, 42.9, 42.7, 42.2, 40.5, 38.6, 35.1, 30.3, 25.2, 24.7, 24.3, 24.0, 23.8, 14.4. HRMS (LSIMS, gly): Calcd. for $C_{20}H_{39}O_4$ (MH+): 343.2848, found: 343.2846.

6.27 2,2,13,13-Tetramethyltetradecane-1,7,14-triol

Under Ar atmosphere, to a stirred suspension of lithium borohydride (0.30 g, 95%, 13 mmol) in dichloromethane (80 mL) was added dropwise methanol (0.42 g, 13 mmol), keeping a gentle reflux while hydrogen gas was formed. The mixture was stirred for 10 min at 45° C. and a solution of 2,2,13,13-tetramethyl-7-oxo-tetradecanedioic acid 1-ethyl ester (1.57 g, 4.36 mmol) in dichloromethane (10 mL) was added dropwise at such a rate as to maintain a gentle reflux. The reaction mixture was heated at reflux for 24 h, then cooled to room temperature and carefully hydrolyzed with 2 N hydrochloric acid (50 mL) and saturated ammonium chloride solution (120 mL). The aqueous layer was extracted with dichloromethane (4×50 mL). The combined organic layers were washed with water (100 mL) and dried over anhydrous magnesium sulfate. The reaction mixture was concentrated to yield the crude product as a yellow oil (1.28 g). Purification by column chromatography on silica gel eluting with hexanes/ethyl acetate (4:1, then 3:1) followed by recrystallization from dichloromethane gave pure 2,2,13, 13-tetramethyltetradecane-1,7,14-triol (0.86 g, 65%) as white needles. M.p.: 79-80° C. $^1$H NMR (300 MHz, CDCl$_3$/TMS): δ (ppm): 3.57 (br. s, 1H), 3.29 (s, 4H), 2.17 (br. s, 3H), 1.46-1.40 (m, 4H), 1.33-1.24 (m, 12H), 0.85 (s, 12H). $^{13}$C NMR (75 MHz, CDCl$_3$/TMS): δ (ppm): 71.8, 71.7, 71.5, 38.7, 37.5, 37.3, 35.1, 30.7, 26.6, 25.7, 24.2, 24.0, 23.9, 23.8. HRMS (LSIMS, gly): Calcd. for $C_{18}H_{39}O_3$ (MH+): 303.2899, found: 303.2897. HPLC: 97% purity.

6.28 2,2,13,13-Tetramethyl-1,14-bis(tetrahydropyran-2-yloxy)tetradecan-6,9-diol A mixture of 2,5-dimethoxytetrahydrofuran (26.43 g, 0.2 mmol) and 0.6 N hydrochloric acid (160 mL) was stirred at room temperature for 1.5 h. The pH was adjusted to 7 by addition of sodium hydrogen carbonate (8.4 g) and the solution was extracted with dichloromethane (3'50 mL). The aqueous phase was acidified with concentrated hydrochloric acid (10 mL) and stirred for another 1.5 h. Basification with sodium hydrogen carbonate (10.1 g) and extraction with dichloromethane was repeated. In total, the acidification-basification-extraction sequence was repeated four times. The combined organic extracts were dried over magnesium sulfate and the dichloromethane was distilled off under atmospheric pressure. The residue was distilled under reduced pressure (b.p.: 75-77° C./15 mm Hg) (House, H. O. et al., J. Org. Chem. 1965, 30, 1061. B.p.=55-60° C./12 mm Hg) to give succinaldehyde as a foul smelling, colorless liquid (5.71 g, 33%), which was used immediately after distillation.

Under nitrogen atmosphere, to a stirred suspension of magnesium powder (3.65 g, 0.15 mol) in anhydrous THF (200 mL) was added 2-(5-bromo-2,2-dimethylpentyl)-tetrahydropyran (27.9 g, 0.1 mol) at such a rate as to maintain a gentle reflux. The reaction mixture was heated at reflux for additional 2 h, allowed to cool to room temperature, and then cooled in an ice-water bath. A solution of freshly distilled succinaldehyde (3.44 g, 0.04 mol) in THE (30 mL) was added dropwise. The reaction mixture was left to stir at room temperature overnight. The solution was decanted off the excess magnesium and poured into an aqueous saturated ammonium chloride solution (300 mL). The pH was carefully adjusted to 1-2 with 2 N hydrochloric acid. The reaction mixture was extracted with diethyl ether and the organic extracts were washed with brine and dried over MgSO4. After solvent removal, a light-yellow oil (23.88 g) was obtained which was purified by flash column chromatography (SiO$_2$, ethyl acetate:hexanes=1:3 to 1:1) to afford the pure product as an almost colorless, very viscous oil (18.04 g, 92%). $^1$H NMR (300 MHz, CDCl$_3$/TMS): δ (ppm): 4.54-4.50 (m, 2H), 3.89-3.82 (m, 2H), 3.66 (br. s, 2H), 3.48 (pseudo-t, 4H, J=9.6 Hz), 2.99 (dd, 2H, J=9.1, 3.5 Hz), 2.60 (br. s, 2H), 1.90-1.20 (m, 28H), 0.90-0.88 (m, 12H). $^{13}$C NMR (75 MHz, CDCl$_3$/TMS): F (ppm): 99.4, 99.2, 76.4, 76.1, 72.1, 71.7, 71.3, 62.4, 62.0, 39.2, 38.8, 38.3, 38.2, 34.1, 33.4, 30.7, 30.6, 25.5, 24.9, 24.6, 24.5, 24.4, 20.0, 19.7, 19.5, 14.2. HRMS (LSIMS, nba): Calcd. for $C_{28}H_{55}O_6$ (MH+): 487.3998, found: 487.3995.

6.29 Ethyl 8-bromo-2,2-dimethyloctanoate

Under N$_2$ atmosphere, a solution of LDA (2.0 M in heptane/tetrahydrofuran/ethylbenzene, 2.94 L, 5.9 mol) was added dropwise to a stirred solution of ethyl isobutyrate (720 g, 6.2 mol) in anhydrous THF (4.7 L) at −45° C. After 1 h, 1,6-dibromohexane (2400 g, 9.8 mol) was added dropwise, followed by the addition of DMPU (320 mL). The reaction mixture was stirred for 1 h and then allowed to warm to room temperature overnight. Saturated NH$_4$Cl solution (3 L) was added and the mixture was extracted with ethyl acetate (3×6 L). The combined organic layers were washed with brine (4.5 L), 1 M aqueous HCl (6 L), saturated NaHCO$_3$ solution (6 L), and brine (4.5 L). The solution was dried over MgSO$_4$ and concentrated in vacuo. The residue was distilled under high vacuo to furnish ethyl 8-bromo-2,2-dimethyloctanoate (856 g, 52%) as a light yellowish oil. Bp 95-100° C./0.2 mm. $^1$H NMR (300 MHz, CDCl$_3$/TMS): δ (ppm): 4.13 (q, J=7.1, 2H), 3.39 (t, J=6.9, 2H), 1.92-1.75 (m, 2H), 1.58-1.25 (m, 8H), 1.25 (t, J=7.1, 3H), 1.12 (s, 6H). $^{13}$C NMR (75 MHz, CDCl$_3$=77.52 ppm): δ (ppm): 177.62, 60.01, 42.08, 40.50, 33.63, 32.68, 29.13, 27.93, 25.00, 24.66, 14.22. HRMS (LSIMS, nba): Calcd for $C_{12}H_{24}BrO_2$ (MH+): 279.0960, found: 279.0957.

6.30 9-Isocyano-2,2,16,16-tetramethyl-9-(toluene-4-sulfonyl-heptadecanedioic Acid Diethyl Ester To a solution of ethyl 8-bromo-2,2-dimethyloctanoate (35.0 g, 125.4 mmol), tetrabutylammonium iodide (4.6 g, 12.5 mmol), and p-toluenesulphonylmethyl isocyanide (TosMIC, 12.2 g, 62.7 mmol) in anhydrous DMSO (450 mL) was added sodium hydride (60% dispersion in mineral oil, 6.3 g, 158 mmol) under cooling with an ice-water bath and under N$_2$ atmosphere. The reaction mixture was stirred for 23 h at room temperature, then carefully hydrolyzed with ice-water (500 mL) and extracted with MTBE (3×200 mL). The organic layers were washed with water (300 mL) and brine (150 mL), dried over MgSO$_4$, and concentrated in vacuo to give crude 9-isocyano-2,2,16,16-tetramethyl-9-(toluene-4-sulfonyl)-heptadecanedioic acid diethyl ester (37.0 g, 100%). H NMR (300 MHz, CDCl$_3$/TMS): δ (ppm): 7.88 (d, J=7.9 Hz, 2H), 7.42 (d, J=7.9 Hz, 2H), 4.10 (q, J=7.5 Hz, 4H), 2.48 (s, 3H), 2.05-1.75 (m, 3H), 1.65-1.20 (m, 21H), 1.15 (t, J=7.5 Hz, 6H), 1.10 (s, 12H). $^{13}$C NMR (75 MHz, CDCl$_3$/TMS): δ (ppm): 177.89, 163.75, 146.23, 131.35, 130.28, 129.82, 81.79, 60.17, 42.09, 40.57, 33.09, 29.68, 25.17, 24.78, 23.66, 14.31. HRMS (LSIMS, gly): Calcd for $C_{37}H_{54}NO_6S$ (MH$^+$): 592.3672, found: 592.3667.

6.31 2,2,16,16-Tetramethyl-9-oxoheptadecanedioic Acid diethyl Ester

To a solution of 9-isocyano-2,2,16,16-tetramethyl-9-(toluene-4-sulfonyl)-heptadecanedioic acid diethyl ester (12.0 g, 20.3 mmol) in methylene chloride (200 mL) was added coned HCl (47 mL). The reaction mixture was stirred for 80 min at room temperature. The mixture was diluted with water (200 mL), the layers were separated, and the aqueous layer was extracted with methylene chloride (3×70 mL). The combined organic layers were washed with saturated NaHCO$_3$ solution (3×40 mL) and brine (50 mL). The solution was dried over MgSO$_4$, and concentrated in vacuo to yield the crude product (7.52 g). Purification by column chromatography (silica gel, ethyl acetate/hexanes=1/9) gave 2,2,16,16-tetramethyl-9-oxoheptadecanedioic acid diethyl ester (3.5 g, 40%) as a colorless oil. H NMR (300 MHz, CDCl$_3$/TMS): δ (ppm): 4.14 (q, J=7.1 Hz, 4H), 2.41 (t, J=7.0 Hz, 4H), 1.66-1.35 (m, 20H), 1.25 (t, J=7.1 Hz, 6H), 1.17 (s, 12H). $^{13}$C NMR (75 MHz, CDCl$_3$/TMS): δ (ppm): 211.24, 177.89, 60.01, 42.69, 42.07, 40.64, 29.86, 29.07, 25.13, 24.73, 23.74, 14.24. HRMS (LSIMS, gly): Calcd for C$_{25}$H$_{47}$O$_5$(MH$^+$): 427.3423, found: 427.3430.

6.32 2,2,16,16-Tetramethylheptadecane-1,9,17-triol

Under N$_2$-atmosphere, methyl tert-butyl ether (MTBE, 80 mL) was added to lithium aluminum hydride (0.67 g, 17.60 mmol) and the suspension was stirred under cooling with an ice-water bath (0° C.). A solution of 2,2,16,16-tetramethyl-9-oxoheptadecanedioic acid diethyl ester (3.0 g, 7.04 mmol) in MTBE (20 mL) was added dropwise, followed by additional MTBE (40 mL). After 2 h at 0° C., the reaction mixture was carefully quenched by addition of ethyl acetate (8 mL, 80 mmol) and allowed to warm to room temperature overnight. The mixture was cooled with an ice-water bath and carefully hydrolyzed by addition of crushed ice (15 g) and water (15 mL). The pH was adjusted to 1 by addition of 2 N sulfuric acid (28 mL) and the solution was stirred at room temperature for 15 min. The layers were separated and the aqueous layer was extracted with MTBE (40 mL). The combined organic layers were washed with deionized water (50 mL), saturated NaHCO$_3$ solution (40 mL), brine (40 mL), dried over MgSO$_4$, concentrated in vacuo and dried in high vacuo to yield a crude product (2.65 g). The crude product was purified by recrystallization from hot CH$_2$Cl$_2$ (20 mL), which was cooled to room temperature and then kept at −5 OC. The crystals were filtered, washed with ice-cold CH$_2$Cl$_2$ (20 mL) and dried in high vacuo. This process was repeated to furnish 2,2,16,16-tetramethylheptadecane-1,9,17-triol (1.59 g, 65%) as a white solid. Mp 75-77 OC. $^1$H NMR (300 MHz, CDCl$_3$/TMS): δ (ppm): 3.57 (m, 1H), 3.30 (s, 4H), 1.72 (br, 2H), 1.50-1.16 (min, 25H), 0.85 (s, 12H). $^{13}$C NMR (75 MHz, CDCl$_3$/TMS): δ (ppm): 72.09, 38.79, 37.61, 35.21, 30.70, 29.85, 25.78, 24.06, 23.92. HRMS (LSIMS, gly): Calcd for C$_{21}$H$_{45}$O$_3$(MH$^+$): 345.3369, found: 345.3364. HPLC: 95% pure.

6.33 8-Hydroxy-2,2,12,12-tetramethylpentadecanedioic Acid diethyl Ester

To a solution of 2,2,12,12-tetramethyl-8-oxopentadecanedioic acid diethyl ester (33.6 g, 84.3 mmol) in 60% aqueous isopropanol (337 mL) was added sodium borohydride (1.6 g, 41 mmol). The reaction mixture was heated to 45° C. for 2 h, diluted with water (400 mL), and extracted with MTBE (2×200 mL). The combined organic layers were washed with water (200 mL), dried over sodium sulfate, and concentrated in vacuo to give the crude product (33.0 g, 98%). $^1$H NMR (300 MHz, CDCl$_3$/TMS): δ (ppm): 4.11 (q, J=7.2 Hz, 4H), 3.55-3.45 (m, 1H), 1.60-1.18 (m, 26H), 1.15 (s, 12H). $^{13}$C NMR (75 MHz, CDCl$_3$/TMS): δ (ppm): 178.1, 72.0, 60.3, 42.4, 40.9, 37.7, 30.4, 25.8, 25.4, 25.1, 14.5. HPLC: 87.5% pure.

6.34 2,2,14,14-Tetramethyl-8-tetrahydropyran-2-yloxy)-pentadecanedioic Acid Diethyl Ester Under nitrogen atmosphere, 3,4-dihydro-2H-pyran (10.2 g, 121 mmol) was added dropwise to a stirred solution of 8-hydroxy-2,2,14,14-tetramethylpentadecanedioic acid diethyl ester (16.1 g, 40 mmol) and p-toluenesulfonic acid monohydrate (catalytic amounts) in methylene chloride (100 mL) under cooling with an ice bath. The reaction mixture was allowed to warm to room temperature and stirred overnight. After the reaction was completed (TLC), the solution was filtered through basic aluminum oxide (50 g), which was washed with methylene chloride (4×30 mL). The filtrate was concentrated in vacuo to give crude product (19.5 g), which was purified by chromatography (silica gel, 200 g, heptanes/ethyl acetate=20:1, 10:1) yielding 2,2,14, 14-tetramethyl-8-(tetrahydropyran-2-yloxy)-pentadecanedioic acid diethyl ester as a colorless oil (12.1 g, 62%). $^1$H NMR (300 MHz, CDCl$_3$/TMS): δ (ppm): 4.69-4.59 (m, 1H), 4.11 (q, J=7.3 Hz, 4H$_1$), 3.98-3.82 (m, 1H), 3.65-3.40 (m, 2H), 2.00-1.18 (m, 26H), 1.24 (t, 0.1===7.1 Hz, 6H), 1.15 (s, 12H). $^{13}$C NMR (75 MHz, CDCl$_3$/TMS): δ (ppm): 177.74, 97.36, 76.48, 62.61, 60.02, 42.05, 40.70, 40.63, 34.90, 33.38, 31.16, 30.32, 30.26, 25.48, 25.10, 24.86, 19.96, 14.23.

6.35 2,2,14,14-Tetramethyl-8(tetrahydropyran-2-yloxy)-pentadecane-1,15-diol

Under nitrogen atmosphere, LiAlH$_4$ (2.2 g, 58 mmol) was suspended in anhydrous MTBE (250 mL) and cooled with an ice/water bath. 2,2,14,14-Tetramethyl-8-(tetrahydropyran-2-yloxy)-pentadecanedioic acid diethyl ester (12.0 g, 24.7 mmol) in anhydrous MTBE (100 mL) was added dropwise over 1.5 h. This mixture was left overnight at ambient temperature. After the reaction was completed, deionized water (4 mL) was added followed by 20% aqueous NaOH solution (5 mL) and water (14 mL). The ether solution was decanted from the formed white residue. The residue was washed with MTBE (4×20 mL) and the combined ether solutions were dried over MgSO$_4$. The solvent was removed under reduced pressure to give crude 2,2,14, 14-tetramethyl-8-(tetrahydropyran-2-yloxy)-pentadecane-1, 15-diol as a colorless oil (8.9 g, 90%), which was used without further purification. $^1$H NMR (300 MHz, CDCl$_3$/TMS): δ (ppm): 4.72-4.59 (m, 1H), 4.03-3.84 (m, 1H), 3.69-3.38 (m, 2H), 3.31 (s, 4H), 2.00-1.15 (m, 28H), 0.87 (s, 12H). $^{13}$C NMR (75 MHz, CDCl$_3$/TMS): δ (ppm): 97.38, 76.57, 71.83, 62.65, 38.55, 34.96, 34.84, 33.33, 31.17, 30.75, 30.63, 26.92, 25.52, 24.95, 23.84, 23.70, 19.96. HRMS (EI, POS): Calcd for C$_{24}$H$_{48}$O$_4$(M+): 400.3553, found: 400.3564.

6.36 Nicotinic acid 8-(tetrahydropyran-2-yloxy)-2,2, 14,14-tetramethyl-15-nicotinoylpentadecyl Ester Anhydrous tert-butyl methyl ether (MTBE, 200 mL) and anhydrous pyridine (30 mL) were added to nicotinoyl chloride hydrochloride (12.3 g, 69 mmol). The mixture was stirred at room temperature under nitrogen atmosphere for 1 h, then cooled to 0° C., A solution of 2,2,14,14-tetramethyl-8-(tetrahydropyran-2-yloxy)-pentadecane-1,15-diol (8.8 g, 21.9 mmol) in anhydrous MTBE (50 mL) was added and the mixture was stirred overnight at room temperature. The mixture was washed with deionized water (3×50 mL), saturated NaHCO$_3$ solution (2×50 mL) and brine (50 mL), and dried over magnesium sulfate. The solvent was removed under reduced pressure to give the crude product as a light yellow oil (11.1 g), which was purified by chromatography (silica gel, 75 g, heptanes:ethyl acetate=10:1, 7:1, 5:1) to give nicotinic acid 8-(tetrahydropyran-2-yloxy)-2,2,14,14-tetramethyl-15-nicotinoylpentadecyl ester (9.2 g, 69%) as a viscous, yellow oil. $^1$H NMR (300 MHz, CDCl$_3$/TMS): δ (ppm): 9.37-9.15 (m, 2H), 8.79 (dd, J=4.8, 1.7 Hz, 2H), 8.30 (dt, J=7.9, 1.9 Hz, 2H), 7.41 (dd, J=4.8, 7.9 Hz, 2H), 4.71-4.55 (m, 1H), 4.07 (s, 4H), 3.99-3.80 (m, 1H), 3.69-3.52 (m, 1H), 3.52-3.35 (m, 1H), 1.92-1.08 (m, 26H), 1.00 (s, 12H). $^{13}$C NMR (75 MHz, CDCl$_3$/TMS): δ (ppm): 165.23, 153.34, 150.85, 136.99, 126.40, 123.36, 97.69, 76.77, 73.45, 62.91, 39.54, 39.49, 35.19, 34.23, 33.70, 31.42, 30.97, 30.88, 25.84, 25.74, 25.26, 24.61, 24.07, 20.25. HRMS (EI, POS): Calcd for C$_{36}$H$_{54}$N$_2$O$_6$ (M$^+$): 610.3982, found: 610.3977. Elemental analysis (C$_{36}$H$_{54}$N$_2$O$_6$): Calcd for C, 70.79; H, 8.91; N, 4.59. Found: C, 70.71; H, 9.06; N, 4.48.

6.37 Nicotinic acid 8-hydroxy-2,2,14,14-tetramethyl-15-nicotinoylpentadecyl Ester Nicotinic acid 8-(tetrahydropyran-2-yloxy)-2,2,14,14-tetramethyl-15 nicotinoylpentadecyl ester (9.0 g, 14.7 mmol) was heated in a mixture of glacial acetic acid, THF, and water (160 mL/80 mL/40 mL) to 45° C. for 6 h, then stirred overnight at ambient temperature. After the reaction was completed (TLC), the reaction mixture was poured onto ice (220 g), stirred for 30-45 min and extracted with methylene chloride (4×100 mL). The combined organic layers were washed with saturated NaHCO$_3$ solution (4×100 mL) and brine (100 mL), dried over MgSO$_4$, and concentrated to give a crude oil (7.9 g). Purification by chromatography (silica gel, 75 g, heptanes:ethyl acetate=1:1) afforded nicotinic acid 8-hydroxy-2,2,14,14-tetramethyl-1 5-nicotinoylpentadecyl ester (4.5 g, 58%) as a white solid. Mp 65-67° C. $^1$H NMR (300 MHz, CDCl$_3$/TMS): δ (ppm): 9.24 (s, 2H), 8.78 (d, J=3.8 Hz, 2H), 8.31 (d, J=8.0 Hz, 2H), 7.42 (dd, J=8.0, 4.9 Hz, 2H), 4.08 (s, 4H), 3.58 (br s, 1H), 2.02 (br s, 1H, OH), 1.62-1.08 (m, 20H), 1.00 (s, 12H). $^{13}$C NMR (75 MHz, CDCl$_3$/TMS): δ (ppm): 164.96, 153.03, 150.53, 136.81, 126.17, 123.16, 73.18, 71.58, 39.17, 37.41, 33.96, 30.44, 25.61, 24.37, 23.78. HRMS (EI, nba): Calcd for C$_3$H$_{47}$N$_2$O$_5$ (MH+): 527.3485, found: 527.3482. HPLC: 99.7% pure. Elemental analysis (C$_{31}$H$_{46}$N$_2$O$_5$): Calcd for C, 70.69; H, 8.80; N, 5.32. Found: C, 70.63; H, 8.83; N, 5.41.

6.38 Bis-(4-bromomethylphenyl)-methanone

Under irradiation with a 100-W white lamp, a mixture of 4,4'-dimethylbenzophenone (40.0 g, 190.2 mmol), NBS (71.10 g, 399.5 mmol), and dichloromethane (700 mL) was heated to reflux for 8 h and stirred at room temperature for 12 h. The white precipitate was removed by filtration and the filtrate was concentrated. The residue (70 g) was purified by column chromatography on silica using hexanes/ethyl acetate (8:1, 6:1, then 4:1) as eluent to afford bis-(4-bromomethylphenyl)-methanone (52.3 g, 75%) as a colorless solid. Mp 118-119° C. $^1$H NMR (300 MHz, CDCl$_3$/TMS): δ (ppm): 7.83 (d, 4H, J=7.8 Hz), 7.53 (d, 4H, J=7.8 Hz), 4.56 (s, 4H). $^{13}$C NMR (75 MHz, CDCl$_3$=77.00 ppm): δ (ppm): 195.3, 142.4, 137.3, 130.6, 129.2, 32.4.

6.39 3-{4-[4-(2-Ethoxycarbonyl-2-methylpropyl)-benzoyl]-benzoyl}-2,2-dimethylpropionic Acid Ethyl Ester Under Ar atmosphere, to a solution of ethyl isobutyrate (18.2 g, 156.6 mmol) and DMPU (1 mL) in THF (30 mL) was added LDA (80 mL, 2 M in heptanes, 160 mmol) at −78° C. The mixture was stirred for 30 min. A solution of bis-(4-bromomethylphenyl)-methanone (21.1 g, 57.3 mmol) in THF (100 mL) was added dropwise. The reaction mixture was allowed to stir overnight, gradually warming to room temperature. Most of the THF (120 mL) was removed under reduced pressure. The mixture was hydrolyzed with 6 N aqueous HCl (30 mL), water (170 g), and saturated NH$_4$Cl solution (200 mL). The solution was extracted with ethyl acetate (200 mL, 2×100 mL). The organic layers were washed with half-saturated NaCl solution (100 mL), dried over MgSO$_4$, and concentrated under vacuum to give a crude oil (35.8 g). Purification by column chromatography on silica (800 g) using hexanes/ethyl acetate (10:1) as eluent afforded 3-{4-[4-(2-ethoxycarbonyl-2-methylpropyl)-benzoyl]-phenyl}-2,2-dimethylpropionic acid ethyl ester (8.50 g, 34%) as a colorless oil. $^1$H NMR (300 MHz, CDCl$_3$/TMS): δ (ppm): 7.73 (d, 4H, J=8.1 Hz), 7.26 (d, 4H, J=8.1 Hz), 4.19-4.11 (m, 4H), 2.97 (s, 4H), 1.29-1.15 (m, 18H). $^{13}$C NMR (75 MHz, CDCl$_3$=77.00 ppm): δ (ppm): 195.8, 176.8, 142.9, 135.8, 129.9, 129.7, 60.4, 46.0, 43.4, 24.8, 14.1. HRMS (LSIMS, nba): Calcd for C$_{27}$H$_{35}$O$_5$ (M+H): 439.2484, found: 439.2487.

6.40 3-(4-{Hydroxy-[4-(3-hydroxy-2,2-dimethylpropyl)-phenyl]-methyl}-phenyl)-2,2-dimethylpropan-1-ol Under Ar atmosphere, to a suspension solution of LiBH$_4$ (1.55 g, 71.2 mmol) in CH$_2$Cl$_2$ (100 mL) was added methanol (2.28 g, 71.2 mmol) at room temperature. The mixture was stirred under reflux for 30 min. A solution of 3-{4-[4-(2-ethoxycarbonyl-2-methylpropyl)-benzoyl]-phenyl}-2,2-dimethylpropionic acid ethyl ester (4.0 g, 9.1 mmol) in CH$_2$Cl$_2$ (50 mL) was added dropwise. The reaction mixture was heated to reflux for 100 h. The mixture was hydrolyzed with 6 N HCl (10 mL), water (125 mL), and saturated NH$_4$Cl solution (125 mL). The solution was extracted with CH$_2$Cl$_2$ (2×50 mL). The combined organic layers were washed with saturated NaHCO$_3$ solution (150 mL), dried over MgSO$_4$, and concentrated under vacuum to give a mixture of 3-(4-{hydroxy-[4-(3-hydroxy-2,2-dimethyl-propyl)phenyl]-methyl}-phenyl)-2,2-dimethylpropan-1-ol and 3-(4-{hydroxy-[4-(3-hydroxy-2,2-dimethyl-propyl)-phenyl]-methyl}-phenyl)-2,2-dimethyl-propionic Acid ethyl ester (2.7 g, ratio 40/60) as a colorless oil. Under Ar atmosphere, to a suspension solution of LiBH$_4$ (2.52 g, 116 mmol) in CH$_2$Cl$_2$ (80 mL) was added methanol (3.7 g, 116 mmol) at room temperature. The mixture was stirred at 45° C. for 30 min. A solution of the above mixture (2.70 g) in CH$_2$Cl$_2$ (20 mL) was added dropwise. The reaction mixture was heated to reflux for 76 h. The mixture was hydrolyzed with 6 N HCl (10 mL), water (150 g), and saturated NH$_4$Cl (150 mL), and the solution was extracted with CH$_2$Cl$_2$ (2×80 mL). The organic layers were washed with saturated NaCl (140 mL), dried over MgSO$_4$, and concentrated under vacuum. The residue was subjected to column chromatography on silica gel using hexanes/ethyl acetate (2:1, 1:1) as eluent to afford 3-(4-{hydroxy-[4-(3-hydroxy-2,2-dimethyl-propyl)-phenyl]-methyl}-phenyl)-2,2-dimethylpropan-1-ol (0.45 g, 14%) as a white solid. Mp 169-170° C. $^1$H NMR (300 MHz, CD$_3$OD/TMS): δ (ppm): 7.15 (d, 4H, J=7.8 Hz), 7.01 (d, 4H, J=7.8 Hz), 5.62 (s, 1H), 3.11 (s, 4H), 2.42 (s, 4H), 0.71 (s, 12H). $^{13}$C NMR (75 MHz, CD$_3$OD=49.15 ppm): δ (ppm): 143.6, 139.2, 131.6, 127.3, 76.8, 71.4, 45.2, 37.3, 24.5. HRMS (LSIMS, gly): Calcd for $C_{23}H_{31}O_2$(M+H–$H_2O$): 339.2324, found: 339.2323. HPLC: 98.1% pure.

6.41 3-(4-{[4-(2-Ethoxycarbonyl-2-methylpropyl)-phenyl]-hydroxymethyl}-phenyl)-2,2-dimethylpropionic Acid Ethyl Ester A solution of 3-{4-[4-(2-ethoxycarbonyl-2-methylpropyl)-benzoyl]-phenyl}-2,2-dimethyl-propionic acid ethyl ester (4.40 g, 10.0 mmol) in methanol (80 mL) was cooled in an ice-water bath. Sodium borohydride (0.45 g, 13.7 mmol) was added and the mixture was stirred for 5 h. Water (150 mL) and dichloromethane (65 mL) were added and the layers were separated. The aqueous layer was washed with dichloromethane (2×65 mL). The combined organic layers were washed with saturated NaCl solution (100 mL), dried over $MgSO_4$, and concentrated under vacuum. The residue was subjected to column chromatography on silica using hexanes/ethyl acetate (9:1 and 6:1) as eluent to afford 3-(4-{[4-(2-ethoxycarbonyl-2-methylpropyl)-phenyl]-hydroxymethyl}-phenyl)-2,2-dimethylpropionic acid ethyl ester (3.63 g, 82%) as a colorless oil. $^1$H NMR (300 MHz, $CDCl_3$/TMS): δ (ppm): 7.24 (d, 4H, J==8.0 Hz), 7.07 (d, 4H, J=8.0 Hz), 5.77 (s, 1H), 4.08 (q, 4H, J=7.1 Hz), 2.83 (s, 4H), 2.62 (s, 1H), 1.21 (t, 6H, J=7.1 Hz), 1.16 (s, 12H). $^{13}$C NMR (75 MHz, $CDCl_3$=77.23 ppm): δ (ppm): 177.6, 142.2, 137.3, 130.3, 126.3, 75.9, 60.5, 46.0, 43.4, 25.1, 14.3. HRMS (LSIMS, nba): Calcd for $C_{27}H_{35}O_4$ (M+H–$H_2O$): 423.2535, found: 423.2520.

6.42 3-{4-[4-(2-Carboxy-2-methylpropyl)-phenyl]-hydroxymethyl]-phenyl}-2,2-dimethylpropionic Acid A solution of 3-(4-{[4-(2-ethoxycarbonyl-2-methylpropyl)-phenyl]-hydroxymethyl}-phenyl)-2,2-dimethylpropionic acid ethyl ester (3.6 g, 8.2 mmol) and potassium hydroxide (85%, 2.16 g, 33.0 mmol) in ethanol (9 mL) and water (2.5 mL) was heated to reflux for 5 h. Diethyl ether (20 mL) was added and the mixture was stirred for 1 h, then diluted with water (50 mL). The mixture was extracted with diethyl ether (2×20 mL). The aqueous solution was acidified with 6 N HCl (ca. 8 mL) to pH 1 and extracted with dichloromethane (4×35 mL). The organic extracts were washed with saturated NaCl solution (50 mL), dried over $MgSO_4$, and concentrated in vacuum to give 3-{4-[4-(2-carboxy-2-methylpropyl)-phenyl]-hydroxymethyl]-phenyl}-2,2-dimethylpropionic acid (3.18 g, 100%) as colorless needles. Mp 114-116° C. $^1$H NMR (300 MHz, $CDCl_3$/TMS): δ (ppm): 10.0-8.0 (br, 2H), 7.18 (d, 4H, J=8.0 Hz), 7.17 (d, 4H, J=8.0 Hz), 5.67 (s, 1H), 2.81 (s, 4H), 1.15 (s, 12H). $^{13}$C NMR (75 MHz, $CDCl_3$=77.23 ppm): δ (ppm): 184.3, 142.0, 136.9, 130.3, 126.5, 75.8, 45.8, 43.6, 24.9, 24.8. HRMS (LSIMS, nba): Calcd for $C_{23}H_{27}O_4$ (M+H): 367.1909, found: 367.1906. HPLC: 99.3% pure.

6.43 Di-m-tolyl-methanone

An oven-dried, three-necked 1-L flask equipped with magnetic stirring bar, gas inlet, dropping funnel, and condenser was flushed with nitrogen and loaded with m-tolunitrile (49.1 g, 419 mmol) and THF (30 mL). A solution of m-tolyl magnesium chloride in THF (1 M, 440 mL) was added dropwise at such a rate that the internal temperature was kept below 50° C. The mixture was heated to reflux for 18 h, then cooled to –15° C., and hydrolyzed with ice-water (210 mL) and aqueous HCl (36.5%, 300 mL). The mixture was stirred at room temperature for 30 min and heated to 80° C. for 18 h. Most of the THF (400 mL) was removed by distillation. The solution was extracted with MTBE (250 mL, 3×200 mL). The combined organic layers were washed with saturated $NaHCO_3$ solution (200 mL) and saturated NaCl solution (200 mL), dried over $MgSO_4$, and concentrated under vacuum to give di-m-tolyl-methanone (99.5 g, quantitative) as a red oil, which was used without further purification for the next step. $^1$H NMR (300 MHz, $CDCl_3$/TMS): δ (ppm): 7.62 (s, 2H), 7.54 (d, 2H, J=7.0 Hz), 7.36-7.31 (m, 4H), 2.37 (s, 6H). $^{13}$C NMR (75 MHz, $CDCl_3$=77.23 ppm): δ (ppm): 197.1, 138.1, 133.2, 130.5, 128.3, 127.4, 21.4 [lit. ref.: Coops, J.; Nauta, W. Th.; Ernsting, M. J. E.; Faber, M. A. C. *Recueil* 1940, 57, 1109].

6.44 Bis-(3-bromomethylphenyl)-methanone

Under irradiation with a 100-W white lamp, a mixture of di-m-tolyl-methanone (99.5 g, 473 mmol), NBS (195 g, 1096 mmol), and dichloromethane (1.4 L) was heated to reflux for 20 h. The precipitate was removed by filtration. The filtrate was washed with aqueous sodium hydroxide solution (8%, 3×550 mL) and concentrated in vacuo to give the crude product as a pale yellow solid (130 g), which was recrystalized from methylene chloride/hexanes (800 mL/200 mL) affording bis-(3-bromomethylphenyl)-methanone (66.20 g, 38%) as white crystals. Mp 147-148° C. (lit. mp 149-151° C.; Atzmuller, M.; Vogtle, F. *Chem. Ber.* 1978, 111, 2547-2556). $^1$H NMR (300 MHz, $CDCl_3$/TMS): δ (ppm): 7.84 (s, 2H), 7.75-7.64 (m, 4H), 7.49 (t, 2H, J=7.7 Hz), 4.54 (s, 4H). $^{13}$C NMR (75 MHz, $CDCl_3$=77.00 ppm): δ (ppm): 195.6, 138.5, 138.0, 133.3, 130.6, 130.2, 129.1, 32.4.

6.45 3-{3-[3-(2-Ethoxycarbonyl-2-methylpropyl)-benzoyl]-phenyl}-2,2-dimethylpropionic Acid Ethyl Ester Under Ar atmosphere, to a solution of ethyl isobutyrate (59 g, 513 mmol) in THF (100 mL) was added LDA (256 mL, 2 M in heptanes, 512 mmol) at –78° C. The mixture was stirred for 30 min and a solution of bis-(3-bromomethylphenyl)-methanone (66.0 g, 179 mmol) in THF (100 mL) was added dropwise. The reaction mixture was allowed to stir overnight, gradually warming to room temperature. The mixture was hydrolyzed with ice (500 g) and water (800 g). The solution was extracted with MTBE (5×200 mL). The organic layers were washed with saturated $NaHCO_3$ solution (100 mL) and saturated NaCl solution (100 mL), dried over $MgSO_4$, and concentrated under vacuum. The residual oil (95 g) was subjected to column chromatography on silica (800 g) using hexanes/ethyl acetate (10:1) as eluent to afford 3-{3-[3-(2-ethoxycarbonyl-2-methylpropyl)-benzoyl]-phenyl}-2,2-dimethylpropionic acid ethyl ester (49.4 g, 63%) as a pale yellow oil. $^1$H NMR (300 MHz, $CDCl_3$/TMS): δ (ppm): 7.67 (m, 2H), 7.59 (s, 2H), 7.40-7.38 (m, 4H), 4.11 (q, 4H, J=7.2 Hz), 2.96 (s, 4H), 1.23 (s, 12H), 1.22 (t, 6H, J=7.2 Hz). $^{13}$C NMR (75 MHz, $CDCl_3$=77.00 ppm): δ (ppm): 196.6, 176.9, 138.2, 137.4, 134.1, 131.5, 128.3, 127.9, 60.4, 45.9, 43.5, 25.0, 14.1. HRMS (LSIMS, gly): Calcd for $C_{27}H_{35}O_5$ (M+H): 439.2484, found: 439.2484.

6.46 3-(3-{Hydroxy-[3-(3-hydroxy-2,2-dimethylpropyl)-phenyl]-methyl}phenyl)-2,2-dimethylpropan-1-ol Under Ar atmosphere, to a suspension of $LiAlH_4$ (7.90 g, 208 mmol) in MTBE (200 mL) was added dropwise a solution of 3-{3-[3-(2-ethoxycarbonyl-2-methylpropyl)-benzoyl]-phenyl}-2,2-dimethylpropionic acid ethyl ester (25.9 g, 59 mmol) in MTBE (150 mL). The reaction mixture was stirred at room temperature for 16 h and heated to reflux for 3 h. Ethyl acetate (100 mL) was added and the reaction mixture was heated to reflux for 1 h and cooled to room temperature. The reaction mixture was poured into ice (500 g) and acidified with hydrochloric acid solution (2 N, 800 mL). The aqueous solution was extracted with MTBE (4×200 mL). The combined organic layers were washed with saturated NaHCO$_3$ solution (200 mL) and saturated NaCl solution (200 mL), dried over MgSO$_4$, and concentrated under vacuum. The residue (22.6 g) was subjected to column chromatography on silica gel using hexanes/ethyl acetate (3:2) as eluent to afford 3-(3-{hydroxy-[3-(3-hydroxy-2,2-dimethylpropyl)-phenyl]-methyl}-phenyl)-2,2-dimethylpropan-1-ol (19.0 g, 90%) as a white solid. Mp 98-99° C. $^1$H NMR (300 MHz, CDCl$_3$/TMS): δ (ppm): 7.26-7.19 (m, 6H), 7.06-7.03 (m, 2H), 5.80 (d, 1H, J=3.4 Hz), 3.23 (s, 4H), 3.05 (d, 1H, J=3.4 Hz), 2.56 (s, 4H), 2.07 (br d, 2H, J=4.4 Hz), 0.85 (s, 12H). $^{13}$C NMR (75 MHz, CD$_3$OD=49.15 ppm): δ (ppm): 145.5, 140.2, 130.5, 130.1, 128.7, 125.4, 77.1, 71.5, 45.6, 37.4, 24.6, 24.5. HRMS (FAB, gly): Calcd for C$_{23}$H$_{33}$O$_3$ (M+H): 357.2430, found: 357.2388. HPLC: 99.8% pure.

6.47 3-(3-{[3-(2-Ethoxycarbonyl-2-methylpropyl)-phenyl]-hydromethyl}-phenyl)-2,2-dimethylpropionic Acid Ethyl Ester Under Ar atmosphere, to a solution of 3-{3-[3-(2-ethoxycarbonyl-2-methyl-propyl)-benzoyl]-phenyl}-2,2-dimethylpropionic acid ethyl ester (12.37 g, 28.2 mmol) in methanol (240 mL) was added sodium borohydride (0.45 g, 13.7 mmol) under cooling with an ice water bath. The mixture was stirred for 5 h and water (480 mL) and dichloromethane (200 mL) were added. The aqueous layer was extracted with dichloromethane (2×200 mL). The combined organic layers were washed with saturated NaHCO$_3$ solution (150 mL and saturated NaCl solution (150 mL), dried over MgSO$_4$, and concentrated under vacuum to give 3-(3-{[3-(2-ethoxycarbonyl-2-methylpropyl)-phenyl]-hydroxymethyl}-phenyl)-2,2-dimethylpropionic acid ethyl ester (12.4 g, 100%) as a colorless oil, which was used for the next step without further purification. $^1$H NMR (300 MHz, CDCl$_3$/TMS): δ (ppm): 7.20-7.18 (m, 4H), 7.10 (s, 2H), 7.00-6.98 (min, 2H), 5.69 (d, 1H, J=3.2 Hz), 4.02 (q, 4H, J=7.1 Hz), 2.97 (d, 1H, J=3.2 Hz), 2.81 (s, 4H), 1.19 (t, 6H, J=7.1 Hz), 1.13 (s, 12H). 3C NMR (75 MHz, CDCl$_3$=77.23 ppm): δ (ppm): 177.6, 143.8, 138.2, 129.3, 128.5, 128.1, 124.8, 76.1, 60.5, 46.3, 43.6, 25.1, 25.0, 14.3. HRMS (LSIMS, gly): Calcd for C$_{27}$H$_{35}$O$_4$ (M+H–H$_2$O): 423.2535, found: 423.2542.

6.48 3-{3-[3-(2-Carboxy-2-methylpropy)-phenyl]-hydroxymethyl]-phenyl}-2,2-dimethylpropionic Acid A solution of 3-(3-{[3-(2-Ethoxycarbonyl-2-methylpropyl)-phenyl]-hydroxymethyl}-phenyl)-2,2-dimethylpropionic acid ethyl ester (12.8 g, 29.1 mmol) and potassium hydroxide (85%, 7.4 g, 112.0 mmol) in ethanol (21 mL) and water (9 mL) was heated to reflux for 4 h. MTBE (100 mL) was added and the mixture was stirred for 72 h, then diluted with water (50 mL). The aqueous layer was extracted with MTBE (2×50 mL). The aqueous solution was acidified with 6 N HCl (ca. 20 mL) to pH 1 and extracted with dichloromethane (4×100 mL). The organic extracts were washed with saturated NaCl solution (50 mL), dried over MgSO$_4$, and concentrated in vacuum to give a colorless solid (10.5 g, 94%). Recrystallization from dichloromethane (50 mL) and ethanol (10 mL) yielded 3-{3-[3-(2-carboxy-2-methylpropyl)-phenyl]-hydroxymethyl]-phenyl}-2,2-dimethylpropionic acid (6.7 g, 60%) in form of colorless crystals. Mp 116-117° C. $^1$H NMR (300 MHz, CDCl$_3$/TMS): δ (ppm): 7.44-7.41 (m, 2H), 7.26-7.22 (m, 4H) 7.06-7.03 (m, 2H), 5.73 (s, 1H), 2.83 (m, 4H), 1.27 (s, 6H), 1.25 (s, 6H). $^{13}$C NMR (75 MHz, DMSO-d$_6$/TMS): δ (ppm): 178.9, 145.6, 138.2, 128.8, 128.5, 128.1, 124.7, 74.8, 45.9, 43.0, 25.2, 25.1. HRMS (LSIMS, EI): Calcd for C$_{23}$H$_{26}$O$_4$[M–H$_2$O]$^+$: 366.1831, found: 366.1821. HLPC: 99.3% pure.

6.49 2 2-Dimethyl-8-oxododecanoic Acid Ethyl Ester

An aqueous solution of NaOH (30%, 240 mL) was added dropwise to a stirred solution of 4-iodobutane (110.5 g, 0.6 mol), p-toluenesulfonyl methyl isocyanide (58.6 g, 0.3 mol), and tetrabutylammonium iodide (8.0 g, 21.6 mmol) in CH$_2$Cl$_2$ (300 mL) at room temperature. The reaction mixture was stirred overnight and diluted with water (200 mL). The organic layer was separated and the aqueous layer was extracted with CH$_2$Cl$_2$ (3×100 mL). The organic layers were combined, washed with saturated NaCl solution (100 mL), dried over MgSO$_4$, and concentrated in vacuo. The residue was taken up in diethyl ether (3×200 mL) and filtered. The filtrate was concentrated and purified by column chromatography (silica gel, ethyl acetate/hexanes=1:3) to give 1-(1-isocyanopentane-1-sulfonyl)-4-methylbenzene (65.7 g, 87%) as an oil. Under N$_2$-atmosphere, sodium hydride (60% dispersion in mineral oil, 11.0 g, 0.275 mol) was added in portions to a solution of ethyl 7-bromo-2,2-dimethylheptanoate (72.8 g, 0.27 mol) and 1-(1-isocyanopentane-1-sulfonyl)-4-methylbenzene (69.0 g, 0.27 mol) in DMSO (500 mL) and diethyl ether (500 mL) at room temperature. After 30 min, tetrabutylammonium iodide (8.0 g, 21.7 mmol) was added and the mixture was stirred for 5 h. A precipitate formed and additional DMSO (500 mL) was added. After stirring overnight at room temperature, the mixture was heated to reflux for 3 h. Water (500 mL) and diethyl ether (500 mL) were added and the layers were separated. The aqueous layer was extracted with diethyl ether (4×200 mL). The combined organic layers were washed with water (500 mL) and saturated NaCl solution (300 mL), dried over MgSO$_4$, and concentrated in vacuo to give crude 8-isocyano-2,2-dimethyl-8-(toluene-4-sulfonyl)-dodecanoic acid ethyl ester (126.2 g) as a dark oil, which was used without further purification. Concentrated, hydrochloric acid (200 mL) was added slowly to a solution of crude 8-isocyano-2,2-dimethyl-8-(toluene-4-sulfonyl)-dodecanoic acid ethyl ester (126.2 g, 0.29 mol) in methylene chloride (300 mL). The reaction mixture was stirred at room temperature for 4 h. Water (500 mL) was added. The aqueous layer was separated and extracted with methylene chloride (3×100 mL). The organic solutions were combined, washed with water (300 mL) and saturated, aqueous NaHCO$_3$ solution (200 mL) and dried over MgSO$_4$. The solvent was evaporated and the residue was purified by column chromatography (silica gel, ethyl acetate/hexanes=1:10) to yield 2,2-dimethyl-8-oxododecanoic acid ethyl ester (69.6 g, 89%) as an oil. $^1$H NMR (300 MHz, CDCl$_3$/TMS): δ (ppm): 4.1 (q, J=7.3 Hz, 2H), 2.40-2.31 (m, 4H), 1.58-1.45 (m, 6H), 1.31-1.19 (m, 6H$_1$), 1.22 (t, 3H, J=7.3 Hz), 1.12 (s, 6H), 0.88 (t, J=7.3 Hz, 3H). $^{13}$C NMR (75 MHz, CDCl$_3$/TMS): δ (ppm): 210.5, 178.0, 60.5, 42.5, 42.0, 30.0, 27.0, 26.0, 25.5, 24.0, 23.0, 14.5, 14.0. HRMS (LSIMS, gly): Calcd for $C_{16}H_{31}O_3$ (MH$^+$): 271.2273, found: 271.2275. HPLC: 84% pure.

6.50 2,2-Dimethyldodecane-1,8-diol

A solution of 2,2-dimethyl-8-oxododecanoic acid ethyl ester (14.33 g, 5.3 mmol) in Et$_2$O (30 mL) was added to a suspension of LiAlH$_4$ (4.6 g, 12 mmol) in Et$_2$O (200 mL). The reaction mixture was heated to reflux for 2 h. Water (100 mL) and aqueous HCl (10%, 200 mL) were added. The aqueous solution was separated and extracted with Et$_2$O (2×100 mL). The combined organic solutions were washed with saturated, aqueous NaHCO$_3$ solution (100 mL) and brine (50 mL) and dried over MgSO$_4$. The solvent was evaporated and the residue was purified by column chromatography (silica gel, ethyl acetate/hexanes=1:10, 200 mL, then 1:3, 150 mL) to yield 2,2-dimethyldodecan-1,8-diol (9.9 g, 81%) as a colorless oil. $^1$H NMR (300 MHz, CDCl$_3$/TMS): d (ppm): 3.55 (br s, 1H), 3.29 (s, 2H), 1.7 (br. s, 2H), 1.42-1.20 (m, 16H), 0.89 (t, J=7.2 Hz, 3H), 0.84 (s, 6H). $^{13}$C NMR (75 MHz, CDCl$_3$/TMS): δ (ppm): 72.1, 72.0, 38.7, 37.6, 37.3, 35.2, 30.8, 28.0, 25.8, 24.0, 23.9, 22.9, 14.3. HRMS (LSIMS, gly): Calcd for $C_{14}H_{31}O_2$(MH$^+$): 231.2324, found: 231.2324. HPLC: 99.8% pure. Elemental analysis ($C_4H_{30}O_2$): Calcd for C, 72.99; H, 13.12. Found: C, 72.75; H, 13.23.

6.51 8-Hydroxy-2,2-dimethyldodecanoic Acid

Sodium borohydride (8.0 g, 0.21 mol) was added in portions to 2,2-dimethyl-8-oxododecanoic acid (27.02 g, 0.11 mol) in ethanol (200 mL), followed by addition of Na$_2$CO$_3$ (5 g) while the reaction mixture was gently refluxed. The reaction mixture was stirred at 40-50° C. for 3.5 h and at 60° C. for 1 h. Water (100 mL) and aqueous HCl (10%, 100 mL) were added. The mixture was extracted with ethyl acetate (3×80 mL). The organic solutions were combined, washed with water (100 mL) and brine (2×50 mL), and dried over MgSO$_4$. The solvent was evaporated and the residue was purified twice by column chromatography (silica gel, ethyl acetate/heptane=1:3). Coevaporation with toluene and drying in high vacuo at 70° C. for 1 h gave 8-hydroxy-2,2-dimethyldodecanoic acid (9.6 g, 35%) as an oil. $^1$H NMR (300 MHz, CDCl$_3$/TMS): δ (ppm): 7.5-6.5 (br, 1H), 3.60 (m, 1H), 1.53-1.29 (m, 17H), 1.21 (s, 6H), 0.91 (t, J=6.6 Hz, 3H). $^{13}$C NMR (75 MHz, CDCl$_3$/TMS): δ (ppm): 185.0, 73.0, 43.1, 41.5, 38.2, 38.0, 31.2, 28.8, 26.5, 26.0, 25.9, 23.8, 15.1. HRMS (LSIMS, gly): Calcd for $C_4H_{29}O_3$ (MH$^+$): 245.2116, found: 245.2107. HPLC: 97.1% pure. Elemental analysis ($C_{14}H_{28}O_3$): Calcd for C, 68.81; H, 68.67. Found: C, 68.67; H, 11.64.

7. BIOLOGICAL ASSAYS

7.1 Effects of Illustrative Compounds of the Invention on NonHDL Cholesterol, HDL Cholesterol, Triglyceride Levels, Glycemic Control Indicators and Body Weight Control in Obese Female Zucker Rats In a number of different experiments, illustrative compounds of the invention are administered daily at a dose of up to 100 mg/kg to chow fed obese female Zucker rats for fourteen days in the morning by oral gavage in 1.5% carboxymethylcellulose/0.2% Tween 20 or 20% ethanol/80% polyethylene glycol (dosing vehicles). Animals are weighed daily. Animals are allowed free access to rodent chow and water throughout the study except on days of blood sampling where food is restricted for six hours prior to blood sampling. Blood glucose is determined after the 6 hour fast in the afternoon without anesthesia from a tail vein. Serum is also prepared from pretreatment blood samples subsequently obtained from the orbital venous plexus (with O$_2$/CO$_2$ anesthesia) and following the fourteenth dose at sacrifice from the heart following O$_2$/C$_2$ anesthesia. Serums are assayed for lipoprotein cholesterol profiles, triglycerides, total cholesterol, Non-HDL cholesterol, HDL cholesterol, the ratio of HDL cholesterol to that of Non-HDL cholesterol, insulin, non-esterified fatty acids, and beta-hydroxy butyric acid. The percent body weight gain and the ratio of liver to body weight is also determined. These are shown as absolute values or as a percent change of the pretreatment values in Table 1 for compounds A-K and in Table 2 for compounds L-M.

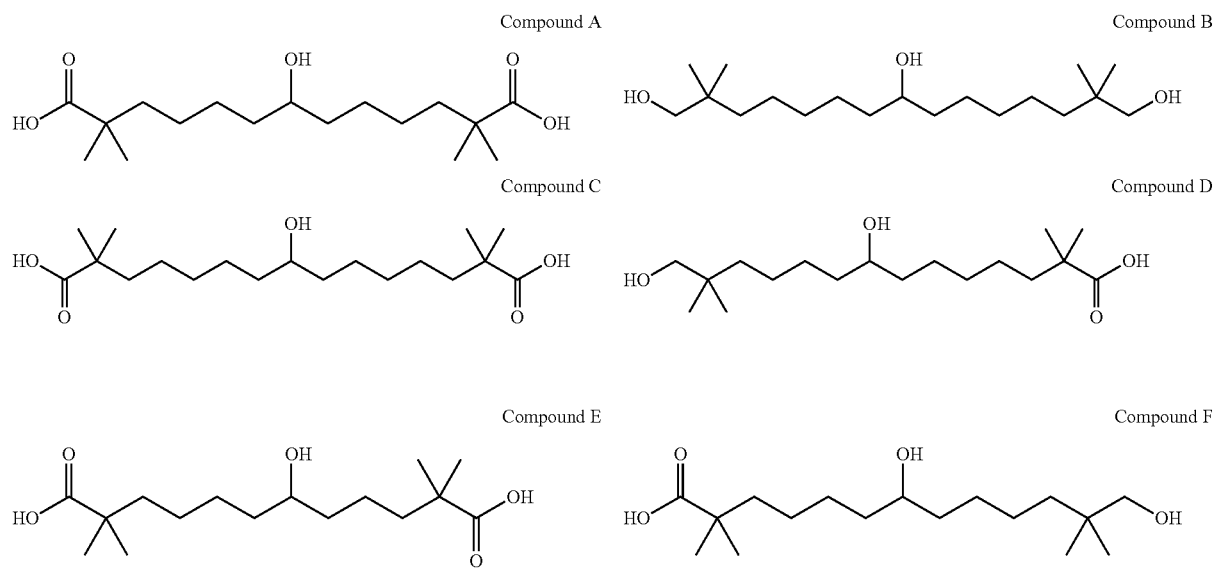

Compound A

Compound B

Compound C

Compound D

Compound E

Compound F

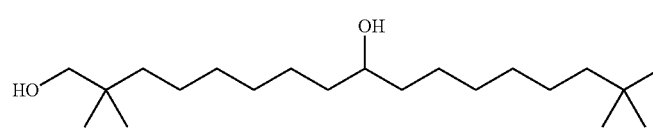

Compound G

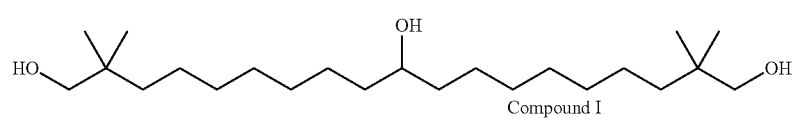

Compound H

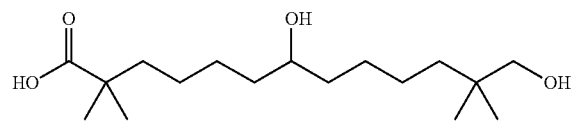

Compound I

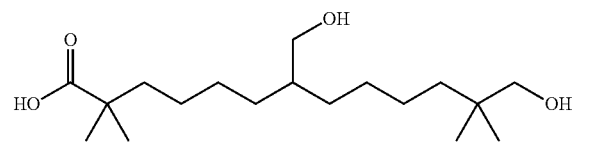

Compound J

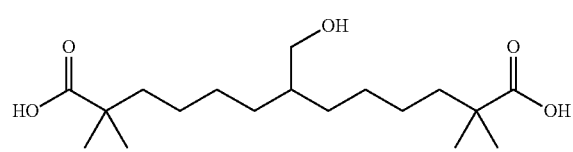

Compound K

Compound L

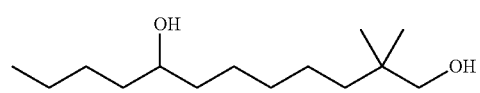

Compound M

7.2 Effects of Illustrative Compounds of the Invention on the In Vitro Lipid Synthesis in Isolated Hepatocytes Compounds were tested for inhibition of lipid synthesis in primary cultures of rat hepatocytes. Male Sprague-Dawley rats were anesthetized with intraperitoneal injection of sodium pentobarbital (80 mg/kg). Rat hepatocytes were isolated essentially as described by the method of Seglen (Seglen, P. O. Hepatocyte suspensions and cultures as tools in experimental carcinogenesis. *J. Toxicol. Environ. Health* 1979, 5, 551-560). Hepatocytes were suspended in Dulbecco's Modified Eagles Medium containing 25 mM D-glucose, 14 mM HEPES, 5 mM L-glutamine, 5 mM leucine, 5 mM alanine, 10 mM lactate, 1 mM pyruvate, 0.2% bovine serum albumin, 17.4 mM non-essential amino acids, 20% fetal bovine serum, 100 nM insulin and 20 µg/mL gentamycin) and plated at a density of $1.5 \times 10^5$ cells/cm² on collagen-coated 96-well plates. Four hours after plating, media was replaced with the same media without serum. Cells were grown overnight to allow formation of monolayer cultures. Lipid synthesis incubation conditions were initially assessed to ensure the linearity of [1-$^{14}$C]-acetate incorporation into hepatocyte lipids for up to 4 hours. Hepatocyte lipid synthesis inhibitory activity was assessed during incubations in the presence of 0.25 µCi [1-$^{14}$C]-acetate/well (final radio-specific activity in assay is 1 Ci/mol) and 0, 1, 3, 10, 30, 100 or 300 µM of compounds for 4 hours. At the end of the 4-hour incubation period, medium was discarded and cells were washed twice with ice-cold phosphate buffered saline and stored frozen prior to analysis. To determine total lipid synthesis, 170 µl of MicroScint-E® and 50 µl water was added to each well to extract and partition the lipid soluble products to the upper organic phase containing the scintillant. Lipid radioactivity was assessed by scintillation spectroscopy in a Packard TopCount NXT. Lipid synthesis rates were used to determine the $IC_{50}$s of the compounds that are presented in Table 3.

TABLE 1

Examples of effects of oral daily treatment of obese female Zucker rats with compounds A-K of the invention for fourteen days
Percent of Pre-treatment

| Compound | Expt. # | n | Dose (mg/kg/day) | % wt. gain | HDL-C/ non-HDL-C | TG | TC | Non-HDL-C | HDL-C | Glucose | Insulin | NEFA | BHA |
|---|---|---|---|---|---|---|---|---|---|---|---|---|---|
| Vehicle | LR63 | 5 | | 13 | 2 | 6 | −17 | 7 | −22 | 2 | −1 | 50 | 211 |
| A | | 4 | 100 | 12 | 5 | −59 | 14 | −41 | 50 | −2 | 4 | −11 | 231 |
| Vehicle | LR92 | 4 | | 7 | 2 | 1 | −3 | 24 | −10 | −5 | −9 | 11 | 62 |
| B | | 4 | 100 | 1 | 35 | −87 | 105 | −81 | 237 | −3 | −52 | −28 | 199 |
| Vehicle | LR107 | 4 | | 8 | 8 | 3 | −4 | 3 | −3 | −14 | −11 | −13 | 139 |
| C | | 4 | 100 | 3 | 40 | −90 | 105 | −80 | 169 | −11 | −57 | −42 | 171 |
| Vehicle | LR28 | 5 | | 1 | 1 | −41 | −14 | −39 | 58 | −16 | −43 | −37 | 236 |
| F | | 2 | 100 | 3 | 2 | −46 | 53 | −15 | 222 | 10 | −4 | −43 | 1056 |
| Vehicle | LR98 | 5 | | 9 | 2 | 23 | 1 | 116 | −26 | 8 | 19 | 6 | 29 |
| G | | 2 | 100 | 9 | 12 | −80 | 21 | −68 | 68 | 14 | −38 | −62 | 163 |
| Vehicle | LR98 | 5 | | 9 | 2 | 23 | 1 | 116 | −26 | 8 | 19 | 6 | 29 |
| H | | 3 | 100 | 9 | 3 | −36 | 61 | −5 | 115 | 19 | −30 | −30 | 97 |

TABLE 1-continued

Examples of effects of oral daily treatment of obese female Zucker rats with compounds A-K of the invention for fourteen days
Percent of Pre-treatment

| Compound | Expt. # | n | Dose (mg/kg/day) | % wt. gain | HDL-C/ non-HDL-C | TG | TC | Non-HDL-C | HDL-C | Glucose | Insulin | NEFA | BHA |
|---|---|---|---|---|---|---|---|---|---|---|---|---|---|
| Vehicle | LR52 | 4 | | 8 | 2 | −6 | −14 | −16 | −7 | 3 | −36 | −7 | 31 |
| J | | 3 | 100 | 12 | 2 | −23 | −6 | −12 | −2 | 21 | −11 | −32 | 183 |
| Vehicle | LR119 | 5 | | 11 | 4 | 9 | 20 | −6 | 28 | 6 | 3 | −2 | 65 |
| K | | 3 | 100 | 10 | 9 | −45 | 35 | −38 | 62 | 3 | 41 | −32 | 253 |

TABLE 2

Examples of effects of oral daily treatment of obese female Zucker rats with compounds
L and M of the invention for fourteen days days
Percent of Pre-treatment

| Compound | Expt. # | n | Dose (mg/kg/day) | % wt. gain | HDL-C/ non-HDL-C | TG | TC | Non-HDL-C | HDL-C | Glucose | Insulin | NEFA | BHA |
|---|---|---|---|---|---|---|---|---|---|---|---|---|---|
| Vehicle | LR118 | 5 | | 10 | 4 | 8 | 1 | 43 | −8 | −2 | −24 | 14 | 81 |
| L | | 3 | 100 | 12 | 4 | −37 | −3 | −11 | −2 | 13 | −37 | −27 | 88 |
| Vehicle | LR118 | 5 | | 10 | 4 | 8 | 1 | 43 | −8 | −2 | −24 | 14 | 81 |
| M | | 3 | 100 | 10 | 3 | −11 | 15 | 7 | 19 | 5 | −5 | −23 | 63 | n is number of animals per experiment

TABLE 3

Effect of Illustrative Compounds of the Invention on the Lipid Synthesis in Primary Rat Hepatocytes.

| Compound | IC$_{50}$ (μM) | 95% Confidence Interval Lower | Upper | r$^2$ |
|---|---|---|---|---|
| A | 3.4 | 2.5 | 4.5 | 0.99 |
| B | 5.1 | 3.6 | 7.3 | 0.99 |
| C | 1.0 | 0.5 | 2.0 | 0.99 |
| D | 1.6 | 1.2 | 2.0 | 0.99 |
| E | 8.3 | 4.6 | 15.1 | 0.98 |
| F | 6.4 | 3.7 | 11.1 | 0.99 |
| G | 7.8 | 6.7 | 8.9 | 0.99 |
| H | 2.6 | 1.5 | 4.4 | 0.98 |
| I | 2.3 | 1.4 | 3.7 | 0.99 |
| J | 17 | 8.7 | 34.4 | 0.98 |
| K | 14 | 12.2 | 15.8 | 0.99 | rodent chow (Purina 5001) and water except for a 6 hour period prior to blood sampling. Following the 21 day acclimation period ESP 55015 was administered daily for three weeks, between 8 10 AM, at a dose of 100 mg/Kg by oral gavage in a dosing vehicle consisting of 20% Ethanol/ 80% Polyethylene glycol 200 [v/v]. Prior to and in the afternoon following the 13th and 21st doses blood samples were collected, between 2 PM and 4 PM, by administering $O_2/CO_2$ anesthesia and bleeding from the orbital venous plexus. All blood samples were processed for separation of serum. Serum samples were subsequently assayed for total cholesterol, total cholesterol lipoprotein profiles (HDL cholesterol, LDL cholesterol and VLDL cholesterol), the ratio of HDL cholesterol, LDL cholesterol and VLDL cholesterol), the ratio of HDL cholesterol to non HDL cholesterol (LDL C, VLDL C) and triglycerides (Table 4). Percent body weight gain and ratio of liver weight to body weight were also determined.

TABLE 4

Effect of Compound B in chow-fed hamster after 3 weeks of dosing

| Compound | Expt. # | n | Dose (mg/kg/day) | Body wt. (gm) | VLDL-C (mg/dl) | LDL-C (mg/dl) | HDL-C (mg/dl) | TG (mg/dl) | Glucose | Insulin | Bile Acids (ng/ml) |
|---|---|---|---|---|---|---|---|---|---|---|---|
| Vehicle | LR100 | 5 | 0 | 148 ± 4 | 9 ± 1 | 41 ± 2 | 83 ± 4 | 325± | 122 ± 4 | | 30,600± |
| B | LR100 | 5 | 100 | 146 ± 2 | 4 ± 2 | 44 ± 4 | 63 ± 4 | 128 ± 37 | 122 ± 3 | 2.4 ± 07 | 67,108 ± 17,529 |

7.3 Effects of Compound B of the Invention on VLDL Cholesterol, LDL Cholesterol HDL Cholesterol Triglyceride Levels, Glycemic Control Indicators Body Weight and Bile Acids in Female Syrian Hamsters Ten week old female Syrian hamsters were acclimated for 21 days to a shortened light and dark cycle (10 hours of light/14 hours of darkness). During the acclimation and drug intervention period animals were allowed free access to The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

The invention claimed is:

1. A method of lowering LDL cholesterol in a human in need thereof, comprising administering to the human a therapeutically effective amount of a compound of formula I, wherein formula I is represented by:

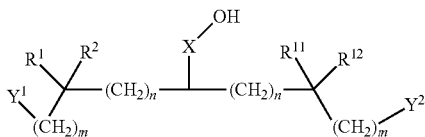

or a pharmaceutically acceptable salt thereof, wherein:
(a) each occurrence of m is independently an integer ranging from 0 to 5;
(b) each occurrence of n is independently an integer ranging from 3 to 7;
(c) X is $(CH_2)_z$, wherein z is an integer from 0 to 4;
(d) each occurrence of $R^1$, $R^2$, $R^{11}$, and $R^{12}$ is independently H, $(C_1-C_6)$alkyl, or phenyl, wherein $R^1$, $R^2$, $R^{11}$, and $R^{12}$ are not each simultaneously H; and
(e) each occurrence of $Y^1$ and $Y^2$ is independently OH, COOH, $COOR^3$,

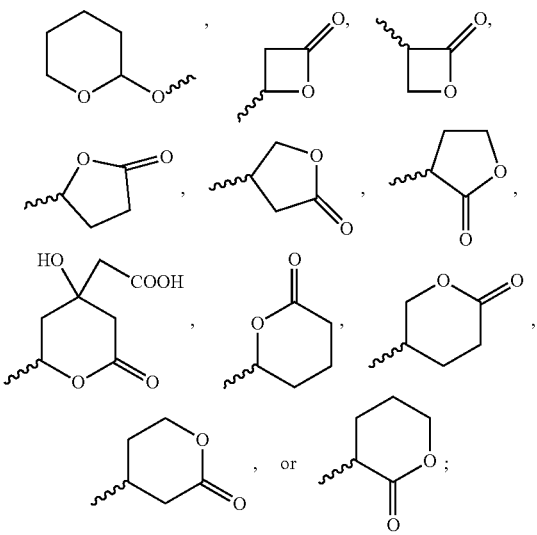

wherein $R^3$ is $(C_1-C_6)$alkyl, phenyl, or benzyl and is unsubstituted or substituted with one or more halo, OH, or $(C_1-C_6)$alkoxy.

2. The method of claim 1, wherein each occurrence of $Y^1$ and $Y^2$ is independently OH, $COOR^3$, or COOH.

3. The method of claim 1, wherein m is 0.

4. The method of claim 1, wherein n is 5.

5. The method of claim 1, wherein z is 0.

6. The method of claim 5, wherein $R^1$, $R^2$, and $R^{11}$ are $(C_1-C_6)$alkyl.

7. The method of claim 6, wherein $Y^1$ and $Y^2$ is COOH.

8. The method of claim 1, wherein the compound of formula I is the following:

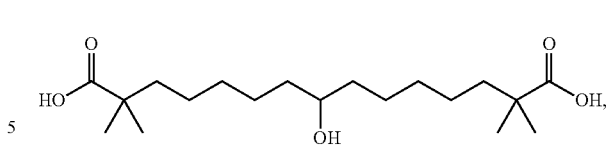

or a pharmaceutically acceptable salt thereof.

9. The method of claim 1, wherein the compound of formula I is the following:

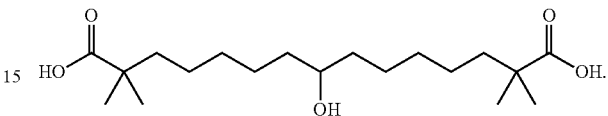

10. The method of claim 1, wherein the compound is administered orally to the human.

11. A method of lowering LDL cholesterol in a human in need thereof, comprising administering to the human a therapeutically effective amount of a compound of formula I, wherein formula I is represented by:

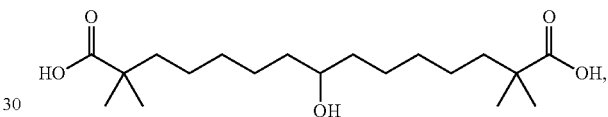

or a pharmaceutically acceptable salt thereof.

12. The method of claim 11, wherein the compound of formula I is:

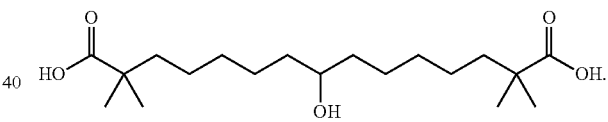

13. The method of claim 1, wherein the compound of formula I is orally administered to the human in the form of a pharmaceutical composition comprising the compound of formula I, and a pharmaceutically acceptable vehicle.

14. The method of claim 11, wherein the compound of formula I is orally administered to the human in the form of a pharmaceutical composition comprising the compound of formula I, and a pharmaceutically acceptable vehicle.

15. The method of claim 12, wherein the compound of formula I is orally administered to the human in the form of a pharmaceutical composition comprising the compound of formula I, and a pharmaceutically acceptable vehicle.

16. The method of claim 1, wherein the human has familial hypercholesterolemia.

17. The method of claim 1, wherein the human has cardiovascular disease.

18. The method of claim 17, wherein the cardiovascular disease is atherosclerotic cardiovascular disease.

19. The method of claim 11, wherein the human has familial hypercholesterolemia.

20. The method of claim 11, wherein the human has cardiovascular disease.

21. The method of claim 20, wherein the cardiovascular disease is atherosclerotic cardiovascular disease.

22. The method of claim 12, wherein the human has familial hypercholesterolemia.

23. The method of claim 12, wherein the human has cardiovascular disease.

24. The method of claim 23, wherein the cardiovascular disease is atherosclerotic cardiovascular disease.

* * * * *